(12) United States Patent
Zhang et al.

(10) Patent No.: US 11,071,585 B2
(45) Date of Patent: Jul. 27, 2021

(54) SYSTEMS AND METHODS OF ABLATING CARDIAC TISSUE

(71) Applicant: Biosense Webster (Israel) Ltd., Yokneam (IL)

(72) Inventors: Xiangming Zhang, Irvine, CA (US); Nader Ghaly, Irvine, CA (US); Eid Adawi, Tur'an (IL); Moe Habib Bishara, Irvine, CA (US); Kendra Anita McInnis, Irvine, CA (US); Assaf Govari, Haifa (IL); Christopher Thomas Beeckler, Brea, CA (US); Joseph Thomas Keyes, Sierra Madre, CA (US); Rowan Olund Hettel, Irvine, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/569,608

(22) Filed: Sep. 12, 2019

(65) Prior Publication Data
US 2020/0085497 A1    Mar. 19, 2020

Related U.S. Application Data

(60) Provisional application No. 62/731,525, filed on Sep. 14, 2018, provisional application No. 62/754,275, (Continued)

(51) Int. Cl.
*A61B 18/00* (2006.01)
*A61B 18/12* (2006.01)
(Continued)

(52) U.S. Cl.
CPC ...... *A61B 18/1492* (2013.01); *A61B 18/1206* (2013.01); *A61M 25/10* (2013.01);
(Continued)

(58) Field of Classification Search
CPC ...... A61B 18/1206; A61B 2018/00351; A61B 2018/00375; A61B 2018/00755
See application file for complete search history.

(56) References Cited

U.S. PATENT DOCUMENTS 5,718,241 A    2/1998 Ben-Haim et al.
6,198,974 B1   3/2001 Webster, Jr.
(Continued)

FOREIGN PATENT DOCUMENTS

EP    2 749 214 A1    7/2014
EP    2 875 790 A2    5/2015
WO    2018/129133 A1  7/2018

OTHER PUBLICATIONS

"Multi-Electrode RF Balloon Efficient for Acute Pulmonary Vein Isolation." DAIC, May 17, 2017, www.dicardiology.com/article/multi-electrode-rf-balloon-efficient-acute-pulmonary-vein-isolation. (Year: 2017).*

(Continued)

*Primary Examiner* — Jaymi E Della
(74) *Attorney, Agent, or Firm* — Troutman Pepper Hamilton Sanders LLP

(57) ABSTRACT

The subject of this disclosure includes systems, devices and methods to treat a predetermined patient population for paroxysmal atrial fibrillation, the method including ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently control- (Continued)

lable; determining a predictor, based on ablation parameters of the balloon catheter, of single shot pulmonary vein isolation (PVI) success rate; and achieving, based on the predictor and step of ablating tissue, a single shot isolation PVI success rate in the isolation of all targeted pulmonary veins for the predetermined patient population.

11 Claims, 128 Drawing Sheets

Related U.S. Application Data filed on Nov. 1, 2018, provisional application No. 62/771,896, filed on Nov. 27, 2018, provisional application No. 62/886,729, filed on Aug. 14, 2019, provisional application No. 62/889,471, filed on Aug. 20, 2019, provisional application No. 62/873,636, filed on Jul. 12, 2019.

(51) Int. Cl.
*A61B 18/14* (2006.01)
*A61M 25/10* (2013.01)

(52) U.S. Cl.
CPC ............... *A61B 2018/00351* (2013.01); *A61B 2018/00375* (2013.01); *A61B 2018/00577* (2013.01); *A61B 2018/00755* (2013.01); *A61B 2018/00791* (2013.01); *A61B 2018/1417* (2013.01); *A61M 2025/1079* (2013.01)

(56) References Cited

U.S. PATENT DOCUMENTS

| | | | |
|---|---|---|---|
| 6,322,558 B1 | 11/2001 | Taylor et al. | |
| 6,484,118 B1 | 11/2002 | Govari | |
| 6,987,995 B2 | 1/2006 | Drysen | |
| 7,142,903 B2 | 11/2006 | Rodriguez et al. | |
| 7,274,957 B2 | 9/2007 | Drysen | |
| 7,377,906 B2 | 5/2008 | Selkee | |
| 7,591,799 B2 | 9/2009 | Selkee | |
| 7,593,760 B2 | 9/2009 | Rodriguez et al. | |
| 7,720,517 B2 | 5/2010 | Drysen | |
| 7,853,302 B2 | 12/2010 | Rodriguez et al. | |
| 8,000,765 B2 | 8/2011 | Rodriguez et al. | |
| 8,021,327 B2 | 9/2011 | Selkee | |
| 8,275,440 B2 | 9/2012 | Rodriguez et al. | |
| 8,348,888 B2 | 1/2013 | Selkee | |
| 9,907,610 B2 | 3/2018 | Beeckler et al. | |
| 9,956,035 B2 | 5/2018 | Govari et al. | |
| 2002/0068931 A1 | 6/2002 | Wong et al. | |
| 2003/0028183 A1 | 2/2003 | Sanchez et al. | |
| 2003/0144658 A1* | 7/2003 | Schwartz ........... | A61B 18/1492 606/41 |
| 2004/0147920 A1 | 7/2004 | Keidar | |
| 2012/0101538 A1 | 4/2012 | Ballakur et al. | |
| 2012/0143177 A1 | 6/2012 | Avitall | |
| 2012/0143293 A1 | 6/2012 | Mauch et al. | |
| 2012/0209260 A1* | 8/2012 | Lambert ............ | A61B 18/1492 606/41 |
| 2013/0150693 A1 | 6/2013 | D'Angelo et al. | |
| 2013/0169624 A1 | 7/2013 | Bourier et al. | |
| 2014/0012242 A1 | 1/2014 | Lee et al. | |
| 2014/0275993 A1 | 9/2014 | Ballakur | |
| 2015/0112321 A1 | 4/2015 | Cadouri | |
| 2015/0272667 A1 | 10/2015 | Govari et al. | |
| 2015/0327805 A1 | 11/2015 | Ben-Haim | |
| 2016/0175041 A1 | 6/2016 | Govari et al. | |
| 2017/0311829 A1 | 11/2017 | Beeckler et al. | |
| 2017/0311893 A1 | 11/2017 | Beeckler et al. | |
| 2017/0312022 A1 | 11/2017 | Beeckler et al. | |
| 2017/0347896 A1 | 12/2017 | Keyes et al. | |
| 2017/0348049 A1 | 12/2017 | Vrba et al. | |
| 2018/0125575 A1 | 5/2018 | Schwartz et al. | |
| 2018/0161093 A1 | 6/2018 | Basu et al. | |
| 2018/0280080 A1 | 10/2018 | Govari et al. | |
| 2019/0060622 A1 | 2/2019 | Beeckler | |
| 2019/0143079 A1 | 5/2019 | Beeckler et al. | |
| 2019/0175262 A1 | 6/2019 | Govari et al. | |
| 2019/0183567 A1 | 6/2019 | Govari et al. | |
| 2019/0217065 A1 | 7/2019 | Govari et al. | |
| 2019/0298441 A1 | 10/2019 | Clark et al. | |
| 2019/0365451 A1* | 12/2019 | Jung, Jr. ............ | A61B 18/1492 |
| 2020/0001054 A1 | 1/2020 | Jimenez et al. | |
| 2020/0155226 A1 | 5/2020 | Valls et al. | |

OTHER PUBLICATIONS

O'Neill, Angela. "AF Symposium 2017: First-in-Man Study Shows Promising Results with a Multi-Electrode Radiofrequency Balloon for Paroxysmal AF Treatment." Cardiac Rhythm News, Jan. 20, 2017, https://cardiacrhythmnews.com/(Year: 2017).*

Vivek Y. Reddy, Petr Neuzil, Andre d'Avila, Margaret Laragy, Zachary J. Malchano, Stepan Kralovec, Steven J. Kim, Jeremy N. Ruskin, Balloon catheter ablation to treat paroxysmal atrial fibrillation: What is the level of pulmonary venous isolation?, Heart Rhythm. Vol. 5:3. Mar. 2008. pp. 353-360. (Year: 2008).*

International Search Report and Written Opinion issued in corresponding International Patent Application No. PCT/IB2019/057743 dated Dec. 6, 2019.

"Multi-Electrode RF Balloon Efficient for Acute Pulmonary Vein Isolation." Daic, May 17, 2017, www.dicardiology.com/article/multi-electrode-rf-balloon-efficient-acute-pulmonary-vei n-isolation. (Year: 2017) cited in OA issued in corresponding U.S. Appl. No. 17/096,484 dated Dec. 28, 2021.

O'Neill, Angela. "AF Symposium 2017: First-in-Man Study Shows Promising Results with a Multi-Electrode Radiofrequency Balloon for Paroxysmal AF Treatment." Cardiac Rhythm News, Jan. 20, 2017, (Year: 2017) https://cardiacrhythmnews.com/fist-in-man-study-shows-promising-results-with-a-multi-electrode-radiofrequency-balloon-for-paroxysmal-af-treatment/ (Year: 2017) cited in OA issued in corresponding U.S. Appl. No. 17/096,484 dated Dec. 28, 2021.

Vivek Y. Reddy, Petr Neuzil, Andre d'Avila, Margaret Laragy, Zachary J. Malchano, Stepan Kralovec, Steven J. Kim, Jeremy N. Ruskin, Balloon catheter ablation to treat paroxysmal atrial fibrillation: What is the level of pulmonary venous isolation?, Heart Rhythm. vol. 5:3. Mar. 2008. pp. 353-360. (Year: 2008) cited in OA issued in corresponding U.S. Appl. No. 17/096,484 dated Dec. 28, 2021.

Nagashima, Koichi, et al. Hot Balloon Versus Cryoballoon Ablation for Atrial Fibrillation. Circulation: arrhythmia and Electrophysiology. vol. 11 :5. May 2018. (Year: 2018) cited in OA issued in corresponding U.S. Appl. No. 17/096,484 dated Dec. 28, 2020.

International Search Report and Written Opinion issued in corresponding International Application No. PCT/IB2019/057742 dated Nov. 28, 2019.

Casella, M., et al. "Ablation Index as a predictor of long-term efficacy in premature ventricular complex ablation: A regional target value analysis" Heart Rhythm Society pp. 888-895 (2019).

Das. M., et al. "Ablation index, a novel marker of ablation lesion quality: prediction of pulmonary vein reconnection at repeat electrophysiology study and regional differences in target values" Europace 19:775-783 (2017).

* cited by examiner

| Parameter | Unipolar Mode |
|---|---|
| Inside Sheath Flow Rate | 5 ml/min |
| Idle Flow Rate | 5 ml/min |
| Irrigation Flow Rate During RF Application | 35 ml/min |
| Power Setting | Max 15 W |
| Temperature Setting* | Max 55 °C |
| Application Time Anterior Electrodes | Max 60 sec |
| Application Time Posterior Electrodes | Max 20 sec |

Fig. 14

| Mild | Awareness of signs, symptoms, or events that are otherwise easily tolerated that may result in minimal transient impairment of a body function or damage to a body structure, but do not require intervention other than monitoring. |
|---|---|
| Moderate | Any event that results in moderate transient impairment of a body function or damage to a body structure that causes interference with usual activities, or that warrants possible intervention, such as the administration of medication, to prevent permanent impairment of a body function or damage to a body structure. |
| Severe | Any event that is incapacitating (an inability to do usual activities) or is life-threatening and results in permanent impairment of a body function or damage to a body structure, or requires intervention, such as major surgery, to prevent permanent impairment of a body function or damage to a body structure. |

Fig. 15

| | Blanking period (≤ 90 days post procedure) | Post blanking period (> 90 days post procedure) |
|---|---|---|
| New Class I and/or Class III AAD | Can be initiated; subject will not be classified as a primary effectiveness failure. | Should NOT be initiated in the absence of AF recurrence; subject will be classified as a primary effectiveness failure.<br><br>Should NOT be continued past 90-days post-ablation (if initiated in blanking). Subject will be classified as a primary effectiveness failure |
| Previously failed Class I and/or Class III AAD (> highest historically failed dose) | Can be initiated; subject will not be classified as a primary effectiveness failure.<br><br>Can be continued (from prior to study enrollment); subject will not be classified as a primary effectiveness failure. | Should NOT be initiated in the absence of AF recurrence; subject will be classified as a primary effectiveness failure.<br><br>Should NOT be continued past 90-days post-ablation (if initiated in blanking). Subject will be classified as a primary effectiveness failure |
| Previously failed Class I and/or Class III AAD (≤ highest historically failed dose) | Can be initiated; subject will not be classified as a primary effectiveness failure.<br><br>Can be continued (from prior to study enrollment); subject will not be classified as a primary effectiveness failure. | Can be initiated; subject will not be classified as a primary effectiveness failure.<br><br>Can be continued past 90-days postablation (if initiated in blanking). Subject will not be classified as a primary effectiveness failure. |
| Class II and/or Class IV AAD | Can be initiated, continued, or increased and subject will not be classified as a primary effectiveness failure. | Can be initiated, continued, or increased and subject will not be classified as a primary effectiveness failure. |

Fig. 16

1700
delivering a multi-electrode radiofrequency balloon catheter to one or more targeted pulmonary veins
1710
ablating tissue of the pulmonary vein using the multi-electrode radiofrequency balloon catheter
1720
achieving a predetermined effectiveness rate of pulmonary vein isolation
1730
Fig. 17

1800
delivering a multi-electrode radiofrequency balloon catheter to a pulmonary vein
1810
ablating tissue of the pulmonary vein using the multi-electrode radiofrequency balloon catheter
1820
achieving a predetermined success rate of pulmonary vein isolation
1830
Fig. 18

1900
delivering a multi-electrode radiofrequency balloon catheter to a pulmonary vein
1910
ablating tissue of the pulmonary vein using the multi-electrode radiofrequency balloon catheter
1920
achieving pulmonary vein isolation and at least a 97% safety endpoint within seven (7) days of successful pulmonary vein isolation
1930
Fig. 19

```
2000 ─┐
        ↓
┌─────────────────────────────────────────────────┐
│ delivering a multi-electrode radiofrequency balloon │
│           catheter to a pulmonary vein          │
│                     2010                        │
└─────────────────────────────────────────────────┘
                        │
                        ▼
┌─────────────────────────────────────────────────┐
│ ablating tissue of the pulmonary vein using the multi- │
│      electrode radiofrequency balloon catheter   │
│                     2020                        │
└─────────────────────────────────────────────────┘
                        │
                        ▼
┌─────────────────────────────────────────────────┐
│ achieving pulmonary vein isolation and at least a 90% │
│  safety endpoint within seven (7) days of successful  │
│              pulmonary vein isolation            │
│                     2030                        │
└─────────────────────────────────────────────────┘
```

--- delivering a multi-electrode radiofrequency balloon catheter having a plurality of independently controllable electrodes for radiofrequency ablation and a multi-electrode diagnostic catheter to one or more targeted pulmonary veins
2110

↓ ablating tissue of the one or more targeted pulmonary veins with one or more of the plurality of the electrodes independently controlled multi-electrode radiofrequency balloon catheter
2120

↓ diagnosing the one or more targeted pulmonary veins using the multi-electrode diagnostic catheter
2130

↓ achieving at least one of a predetermined clinical effectiveness and acute effectiveness of the method based on use of the multi-electrode radiofrequency balloon catheter and the multi-electrode diagnostic catheter in the isolation of the one or more targeted pulmonary veins
2140

```
┌─────────────────────────────────────────────────────────────┐
│ delivering a multi-electrode radiofrequency balloon catheter having a │
│ plurality of independently controllable electrodes for radiofrequency │
│ ablation and a multi-electrode diagnostic catheter to one or more │
│ targeted pulmonary veins                                    │
│ 2210                                                        │
└─────────────────────────────────────────────────────────────┘
                              ↓
┌─────────────────────────────────────────────────────────────┐
│ ablating tissue of one or more targeted pulmonary veins with one or │
│ more of the plurality of the electrodes independently controlled multi- │
│ electrode radiofrequency balloon catheter                   │
│ 2220                                                        │
└─────────────────────────────────────────────────────────────┘
                              ↓
┌─────────────────────────────────────────────────────────────┐
│ diagnosing all targeted pulmonary veins using the multi-electrode │
│ diagnostic catheter                                         │
│ 2230                                                        │
└─────────────────────────────────────────────────────────────┘
                              ↓
┌─────────────────────────────────────────────────────────────┐
│ achieving a predetermined rate of adverse events based on use of the │
│ multi-electrode radiofrequency balloon catheter and the multi- │
│ electrode diagnostic catheter in the isolation of all targeted pulmonary │
│ veins, during and approximately 6 months after the method   │
│ 2240                                                        │
└─────────────────────────────────────────────────────────────┘
```

Fig. 22

| Population | N = 87 (Excluding roll-in cases) | | | | | |
|---|---|---|---|---|---|---|
| | Single shot Isolation (no reconnection) | | Isolation-Reconnection | | Non-Isolation | |
| Balloon Inflation Index | $0.94 \pm 0.08$ | | $0.92 \pm 0.10$ | | $0.92 \pm 0.09$ | |
| Ablation location | Ant. | Post. | Ant. | Post. | Ant. | Post. |
| # of Electrode Ablations | 1078 (74.3%) | 372 (25.7%) | 90 (75.0%) | 30 (25.0%) | 421 (69.0%) | 189 (31.0%) |
| Initial Impedance ($\Omega$) | $98.4 \pm 12.0$ | $104.2 \pm 13.0$ | $95.5 \pm 12.0$ | $104.9 \pm 10.5$ | $102.2 \pm 13.6$ | $109.3 \pm 16.2$ |
| Impedance Drop ($\Omega$) | $19.6 \pm 9.1$ | $21.9 \pm 9.2$ | $17.7 \pm 8.8$ | $23.1 \pm 9.0$ | $18.4 \pm 10.2$ | $22.8 \pm 12.8$ |
| Max Temperature (°C) | $41.4 \pm 5.5$ | $41.4 \pm 5.1$ | $40.1 \pm 5.8$ | $42.0 \pm 6.4$ | $40.4 \pm 5.1$ | $40.3 \pm 5.8$ |
| Temperature rise (°C) | $11.6 \pm 6.4$ | $11.5 \pm 5.5$ | $9.8 \pm 6.4$ | $12.6 \pm 12.6$ | $10.2 \pm 5.9$ | $10.1 \pm 6.3$ |

Fig. 24

| Initial Impedance Variation (Ω) | N= | 1-shot PVI rate |
|---|---|---|
| < 20 | 27 | 85.2% |
| 20-30 | 77 | 77.9% |
| 30-40 | 61 | 75.4% |
| 40-50 | 34 | 67.6% |
| 50-60 | 11 | 36.4% |
| ≥ 60 | 9 | 33.3% |
| Total | 219 | 72.6% |

| Potential Predictors | | Pearson Correlation | | Binary logistic regression | |
|---|---|---|---|---|---|
| | | Coefficient * | P-value* | Odds ratio (95% CI) | P-value |
| Pre-ablation Parameters | Lowest Ant. Imp | -0.159 | 0.019 | 0.952 (0.913 – 0.992) | 0.018 |
| | Ant. Imp variation | -0.219 | 0.001 | 0.961 (0.937 – 0.985) | 0.001 |
| | Lowest initial Imp | -0.131 | 0.053 | 0.958 (0.916 – 1.00) | 0.051 |
| | Mean initial Imp | -0.267 | 0.000 | 0.925 (0.888 – 0.963) | 0.000 |
| | Initial Imp Variation | -0.284 | 0.000 | 0.952 (0.929 – 0.976) | 0.000 |
| Post-ablation Parameters | Lowest max temp | 0.152 | 0.024 | 1.240 (1.025 – 1.499) | 0.020 |
| | Lowest Imp drop | 0.259 | 0.000 | 1.162 (1.073 – 1.258) | 0.000 |
| | Mean Imp drop | 0.032 | 0.639 | 1.015 (0.954 – 1.080) | 0.635 |
| | Imp drop variation | -0.267 | 0.000 | 0.944 (0.915 – 0.973) | 0.000 |

Fig. 33

| Potential Predictors | | | Pearson Correlation | | Binary logistic regression | |
|---|---|---|---|---|---|---|
| | | Among 10 electrodes | Coefficient* | P-value* | Odds ratio (95% CI) | P-value |
| Pre-Ablation Parameters | Initial Temp | Mean | -0.161 | 0.019 | 0.714 (0.536 – 0.951) | 0.016 |
| | | Lowest value | -0.089 | 0.196 | 0.815 (0.580 – 1.111) | 0.191 |
| | | Highest value | -0.227 | 0.001 | 0.609 (0.448 – 0.828) | 0.000 |
| | | Variation | -0.214 | 0.002 | 0.624 (0.460 – 0.847) | 0.002 |
| | Initial Imp | Mean | -0.288 | 0.000 | 0.916 (0.877 – 0.956) | 0.000 |
| | | Lowest value | -0.152 | 0.027 | 0.950 (0.906 – 0.995) | 0.026 |
| | | Highest value | -0.335 | 0.000 | 0.945 (0.922 – 0.969) | 0.000 |
| | | Variation | -0.288 | 0.000 | 0.950 (0.927 – 0.975) | 0.000 |
| | Initial anterior wall Imp# | Mean | -0.258 | 0.000 | 0.924 (0.885 – 0.964) | 0.000 |
| | | Lowest value | -0.190 | 0.006 | 0.940 (0.898 – 0.983) | 0.005 |
| | | Highest value | -0.291 | 0.000 | 0.950 (0.926 – 0.974) | 0.000 |
| | | Variation | -0.207 | 0.003 | 0.962 (0.936 – 0.988) | 0.003 |

Fig. 34

| Potential Predictors | | Pearson Correlation | | Binary logistic regression | |
|---|---|---|---|---|---|
| | Among 10 electrodes | Coefficient | P-value | Odds ratio (95% CI) | P-value |
| Temp slope | Mean | 0.201 | 0.004 | 6.145 (1.754 – 21.529) | 0.003 |
| | Lowest value | 0.217 | 0.002 | 7.251 (2.023 – 25.983) | 0.001 |
| | Highest value | 0.104 | 0.135 | 1.614 (0.860 – 3.029) | 0.129 |
| | Variation | -0.014 | 0.838 | 0.943 (0.541 – 1.644) | 0.837 |
| Temp rise | Mean | 0.199 | 0.004 | 1.170 (1.050 – 1.304) | 0.003 |
| | Lowest value | 0.244 | 0.000 | 1.320 (1.122 – 1.553) | 0.000 |
| | Highest value | 0.106 | 0.126 | 1.053 (0.985 – 1.125) | 0.126 |
| | Variation | -0.042 | 0.548 | 0.979 (0.914 – 1.049) | 0.546 |
| Max Temp | Mean | 0.176 | 0.011 | 1.189 (1.039 – 1.359) | 0.010 |
| | Lowest value | 0.152 | 0.027 | 1.250 (1.022 – 1.528) | 0.022 |
| | Highest value | 0.096 | 0.163 | 1.050 (0.980 – 1.125) | 0.162 |
| | Variation | 0.038 | 0.579 | 1.021 (0.950 – 1.097) | 0.576 |
| Imp drop | Mean | 0.017 | 0.807 | 1.008 (0.944 – 1.077) | 0.805 |
| | Lowest value | 0.234 | 0.001 | 1.146 (1.057 – 1.243) | 0.000 |
| | Highest value | -0.160 | 0.020 | 0.964 (0.934 – 0.995) | 0.022 |
| | Variation | -0.264 | 0.000 | 0.941 (0.911 – 0.972) | 0.000 |
| Imp drop Percent (imp drop/initial imp) | Mean | 0.155 | 0.024 | 1.105 (1.012 – 1.206) | 0.022 |
| | Lowest value | 0.270 | 0.000 | 1.166 (1.077 – 1.263) | 0.000 |
| | Highest value | -0.005 | 0.984 | 0.998 (0.945 – 1.054) | 0.941 |
| | Variation | -0.199 | 0.004 | 0.931 (0.887 – 0.978) | 0.004 |

Fig. 35

| | Rank | Potential Predictor (P value <0.01) | Implication |
|---|---|---|---|
| Pre-ablation parameters | 1 | Initial Imp - Variation | Initial Impedance variation < 20 Ω, single shot isolation (SSI) rate nearly 90%. Lower variation, higher SSI rate. |
| | 2 | Initial Temp - Highest | Highest Initial temp < 31 °C, SSI rate > 90% |
| | 3 | Initial Temp - Variation | Initial temp variation < 3 °C, SSI rate > 90% |
| | 4 | Ant. Imp - Variation | Ant. Initial Impedance variation < 20 Ω, SSI rate nearly 90% |
| | 5 | Ant. Imp - Lowest | The optimal range: 80-90 Ω, SSI rate >85% |
| Post-Ablation Parameters | 1 | Imp drop - Variation | Impedance drop Variation < 20Ω, SSI rate > 85% |
| | 2 | Temp Rise - Lowest | Lowest Temp rise ≥ 6 °C, SSI rate > 90% |
| | 3 | Imp drop - Lowest | Lowest Impedance drop ≥ 12Ω, SSI rate > 90% |
| | 4 | Temp Slope - Lowest | Lowest Temp slope ≥ 0.75 °C/sec, SSI rate > 90% |
| | 5 | Temp Slope - Mean | Higher mean temp slope, higher SSI isolation rate |
| | 6 | Temp Rise - Mean | Mean Temp rise ≥ 14 °C, SSI rate > 90% |

Fig. 36

| Range of Prob predicted by model | Probability of single shot isolation ||||
|---|---|---|---|---|
| | N = | Mean Model prediction (%) | Actual percentage (%) | Difference |
| prob ≥ 0.9 | 16 | 92 | 100 | -8.0 |
| 0.8 - 0.9 | 74 | 84.9 | 82.4 | 2.5 |
| 0.7 - 0.8 | 58 | 75.2 | 70.7 | 4.5 |
| prob < 0.7 | 63 | 55.4 | 60.3 | -4.9 |
| total | 211 | 73.9 | 73.9 | 0.0 |

| Criterion: | Probability ≥ 0.8 ||
|---|---|---|
| Criterion met/not met: | met | not met |
| # of ablations | 90 | 121 |
| # of single-shots: | 77 | 79 |
| # of non-single-shots: | 13 | 42 |
| Percent of single-shots | 85.6% | 65.3% |

| Range of Prob predicted by model | Probability of single shot isolation | | | |
|---|---|---|---|---|
| | N = | Mean Model prediction (%) | Actual percentage (%) | Difference |
| prob ≥ 0.9 | 46 | 94.2 | 95.6 | -1.4 |
| 0.8 - 0.9 | 51 | 84.8 | 80.4 | 4.4 |
| 0.7 - 0.8 | 41 | 75.1 | 78.0 | -2.9 |
| Prob < 0.7 | 73 | 53.4 | 53.4 | 0.0 |
| total | 211 | 74.1 | 73.9 | 0.2 |

| Criterion: | Probability ≥ 0.8 | |
|---|---|---|
| Criterion met/not met: | met | not met |
| # of ablations | 97 | 114 |
| # of single-shots: | 85 | 71 |
| # of non-single-shots: | 12 | 43 |
| Percent of single-shots | 87.6% | 62.3% |

| Range of Prob predicted by model | Probability of single shot isolation | | | |
|---|---|---|---|---|
| | N = | Mean Model prediction (%) | Actual percentage (%) | Difference |
| prob ≥ 0.9 | 41 | 93.7 | 92.7 | 1.0 |
| 0.8 - 0.9 | 45 | 85.2 | 86.7 | -1.5 |
| 0.7 - 0.8 | 53 | 75.1 | 77.4 | -2.3 |
| Prob < 0.7 | 72 | 54.2 | 52.8 | 1.4 |
| total | 211 | 73.7 | 73.9 | -0.2 |

| Criterion: | Probability ≥ 0.8 | |
|---|---|---|
| Criterion met/not met: | met | not met |
| # of ablations | 86 | 125 |
| # of single-shots: | 77 | 79 |
| # of non-single-shots: | 9 | 46 |
| Percent of single-shots | 89.5% | 63.2% |

| Range of Prob predicted by model | Probability of single shot isolation | | | |
|---|---|---|---|---|
| | N = | Mean Model prediction (%) | Actual percentage (%) | Difference |
| prob ≥ 0.9 | 26 | 92.6 | 96.2 | -3.6 |
| 0.8 - 0.9 | 64 | 85.4 | 85.9 | -0.5 |
| 0.7 - 0.8 | 59 | 75.1 | 71.2 | 3.9 |
| prob < 0.7 | 62 | 53.1 | 54.8 | -1.7 |
| total | 211 | 73.9 | 73.9 | 0.0 |

| Criterion: | Probability ≥ 0.8 | |
|---|---|---|
| Criterion met/not met: | met | not met |
| # of ablations | 90 | 121 |
| # of single-shots: | 80 | 76 |
| # of non-single-shots: | 10 | 45 |
| Percent of single-shots | 88.9% | 62.8% |

| Range of Prob predicted by model | Probability of single shot isolation | | | |
|---|---|---|---|---|
| | N = | Mean Model prediction (%) | Actual percentage (%) | Difference |
| prob ≥ 0.9 | 24 | 92.3 | 95.8 | -3.5 |
| 0.8 - 0.9 | 62 | 85.1 | 90.3 | -5.2 |
| 0.7 - 0.8 | 59 | 75.5 | 71.2 | 4.3 |
| prob < 0.7 | 66 | 55.2 | 53.0 | 2.2 |
| total | 211 | 73.9 | 73.9 | 0.0 |

| Criterion: | Probability ≥ 0.8 | |
|---|---|---|
| Criterion met/not met: | met | not met |
| # of ablations | 86 | 125 |
| # of single-shots: | 79 | 77 |
| # of non-single-shots: | 7 | 48 |
| Percent of single-shots | 91.9% | 61.6% |

| Range of Prob predicted by model | Probability of single shot isolation | | | |
|---|---|---|---|---|
| | N = | Mean Model prediction (%) | Actual percentage (%) | Difference |
| prob ≥ 0.9 | 34 | 94.7 | 97.1 | -2.7 |
| 0.8 - 0.9 | 59 | 85.1 | 74.6 | 10.5 |
| 0.7 - 0.8 | 44 | 75.7 | 86.4 | -10.7 |
| prob < 0.7 | 74 | 54.8 | 55.4 | -0.6 |
| total | 211 | 74.0 | 73.9 | 0.1 |

| Criterion | Probability ≥ 0.8 | |
|---|---|---|
| Criterion met/not met | met | not met |
| # of ablations | 93 | 118 |
| # of single shots | 77 | 79 |
| # of non-single shots | 16 | 39 |
| Percent of single-shots | 82.8% | 66.9% |

| Range of Prob predicted by model | Probability of single shot isolation | | | |
|---|---|---|---|---|
| | N = | Mean Model prediction (%) | Actual percentage (%) | Difference |
| prob ≥ 0.9 | 44 | 94.4 | 95.4 | -1.0 |
| 0.85 - 0.9 | 27 | 87.3 | 77.8 | 9.5 |
| 0.8 - 0.85 | 26 | 82.6 | 80.8 | 1.8 |
| 0.75 - 0.8 | 24 | 77.2 | 70.8 | 6.4 |
| 0.7 - 0.75 | 19 | 72.5 | 89.5 | -17.0 |
| 0.6 - 0.7 | 33 | 65.2 | 75.6 | -10.4 |
| prob < 0.6 | 38 | 42.4 | 34.2 | 8.2 |
| total | 211 | 74.2 | 73.9 | 0.3 |

| Range of Prob predicted by model | Probability of single shot isolation | | | |
|---|---|---|---|---|
| | N = | Mean Model prediction (%) | Actual percentage (%) | Difference |
| prob ≥ 0.9 | 44 | 94.4 | 95.4 | -1.0 |
| 0.8 - 0.9 | 53 | 85.0 | 79.2 | 5.8 |
| 0.7 - 0.8 | 43 | 75.1 | 79.0 | -3.9 |
| prob < 0.7 | 71 | 53.0 | 53.5 | -0.5 |
| total | 211 | 74.2 | 73.9 | 0.3 |

Fig. 67

| Range of Prob predicted by model | N = | Probability of single shot isolation Mean Model prediction (%) | Actual percentage (%) | Difference | reconnection # | reconnection % |
|---|---|---|---|---|---|---|
| prob ≥ 0.9 | 44 | 93.7 | 95.5 | -1.8 | 1 | 2.3 |
| 0.8 - 0.9 | 33 | 84.6 | 81.8 | 2.8 | 3 | 9.1 |
| 0.7 - 0.8 | 60 | 75.4 | 76.7 | -1.3 | 4 | 6.7 |
| Prob < 0.7 | 74 | 56.2 | 55.4 | 0.8 | 3 | 4.1 |
| total | 211 | 73.9 | 73.9 | 0.0 | 11 | 5.2 |

| Criterion: | Probability ≥ 0.8 | |
|---|---|---|
| Criterion met/not met: | met | not met |
| # of ablations | 77 | 134 |
| # of single-shots: | 69 | 87 |
| # of non-single-shots: | 8 | 47 |
| Percent of single-shots | 89.6% | 64.9% |

| Range of Prob predicted by model | Probability of single shot isolation | | | reconnection | |
|---|---|---|---|---|---|
| | N = | Mean Model prediction (%) | Actual percentage (%) | Difference | # | % |
| prob ≥ 0.9 | 30 | 94.0 | 96.7 | -2.7 | 1 | 3.3 |
| 0.8 - 0.9 | 32 | 84.9 | 87.5 | -2.6 | 1 | 3.1 |
| 0.7 - 0.8 | 66 | 74.3 | 65.2 | 9.1 | 4 | 6.1 |
| Prob < 0.7 | 83 | 61.7 | 67.5 | -5.8 | 5 | 6.0 |
| total | 211 | 73.8 | 73.9 | -0.1 | 11 | 5.2 |

| Criterion: | Probability ≥ 0.8 | |
|---|---|---|
| Criterion met/not met: | met | not met |
| # of ablations | 62 | 149 |
| # of single-shots: | 57 | 99 |
| # of non-single-shots: | 5 | 50 |
| Percent of single-shots | 91.9% | 66.4% |

| Range of P predicted by model | Probability of single shot isolation | | | | Reconnection | |
|---|---|---|---|---|---|---|
| | N = | Mean Model prediction (%) | Actual percentage (%) | Difference | # | % |
| p ≥ 0.9 | 43 | 94.0 | 95.3 | -1.3 | 1 | 2.3 |
| 0.8 - 0.9 | 41 | 84.7 | 80.5 | 4.2 | 3 | 7.3 |
| 0.7 - 0.8 | 54 | 74.7 | 75.9 | -1.2 | 3 | 5.6 |
| < 0.7 | 73 | 55.6 | 56.2 | -0.6 | 4 | 5.5 |
| total | 211 | 73.9 | 73.9 | 0 | 11 | 5.2 |

Fig. 70A

| Criterion: | Probability ≥ 0.8 | |
|---|---|---|
| Criterion met/not met: | met | not met |
| # of ablations | 84 | 127 |
| # of single-shots: | 74 | 82 |
| # of non-single-shots: | 10 | 45 |
| Percent of single-shots | 88.1% | 64.6% |

Fig. 70B

| Range of P predicted by model | Probability of single shot isolation | | | Reconnection | |
|---|---|---|---|---|---|
| | N = | Mean Model prediction (%) | Actual percentage (%) | Difference | # | % |
| p ≥ 0.9 | 34 | 93.7 | 94.1 | -0.4 | 1 | 2.9 |
| 0.8 - 0.9 | 31 | 85.0 | 93.5 | -8.5 | 0 | 0 |
| 0.7 - 0.8 | 66 | 74.4 | 68.2 | 6.2 | 5 | 7.6 |
| < 0.7 | 80 | 60.9 | 62.5 | -1.6 | 5 | 6.3 |
| total | 211 | 74.0 | 73.9 | 0.1 | 11 | 5.2 |

| Criterion: | Probability ≥ 0.8 | |
|---|---|---|
| Criterion met/not met: | met | not met |
| # of ablations | 65 | 146 |
| # of single-shots | 61 | 95 |
| # of non-single-shots | 4 | 51 |
| Percent of single-shots | 93.8% | 65.1% |

| Range of P predicted by model | Probability of single shot isolation | | | Reconnection | |
|---|---|---|---|---|---|
| | N = | Mean Model prediction (%) | Actual percentage (%) | Difference | # | % |
| p ≥ 0.9 | 33 | 94.2 | 96.9 | -2.7 | 1 | 3.0 |
| 0.8 - 0.9 | 32 | 84.6 | 87.5 | -2.9 | 0 | 0.0 |
| 0.7 - 0.8 | 70 | 74.2 | 65.7 | 8.5 | 6 | 8.6 |
| < 0.7 | 76 | 60.4 | 65.8 | -5.4 | 4 | 5.3 |
| total | 211 | 73.9 | 73.9 | 0 | 11 | 5.2 |

| Criterion | Probability ≥ 0.8 | |
|---|---|---|
| Criterion met/not met | met | not met |
| # of ablations | 65 | 146 |
| # of single-shots | 60 | 96 |
| # of non-single-shots | 5 | 50 |
| Percent of single-shots | 92.3% | 65.8% |

| Range of P predicted by model | Probability of single shot isolation | | | | Reconnection | |
|---|---|---|---|---|---|---|
| | N = | Mean Model prediction (%) | Actual percentage (%) | Difference | # | % |
| p ≥ 0.9 | 33 | 94.3 | 97 | -2.7 | 33 | 94.3 |
| 0.8 - 0.9 | 36 | 85 | 88.9 | -3.9 | 36 | 85 |
| 0.7 - 0.8 | 67 | 74.1 | 65.7 | 8.4 | 67 | 74.1 |
| < 0.7 | 75 | 59.5 | 64 | -4.5 | 75 | 59.5 |
| total | 211 | 73.9 | 73.9 | 0 | 211 | 73.9 |

Fig. 73A

| Criterion | Probability ≥ 0.8 | |
|---|---|---|
| Criterion met/not met | met | not met |
| # of ablations | 69 | 142 |
| # of single-shots | 64 | 92 |
| # of non-single-shots | 5 | 50 |
| Percent of single-shots | 92.8% | 64.8% |

Fig. 73B

| Range of P predicted by model | Probability of single shot isolation | | | |
|---|---|---|---|---|
| | N = | Mean Model prediction (%) | Actual percentage (%) | Difference |
| p ≥ 0.9 | 44 | 93.5 | 100 | -6.5 |
| 0.8 - 0.9 | 36 | 85 | 72.2 | 12.8 |
| 0.7 - 0.8 | 56 | 74.9 | 80.3 | -5.4 |
| < 0.7 | 75 | 55.1 | 54.7 | 0.4 |
| total | 211 | 73.5 | 73.9 | -0.4 |

Fig. 74

Actual Rate

Actual Rate

| Potential Predictors | | Pearson Correlation | | Binary logistic regression | |
|---|---|---|---|---|---|
| | Among 10 electrodes | Coefficient | P-value | Odds ratio (95% CI) | P-value |
| Initial Imp | # of electrodes with initial impedance at least 10 Ω higher than mean value | -0.165 | 0.016 | 0.684 (0.500 – 0.937) | 0.017 |
| | # of electrodes with initial impedance at least 10 Ω lower than mean value | -0.166 | 0.016 | 0.750 (0.591 – 0.951) | 0.017 |
| | # of electrodes with initial impedance at least 10 Ω higher or lower than mean value | -0.182 | 0.008 | 0.821 (0.708 – 0.953) | 0.009 |

Fig. 109

| Potential Predictors | | Pearson Correlation | | Binary logistic regression | |
|---|---|---|---|---|---|
| | | Coefficient | P-value | Odds ratio (95% CI) | P-value |
| Pre-ablation Parameters | Lowest Ant. Imp | -0.190 | 0.006 | 0.940 (0.898 – 0.983) | 0.005 |
| | Ant. Imp variation | -0.218 | 0.001 | 0.961 (0.936 – 0.986) | 0.002 |
| | Lowest initial Imp | -0.152 | 0.027 | 0.950 (0.906 – 0.995) | 0.026 |
| | Mean initial Imp | -0.292 | 0.000 | 0.916 (0.878 – 0.956) | 0.000 |
| | Initial Imp Variation | -0.299 | 0.000 | 0.949 (0.926 – 0.974) | 0.000 |
| Post-ablation Parameters | Lowest max temp | 0.152 | 0.027 | 1.250 (1.022 – 1.528) | 0.022 |
| | Lowest Imp drop | 0.234 | 0.001 | 1.146 (1.057 – 1.243) | 0.000 |
| | Mean Imp drop | -0.001 | 0.984 | 0.999 (0.938 – 1.064) | 0.984 |
| | Imp drop variation | -0.275 | 0.000 | 0.942 (0.913 – 0.972) | 0.000 |

Fig. 110

|       | $Z_0 [\Omega]$ | $T_0 [°C]$ | $Z \downarrow [\Omega]$ | $T \uparrow [°C]$ |
|-------|-----|------|----|------|
| Max   | 149 | 29.1 | 46 | 16.9 |
| Min   | 86  | 26.6 | 16 | 8.9  |
| Range | 62  | 2.5  | 29 | 8.0  |
| μ     | 107 | 27.9 | 26 | 12.4 |
| σ     | 18  | 0.7  | 8  | 2.2  |

Fig. 121

|  | $Z_0 [\Omega]$ | | $T_0 [°C]$ | | $Z\downarrow [\Omega]$ | | $T\uparrow [°C]$ | |
|---|---|---|---|---|---|---|---|---|
|  | 1-Shot | Non | 1-Shot | Non | 1-Shot | Non | 1-Shot | Non |
| Max | - | - | <29 | >31.5 | <35 | >48 | - | - |
| Min | >70 | - | - | - | >7 | - | >8.3 | <2.6 |
| Range | <25 | >48 | <2.8 | >4.2 | <13 | >35 | - | - |
| μ | >? | - | <27.5 | >28 | >15 | - | >13.8 | <10.4 |
| σ | <7 | >13 | <0.8 | >1.5 | <4 | >9 | <3.8 | >4.2 |

```
┌─────────────────────────────────────────────────────────────┐
│ ablating tissue of one or more targeted pulmonary veins     │
│ with one or more of a plurality of the electrodes of an     │
│ independently controlled multi-electrode radiofrequency     │
│ balloon catheter, the balloon catheter comprising the       │
│ plurality of electrodes for radiofrequency ablation that    │
│ are independently controllable                              │
│                         12510                               │
└─────────────────────────────────────────────────────────────┘
                              │
                              ▼
┌─────────────────────────────────────────────────────────────┐
│ determining a characteristic, based on ablation parameters  │
│ of the balloon catheter, of single shot pulmonary vein      │
│ isolation (PVI) success rate                                │
│                         12520                               │
└─────────────────────────────────────────────────────────────┘
                              │
                              ▼
┌─────────────────────────────────────────────────────────────┐
│ achieving, based on the characteristic and step of ablating │
│ tissue, a single shot isolation PVI success rate in the     │
│ isolation of all targeted pulmonary veins for the           │
│ predetermined patient population                            │
│                         12530                               │
└─────────────────────────────────────────────────────────────┘
                              │
                              ▼
┌─────────────────────────────────────────────────────────────┐
│ displaying the characteristic and the electrodes energized  │
│ during the ablating                                         │
│                         12540                               │
└─────────────────────────────────────────────────────────────┘
```

Fig. 125

12600 ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently controllable
12610

↓ determining a characteristic, based on ablation parameters of the balloon catheter, of single shot pulmonary vein isolation (PVI) success rate
12620

↓ achieving, based on the characteristic and step of ablating tissue, a single shot isolation PVI success rate in the isolation of all targeted pulmonary veins for the predetermined patient population
12630

↓ displaying the characteristic and identity of electrodes that were energized during the ablating
12640

Fig. 126

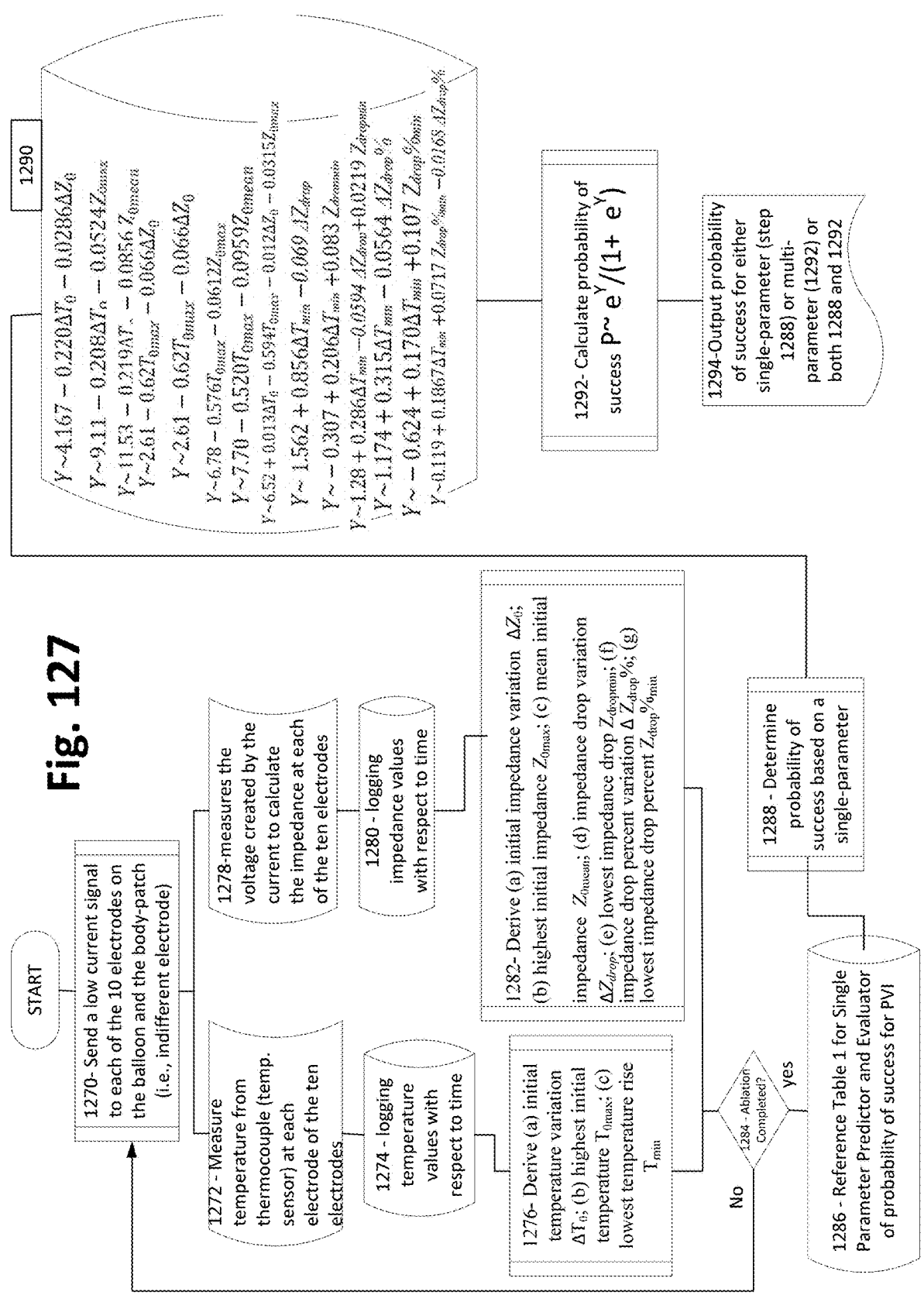

SYSTEMS AND METHODS OF ABLATING CARDIAC TISSUE

PRIORITY AND CROSS-REFERENCE TO RELATED APPLICATIONS

This application claims priority under 35 USC 119 and 365 (as well as the Paris Convention) to U.S. provisional patent application No. 62/731,525 filed Sep. 14, 2018, U.S. provisional patent application No. 62/754,275 filed Nov. 1, 2018, U.S. provisional patent application No. 62/771,896 filed Nov. 27, 2018, U.S. provisional patent application No. 62/886,729 filed Aug. 14, 2019, and to U.S. provisional patent application No. 62/889,471 filed Aug. 20, 2019 and to U.S. provisional patent application No. 62/873,636 filed Jul. 12, 2019. The contents of these United States provisional patent applications are incorporated herein by reference in their entirety as if set forth verbatim.

FIELD

This disclosure relates to medical devices designed to treat cardiac arrhythmia.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist to treat arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

With this in mind, it is understood that AF is the most common sustained arrhythmia in humans. It affects anywhere from 0.4% to 1% of the general population and increases in prevalence with age to approximately 10% in patients over 80 years of age. The primary clinical benefit of AF ablation is improvement in quality of life resulting from the elimination of arrhythmia-related symptoms such as palpitations, fatigue, or effort intolerance.

However, due to variances in human anatomy, ostia and tubular regions in the heart come in all sizes. Thus, conventional balloon or inflatable catheters may not have necessary flexibility to accommodate different shapes and sizes while having sufficient structural support for effective circumferential contact with tissue. In particular, ablation electrodes that provide greater surface contact may lack sufficient flexibility. Moreover, delicate wires such as those of electrode lead wires and/or thermocouple wires and their solder joints need support and protection from breakage and damage during both assembly and use in the patient's body. Additionally, because the balloon configuration is radially symmetrical and multiple electrode elements surround the balloon configuration, determining the orientation of the balloon electrode assembly under fluoroscopy has also posed challenges.

SUMMARY

Accordingly, the inventors of this disclosure have recognized that there is a need for a balloon or a catheter having an inflatable member with contact electrodes that can contact more tissue area while remaining sufficiently flexible to accommodate different anatomy and the tighter space constraints of an ostium and a pulmonary vein. The inventors have recognized a need for a balloon catheter to carry an electrode assembly with adaptations for the ostium and pulmonary vein that can be manufactured from a generic flexible circuit. There is a further desire for a balloon catheter capable of multiple functions including diagnostic and therapeutic functions, such as ablation, pacing, navigation, temperature sensing, electropotential sensing and impedance sensing, and be adaptive for use with other catheters, including a lasso catheter or a focal catheter.

The solution of this disclosure resolves these and other issues of the art.

The subject of this disclosure is the use of a multi-electrode RF balloon catheter and a multi-electrode diagnostic catheter for the treatment of paroxysmal and/or drug refractory atrial fibrillation to achieve at least one of a predetermined clinical effectiveness and acute effectiveness for a predetermined population size. The inventors believe that there are theoretical advantages of a multi-electrode RF balloon catheter in conjunction with the multi-electrode diagnostic catheter of this disclosure, which includes high probability of single-shot pulmonary vein isolation with minimal collateral damage to non-pulmonary vein structures, but without the drawbacks of excessive heating or cooling of the surrounding tissue. In some examples, a multi-electrode RF balloon of the multi-electrode RF balloon catheter is configured to deliver directionally-tailored energy using multiple electrodes, optimizing safety and/or efficacy. In particular, examples of this disclosure are suited for isolation of the atrial pulmonary veins in treatment of subjects with paroxysmal atrial fibrillation.

In some examples, a method or use is disclosed to treat a predetermined patient population for paroxysmal atrial fibrillation. The method or use can include ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently controllable; determining a characteristic, based on ablation parameters of the balloon catheter, of single shot pulmonary vein isolation (PVI) success rate; and achieving, based on the characteristic and step of ablating tissue, a single shot isolation PVI success rate in the isolation of all targeted pulmonary veins for the predetermined patient population.

In some examples, the step of achieving the single shot isolation PVI success rate includes further ablating tissue of one or more targeted pulmonary veins, based on the characteristic, with one or more of a plurality of the electrodes.

In some examples, the step of achieving the single shot isolation PVI success rate includes ceasing further tissue ablation with the multi-electrode radiofrequency balloon catheter, based on the characteristic.

In some examples, the step of achieving the single shot isolation PVI success rate includes achieving at least about a 91.7% success rate by ablating with a pre-ablation mean initial impedance of less than about 95Ω.

In some examples, the step of achieving the single shot isolation PVI success rate includes achieving at least about a 91.7% success rate by ablating with a pre-ablation highest initial impedance of less than about 100Ω.

In some examples, the step of achieving the single shot isolation PVI success rate includes achieving at least about 87% success rate by ablating with a pre-ablation initial anterior wall impedance of less than about 95Ω.

In some examples, the step of achieving the single shot isolation PVI success rate includes achieving at least about 85% success rate by ablating with a pre-ablation lowest initial anterior wall impedance of between about 80-90Ω.

In some examples, the step of achieving the single shot isolation PVI success rate includes achieving at least about 88% success rate by ablating with a pre-ablation highest initial anterior wall impedance of about 110Ω.

In some examples, the step of achieving the single shot isolation PVI success rate includes achieving at least about 87.5% success rate by ablating with a pre-ablation initial anterior wall impedance variation impedance range of less than about 20Ω.

In some examples, the characteristic is a predictor of the single shot isolation PVI success rate before ablation was limiting a highest initial temperature to less than about 31° C. among the electrodes of the balloon catheter.

In some examples, the characteristic is a predictor of the single shot isolation PVI success rate before ablation was permitting a lowest anterior wall impedance between approximately about 80-90Ω.

In some examples, the step of achieving the single shot isolation PVI success rate includes achieving at least about a 90% success rate by ablating with a mean initial impedance of less than about 95Ω for and a highest initial impedance of less than about 110Ω.

In some examples, the characteristic is a predictor is of the single shot isolation PVI success rate before ablation, the predictor being initial temperature and impedance at a lesion site just before the step of ablating.

In some examples, the characteristic is a predictor is of the single shot isolation PVI success rate before ablation, the predictor being relatively low initial temperature (approximately 31 deg centigrade or under) just before the step of ablating. The term "relatively low initial temperature" include a temperature lower than body temperature and in one embodiment, approximately 31 degrees Centigrade or lower.

In some examples, the characteristic is a predictor is of the single shot isolation PVI success rate before ablation, the predictor being initial temperature in a relatively low range with the highest and lowest impedance measured initially (before ablation) from the electrodes being no more than 20-30 ohms (and preferably 20 ohms or less) apart (i.e., impedances measured from all the electrodes are within 20-30 (or less than 30) ohms of each other) at a lesion site just before the step of ablating.

In some examples, the characteristic is a predictor is of the single shot isolation PVI success rate before ablation, the predictor being initial impedance having relatively high values with a relatively narrow range.

In some examples, the characteristic is a predictor is of the single shot isolation PVI success rate before ablation, the predictor being absolute values of impedance readings within a predetermined range.

In some examples, the characteristic is a predictor is of the single shot isolation PVI success rate before and during ablation, the predictor being electrode temperature before and during ablation.

In some examples, the characteristic is a predictor is of the single shot isolation PVI success rate before ablation, the predictor being mean initial temperature, and wherein the mean initial temperature is approximately less than about 28° C. and the single shot isolation PVI success rate is at least approximately about 90%.

In some examples, the characteristic is a predictor is of the single shot isolation PVI success rate before ablation, the predictor being a distributed initial temperature, and wherein the distributed initial temperature is approximately greater than about 31° C., and the single shot isolation PVI success rate is at least approximately about 90%.

In some examples, the characteristic is a predictor is of the single shot isolation PVI success rate before ablation, the predictor being a distributed initial temperature, and wherein the distributed initial temperature is approximately greater than about 30° C., and the single shot isolation PVI success rate is at least approximately about 90%.

In some examples, the characteristic is a predictor is of the single shot isolation PVI success rate before ablation, the predictor being a distributed initial temperature, and wherein the distributed initial temperature is approximately greater than about 29° C., and the single shot isolation PVI success rate is at least approximately about 90%.

In some examples, the characteristic is a predictor is of the single shot isolation PVI success rate before ablation, the predictor being a pre-ablation lowest temperature slope, and wherein the pre-ablation lowest temperature slope is approximately greater than about 0.75° C./sec, and the single shot isolation PVI success rate is at least approximately about 90%.

In some examples, the characteristic is a predictor is of the single shot isolation PVI success rate before ablation, the predictor being a pre-ablation lowest value temperature, and wherein the pre-ablation lowest value temperature is approximately greater than about 6° C., and the single shot isolation PVI success rate is at least approximately about 90%.

In some examples, the characteristic is a predictor of the single shot isolation PVI success rate before ablation, the predictor being a pre-ablation highest initial temperature, and wherein the pre-ablation highest initial temperature is approximately less than about 31° C., and the single shot isolation PVI success rate is at least approximately about 90%.

In some examples, the characteristic is a predictor of the single shot isolation PVI success rate before ablation, the predictor being a pre-ablation initial temperature variation, and wherein the pre-ablation initial temperature variation is approximately less than about 3° C., and the single shot isolation PVI success rate is at least approximately about 95%.

In some examples, the characteristic is a predictor of the single shot isolation PVI success rate before ablation, the predictor being a pre-ablation initial impedance variation, and wherein the pre-ablation initial impedance variation comprises an optimal range of approximately less than about 20Ω, and the single shot isolation PVI success rate is at least approximately about 88.5%.

In some examples, the characteristic is a predictor of the single shot isolation PVI success rate before ablation, the predictor being a pre-ablation lowest value impedance drop, and wherein the pre-ablation lowest value impedance drop is approximately greater than about 12Ω, and the single shot isolation PVI success rate is at least approximately about 90%.

In some examples, the characteristic is a predictor of the single shot isolation PVI success rate before ablation, the predictor being a pre-ablation impedance drop variation, and wherein the pre-ablation impedance drop variation is approximately greater than about 20Ω, and the single shot isolation PVI success rate is at least approximately about 85%.

In some examples, the characteristic is a predictor of the single shot isolation PVI success rate before ablation, the predictor being a pre-ablation lowest value impedance drop percent, and wherein the pre-ablation lowest value impedance drop percent is greater than or equal to approximately about 12%, and the single shot isolation PVI success rate is at least approximately about 90%.

In some examples, the characteristic is a predictor of the single shot isolation PVI success rate before ablation, the predictor being a pre-ablation impedance drop percent variation, and wherein the pre-ablation impedance drop percent variation is less than about 20Ω, and the single shot isolation PVI success rate is at least approximately about 85%.

In some examples, when a number of electrodes with initial impedance deviation from mean value is zero, the single shot isolation PVI success rate is approximately about 92%.

In some examples, the characteristic is a predictor of the single shot isolation PVI success rate before ablation, the predictor being a difference of impedance between anterior and posterior wall.

In some examples, the difference is less than approximately about 20Ω and the single-shot PVI success rate is at least approximately about 85% for the predetermined patient population.

In some examples, the difference is less than approximately about 20Ω and the single-shot PVI success rate is at least approximately about 85% for the predetermined patient population of at least 25 patients.

In some examples, the difference is approximately between 20 to 30Ω and the single-shot PVI success rate is at least approximately about 78% for the predetermined patient population.

In some examples, the difference is approximately between 20 to 30Ω and the single-shot PVI success rate is at least approximately about 78% for the predetermined patient population of at least 75 patients.

In some examples, the difference is approximately between 30 to 40Ω and the single-shot PVI success rate is at least approximately about 75% for the predetermined patient population.

In some examples, the difference is approximately between 30 to 40Ω and the single-shot PVI success rate is at least approximately about 75% for the predetermined patient population of at least 60 patients.

In some examples, the difference is approximately between 40 to 50Ω and the single-shot PVI success rate is at least approximately about 67% for the predetermined patient population.

In some examples, the difference is approximately between 40 to 50Ω and the single-shot PVI success rate is at least approximately about 67% for a predetermined patient population of at least 34 patients.

In some examples, the difference is approximately between 50 to 60Ω and the single-shot PVI success rate is at least approximately about 35% for the predetermined patient population.

In some examples, the difference is approximately between 50 to 60Ω and the single-shot PVI success rate is at least approximately about 35% for the predetermined patient population of at least 11 patients.

In some examples, the difference is greater than approximately about 60Ω and the single-shot PVI success rate is at least approximately about 33% for the predetermined patient population.

In some examples, the difference is greater than approximately about 60Ω and the single-shot PVI success rate is at least approximately about 33% for the predetermined patient population of at least 9 patients.

In some examples, the balloon catheter is a full-circle all electrode burning ablation catheter.

In some examples, the step of ablating tissue is for a duration of 60 seconds.

In some examples, the characteristic is a predictor of the single shot isolation PVI success rate before ablation, and wherein pre-ablation mean initial impedance is the predictor.

In some examples, the characteristic is a predictor of the single shot isolation PVI success rate before ablation, and wherein pre-ablation initial impedance variation is the predictor.

In some examples, the characteristic is an evaluator of the single shot isolation PVI success rate post ablation, and wherein post-ablation lowest impedance drop is the evaluator.

In some examples, the characteristic is an evaluator of the single shot isolation PVI success rate post ablation, and wherein post-ablation impedance drop variation is the evaluator.

In some examples, the characteristic is a predictor is of the single shot isolation PVI success rate before ablation, and wherein post-ablation mean temperature slope is the evaluator.

In some examples, the characteristic is an evaluator of the single shot isolation PVI success rate post ablation, and wherein post-ablation lowest temperature slope is the predictor.

In some examples, the characteristic is an evaluator of the single shot isolation PVI success rate post ablation, and wherein post-ablation mean temperature rise is the evaluator.

In some examples, the characteristic is an evaluator of the single shot isolation PVI success rate post ablation, and wherein post-ablation lowest temperature rise is the evaluator.

In some examples, the characteristic is an evaluator of the single shot isolation PVI success rate post ablation, and wherein post-ablation lowest impedance drop percentage is the evaluator.

In some examples, the characteristic is an evaluator of the single shot isolation PVI success rate post ablation, and wherein post-ablation variation of impedance drop percentage is the evaluator.

In some examples, the characteristic is a predictor of the single shot isolation PVI success rate before ablation, and wherein pre-ablation lowest impedance drop is the predictor.

In some examples, the characteristic is a predictor of the single shot isolation PVI success rate before ablation, and wherein pre-ablation initial temperature variation is the predictor.

In some examples, the characteristic is a predictor of the single shot isolation PVI success rate before ablation, and wherein pre-ablation maximum initial impedance is the predictor.

In some examples, the characteristic is a predictor of the single shot isolation PVI success rate before ablation, and wherein pre-ablation mean initial anterior wall impedance is the predictor.

In some examples, the characteristic is a predictor of the single shot isolation PVI success rate before ablation, and wherein pre-ablation lowest anterior wall impedance is the predictor.

In some examples, the characteristic is a predictor of the single shot isolation PVI success rate before ablation, and wherein pre-ablation maximum anterior wall impedance is the predictor.

In some examples, the characteristic is a predictor of the single shot isolation PVI success rate before ablation, and wherein pre-ablation anterior wall impedance variation is the predictor.

In some examples, impedance values were among the electrodes of the anterior wall.

In some examples, the characteristic is a predictor of the single shot isolation PVI success rate before ablation, and wherein the predictor is determined by:

$$\text{Probability} \sim \frac{e^Y}{(1+e^Y)}$$

$$Y \sim -4.367 - 0.420 \Delta T_0 - 0.0486 \Delta Z_0$$

wherein $\Delta T_0$ is initial impedance variation and $\Delta Z_0$ is initial temperature variation. In some examples, the characteristic is a predictor of the single shot isolation PVI success rate before ablation, and wherein the predictor is determined by:

$$Prob \sim \frac{e^Y}{(1+e^Y)}$$

$$Y \sim 26.78 - 0.576 T_{0max} - 0.0632 Z_{0max}$$

wherein $T_{0max}$ is highest initial temperature and $Z_{0max}$ is highest initial impedance.

In some examples, the characteristic is a predictor of the single shot isolation PVI success rate before ablation, and wherein the predictor is determined by:

$$Prob \sim \frac{e^Y}{(1+e^Y)}$$

$$Y \sim 27.70 - 0.540 T_{0max} - 0.09595 Z_{0max}$$

wherein $T_{0max}$ is highest initial temperature and $Z_{0max}$ is highest initial impedance.

In some examples, the characteristic is a predictor of the single shot isolation PVI success rate before ablation, and wherein the predictor is determined by:

$$Prob \sim \frac{e^Y}{(1+e^Y)}$$

$$Y \sim 9.31 - 0.408 \Delta T_0 - 0.0544 Z_{0max}$$

wherein $\Delta T_0$ is initial temperature variation and $Z_{0max}$ is highest initial impedance.

In some examples, the characteristic is a predictor of the single shot isolation PVI success rate before ablation, and wherein the predictor is determined by:

$$Prob \sim \frac{e^Y}{(1+e^Y)}$$

$$Y \sim 22.61 - 0.622 T_{0max} - 0.0626 Z_0$$

wherein $T_{0max}$ is highest initial temperature and $\Delta Z_0$ is initial impedance variation.

In some examples, the characteristic is a predictor of the single shot isolation PVI success rate before ablation, and wherein the predictor is determined by:

$$Prob \sim \frac{e^Y}{(1+e^Y)}$$

$$Y \sim 11.53 - 0.439 \Delta T_0 - 0.0856 \, Z_{0mean}$$

wherein $\Delta T_0$ is initial temperature variation and $Z_{0max}$ is mean initial impedance In some examples, the characteristic is a predictor of the single shot isolation PVI success rate before ablation, and wherein the predictor is determined by:

$$Prob \sim \frac{e^Y}{(1+e^Y)}$$

$$Y \sim 26.52 + 0.013 \Delta T_0 - 0.594 T_{0max} - 0.0122 \Delta Z_0 - 0.0535 Z_{0max}$$

wherein $\Delta T_0$ is initial temperature variation, $T_{0max}$ is highest initial temperature, $\Delta Z_0$ is initial impedance variation, and $Z_{0max}$ is highest initial impedance.

In some examples, the characteristic is an evaluator of the single shot isolation PVI success rate post ablation, and wherein the evaluator is determined by:

$$Prob \sim \frac{e^Y}{(1+e^Y)}$$

$$Y \sim 1.562 + 0.2856 T_{min} - 0.0629 \Delta Z_{drop}$$

wherein $\Delta T_{min}$ is lowest temperature rise and $\Delta Z_{drop}$ is impedance drop variation.

In some examples, the characteristic is an evaluator of the single shot isolation PVI success rate post ablation, and wherein the evaluator is determined by:

$$Prob \sim \frac{e^Y}{(1+e^Y)}$$

$$Y \sim -0.644 + 0.170 \Delta T_{min} + 0.107 \, Z_{drop} \%_{min}$$

wherein $\Delta T_{min}$ is lowest temperature rise and $Z_{drop}\%_{min}$ is lowest impedance drop percent.

In some examples, the characteristic is an evaluator of the single shot isolation PVI success rate post ablation, and wherein the evaluator is determined by:

$$P \sim \frac{e^Y}{(1+e^Y)}$$

$$Y \sim 0.339 + 0.187 \Delta T_{min} + 0.0737 \, Z_{drop} \%_{min} - 0.0368 \Delta Z_{drop} \%$$

wherein $\Delta T_{min}$ is lowest temperature rise, $Z_{drop}\%_{min}$ is lowest impedance drop percent, and $\Delta Z_{drop}\%$) is impedance drop percent variation.

In some examples, the characteristic is an evaluator of the single shot isolation PVI success rate post ablation, and wherein the evaluator is determined by:

$$P \sim \frac{e^Y}{(1+e^Y)}$$
$$Y \sim 1.043 + 0.777 T'_{min} + 0.171\Delta T_{min} + 0.0479 Z_{drop-min} - 0.0589\Delta Z_{drop}$$

wherein $T'_{min}$ is lowest temperature slope, $\Delta T_{min}$ is lowest temperature rise, $Z_{drop-min}$ is lowest impedance drop and $\Delta Z_{drop}$ is impedance drop variation.

In some examples, the characteristic is an evaluator of the single shot isolation PVI success rate post ablation, and wherein the evaluator is determined by:

$$P \sim \frac{e^Y}{(1+e^Y)}$$
$$Y \sim -0.507 + 0.206\Delta T_{min} + 0.083 Z_{dropmin}$$

wherein $\Delta T_{min}$ is lowest temperature rise and $Z_{dropmin}$ is minimum impedance drop.

In some examples, the characteristic is an evaluator of the single shot isolation PVI success rate post ablation, and wherein the evaluator is determined by:

$$P \sim \frac{e^Y}{(1+e^Y)}$$
$$Y \sim 1.248 + 0.2486\Delta T_{min} - 0.0594\Delta Z_{drop} + 0.0419 Z_{dropmin}$$

wherein $\Delta T_{min}$ is lowest temperature rise and $Z_{dropmin}$ is minimum impedance drop.

In some examples, the characteristic is an evaluator of the single shot isolation PVI success rate post ablation, and wherein the evaluator is determined by:

$$P \sim \frac{e^Y}{(1+e^Y)}$$
$$Y \sim 1.174 + 0.2515\Delta T_{min} - 0.0564\Delta Z_{drop} \%$$

wherein $\Delta T_{min}$ is lowest temperature rise and $\Delta Z_{drop}$ is impedance drop percent variation.

In some examples, the method or use includes a step of displaying a graphical representation of the independently controllable electrodes and the ablation parameters.

In some examples, one ablation parameter comprises impedance measured proximate each electrode.

In some examples, the measured impedance comprises impedance measured before ablation.

In some examples, the measured impedance comprises impedance measured after ablation.

In some examples, the measured impedance comprises impedance measured before and impedance measured after ablation.

In some examples, one ablation parameter comprises temperature measured proximate each electrode.

In some examples, one ablation parameter comprises a maximum temperature measured proximate each electrode during the ablating.

In some examples, one ablation parameter comprises a measured temperature rise from a beginning of ablating to an end of the ablating.

In some examples, a method or use is disclosed to treat a plurality of patients for paroxysmal atrial fibrillation. The method or use can include delivering a multi-electrode radiofrequency balloon catheter and a multi-electrode diagnostic catheter to one or more targeted pulmonary veins; ablating tissue of the one or more targeted pulmonary veins using the multi-electrode radiofrequency balloon catheter; diagnosing the one or more targeted pulmonary veins using the multi-electrode diagnostic catheter; and achieving at least one of a predetermined clinical effectiveness and acute effectiveness of the procedure based on use of the multi-electrode radiofrequency balloon catheter and the multi-electrode diagnostic catheter in the isolation of the one or more targeted pulmonary veins.

In some examples, the acute effectiveness is defined by confirming if there is an entrance block in all targeted pulmonary veins after adenosine and/or isoproterenol challenge.

In some examples, the acute effectiveness is further defined by success greater than 90% for the plurality of patients.

In some examples, the acute effectiveness is further defined by success greater than 95% for the plurality of patients.

In some examples, a Type-1 error rate for power the acute effectiveness and the clinical effectiveness of all targeted veins are controlled at approximately a 5% level. The method or use can include determining whether the procedure is clinically successful for the plurality of patients if both the acute effectiveness and the clinical effectiveness indications are controlled at approximately the 5% level.

In some examples, the acute effectiveness is at least 80% for the plurality of patients being at least 80 patients, 130 patients, and/or 230 patients.

In some examples, the acute effectiveness is further defined by confirming if there is an entrance block in all targeted pulmonary veins after adenosine and/or isoproterenol challenge using a focal ablation catheter.

In some examples, the acute effectiveness is further defined by confirming if there is an entrance block in all targeted pulmonary veins after adenosine and/or isoproterenol challenge without using a focal ablation catheter.

In some examples, the procedure is administered on the plurality of patients diagnosed with symptomatic paroxysmal atrial fibrillation.

In some examples, the predetermined effectiveness rate is defined by an average number of RF applications per patient and RF time required to isolate all pulmonary veins the step of diagnosing further comprises: electrophysiological mapping of the heart.

In some examples, the multi-electrode diagnostic catheter further comprises a high torque shaft with a halo-shaped tip section containing a plurality of pairs of electrodes visible under fluoroscopy.

In some examples, the predetermined acute effectiveness is defined by ulceration being absent in the plurality of patients after the procedure.

In some examples, the predetermined acute effectiveness is defined by a complication rate of approximately 13% or fewer of the plurality of patients experiencing esophageal erythema after the procedure.

In some examples, the predetermined acute effectiveness is defined by a complication rate of approximately 25% or fewer of the plurality of patients experiencing new asymptomatic cerebral embolic lesions after the procedure.

In some examples, the predetermined acute effectiveness is defined by a complication rate of approximately 20% or fewer of the plurality of patients experiencing new asymptomatic cerebral embolic lesions after the procedure.

In some examples, wherein the predetermined acute effectiveness is defined by a complication rate of approximately 5-9% or fewer of the plurality of patients experiencing a primary adverse event by approximately 7 or more days after the procedure.

In some examples, inclusion criteria for the plurality of patients includes a diagnosis with symptomatic paroxysmal atrial fibrillation and a patient capability to comply with uninterrupted per-protocol anticoagulation requirements.

In some examples, the predetermined acute effectiveness is defined by a total procedure time.

In some examples, a population size for the predetermined success rate is at least 80 patients, 130 patients, 180 patients, and/or 230 patients.

In some examples, the predetermined acute effectiveness is defined by a total RF application time.

In some examples, the predetermined acute effectiveness is defined by a total dwell time of the multi-electrode radiofrequency balloon catheter.

In some examples, the predetermined acute effectiveness is defined by a total time to isolate all targeted pulmonary veins.

In some examples, the predetermined acute effectiveness is defined by a number and a total time of applications by the multi-electrode radiofrequency balloon catheter per location of all targeted pulmonary veins.

In some examples, the predetermined acute effectiveness is defined by a number and a total time of applications by the multi-electrode radiofrequency balloon catheter per patient.

In some examples, the predetermined acute effectiveness is defined by a number and a total time of applications by the multi-electrode radiofrequency balloon catheter per targeted vein.

In some examples, multi-electrode radiofrequency balloon catheter comprises a compliant balloon with a plurality of electrodes bonded configured to deliver RF energy to tissue of the pulmonary vein and sense temperature at each electrode.

In some examples, clinical effectiveness is defined by an incidence of early onset of one or more adverse events within a predetermined time of the procedure being implemented.

In some examples, the predetermined time is at least 7 days.

In some examples, the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

In some examples, the one or more adverse events comprise: incidence of individual adverse events from a primary composite; incidence of serious adverse device effect; incidence of serious adverse events within 7 days, at least 7–30 days, and at least 30 days following the procedure; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

In some examples, the one or more adverse events for approximately 8% of the plurality of patients, the one or more adverse events comprising: NIHSS (National Institute of Health Stroke Scale) scores at baseline, post-ablation and during follow-up; a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins; a percentage (%) of subjects with use of focal catheter ablations for non-PV triggers; a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180); a percentage (%) of subjects with freedom from documented atrial fibrillation (AF), atrial tachycardia (AT), or atypical (left side) atrial flutter (AFL); one or more episodes that endure for 30 or more seconds on an arrhythmia monitoring device from day 91 to 180 following the procedure; and one or more procedural parameters including total procedure and ablation time, balloon dwell time, RF application time, a number of RF applications, fluoroscopy time and dose.

In some examples, the acute safety rate includes complication rates of 10% or less and is defined by incidence of asymptomatic cerebral embolic lesions at a discharge magnetic resonance imaging (MRI).

In some examples, the acute effectiveness rate includes complication rates of approximately 0% and is defined by existence of esophageal injury erythema.

In some examples, the acute effectiveness rate is 100% and is defined by electrically isolating all targeted pulmonary veins without use of a focal ablation catheter.

In some examples, the acute effectiveness rate is defined by a freedom from documented atrial fibrillation, atrial tachycardia, or atypical atrial flutter episodes based on electrocardiographic data through an effectiveness evaluation period (1 year).

In some examples, the acute effectiveness rate is defined by pulmonary vein isolation touch-up by a focal catheter among all targeted pulmonary veins.

In some examples, the predetermined clinical effectiveness rate is defined by 10% or less complication rates related to incidence of post-ablation symptomatic and asymptomatic cerebral emboli as compared to pre-ablation.

In some examples, the multi-electrode diagnostic catheter is configured for electrophysiological recording and stimulation of the atrial region of the heart and is used in conjunction with the multi-electrode radiofrequency balloon catheter.

In some examples, a method or use of administering a procedure to treat a plurality of patients for paroxysmal atrial fibrillation. The method or use includes delivering a multi-electrode radiofrequency balloon catheter and a multi-electrode diagnostic catheter to one or more targeted pulmonary veins; and ablating tissue of all targeted pulmonary veins using the multi-electrode radiofrequency balloon catheter; diagnosing all targeted pulmonary veins using the multi-electrode diagnostic catheter; and achieving a predetermined rate of adverse events, using the multi-electrode radiofrequency balloon catheter and the multi-electrode diagnostic catheter in the isolation of all targeted pulmonary veins, during and approximately 6 months after the procedure.

In some examples, a method or use of treating a plurality of patients for paroxysmal atrial fibrillation. The method or use includes evaluating a number and size of all targeted pulmonary veins and anatomy of the left atrial; puncturing the transseptal; selectively positioning a multi-electrode esophageal temperature monitoring device in the vasculature with respect to all targeted pulmonary veins; selectively positioning a multi-electrode radiofrequency balloon catheter in the vasculature with respect to all targeted pulmonary veins; selectively positioning a multi-electrode diagnostic catheter in the vasculature with respect to all targeted pulmonary veins; ablating tissue of all targeted pulmonary veins using the multi-electrode radiofrequency balloon catheter; confirming isolation of all targeted pulmonary veins using the multi-electrode diagnostic catheter; confirming existence of an entrance block in all targeted pulmonary veins; achieving a predetermined clinical effectiveness and/or acute effectiveness of the procedure, based on the confirmed existence of the entrance block, regarding the isolation of all targeted pulmonary veins following the procedure.

In some examples, mapping all targeted pulmonary veins using the diagnostic catheter.

In some examples, exclusion criteria for the plurality of patients comprises at least one of the following: atrial fibrillation secondary to electrolyte imbalance, thyroid disease, or reversible or non-cardiac cause; previous surgical or catheter ablation for atrial fibrillation; anticipated to receive ablation outside all targeted pulmonary veins ostia and CTI region; previously diagnosed with persistent, longstanding atrial fibrillation and/or continuous atrial fibrillation >7 days, or >48 hrs terminated by cardioversion; any percutaneous coronary intervention (PCI) within the past 2 months; valve repair or replacement and presence of a prosthetic valve; any carotid stenting or endarterectomy; coronary artery bypass grafting, cardiac surgery, valvular cardiac surgical or percutaneous procedure within the past 6 months; documented left atrium thrombus on baseline imaging; LA antero posterior diameter greater than 50 mm; any pulmonary vein with a diameter greater than or equal to 26 mm; left ventricular ejection fraction less than 40%; contraindication to anticoagulation; history of blood clotting or bleeding abnormalities; myocardial infarction within the past 2 months; documented thromboembolic event within the past 12 months; rheumatic heart disease; awaiting cardiac transplantation or other cardiac surgery within the next 12 months; unstable angina; acute illness or active systemic infection or sepsis; diagnosed atrial myxoma or interatrial baffle or patch; presence of implanted pacemaker, implantable cardioverter defibrillator, tissue-embedded, or iron-containing metal fragments; significant pulmonary disease or any other disease or malfunction of the lungs or respiratory system that produces chronic symptoms; significant congenital anomaly; pregnancy or lactating; enrollment in an investigational study evaluating another device, biologic, or drug; pulmonary vein stenosis; presence of intramural thrombus, tumor or other abnormality that precludes vascular access, or manipulation of the catheter; presence of an IVC filter; presence of a condition that precludes vascular access; life expectancy or other disease processes likely to limit survival to less than 12 months; contraindication to use of contrast agents for MRI; presence of iron-containing metal fragments in the patient; or unresolved pre-existing neurological deficit.

In some examples, the multi-electrode radiofrequency balloon catheter includes a compliant balloon with a plurality of electrodes configured to deliver RF energy to tissue of all targeted pulmonary veins and sense temperature at each electrode. In some examples, the plurality of electrodes is oriented circularly to circumferentially contact with an ostia of the pulmonary vein. In some examples, the method or use includes using the plurality of electrodes for visualization, stimulation, recording, and ablation. In some examples, each electrode is configured so an amount of power delivered to each electrode is controlled independently. In some examples, the multi-electrode radiofrequency balloon catheter further comprises a proximal handle, a distal tip, and a middle section disposed therebetween. In some examples, the proximal handle is a deflection thumb knob allowing for unidirectional deflection, a balloon advancement mechanism, and a luer fitting for balloon inflation and irrigation. In some examples, the multi-electrode radiofrequency balloon catheter further comprises a high-torque shaft configured to be rotated to facilitate accurate positioning of the catheter tip to a desired; and a unidirectional braided deflectable tip section.

In some examples, the method or use also includes controlling irrigation to the multi-electrode radiofrequency balloon catheter with an irrigation pump.

In some examples, the method or use also includes administering uninterrupted anticoagulation therapy at least 1 month prior to the procedure.

In some examples, if the patient is receiving warfarin/coumadin therapy, the patient must have an international normalized ratio (INR)≥2 for at least 3 weeks prior to the procedure.

In some examples, if the patient is receiving warfarin/coumadin therapy, the patient must be confirmed to have an international normalized ratio (INR)≥2 within 48 hours pre-procedure.

In some examples, the method or use also includes continuing anticoagulation therapy prior to the procedure.

In some examples, the method or use also includes administering a transseptal puncture; confirming an activated clotting time target of ≥350 sec. prior to inserting the multi-electrode radiofrequency balloon catheter into the left atrium and maintaining throughout the procedure; introducing the multi-electrode radiofrequency balloon catheter; introducing of a multi-electrode circular diagnostic catheter; ablating the pulmonary vein with the multi-electrode radiofrequency balloon catheter; determining in real time pulmonary vein isolation with the multi-electrode circular diagnostic catheter; and confirming whether an entrance is blocked in the pulmonary vein.

In some examples, the method or use also includes the multi-electrode circular diagnostic catheter comprises: an elongated body having a longitudinal axis; a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

In some examples, a method or use of treating a plurality of patients for paroxysmal atrial fibrillation by applying energy to tissue of a subject's heart proximate to an esophagus, phrenic nerve, or lung, the method or use comprising the steps of achieving at least one of a predetermined clinical effectiveness and acute effectiveness of the procedure based on use of a multi-electrode radiofrequency balloon catheter and a multi-electrode diagnostic catheter in the isolation of the one or more targeted pulmonary veins by positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker; viewing an image of the expandable member as well as the first and second radiopaque markers in the left atrium; determining an orientation of the first and second radiopaque markers with respect to a portion of the left atrium closest to the esophagus, phrenic nerve, or lung, of the subject; moving one of the first and second radiopaque markers to a portion of the left atrium closest to the esophagus, phrenic nerve or lung; energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and electrophysiologically recording and stimulating the atrial region of the tissue proximate to the esophagus, phrenic nerve, or lung using the multi-electrode diagnostic catheter.

In some examples, a clinically effective device is disclosed to treat atrial fibrillation in a group of patients. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane. The device can achieve a predetermined effectiveness rate of pulmonary vein isolation in the group of patients.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve a predetermined effectiveness rate of pulmonary vein isolation.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 97% safety endpoint within seven (7) days of successful pulmonary vein isolation.

In some examples, a clinically effective device is disclosed to administer a procedure for cardiac electrophysiological ablation of pulmonary veins of the atria and treatment of drug refractory recurrent symptomatic pulmonary atrial fibrillation. The device can include an end probe coupled to a tubular member that extends along a longitudinal axis from a proximal portion to a distal portion. The end probe can include a first expandable membrane coupled to the tubular member; a plurality of electrodes disposed generally equiangularly about the longitudinal axis on an outer surface of the first expandable membrane; at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 90% safety endpoint within seven (7) days of successful pulmonary vein isolation.

In some examples, the predetermined effectiveness rate includes complication rates of 10% or less and is defined by existence or non-existence of asymptomatic cerebral embolic lesions at a discharge magnetic resonance imaging (MRI).

In some examples, the predetermined effectiveness rate includes complication rates of approximately 0% and is defined by existence or non-existence of esophageal injury erythema.

In some examples, the predetermined effectiveness rate is approximately 100% and is defined by electrically isolating all targeted pulmonary veins without use of a focal ablation catheter.

In some examples, the predetermined effectiveness rate is defined by a freedom from documented atrial fibrillation, atrial tachycardia, or atypical atrial flutter episodes based on electrocardiographic data through an effectiveness evaluation period. In some examples, the effectiveness evaluation period is approximately one year.

In some examples, the predetermined effectiveness rate is defined by pulmonary vein isolation touch-up by a focal catheter among all targeted pulmonary veins.

In some examples, the predetermined effectiveness rate is defined by using focal catheter ablation for non-PV triggers during the index procedure.

In some examples, the predetermined effectiveness rate comprises a long-term effectiveness rate.

In some examples, the predetermined effectiveness rate is defined by an average number of Radio-Frequency applications per patient and Radio-Frequency time required to isolate all pulmonary veins.

In some examples, the predetermined effectiveness rate is defined by an average number of Radio-Frequency applications per vein and Radio-Frequency time required to isolate common pulmonary veins.

In some examples, the predetermined effectiveness rate is defined by an average number of Radio-Frequency applications per patient and Radio-Frequency time required to isolate common pulmonary veins.

In some examples, the predetermined effectiveness rate is defined by determining incidence of complication rates being 10% or less of post-ablation symptomatic and asymptomatic cerebral emboli as compared to pre-ablation.

In some examples, the predetermined effectiveness rate is defined by evaluating a presence of emboli-associated neurological deficits by at least one of NIHSS and mRS assessments.

In some examples, the end probe is configured for use in catheter-based cardiac electrophysiological mapping of the atria.

In some examples, the end probe is configured for cardiac ablation.

In some examples, the end probe comprises: the plurality of electrodes bonded to the first expandable membrane and configured to deliver Radio-Frequency energy to tissue of the pulmonary vein and sense temperature at each electrode.

In some examples, the plurality of electrodes is oriented circularly to circumferentially contact with an ostia of the pulmonary vein.

In some examples, the device is further configured for using the plurality of electrodes for visualization, stimulation, recording, and ablation.

In some examples, each electrode is configured so an amount of power delivered to each electrode is controlled independently.

In some examples, the end probe further comprises a proximal handle, a distal tip, and a middle section disposed therebetween.

In some examples, the proximal handle is a deflection thumb knob allowing for unidirectional deflection, a balloon advancement mechanism, and a luer fitting for balloon inflation and irrigation.

In some examples, the end probe further includes a high-torque shaft configured to be rotated to facilitate accurate positioning of the catheter tip to a desired; and a unidirectional braided deflectable tip section.

In some examples, the end probe further includes a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

In some examples, the device further includes an irrigation pump to provide irrigation fluid to the first expandable membrane and out of the first expandable membrane.

In some examples, the effectiveness evaluation period is at least 91 days following a delivery of the end probe to the pulmonary vein; and ablation of tissue proximate the pulmonary vein with the end probe.

In some examples, the effectiveness evaluation period is less than or equal to one year following a delivery of the end probe to the pulmonary vein; and ablation of tissue proximate the pulmonary vein with the end probe.

In some examples, the predetermined success rate is 60% for a population size of at least 40 patients.

In some examples, a population size for the predetermined success rate is at least 300 patients, 200 patients, 100 patients, or 50 patients.

In some examples, the predetermined success rate is at least 60%.

In some examples, the predetermined success rate is determined by evaluation of the patient 7 days following a delivery of the end probe to the pulmonary vein and ablation of tissue proximate the pulmonary vein with the end probe.

In some examples, the predetermined success rate is determined by evaluation of the patient 1 month following a delivery of the end probe to the pulmonary vein; and ablation of tissue proximate the pulmonary vein with the end probe.

In some examples, the predetermined success rate is determined by evaluation of the patient 6 months following a delivery of the end probe to the pulmonary vein; and ablation of tissue proximate the pulmonary vein with the end probe.

In some examples, the predetermined success rate is determined by evaluation of the patient 12 months following a delivery of the end probe to the pulmonary vein; and ablation of tissue proximate the pulmonary vein with the end probe.

In some examples, the predetermined success rate further includes confirmation of an entrance block in the pulmonary vein after at least one of adenosine and isoproterenol challenge.

In some examples, the patient suffering at least one of the following events is deemed as an unsuccessful pulmonary vein isolation, including: device or procedure related death; atrio-esophageal fistula, myocardial infarction; cardiac Tamponade/Perforation; thromboembolism; stroke/Cerebrovascular Accident (CVA); transient Ischemic Attach (TIA); phrenic Nerve Paralysis, Pulmonary Vein Stenosis; pericarditis; pulmonary Edema; major Vascular Access Complication/Bleeding; and hospitalization (initial or prolonged).

In some examples, the patient suffering at least one of the following events is deemed as an unsuccessful pulmonary vein isolation, whereby those events can include acute procedural failure; repeat ablation or surgical treatment for AF/AT/Atypical (left-side) AFL after the blanking period (after day 90 post index procedure); DC cardioversion for AF/AT/Atypical (left-side) AFL, continuous AF/AT/AFL on a standard 12-lead ECG even if the recording is less than 30 seconds in duration (after day 90 post index procedure); a new Class I and/or Class III AAD is prescribed for AF during effectiveness evaluation period (day 91-365 post index procedure) or prescribed during the blanking period and continued past 90 days; a previously failed Class I and/or Class III AAD (failed at or before screening) is taken for AF at a greater dose than the highest ineffective historical dose during the effectiveness evaluation period; and amiodarone is prescribed post procedure.

In some examples, the safety endpoint is defined by a patient suffering a primary adverse event.

In some examples, at least one risk factor for the patient can be selected as: at least three (3) symptomatic episodes of atrial fibrillation that last lasting ≥1 minute within six (6) months before the device; at least one (1) atrial fibrillation episode electrocardiographically documented within twelve (12) months prior to enrollment (e.g., electrocardiogram (ECG), Holter monitor, telemetry strip, etc.); failing at least one (1) Class I or Class III AAD as evidenced by recurrent symptomatic atrial fibrillation or intolerable side effects to the AAD; age under 18 and 75 or over; secondary to electrolyte imbalance; thyroid disease; reversible or non-cardiac cause; and previous surgical or catheter ablation for atrial fibrillation.

In some examples, for purposes of calculating the effectiveness rate, the patient has at least one of the following risk factors: patients known to require ablation outside the PV ostia and CTI region; previously diagnosed with persistent or long-standing persistent atrial fibrillation and/or continuous atrial fibrillation 7 days following the device procedure; any percutaneous coronary intervention within the past 2 months; repair or replacement or presence of a prosthetic valve; any carotid stenting or endarterectomy within the past 6 months; coronary artery bypass grafting, cardiac surgery or valvular cardiac surgical procedure within the past 6 months; documented left atrium thrombus within 1 day prior to the device procedure; left atrium antero posterior diameter >50 mm; left Ventricular Ejection Fraction <40%; contraindication to anticoagulation; history of blood clotting or bleeding abnormalities; myocardial infarction within the past 2 months; documented thromboembolic event (including transient ischemic attack) within the past 12 months; Rheumatic Heart Disease; Uncontrolled heart failure or New York Heart Association (NYHA) function class III or IV; awaiting cardiac transplantation or other cardiac surgery within the next 12 months; unstable angina; acute illness or active systemic infection or sepsis; diagnosed atrial myxoma or presence of an interatrial baffle or patch; presence of implanted pacemaker or implantable cardioverter defibrillator (ICD); significant pulmonary disease or any other disease or malfunction of the lungs or respiratory system that produces chronic symptoms; significant congenital anomaly; women who are pregnant; enrollment in an investigational study evaluating another device, biologic, or drug; known pulmonary vein stenosis; presence of intramural thrombus, tumor or other abnormality that precludes vascular access, or manipulation of the catheter; presence of an inferior vena cava filter; presence of a condition that precludes vascular access; life expectancy or other disease processes likely to limit survival to less than 12 months; presenting contra-indication for the devices; and patient on amiodarone at any time during the past 3 months prior to enrollment.

In some examples, if the patient is receiving warfarin/coumadin therapy, the patient must have an international normalized ratio ≥2 for at least 3 weeks prior to the procedure.

In some examples, if the patient is receiving warfarin/coumadin therapy, the patient must be confirmed to be ≥2 within 48 hours pre-procedure.

In some examples, wherein anticoagulation therapy is provided prior to the procedure.

In some examples, wherein an activated clotting time of 350-400 seconds is targeted prior to insertion of the catheter and throughout the procedure.

In some examples, wherein an activated clotting time levels are checked every 15-30 minutes during the procedure to ensure an activated clotting time target of 350-400 seconds.

In some examples, wherein the multi-electrode circular diagnostic catheter includes an elongated body having a longitudinal axis and a distal assembly distal the elongated body. The distal assembly can have a helical form comprising a proximal loop, a distal loop, and a shape-memory support member extending through at least the proximal loop. The proximal loop and the distal loop can be oriented obliquely at an angle relative to the longitudinal axis of the elongated body; at least one irrigated ablation ring electrode mounted on the proximal loop; a control handle proximal the elongated body; and a contraction wire having a proximal end in the control handle and a distal end anchored in the proximal loop, the control handle including a first control member configured to actuate the contraction wire to contract the proximal loop. The proximal loop can have a first flexibility and the distal loop has a second flexibility, and the second flexibility can be greater than the first flexibility.

To the accomplishment of the foregoing and related ends, certain illustrative aspects are described herein in connection with the following description and the appended drawings. These aspects are indicative, however, of but a few of the various ways in which the principles of the claimed subject matter can be employed and the claimed subject matter is intended to include all such aspects and their equivalents. Other advantages and novel features can become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 14 shows a table summarizing recommended RF Energy Delivery Parameters in one example.

FIG. 15 shows a table summarizing intensity or severity of each AE assessed according to classifications.

FIG. 16 shows a table illustrating classifications based on AAD therapy administered in the blanking and post-blanking periods in an example study.

FIG. 17 depicts a graphical overview of one method or use according to this disclosure.

FIG. 18 depicts a graphical overview of one method or use according to this disclosure.

FIG. 19 depicts a graphical overview of one method or use according to this disclosure.

FIG. 20 depicts a graphical overview of one method or use according to this disclosure.

FIG. 21 depicts a graphical overview of one method or use according to this disclosure.

FIG. 22 depicts a graphical overview of one method or use according to this disclosure.

FIG. 24 shows a table summarizing single shot isolation versus non-isolation according to the study of this disclosure.

FIG. 33 shows a table summarizing predictors associated with corresponding Pearson correlation and binary logistic regression values in the study of this disclosure with pre- and post-ablation parameters.

FIG. 34 shows a table summarizing predictors associated with corresponding Pearson correlation and binary logistic regression values in the study of this disclosure with pre-ablation parameters.

FIG. 35 shows a table summarizing predictors associated with corresponding Pearson correlation and binary logistic regression values in the study of this disclosure with post-ablation parameters.

FIG. 36 shows a table summarizing rankings of pre- and post-ablation parameters that were single shot predictors observed in the study of this disclosure.

FIG. 67 shows a table summarizing data associated with another simulation.

FIG. 70A shows a table summarizing data associated with a simulation of an example evaluator algorithm.

FIG. 70B shows a table summarizing data associated with the simulation of the example evaluator algorithm of FIG. 70A.

FIG. 73A shows a table summarizing data associated with a simulation of an example evaluator algorithm.

FIG. 73B shows a table summarizing data associated with a simulation of an example evaluator algorithm.

FIG. 74 shows a table summarizing data associated with a simulation of an example evaluator algorithm.

FIG. 85A shows a bar graph summarizing single shot isolation probability versus pre-ablation initial impedance variation in the study of this disclosure.

FIG. 85B shows a binary fitted line plot of single shot isolation probability versus pre-ablation initial impedance variation in the study of this disclosure.

FIG. 86A shows a bar graph summarizing single shot isolation probability versus pre-ablation initial anterior wall impedance in the study of this disclosure.

FIG. 86B shows a binary fitted line plot of single shot isolation probability versus pre-ablation initial anterior wall impedance in the study of this disclosure.

FIG. 87A shows a bar graph summarizing single shot isolation probability versus pre-ablation lowest initial anterior wall impedance in the study of this disclosure.

FIG. 87B shows a binary fitted line plot of single shot isolation probability versus pre-ablation lowest initial anterior wall impedance in the study of this disclosure.

FIG. 88A shows a bar graph summarizing single shot isolation probability versus pre-ablation highest initial anterior wall impedance in the study of this disclosure.

FIG. 88B shows a binary fitted line plot of single shot isolation probability versus pre-ablation highest initial anterior wall impedance in the study of this disclosure.

FIG. 89A shows a bar graph summarizing single shot isolation probability versus pre-ablation initial anterior wall impedance variation in the study of this disclosure.

FIG. 89B shows a binary fitted line plot of single shot isolation probability versus pre-ablation initial anterior wall impedance variation in the study of this disclosure.

FIG. 90A shows a bar graph summarizing single shot isolation probability versus pre-ablation mean temperature slope in the study of this disclosure.

FIG. 90B shows a binary fitted line plot of single shot isolation probability versus pre-ablation mean temperature slope in the study of this disclosure.

Figure 91A:
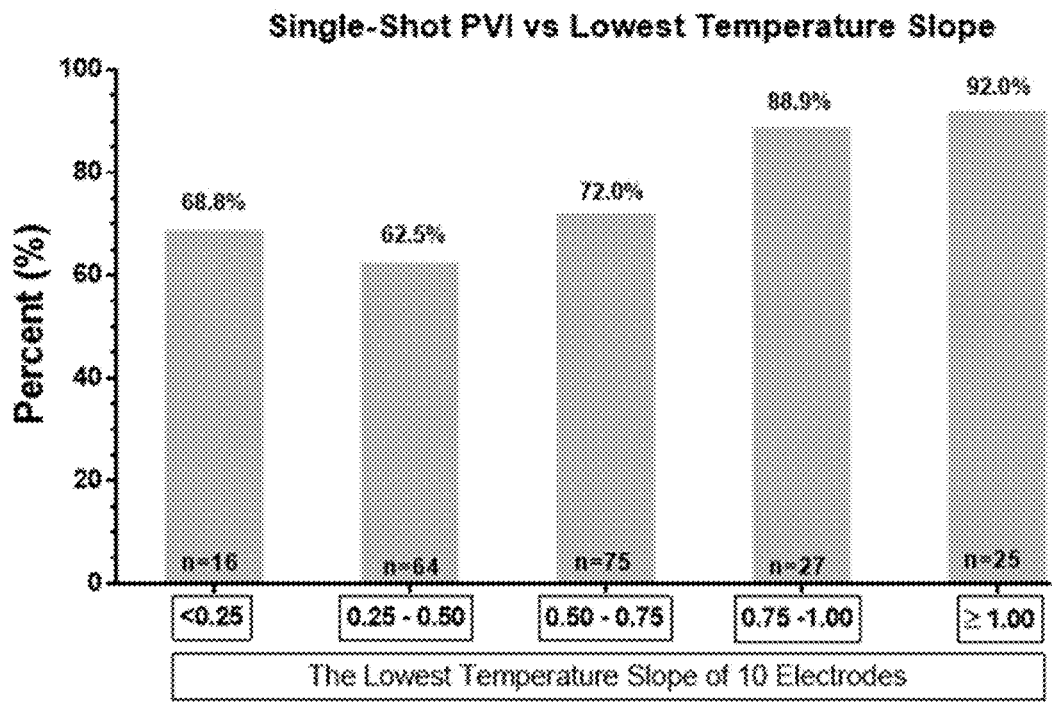

FIG. 91A shows a bar graph summarizing single shot isolation probability versus pre-ablation lowest temperature slope in the study of this disclosure.

Figure 91B:
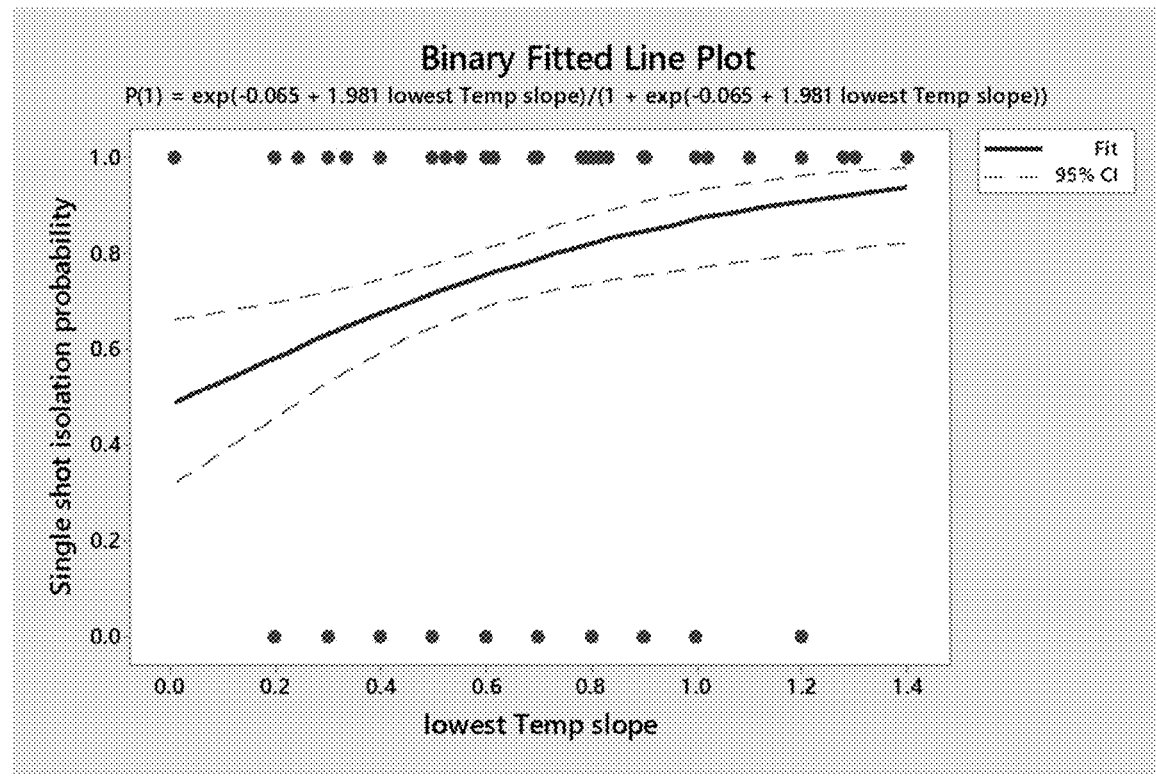

FIG. 91B shows a binary fitted line plot of single shot isolation probability versus pre-ablation lowest temperature slope in the study of this disclosure.

Figure 92A:
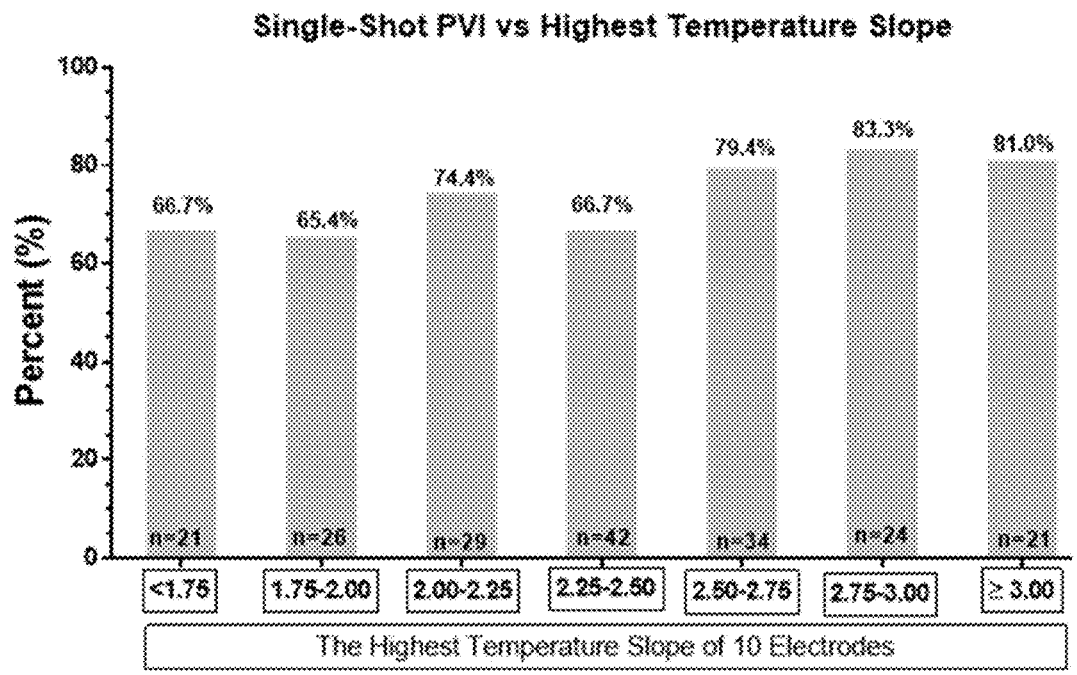

FIG. 92A shows a bar graph summarizing single shot isolation probability versus pre-ablation highest temperature slope in the study of this disclosure.

Figure 92B:
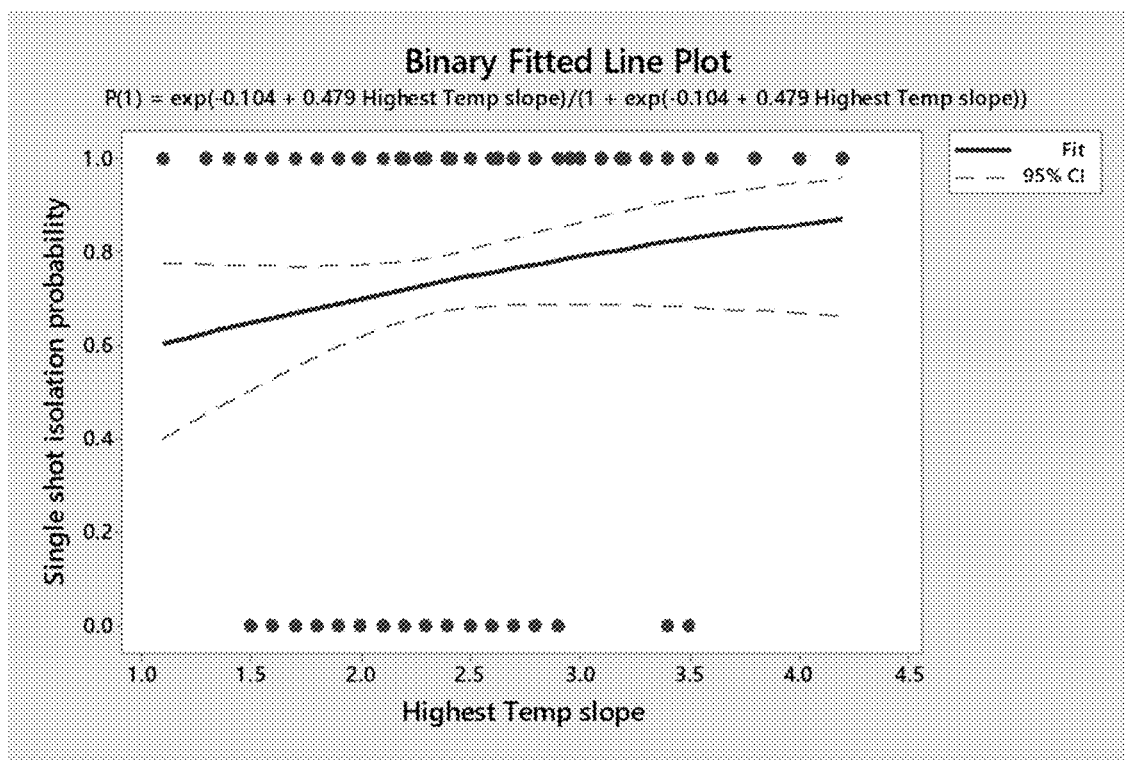

FIG. 92B shows a binary fitted line plot of single shot isolation probability versus pre-ablation highest temperature slope in the study of this disclosure.

Figure 93A:
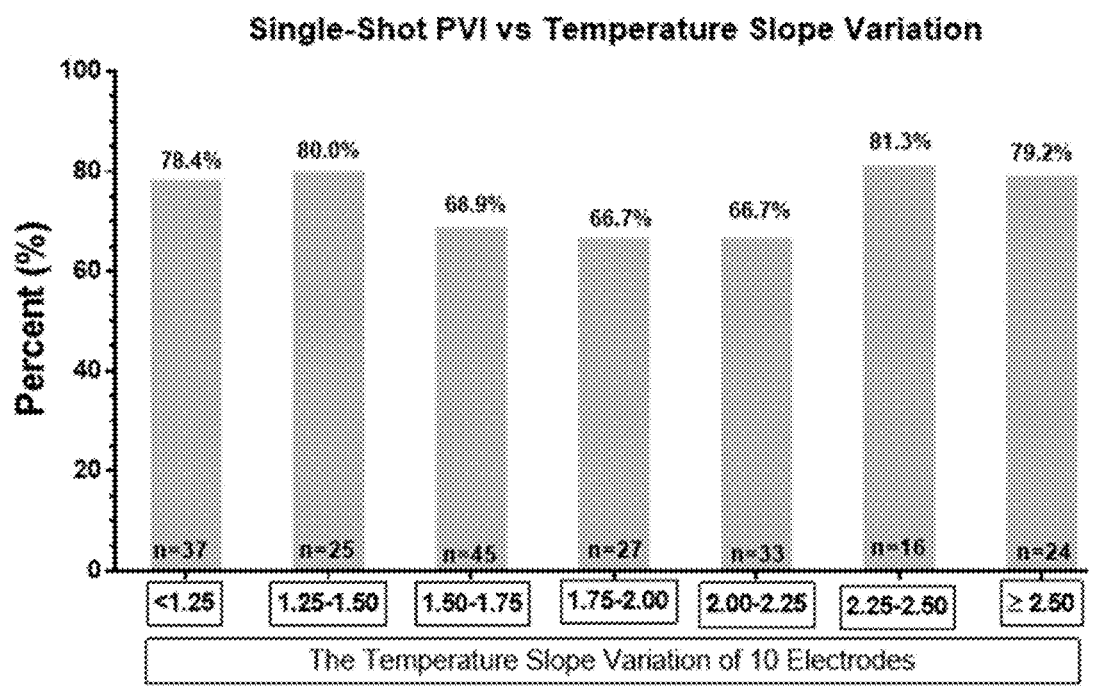

FIG. 93A shows a bar graph summarizing single shot isolation probability versus pre-ablation temperature slope variation in the study of this disclosure.

Figure 93B:
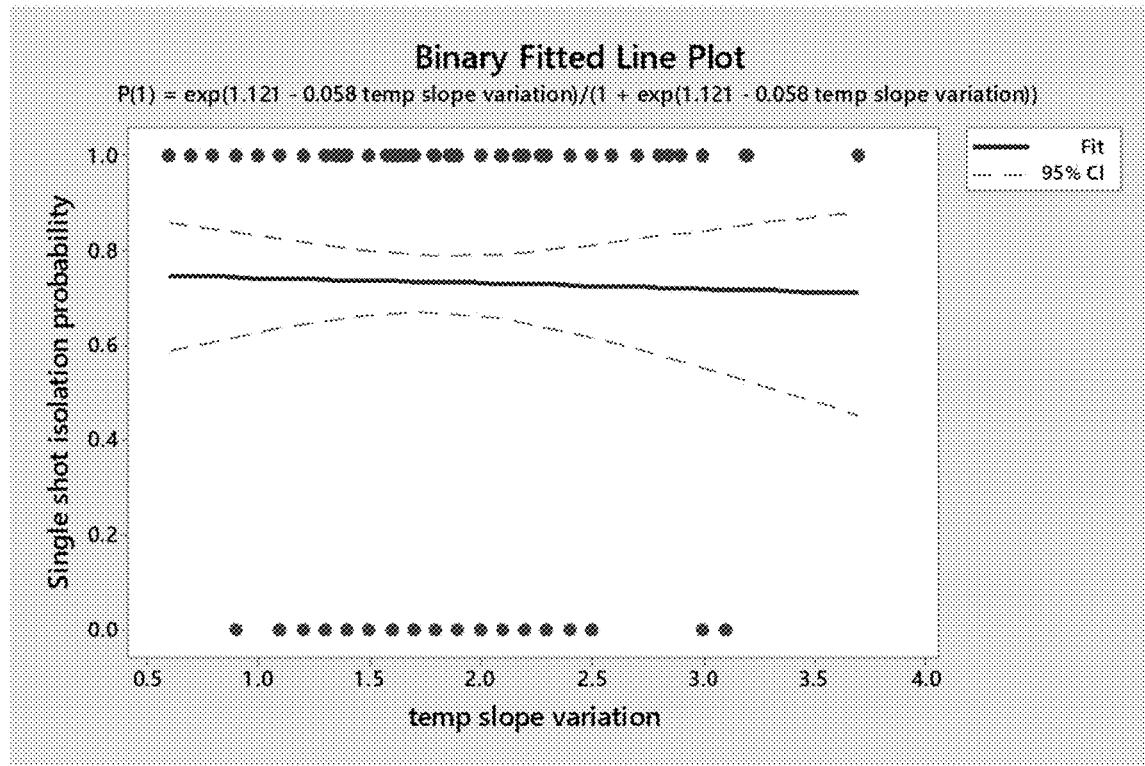

FIG. 93B shows a binary fitted line plot of single shot isolation probability versus pre-ablation temperature slope variation in the study of this disclosure.

Figure 94A:
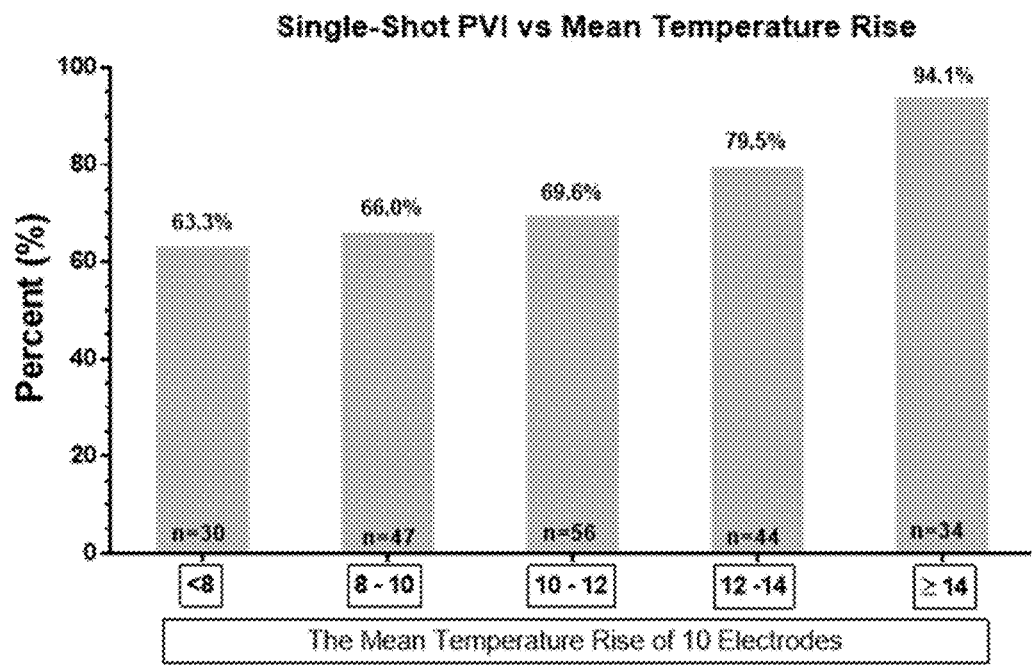

FIG. 94A shows a bar graph summarizing single shot isolation probability versus pre-ablation mean temperature rise in the study of this disclosure.

Figure 94B:
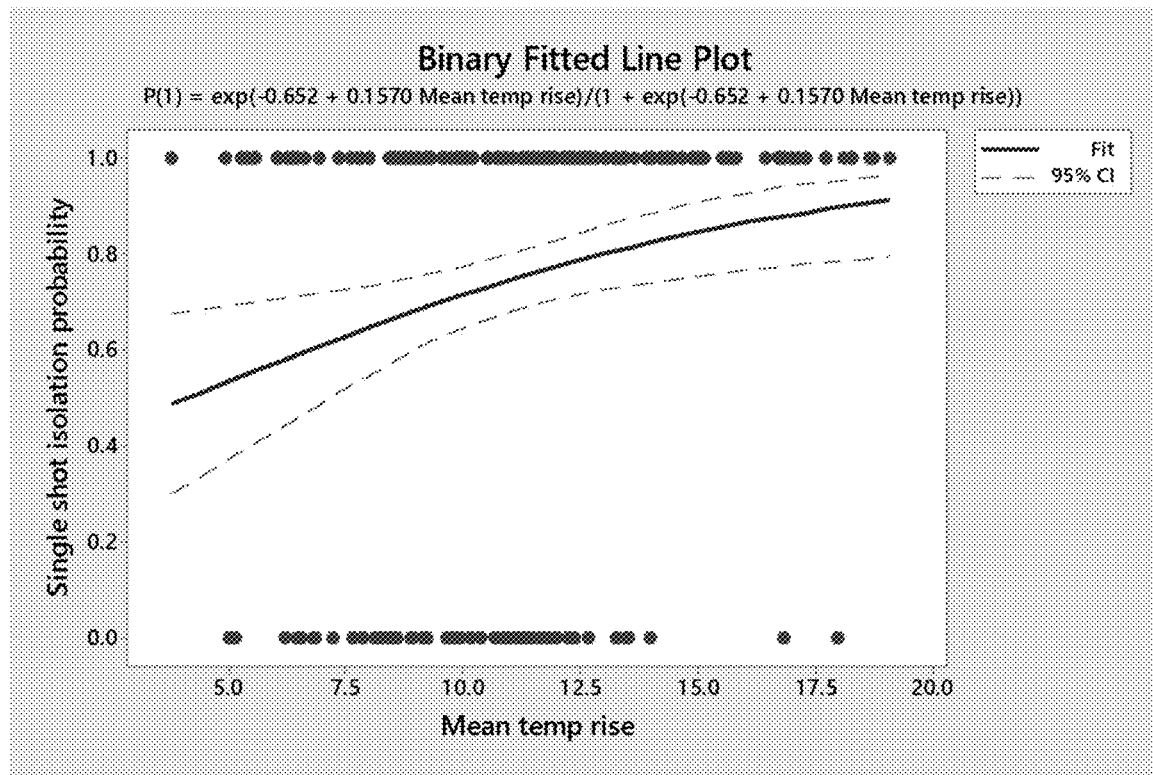

FIG. 94B shows a binary fitted line plot of single shot isolation probability versus pre-ablation mean temperature rise in the study of this disclosure.

Figure 95A:
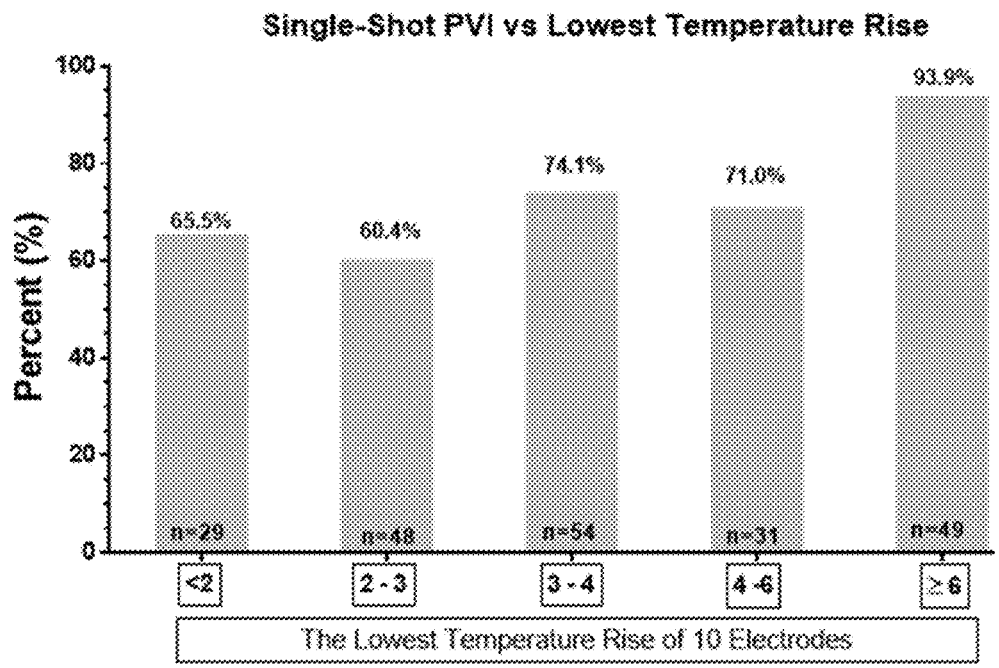

FIG. 95A shows a bar graph summarizing single shot isolation probability versus pre-ablation lowest value temperature rise in the study of this disclosure.

Figure 95B:
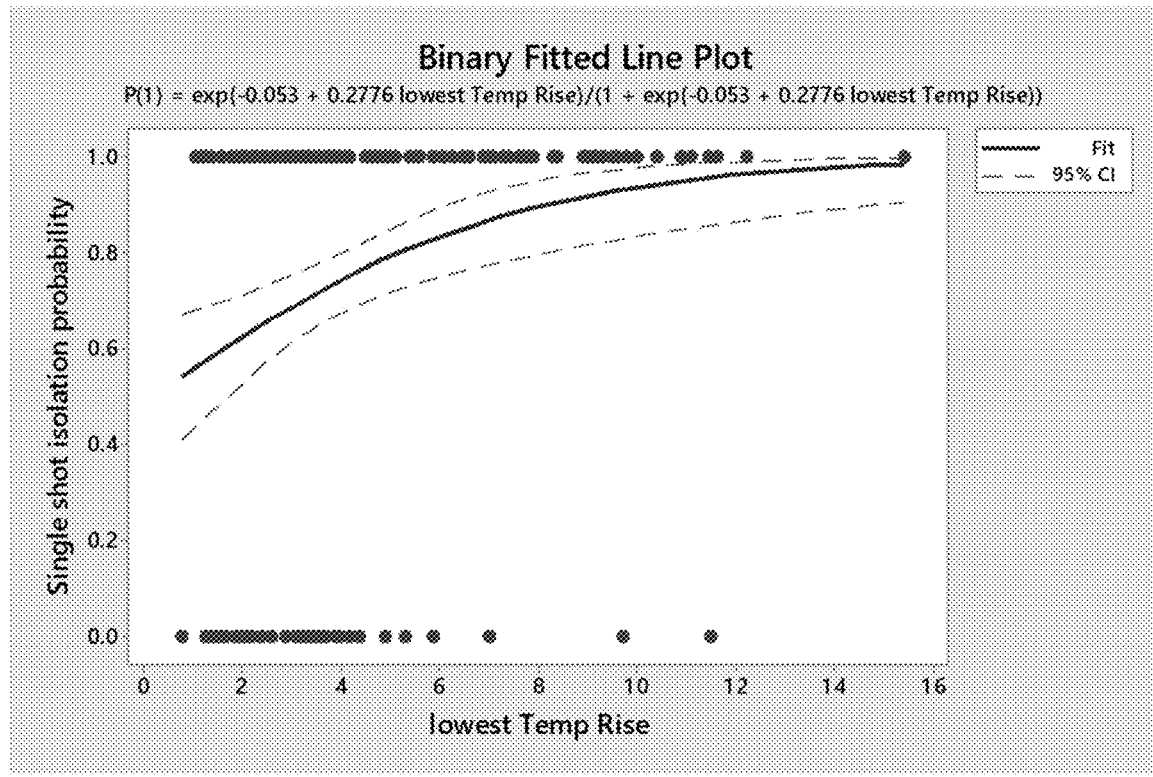

FIG. 95B shows a binary fitted line plot of single shot isolation probability versus pre-ablation lowest value temperature rise in the study of this disclosure.

Figure 96A:
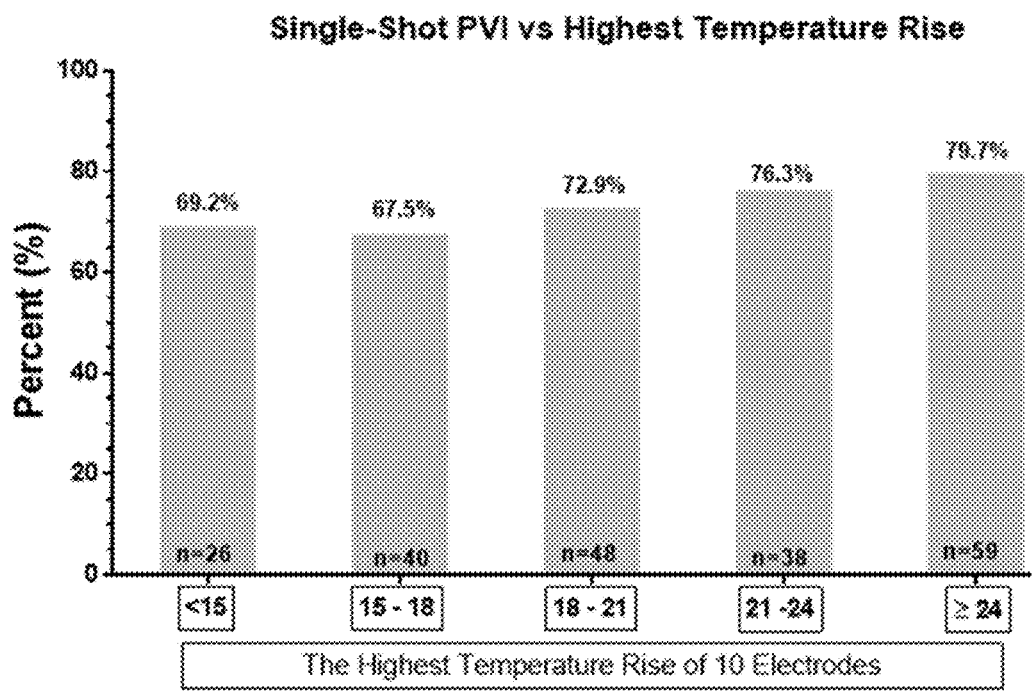

FIG. 96A shows a bar graph summarizing single shot isolation probability versus pre-ablation highest value temperature rise in the study of this disclosure.

Figure 96B:
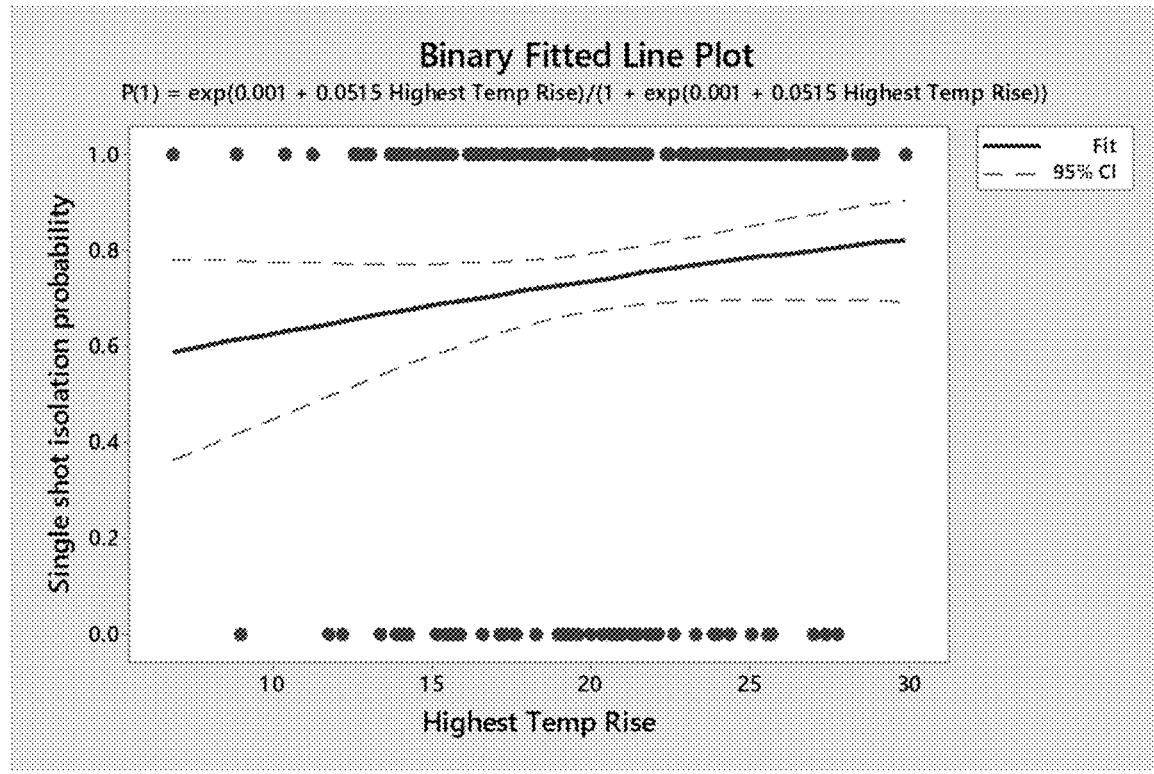

FIG. 96B shows a binary fitted line plot of single shot isolation probability versus pre-ablation highest value temperature rise in the study of this disclosure.

Figure 97A:
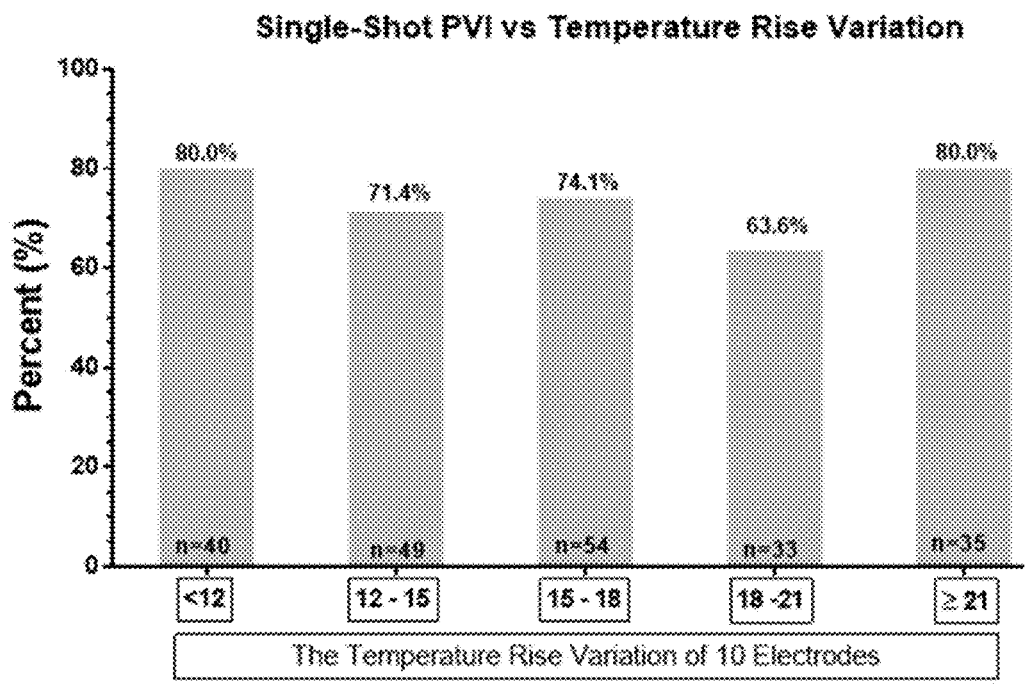

FIG. 97A shows a bar graph summarizing single shot isolation probability versus pre-ablation temperature rise variation in the study of this disclosure.

Figure 97B:
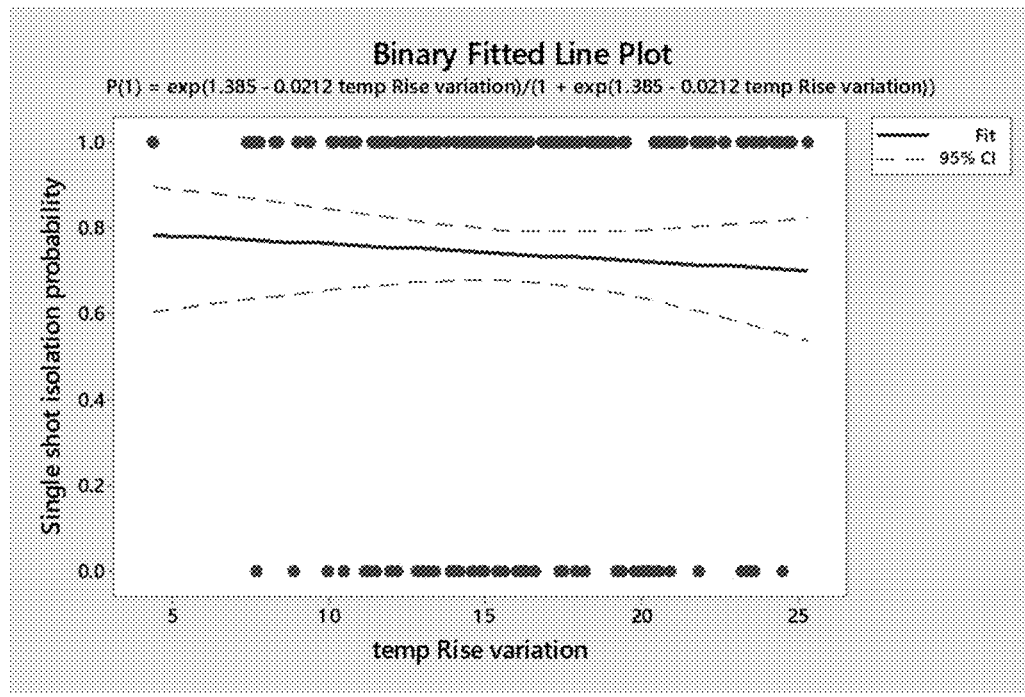

FIG. 97B shows a binary fitted line plot of single shot isolation probability versus pre-ablation temperature rise variation in the study of this disclosure.

Figure 98A:
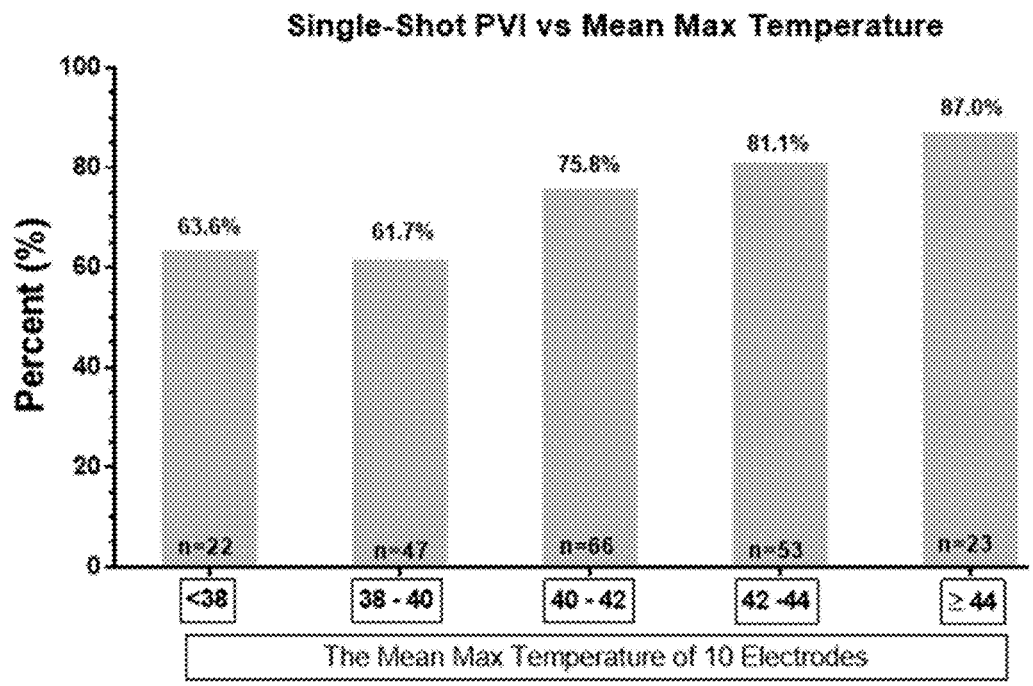

FIG. 98A shows a bar graph summarizing single shot isolation probability versus pre-ablation maximum mean temperature in the study of this disclosure.

Figure 98B:
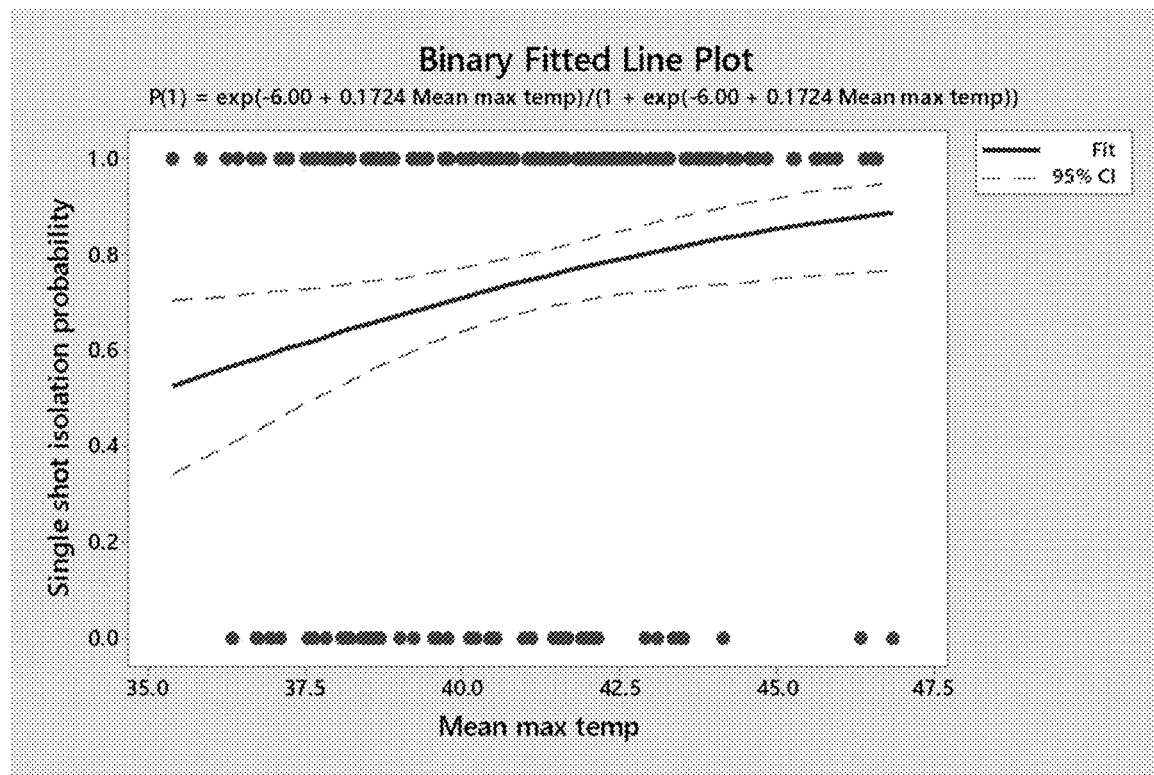

FIG. 98B shows a binary fitted line plot of single shot isolation probability versus pre-ablation maximum mean temperature in the study of this disclosure.

Figure 99A:
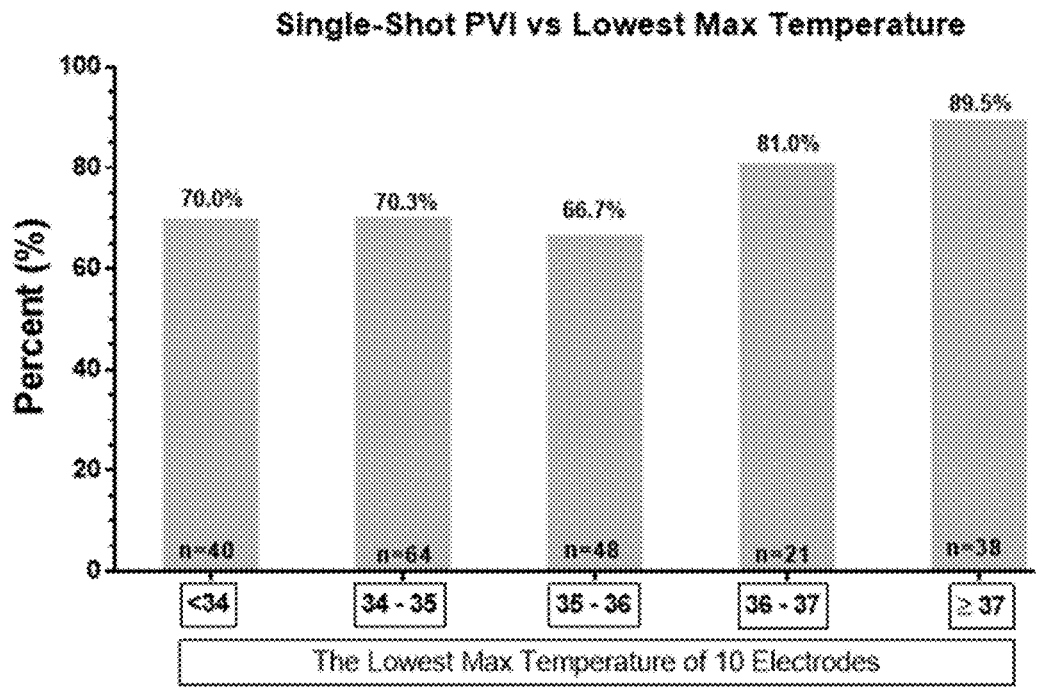

FIG. 99A shows a bar graph summarizing single shot isolation probability versus pre-ablation lowest value maximum temperature in the study of this disclosure.

Figure 99B:
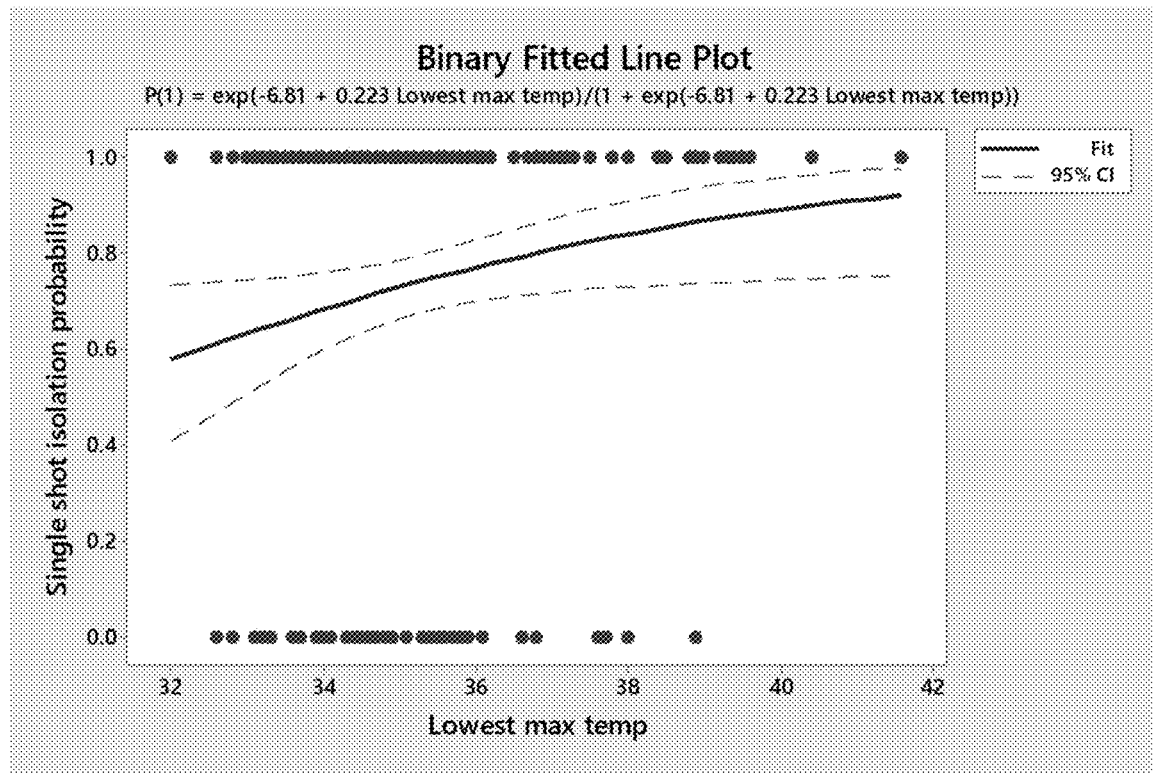

FIG. 99B shows a binary fitted line plot of single shot isolation probability versus pre-ablation lowest value maximum temperature in the study of this disclosure.

Figure 100A:
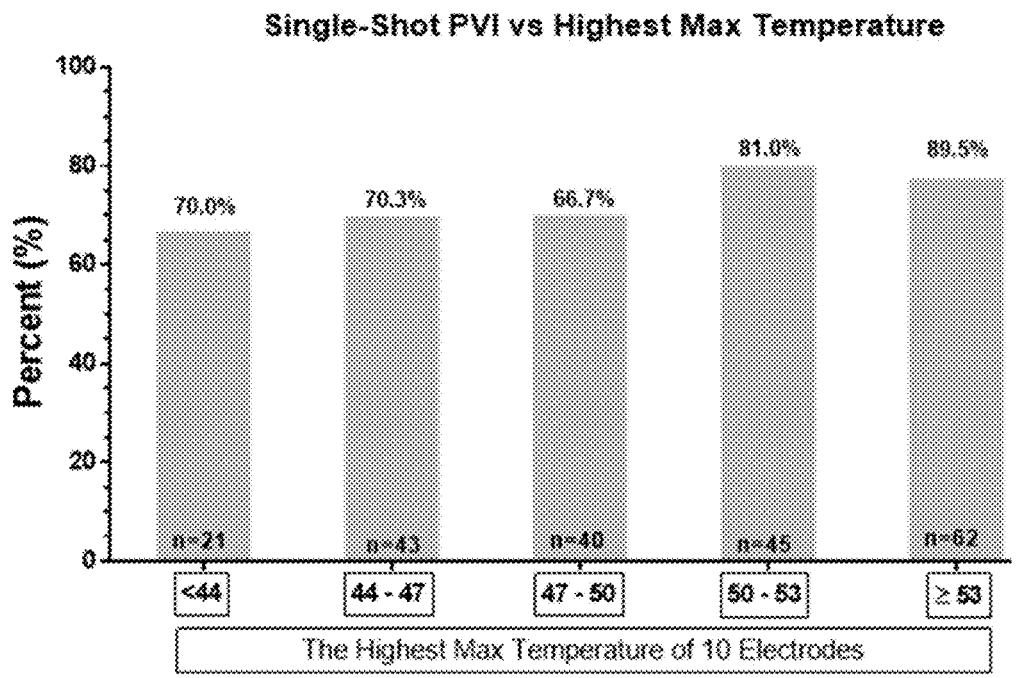

FIG. 100A shows a bar graph summarizing single shot isolation probability versus pre-ablation highest value maximum temperature in the study of this disclosure.

Figure 100B:
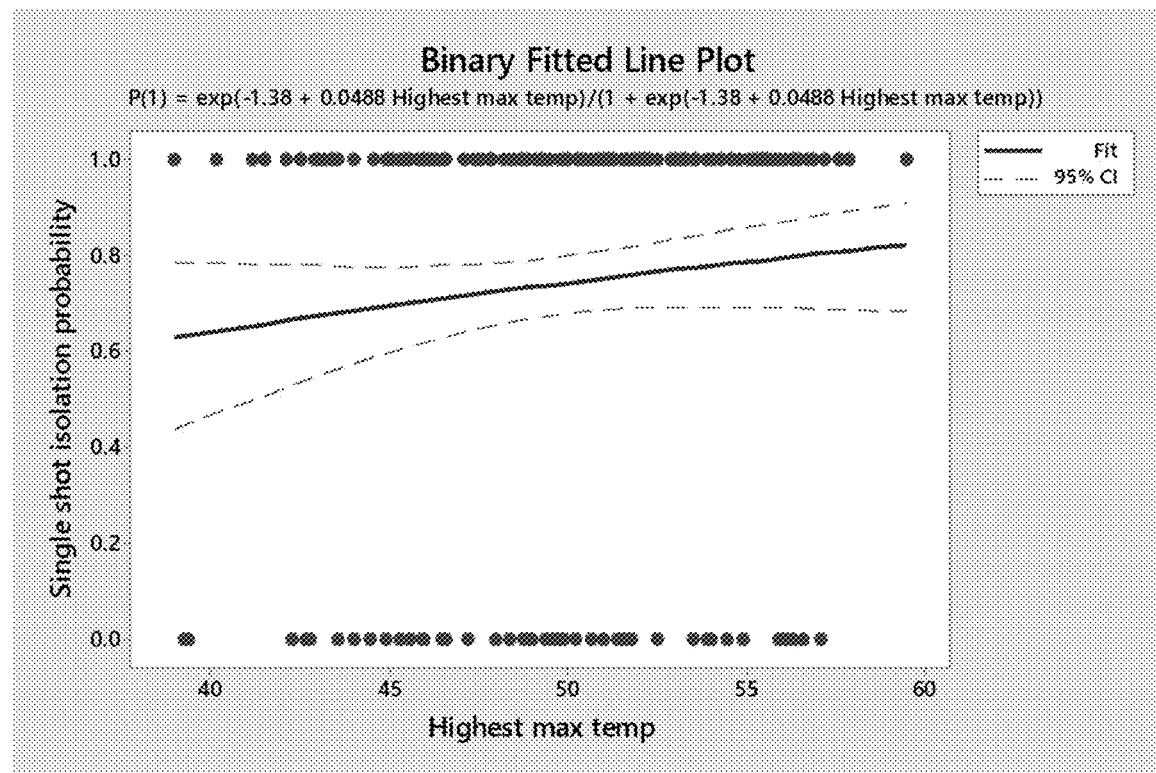

FIG. 100B shows a binary fitted line plot of single shot isolation probability versus pre-ablation highest value maximum temperature in the study of this disclosure.

Figure 101A:
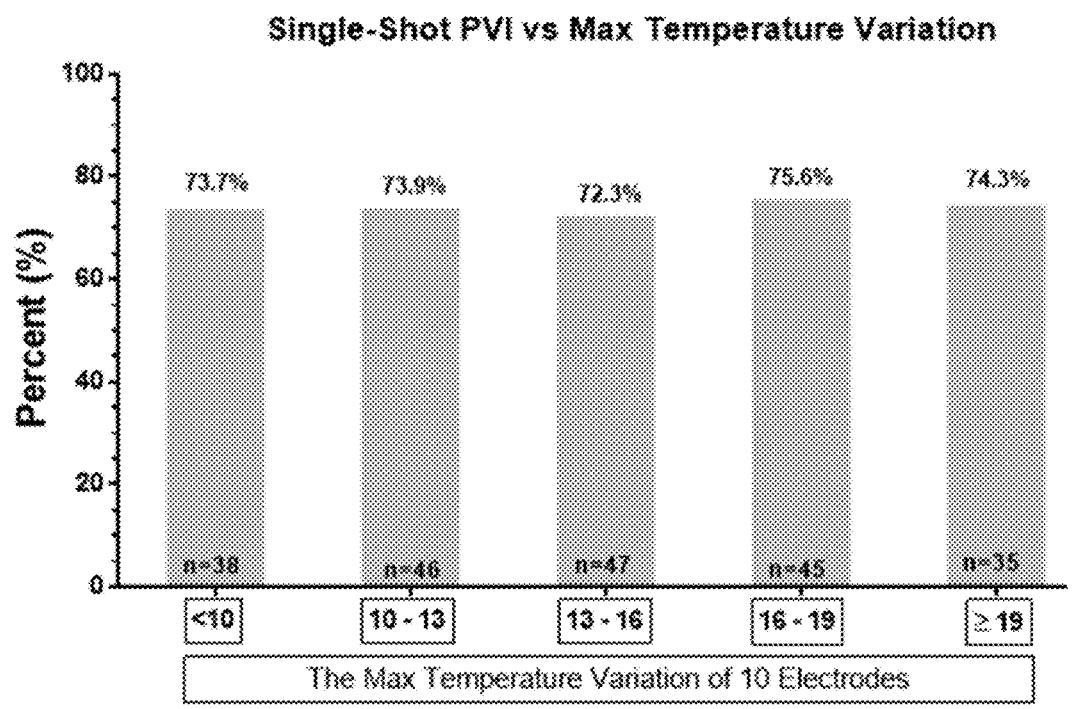

FIG. 101A shows a bar graph summarizing single shot isolation probability versus pre-ablation maximum temperature variation in the study of this disclosure.

Figure 101B:
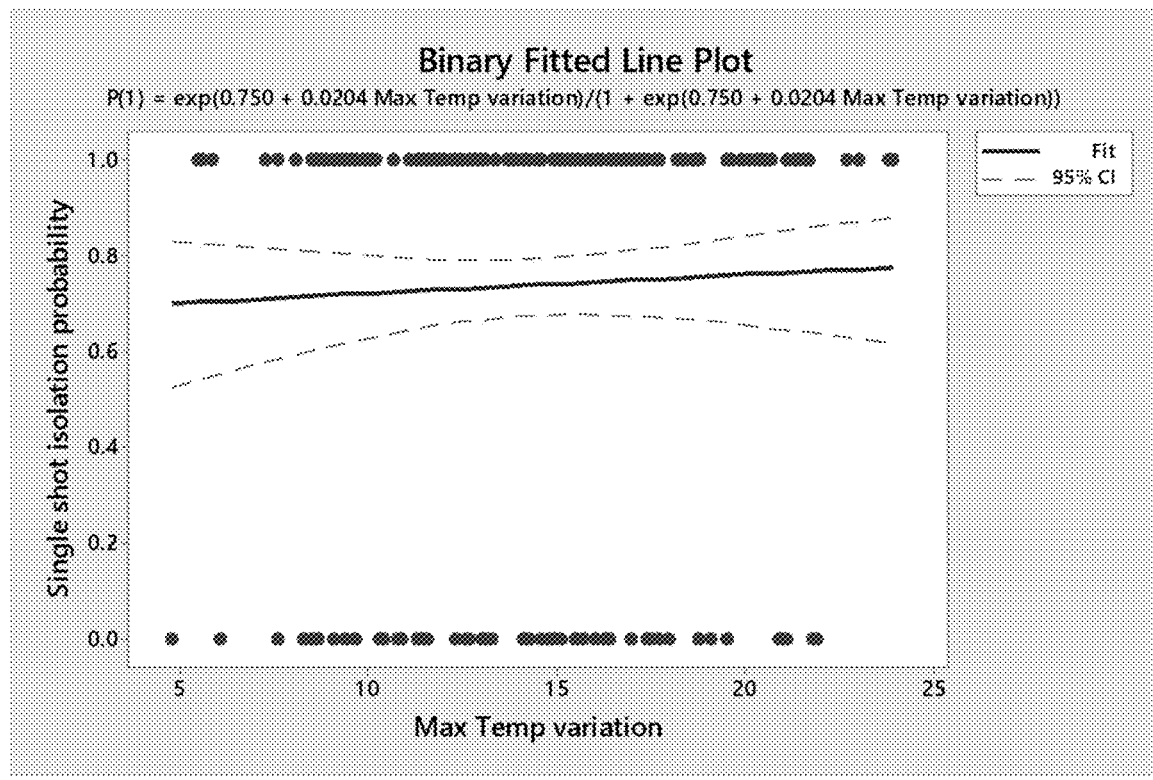

FIG. 101B shows a binary fitted line plot of single shot isolation probability versus pre-ablation maximum temperature variation in the study of this disclosure.

Figure 102A:
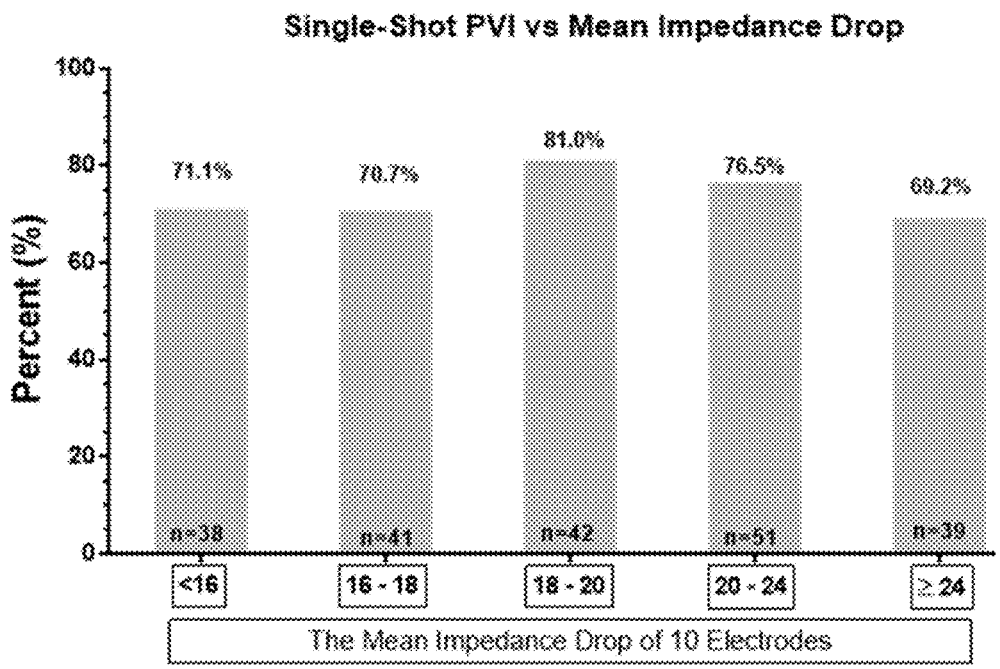

FIG. 102A shows a bar graph summarizing single shot isolation probability versus pre-ablation mean impedance drop in the study of this disclosure.

Figure 102B:
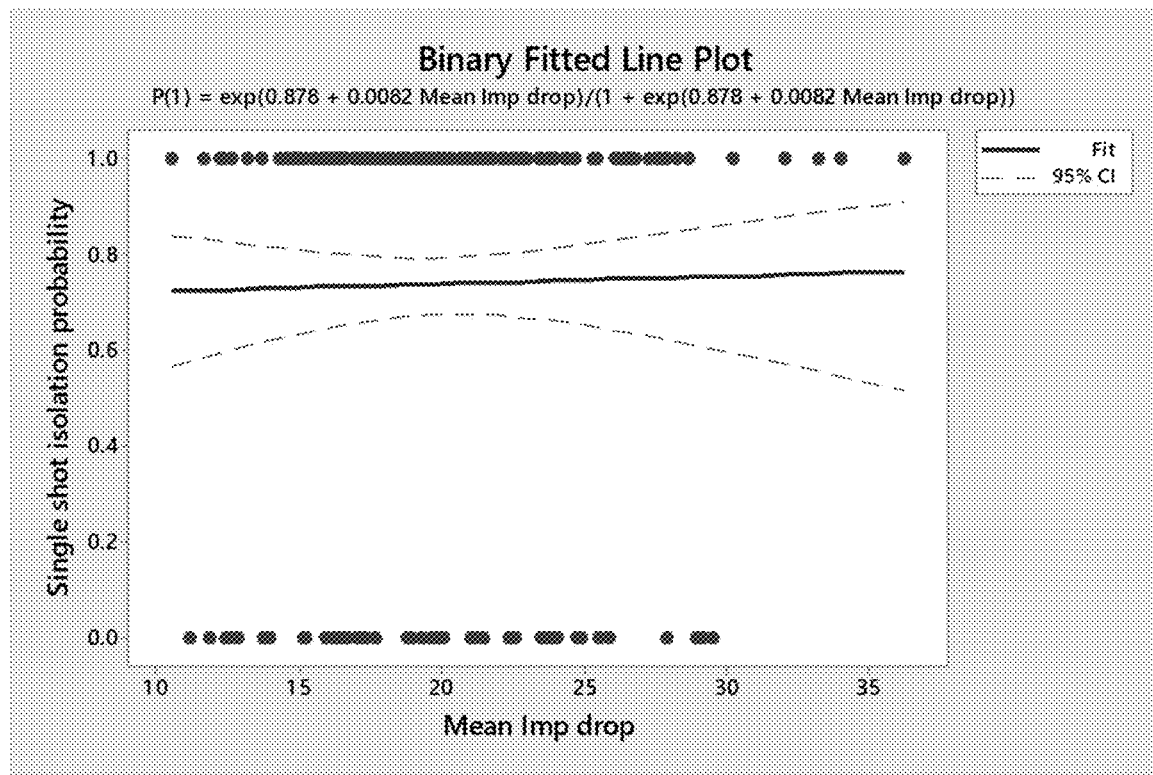

FIG. 102B shows a binary fitted line plot of single shot isolation probability versus pre-ablation mean impedance drop in the study of this disclosure.

Figure 103A:
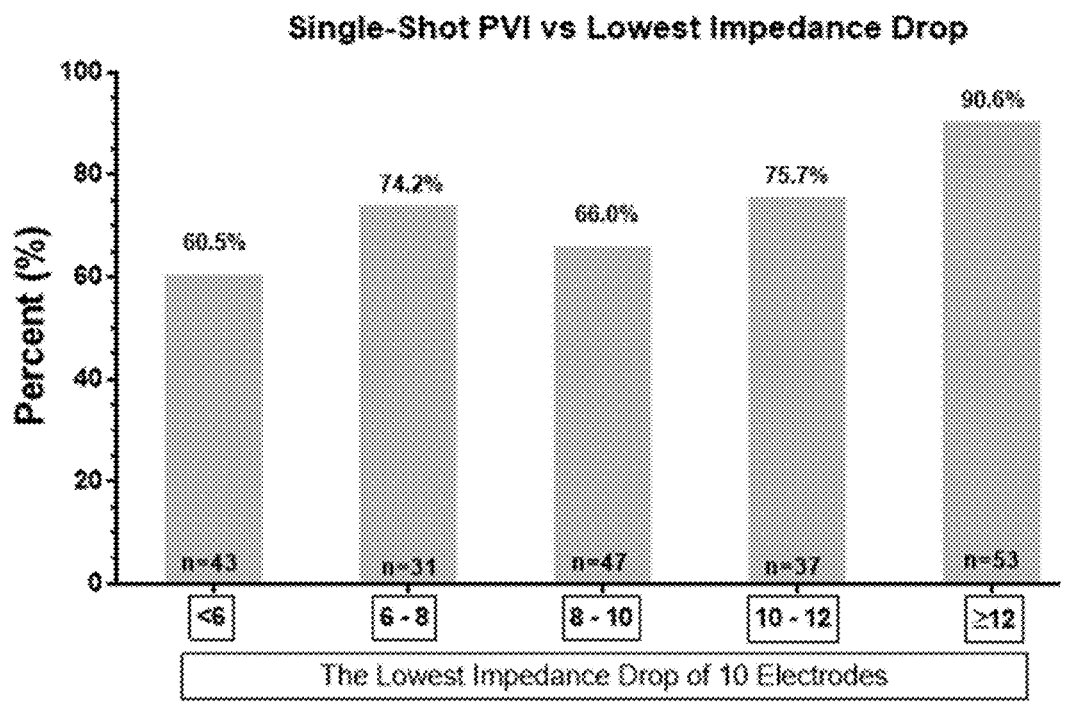

FIG. 103A shows a bar graph summarizing single shot isolation probability versus pre-ablation lowest value impedance drop in the study of this disclosure.

Figure 103B:
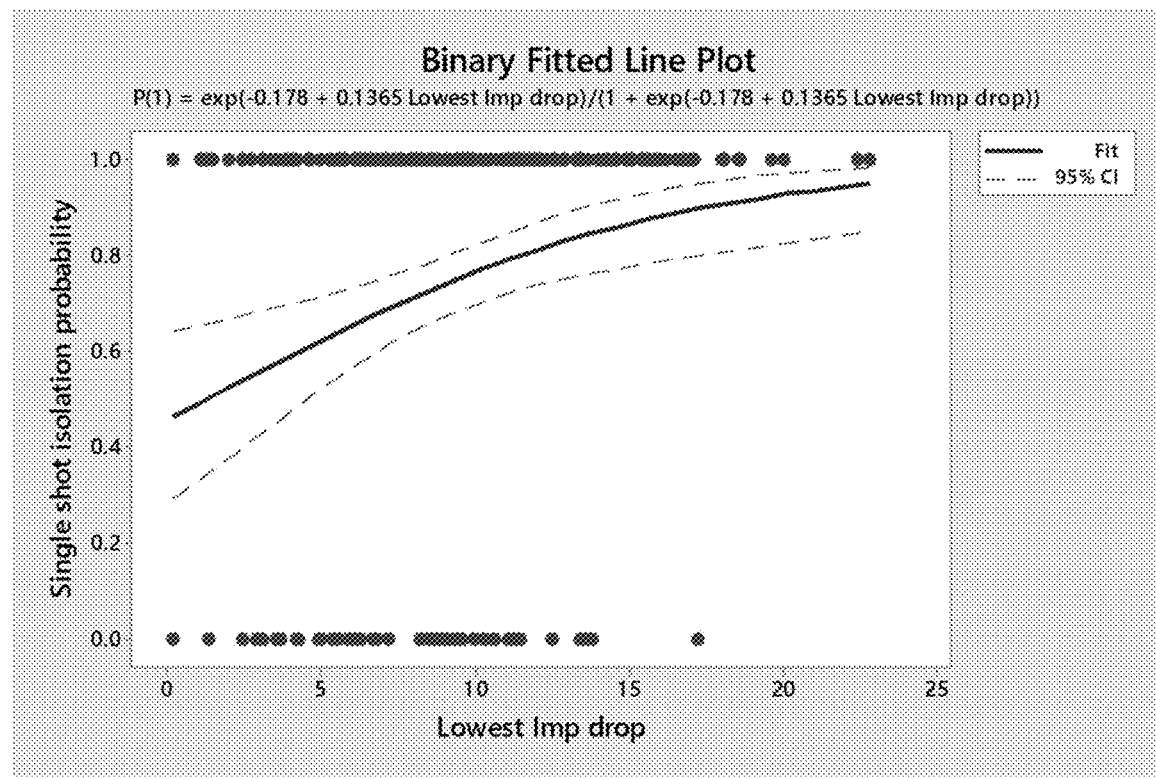

FIG. 103B shows a binary fitted line plot of single shot isolation probability versus pre-ablation lowest value impedance drop in the study of this disclosure.

Figure 104A:
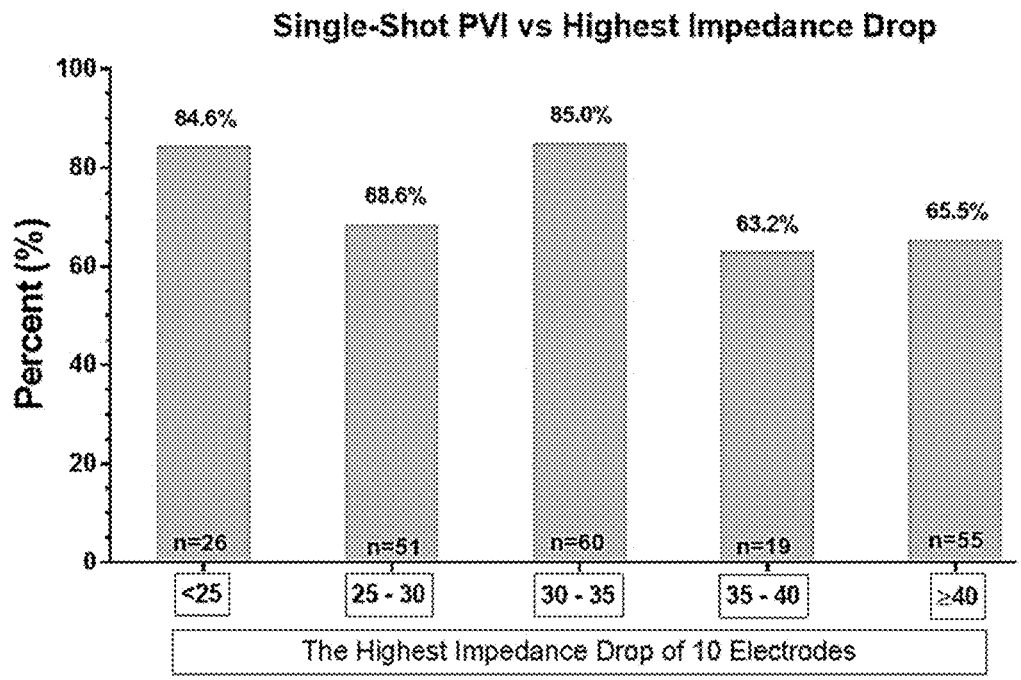

FIG. 104A shows a bar graph summarizing single shot isolation probability versus pre-ablation highest value impedance drop in the study of this disclosure.

Figure 104B:
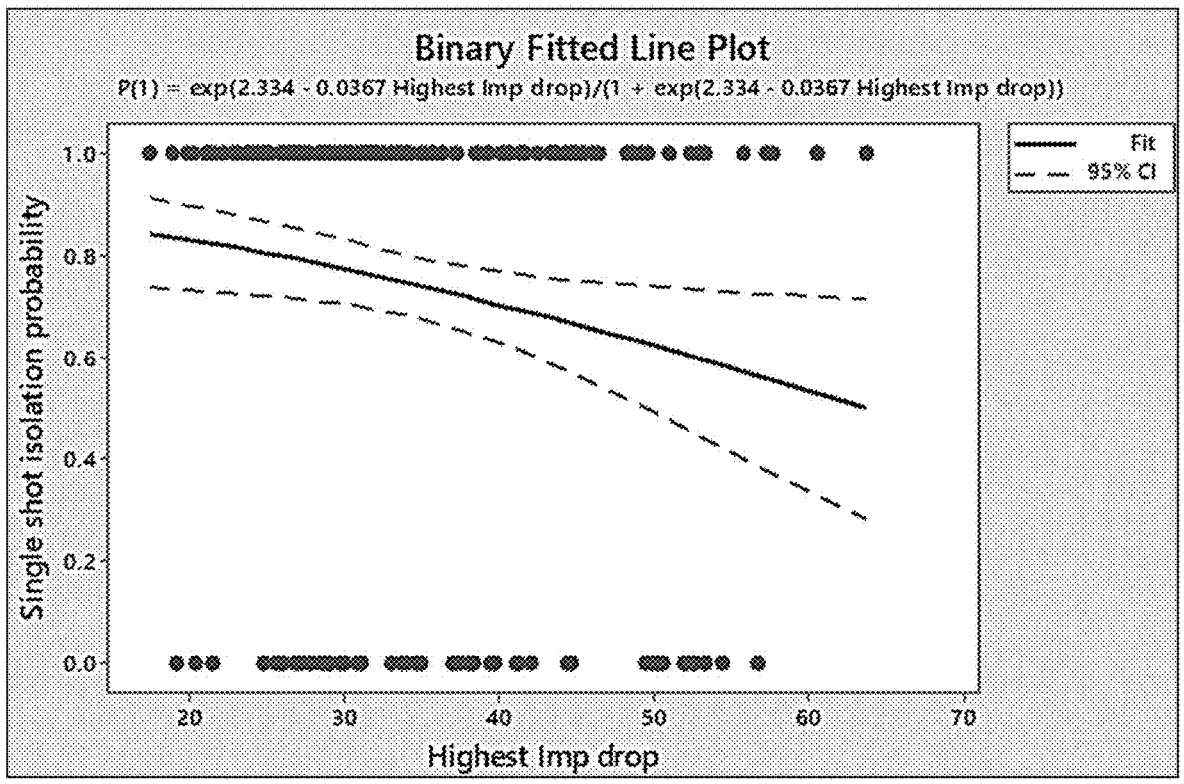

FIG. 104B shows a binary fitted line plot of single shot isolation probability versus pre-ablation highest value impedance drop in the study of this disclosure.

Figure 105A:
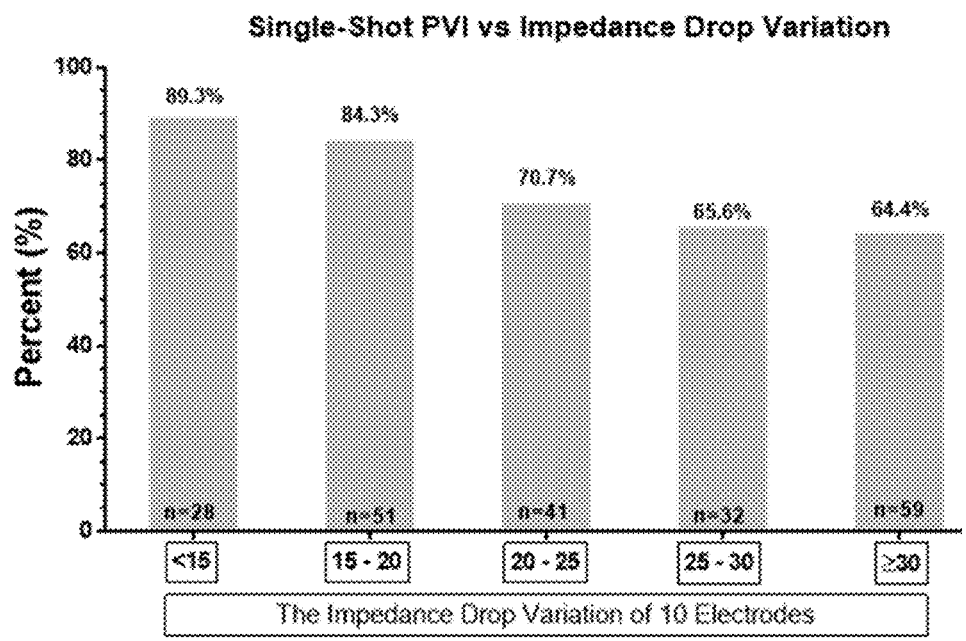

FIG. 105A shows a bar graph summarizing single shot isolation probability versus pre-ablation impedance drop variation in the study of this disclosure.

Figure 105B:
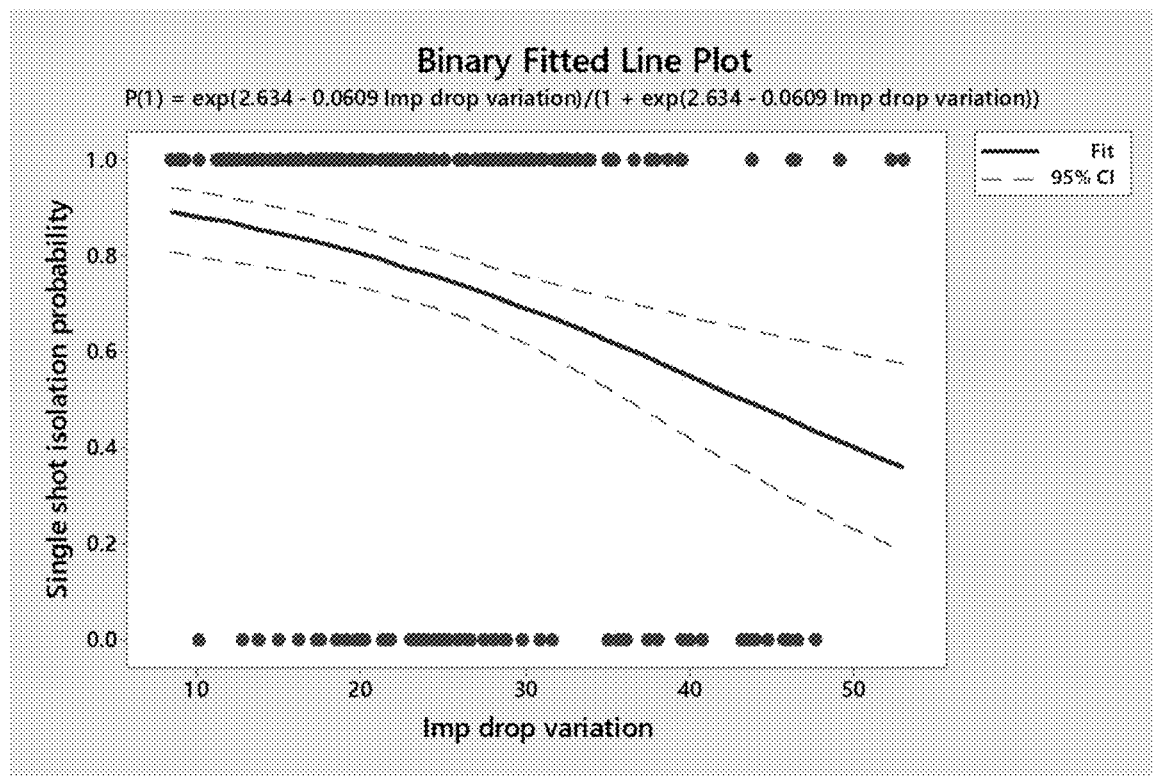

FIG. 105B shows a binary fitted line plot of single shot isolation probability versus pre-ablation impedance drop variation in the study of this disclosure.

Figure 106A:
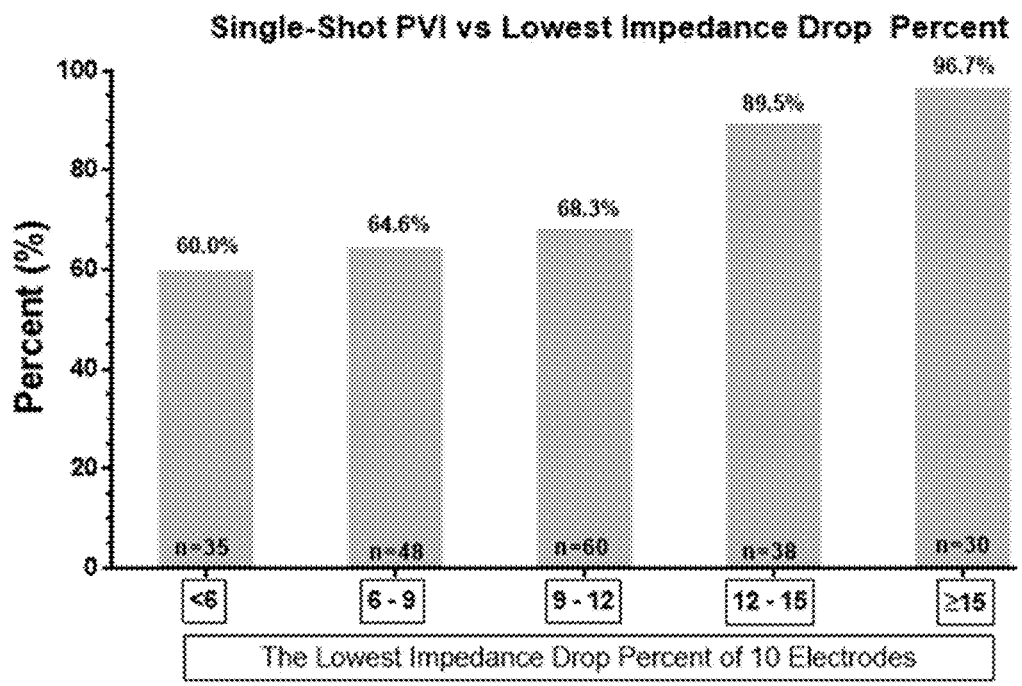

FIG. 106A shows a bar graph summarizing single shot isolation probability versus pre-ablation lowest value impedance drop percent in the study of this disclosure.

Figure 106B:
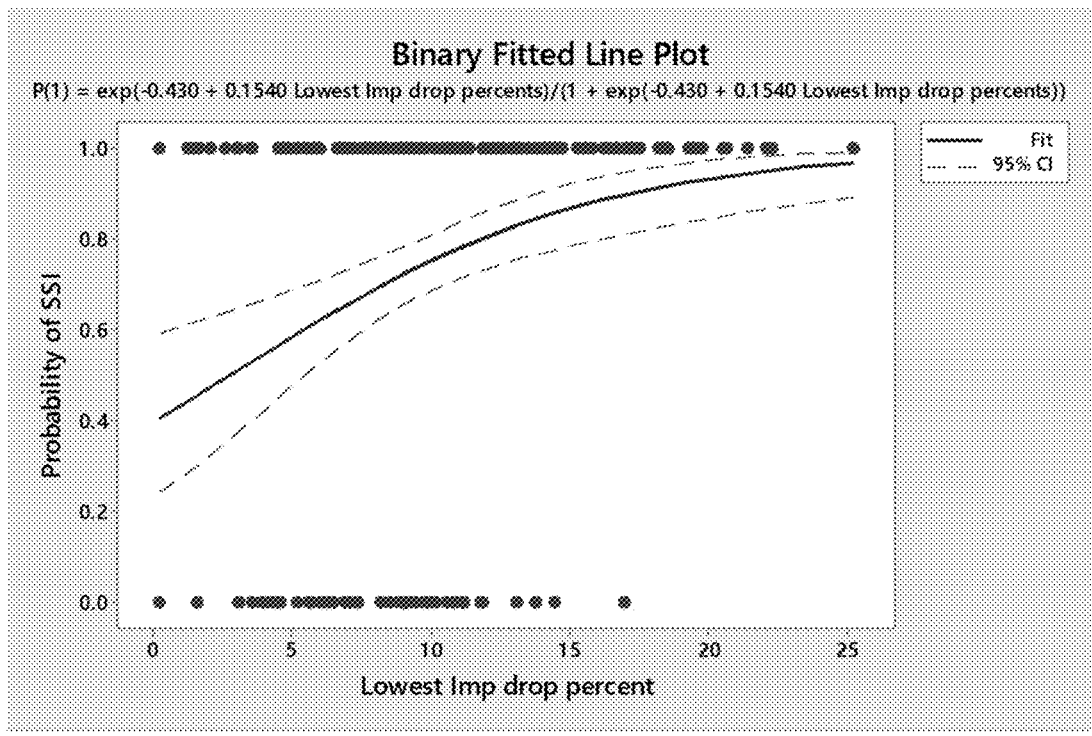

FIG. 106B shows a binary fitted line plot of single shot isolation probability versus pre-ablation lowest value impedance drop percent in the study of this disclosure.

Figure 107A:
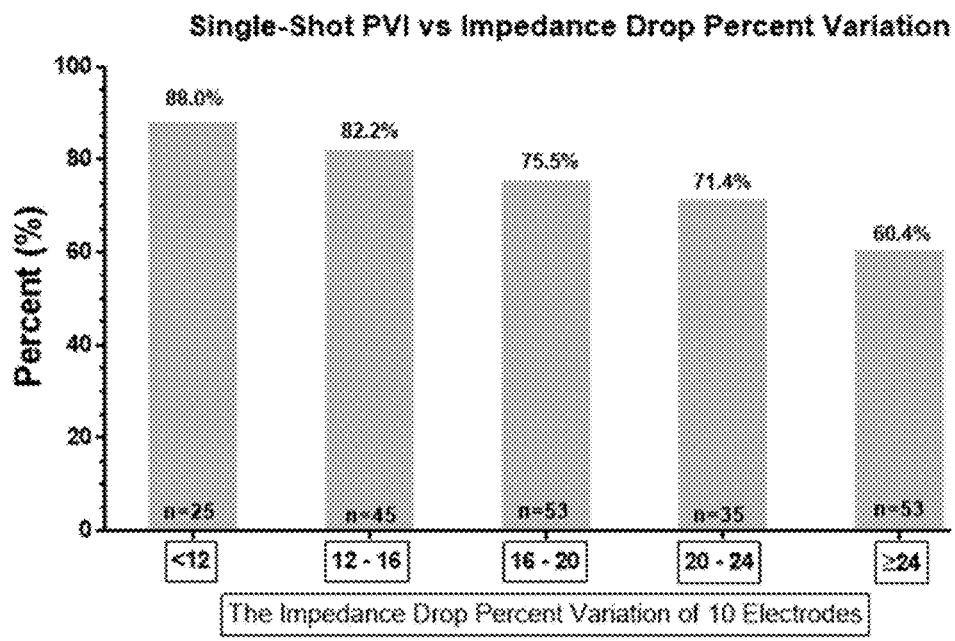

FIG. 107A shows a bar graph summarizing single shot isolation probability versus pre-ablation impedance drop percent variation in the study of this disclosure.

Figure 107B:
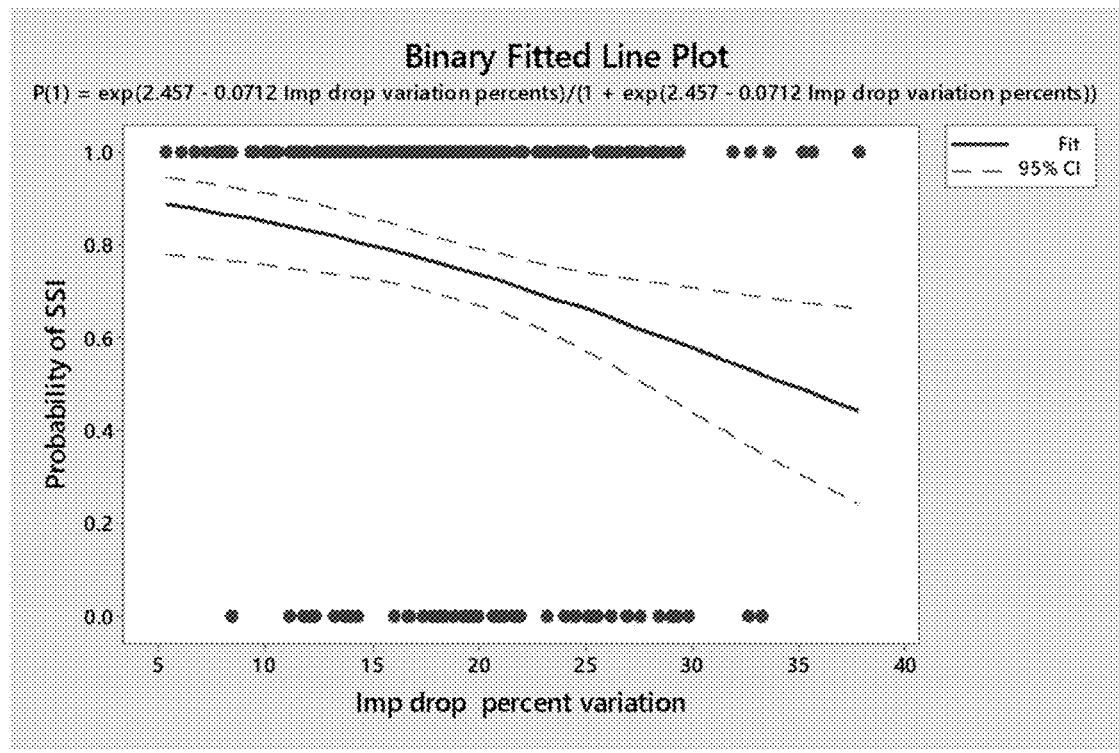

FIG. 107B shows a binary fitted line plot of single shot isolation probability versus pre-ablation impedance drop percent variation in the study of this disclosure.

Figure 108A:
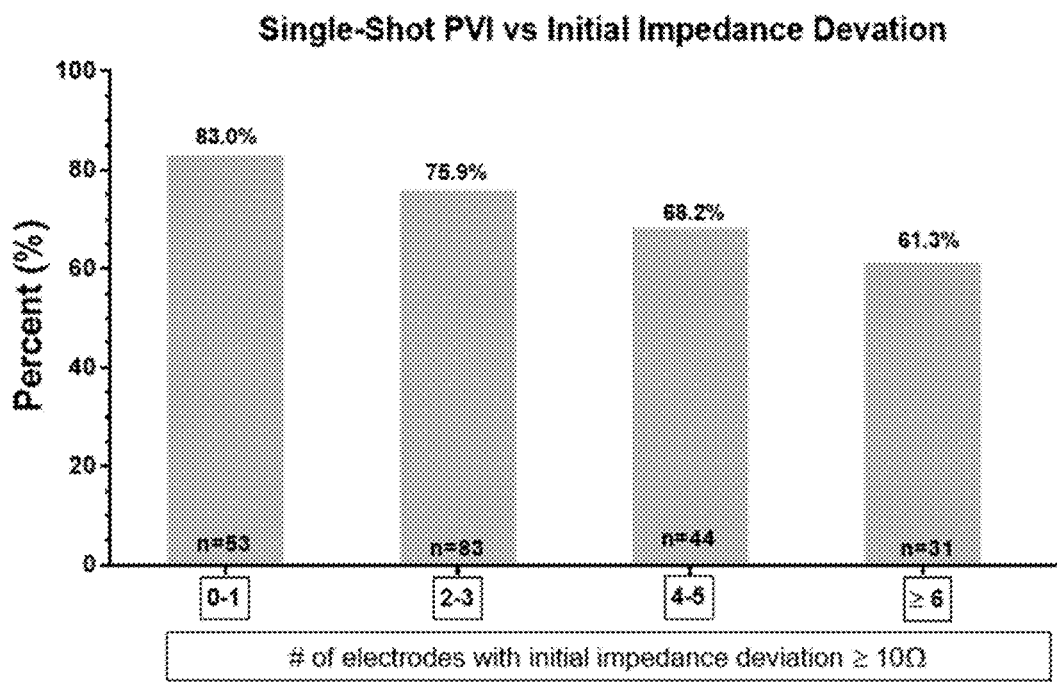

FIG. 108A shows a bar graph summarizing single shot isolation probability versus pre-ablation initial impedance deviation from mean value in the study of this disclosure.

Figure 108B:
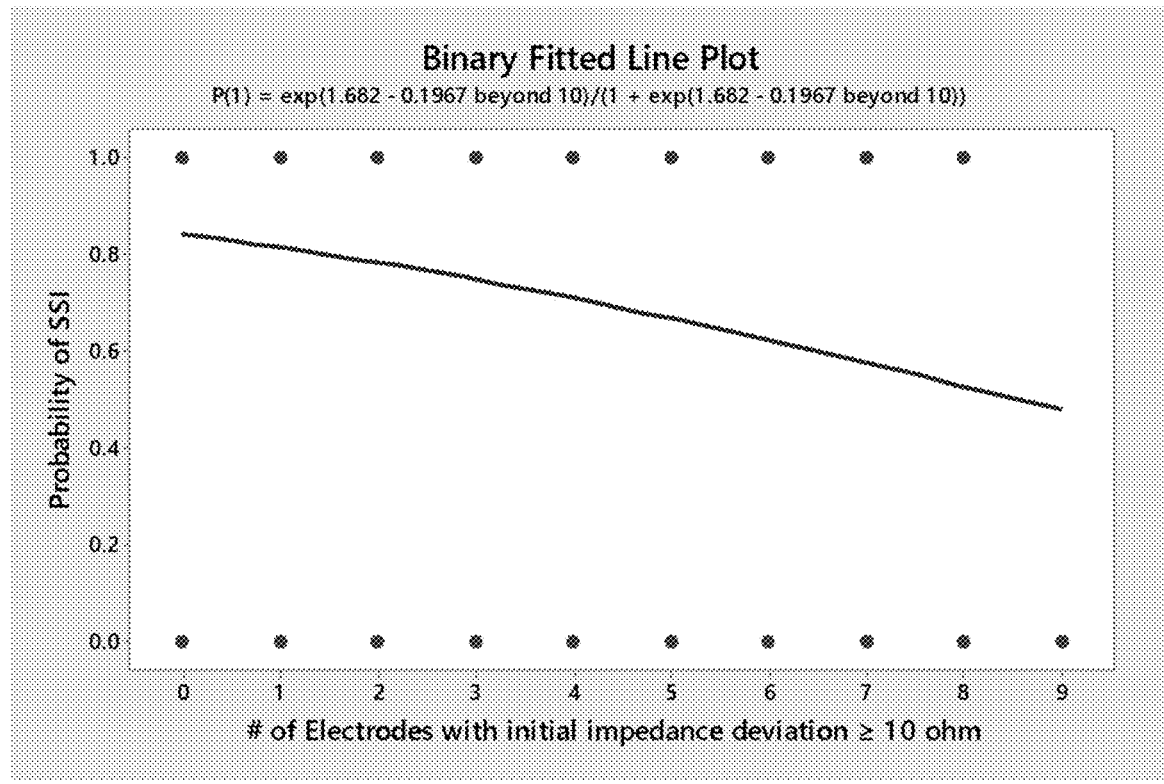

FIG. 108B shows a binary fitted line plot of single shot isolation probability versus pre-ablation initial impedance deviation from mean value in the study of this disclosure.

FIG. 109 shows a table summarizing predictors associated with corresponding Pearson correlation and binary logistic regression values in the study of this disclosure.

FIG. 110 shows a table summarizing pre- and post-ablation parameters in the study of this disclosure.

Figure 111:
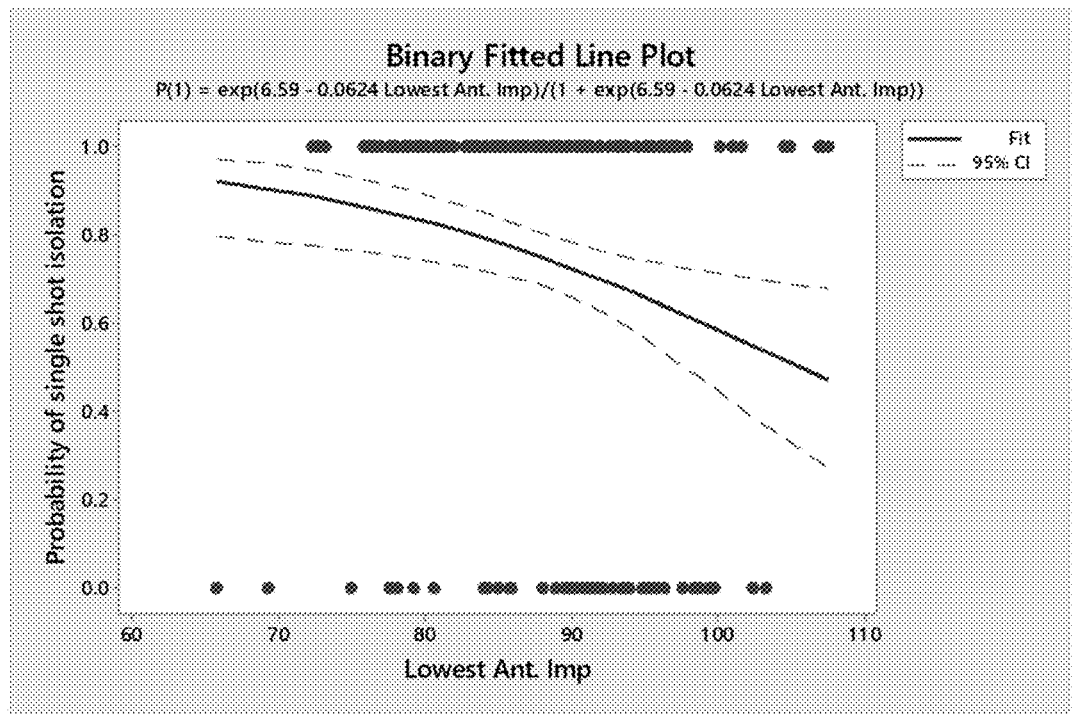

FIG. 111 shows a binary fitted line plot of probability of single shot isolation versus pre-ablation lowest anterior impedance in the study of this disclosure.

Figure 112:
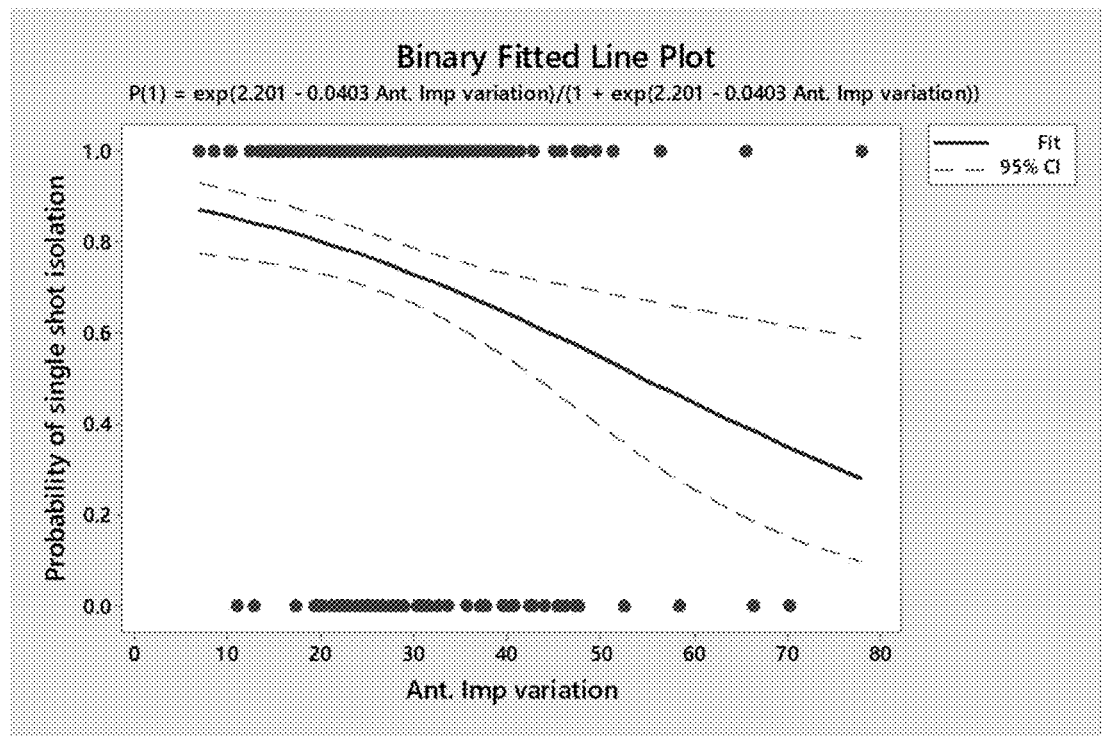

FIG. 112 shows a binary fitted line plot of probability of single shot isolation versus pre-ablation anterior impedance variation in the study of this disclosure.

Figure 113:
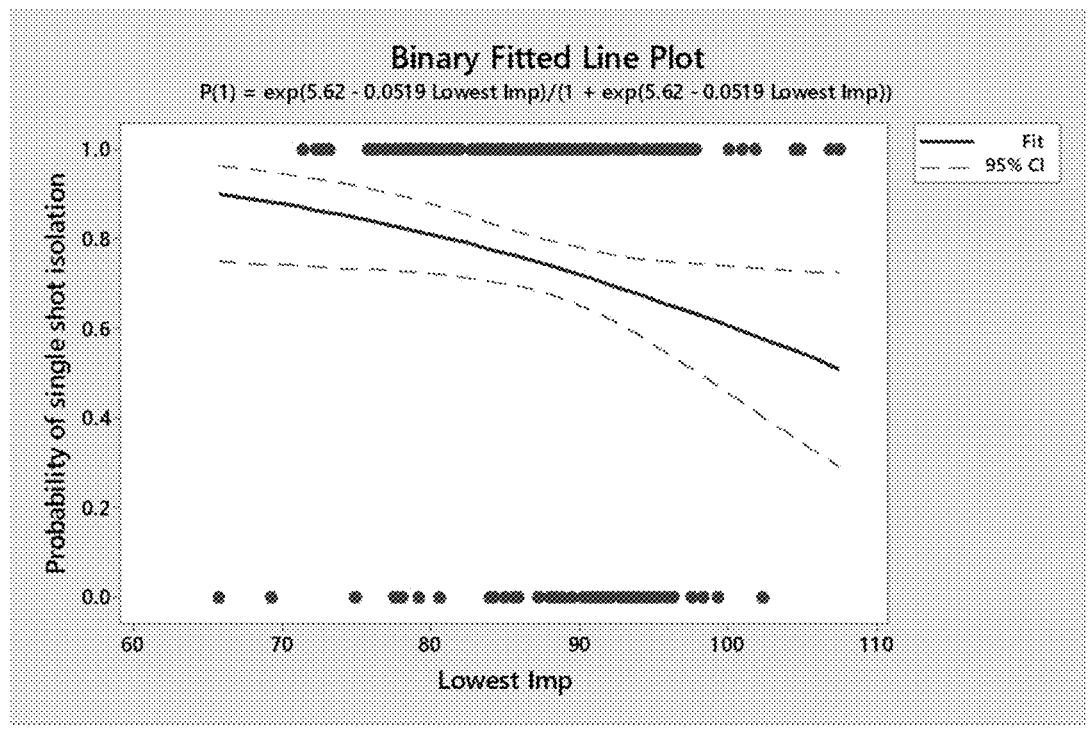

FIG. 113 shows a binary fitted line plot of probability of single shot isolation versus pre-ablation lowest impedance in the study of this disclosure.

Figure 114:
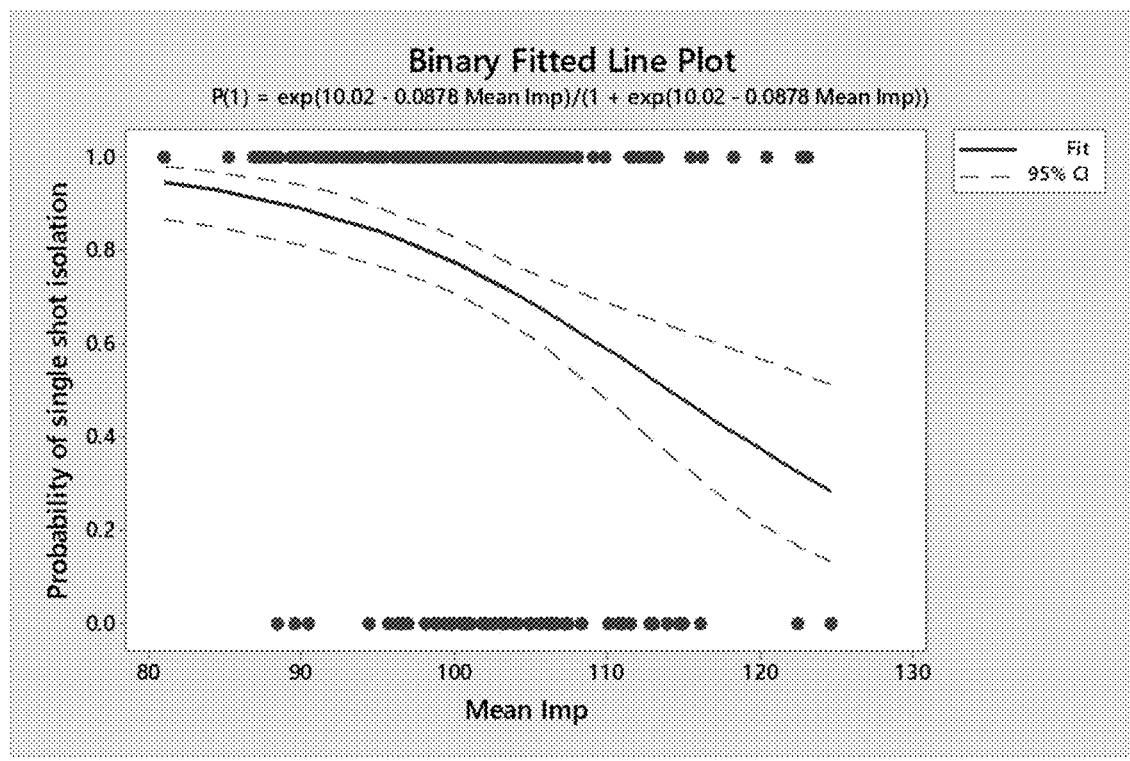

FIG. 114 shows a binary fitted line plot of probability of single shot isolation versus pre-ablation mean impedance in the study of this disclosure.

Figure 115:
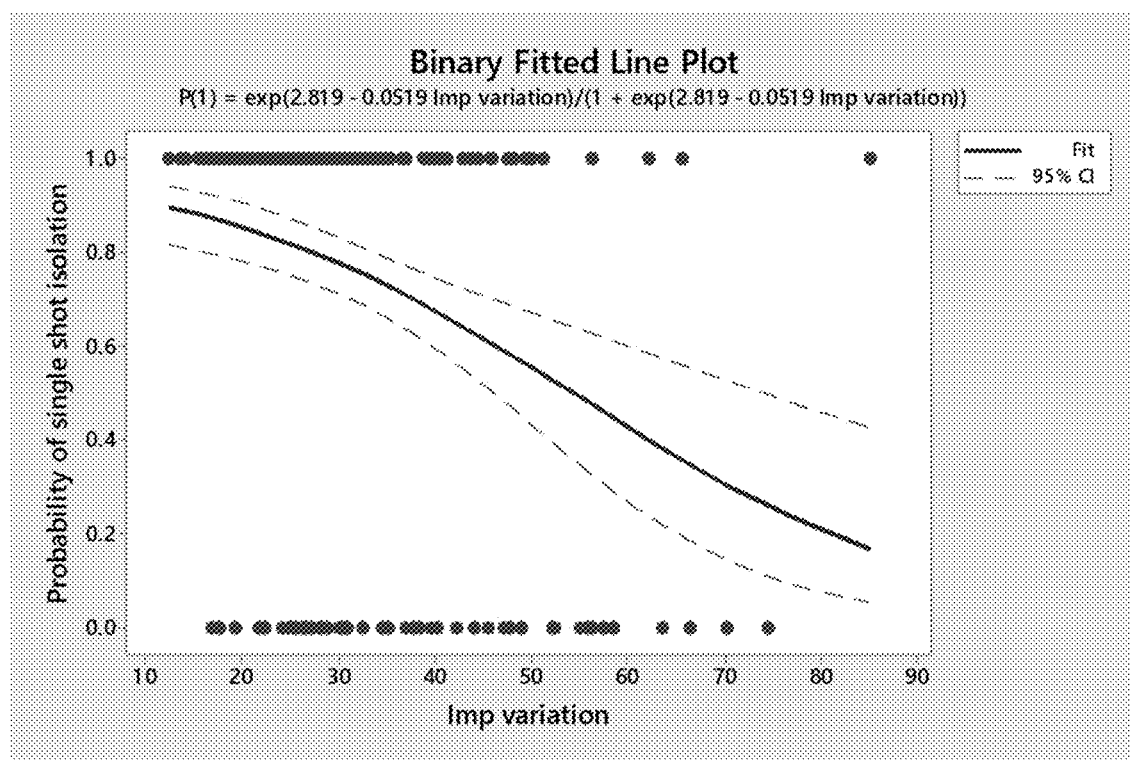

FIG. 115 shows a binary fitted line plot of probability of single shot isolation versus pre-ablation impedance variation in the study of this disclosure.

Figure 116:
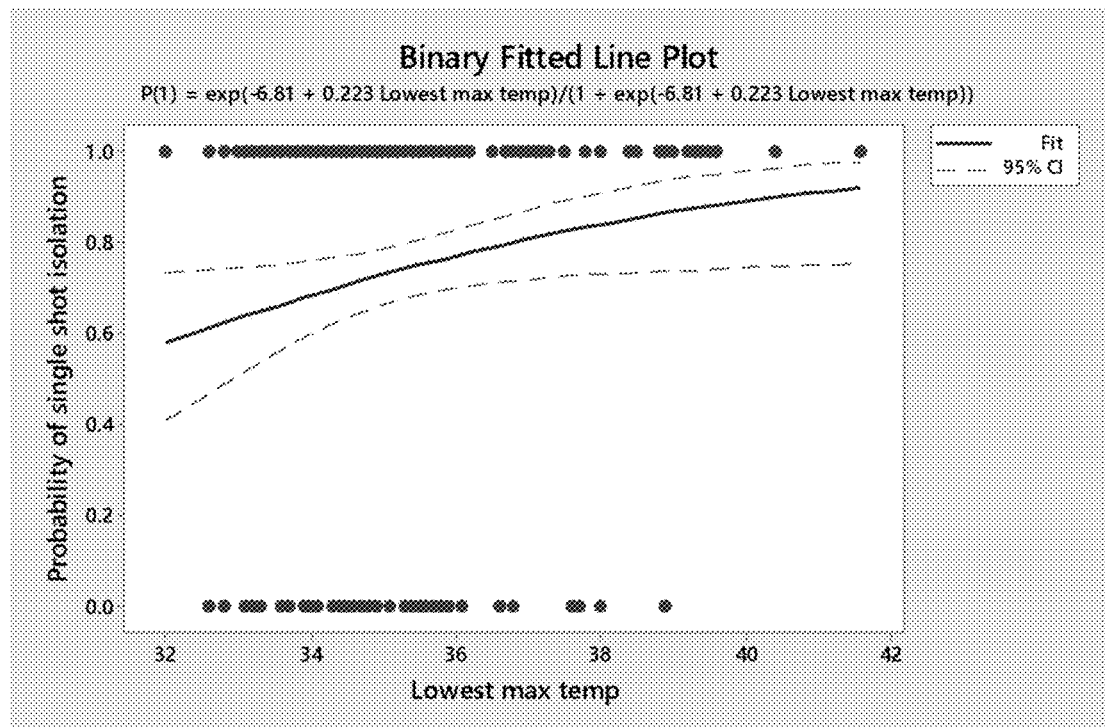

FIG. 116 shows a binary fitted line plot of probability of single shot isolation versus post-ablation lowest maximum temperature in the study of this disclosure.

Figure 117:
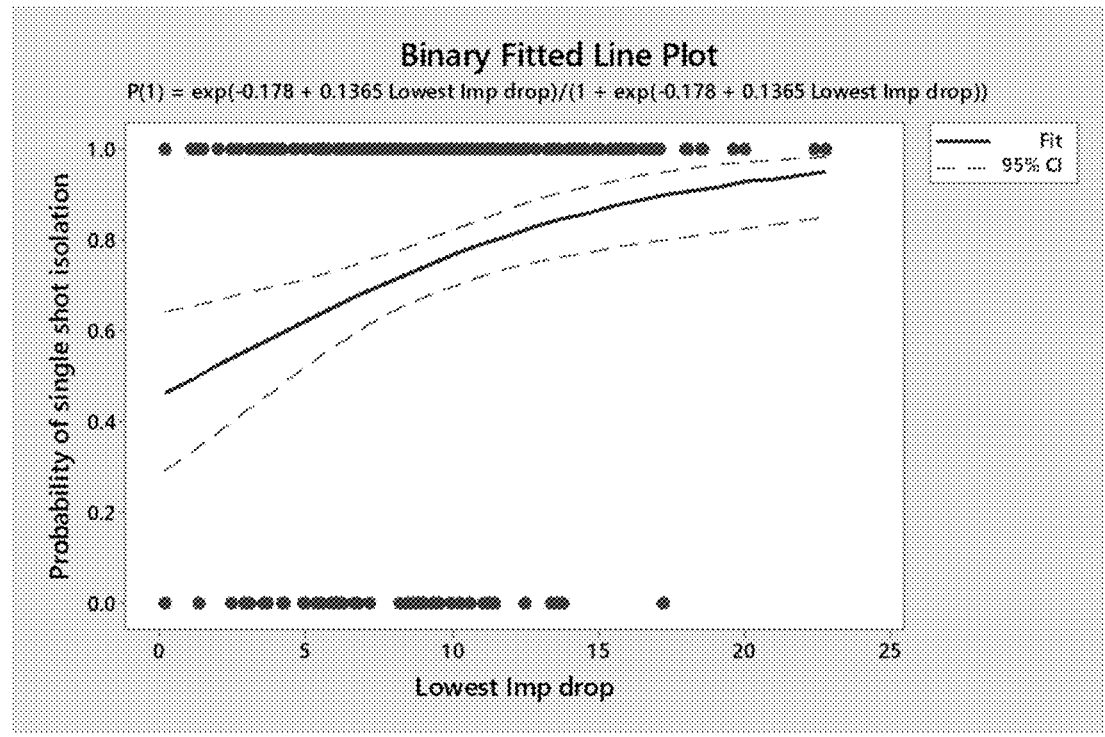

FIG. 117 shows a binary fitted line plot of probability of single shot isolation versus post-ablation lowest impedance drop in the study of this disclosure.

Figure 118:
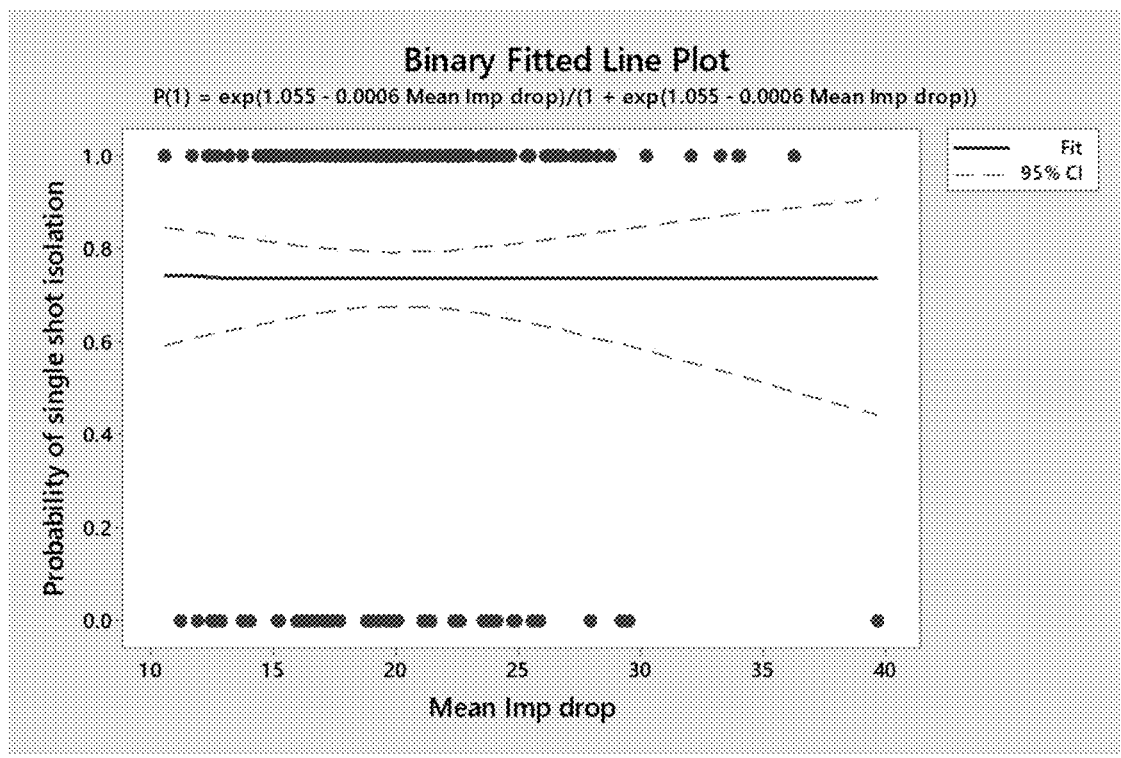

FIG. 118 shows a binary fitted line plot of probability of single shot isolation versus post-ablation mean impedance drop in the study of this disclosure.

Figure 119:
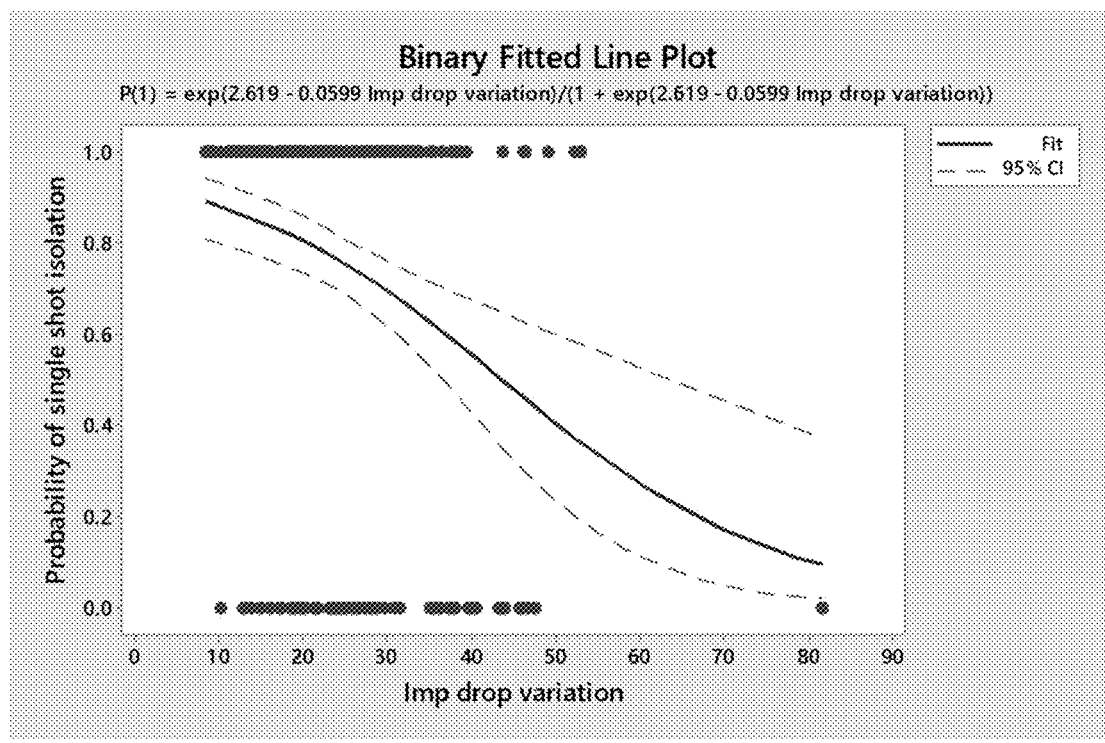

FIG. 119 shows a binary fitted line plot of probability of single shot isolation versus post-ablation impedance drop variation in the study of this disclosure.

Figure 120A:
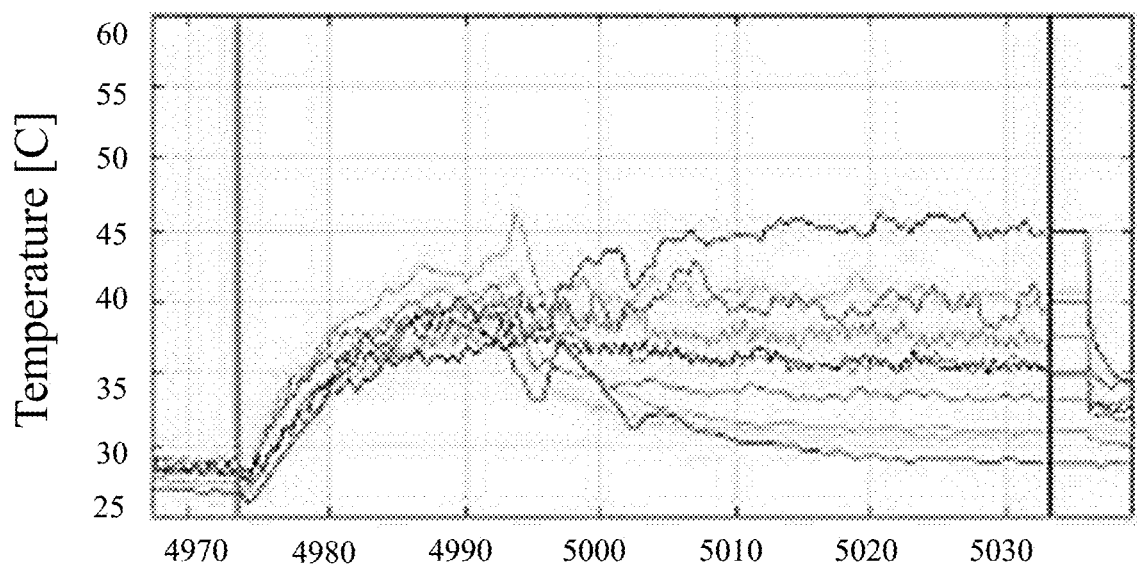

FIG. 120A shows a graph summarizing electrode temperature versus time in the study of this disclosure.

Figure 120B:
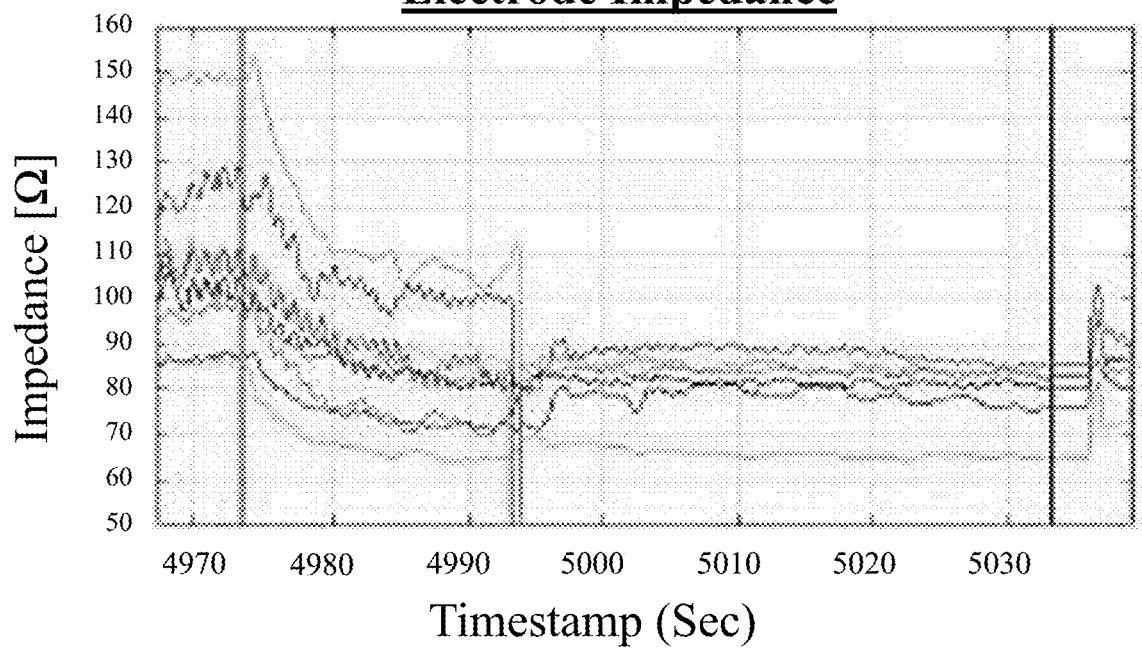

FIG. 120B shows a graph summarizing electrode impedance versus time in the study of this disclosure.

FIG. 121 shows a table summarizing impedance and temperature values from single shot information from the graphs of FIGS. 120A-120B FIG. 122 shows a table demonstrating temperature and impedance trends in electrodes of the balloon catheter as to single shot versus non-isolation comparison for cases of the study of this disclosure.

Figure 123A:
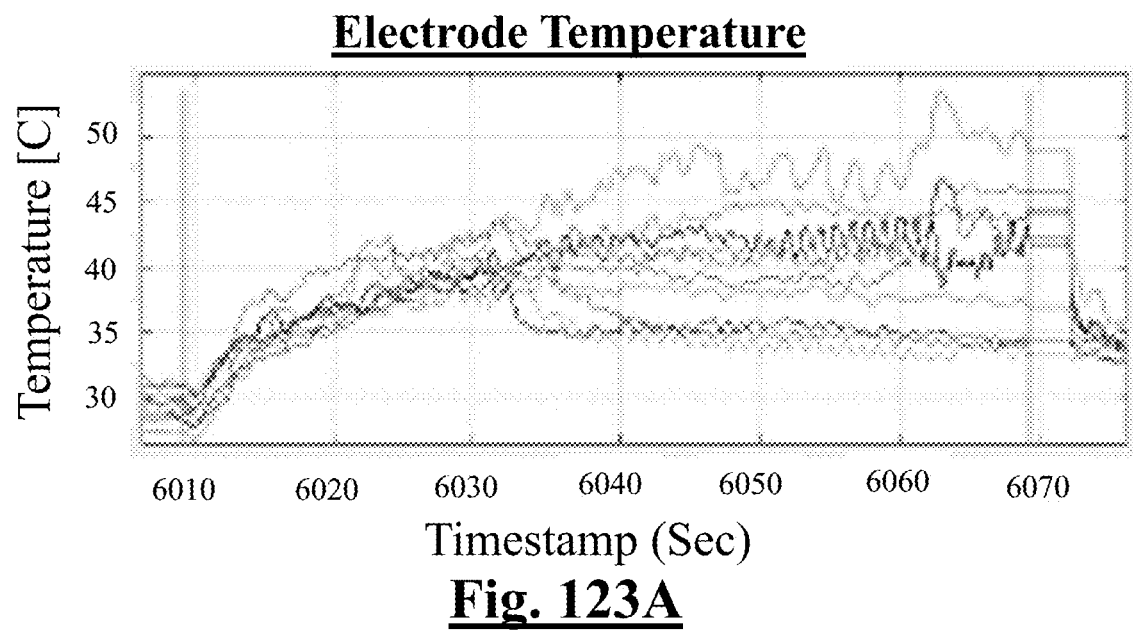

FIG. 123A shows a graph summarizing electrode temperature versus time in the study of this disclosure.

Figure 123B:
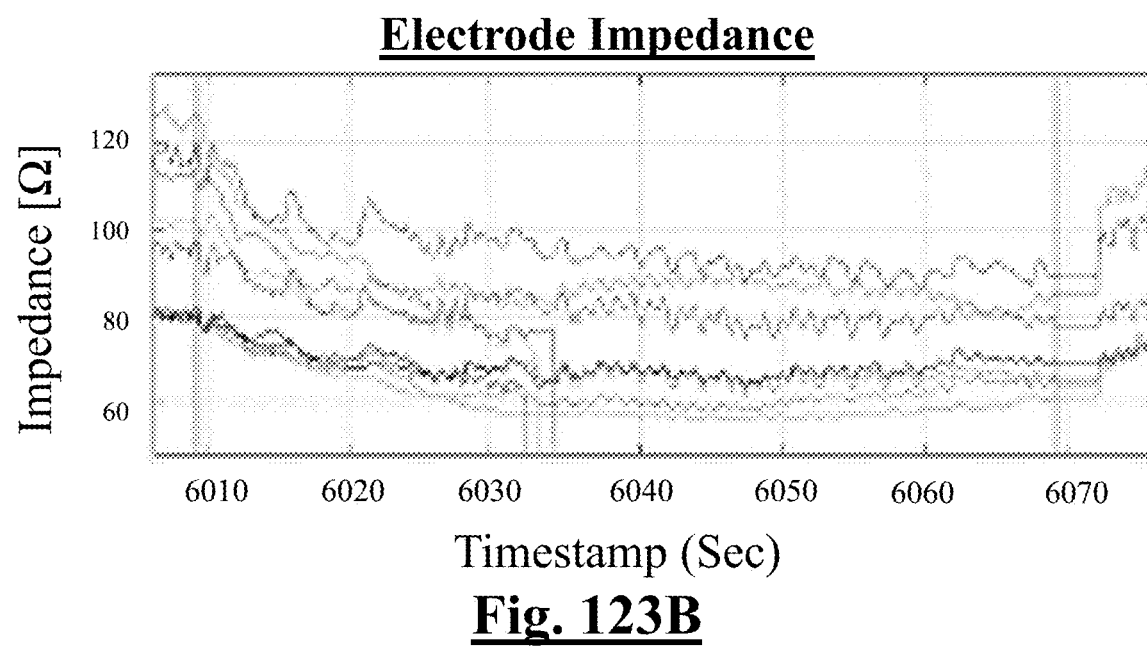

FIG. 123B shows a graph summarizing electrode impedance versus time in the study of this disclosure.

Figure 124:
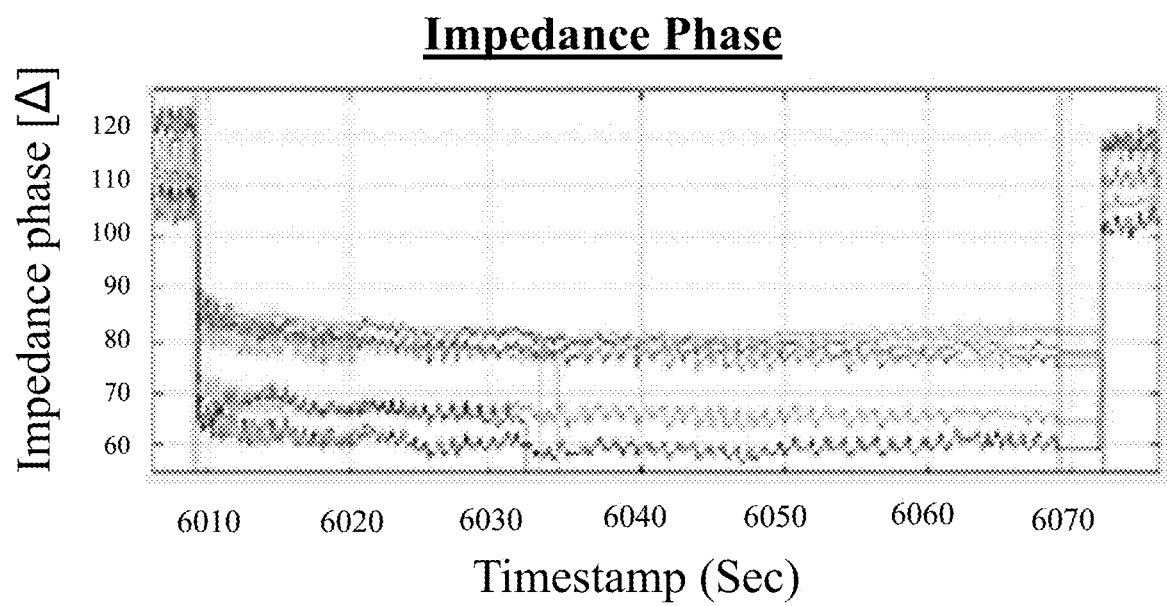

FIG. 124 shows a graph summarizing electrode impedance phase versus time in the study of this disclosure.

FIG. 125 depicts a graphical overview of one method or use according to this disclosure.

FIG. 126 depicts a graphical overview of one method or use according to this disclosure.

FIG. 127 illustrates an exemplary flow chart of the subroutine to determine a probability of success.

Figure 128:
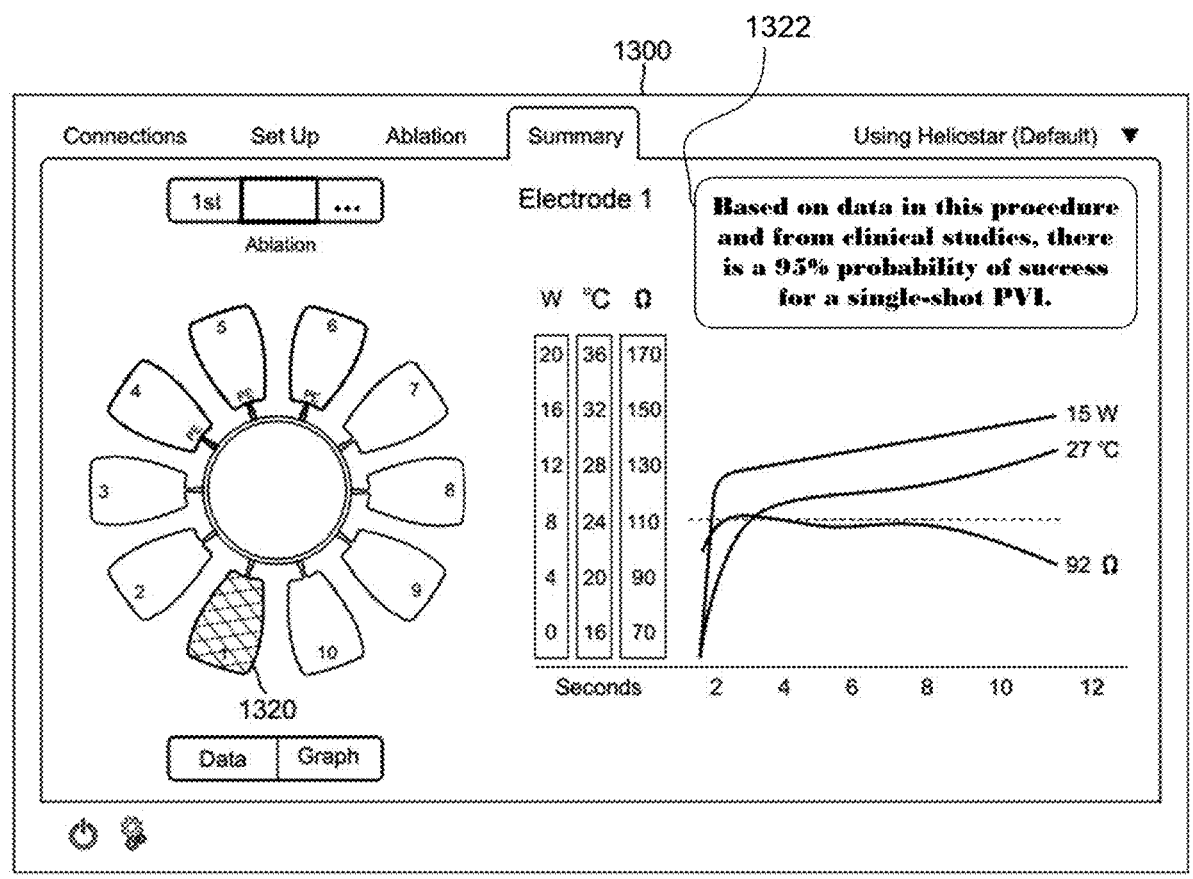

FIG. 128 shows an example graphical display representing a characteristic and the identity of the electrodes energized during an example ablation.

DETAILED DESCRIPTION

Although example embodiments of the disclosed technology are explained in detail herein, it is to be understood that other embodiments are intended to be within the scope of the claimed invention. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method or use step is present in the composition or article or method or use, but does not exclude the presence of other compounds, materials, particles, method or use steps, even if the other such compounds, material, particles, method or use steps have the same function as what is named.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values ±20% of the recited value, e.g. "about 90%" can refer to the range of values from 71% to 99%.

In addition, as used herein, the terms "patient," "host," "user," and "subject" refer to any human or animal subject and are not intended to limit the systems or method or uses to human use, although use of the subject invention in a human patient represents a preferred embodiment.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method or use does not preclude the presence of additional method or use steps or intervening method or use steps between those steps expressly identified. Steps of a method or use can be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, or any other individual or delivery instrumentation associated with delivery of a multi-electrode RF balloon catheter for the treatment of drug refractory atrial fibrillation to a subject.

As discussed herein, "NIHSS Score" means The National Institutes of Health Stroke Scale, or NIH Stroke Scale (NIHSS) and is a tool used by healthcare providers to objectively quantify the impairment caused by a stroke. The NIHSS is composed of 11 items, each of which scores a specific ability between a 0 and 4. For each item, a score of 0 typically indicates normal function in that specific ability, while a higher score is indicative of some level of impairment. The individual scores from each item are summed in order to calculate a patient's total NIHSS score. The maximum possible score is 42, with the minimum score being a 0.

As discussed herein, "mRS" means the modified Rankin Scale (mRS) that is a commonly used scale for measuring the degree of disability or dependence in the daily activities of people who have suffered a stroke or other causes of neurological disability. The mRS scale runs from 0-6, running from perfect health without symptoms to death. An mRS score of 0 is understood as no symptoms being observed. An mRS score of 1 is understood as no significant disability is observed and the patient is able to carry out all usual activities, despite some symptoms. An mRS score of 2 is understood as slight disability and the patient is able to look after own affairs without assistance, but unable to carry out all previous activities. An mRS score of 3 is understood as moderate disability whereby the patient can require some help but is able to walk unassisted. An mRS score of 4 is understood as moderate severe disability and the patient is unable to attend to own bodily needs without assistance or walk unassisted. An mRS score of 5 is understood as severe disability and the patient requires constant nursing care and attention, bedridden, incontinent. An mRS score of 6 is understood as the patient being deceased.

As discussed herein, the term "safety", as it relates to devices used in ablating cardiac tissue, related delivery systems, or method or use of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study can be an adequately sized, randomized, double-blinded controlled study used to clinically prove the effects of the cardiac ablation device(s) and related system(s) of this disclosure. Most preferably to clinically prove the effects of the device(s) with respect to all targeted pulmonary veins, for example, to achieve a clinically effective outcome in for the patient (e.g., mRS less than or equal to 2) and/or achieve pulmonary vein isolation in those afflicted veins.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

The present disclosure is related to systems, method or uses and devices for ablating cardiac tissue to treat cardiac arrhythmias. Ablative energies are typically provided to cardiac tissue by a tip portion which can deliver ablative energy alongside the tissue to be ablated. Some of these catheters administer ablative energy from various electrodes three-dimensional structures. Ablative procedures incorporating such catheters can be visualized using fluoroscopy.

Ablation of cardiac tissue to correct a malfunctioning heart is a well-known procedure. Typically, to successfully ablate, cardiac electropotentials need to be measured at various locations of the myocardium. In addition, temperature measurements during ablation provide data enabling the efficacy of the ablation to be measured. Typically, for an ablation procedure, the electropotentials and the temperatures are measured before, during, and after the actual ablation.

Previous solutions have used two or more separate instructions (e.g., one for the electropotentials and temperature measurements, and another for the ablation), embodiments disclosed herein facilitate the two measurements, and in addition enable ablation using radiofrequency electromagnetic energy, using a single catheter. The catheter has a lumen, and a balloon is deployed through the catheter lumen (the balloon travels through the lumen in a collapsed, uninflated configuration, and the balloon is inflated on exiting the lumen). The balloon has an exterior wall or membrane and has a distal end and a proximal end which define a longitudinal axis that extends the lumen.

Figure 1:
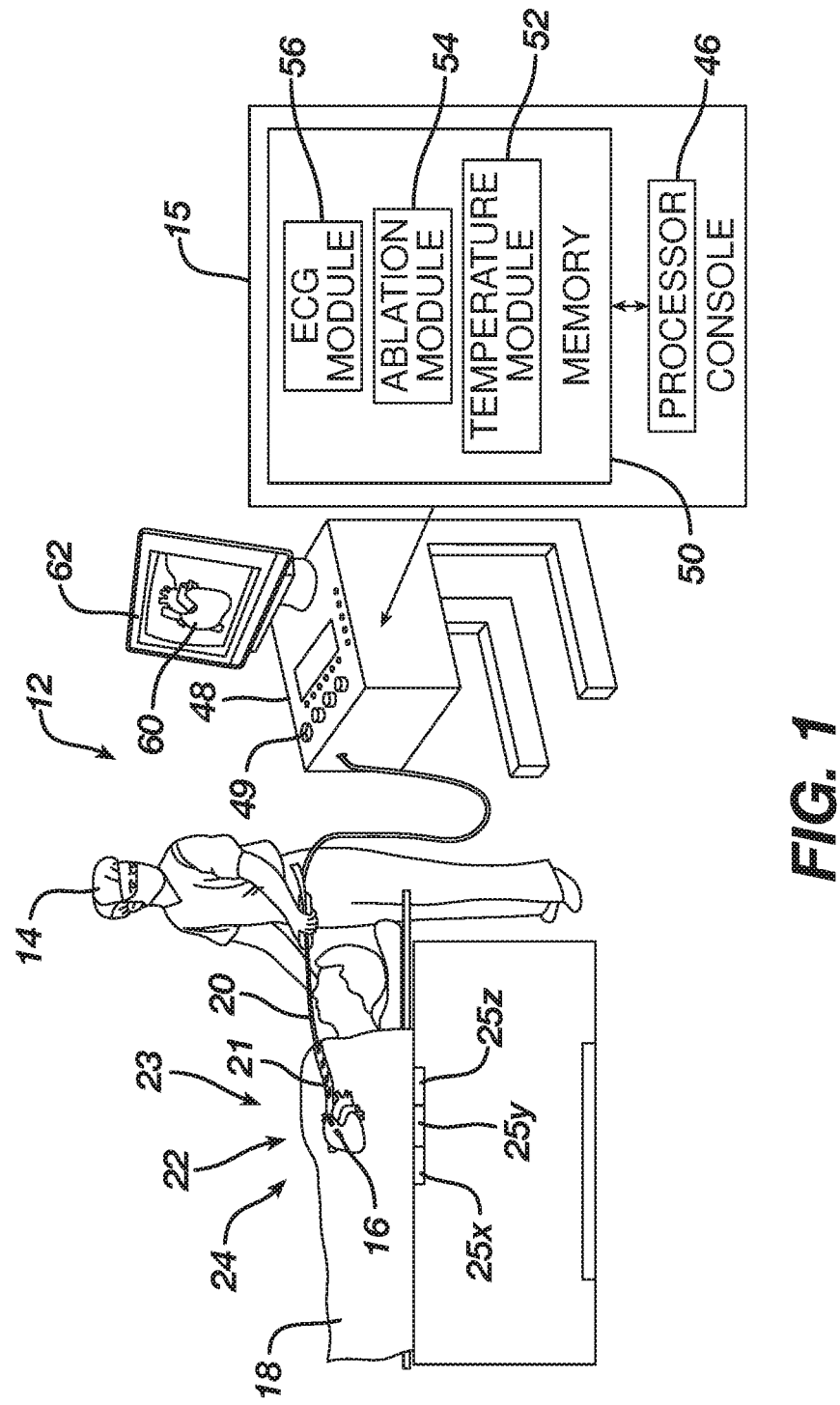
FIG. 1 is a schematic illustration of a medical procedure using example instrumentation of this disclosure.

As an example, FIG. 1 depicts example instrumentations that include an apparatus 12, according to an example embodiment. The procedure is performed by an operator 14, and the procedure in the description hereinbelow is assumed to comprise ablation of a portion of a myocardium 16 of the heart of a human patient 18. However, it is understood that embodiments disclosed herein are not merely applicable to this specific procedure and can include substantially any procedure on biological tissue or on non-biological materials.

To perform the ablation, the operator 14 inserts a probe 20 into a sheath 21 that has been pre-positioned in a lumen of the patient. Sheath 21 is positioned so that a distal end 22 of probe 20 enters the heart of the patient. A multi-electrode radiofrequency balloon catheter 24 (e.g., a balloon catheter), which is described in more detail below, is deployed through a lumen 23 of the probe 20 and exits from a distal end of the probe 20. Catheter 24 can be a multi-electrode radiofrequency balloon catheter for cardiac electrophysiological ablation of pulmonary veins of the atria and, when used with a multi-channel RF generator, for the treatment of drug refractory recurrent symptomatic PAF, as discussed more particularly below. Catheter 24 and variations or updates to catheter 24 can be understood as including features more clearly described in Appendix 1 as incorporated by reference in its entirety from the U.S. Provisional applications from which this application claims priority, which includes U.S. Pat. Nos. 9,907,610; 9,956,035; U.S. Pat. Pubs. 2015/0272667; 2016/0175041; 2017/0311893; 2017/0311829; 2017/0312022A1; 2018/0280080A1 (Ser. No. 15/476,191); 2018/0161093; 2019/0183567 (Ser. No. 15/847,661); 2019/0175262; 2019/0060622 (Ser. No. 15/684,434); 2019/0217065 (Ser. No. 15/870,375); 2019/0143079 (Ser. No. 15/815,394); 2017/0347896; 2016/0175041 each of which are incorporated by reference in their entirety as if set forth verbatim herein. Note that such catheters 24 can be introduced through the femoral artery, wrist artery (radial access) or directly through the carotid artery. While both radial and carotid access avoids the aortic arches, there are other drawbacks. However, all three approaches are considered to be known to ones of skill in this art.

Functionally, catheter 24 seeks to achieve isolation of the pulmonary veins in the subject's LA to eliminate symptoms of AF. The catheter 24 ablates from multiple irrigated, independently-controlled electrodes simultaneously. The amount of power delivered to each electrode is controlled independently to improve safety and lesion quality.

One RF generator intended for use in this disclosure can be for cardiac ablation applications to generate RF energy for delivery to a site in the heart via compatible RF ablation catheters. The generator is capable of independently controlling the delivery of RF energy to electrodes simultaneously. The generator can include functions for controlling ablation parameters at the ablation electrodes of the catheter. Ablation parameters, such as power, impedance, ablation duration, and temperature are recorded and can be exported at the end of the procedure to a USB device. The generator is typically configured to measure and display a magnitude of a complex impedance (Z) at least intended to represent the impedance of the patient's tissue proximate the ablation electrode. To make the impedance measurement, the generator uses each of the plurality of electrodes (i.e., one lead through the catheter to each ablation electrode) and one RF indifferent/dispersive return (i.e., one lead from the RF indifferent return going back to the generator)—a two terminal configuration for measurement for each electrode. With this set up, the generator generates small currents between each electrode and the indifferent electrode and measures the voltage created by the current to calculate the impedance for each electrode. As configured in this system, the impedance of the tissue in contact with each of the ten electrodes can be detected by the processor 46 and analyzed to provide indicators and guidance for the operator during or after a procedure.

Figure 2:
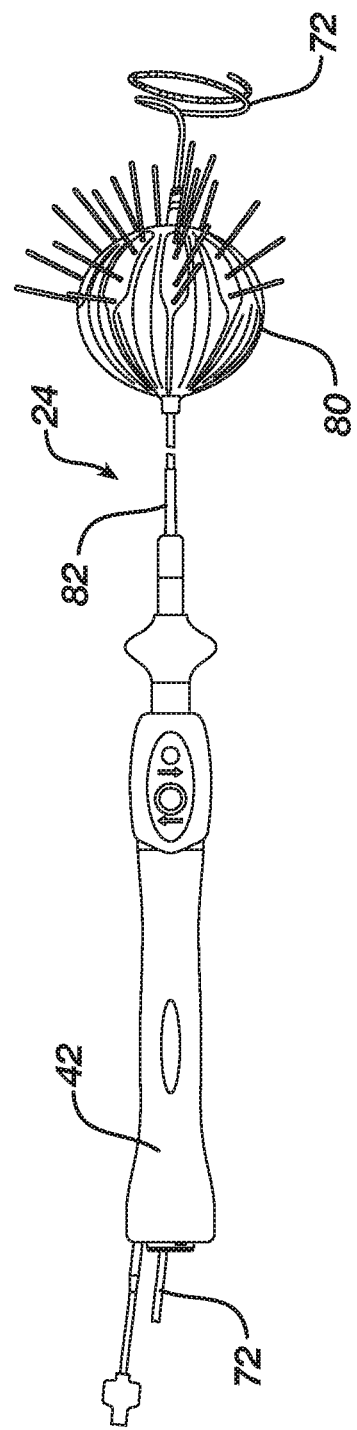
FIG. 2 is a top view of one example catheter of this disclosure with a balloon in an expanded state, in use with a lasso catheter.

As shown in FIGS. 1 to 2, apparatus 12 is controlled by a system processor 46, which is in an operating console 15 of the apparatus. Console 15 comprises controls 49 which are used by professional 14 to communicate with the processor. During the procedure, the processor 46 typically tracks a location and an orientation of the distal end 22 of the probe 20, using any method or use known in the art. For example, processor 46 can use a magnetic tracking method or use, wherein magnetic transmitters 25X, 25Y and 25Z external to the patient 18 generate signals in coils positioned in the distal end of the probe 20. The CARTO® system (available from Biosense Webster, Inc. of Irvine, Calif.) uses such a tracking method or use.

To operate apparatus 12, the processor 46 communicates with a memory 50, which has many modules used by the processor to operate the apparatus. Thus, the memory 50 comprises a temperature module 52, an ablation module 54, and an electrocardiograph (ECG) module 56, the functions of which are described below. The memory 50 typically comprises other modules, such as a force module for measuring the force on the distal end 22, a tracking module for operating the tracking method or use used by the processor 46, and an irrigation module allowing the processor to control irrigation provided for the distal end 22.

While other modules are not illustrated in FIG. 1, others are indeed intended to be within the scope of the claimed invention and can include hardware as well as software elements. For example, module 54 can include a radiofrequency generator with at least one output or output channel, e.g., ten outputs or ten output channels. Each of the outputs can be separately and selectively activated or deactivated by a switch. That is, each switch can be disposed between the signal generator and a respective output. Thus, a generator with ten outputs would include ten switches. These outputs can each be individually coupled to electrodes on an ablation catheter, e.g., the ten electrodes 33 on balloon 80, described in further detail below. Electrodes 33 can be irrigated, flexible gold-plated electrodes bonded thereto and used to deliver RF energy in a unipolar fashion to the tissue and sense temperature at each electrode. Electrodes 33 can be oriented circularly to achieve good circumferential contact with the ostia of the pulmonary veins. The catheter 24 can ablate cardiac tissue from the independently-controlled electrodes simultaneously when paired with a Multi-Channel RF generator and the amount of power delivered to each electrode is controlled independently.

Such an electrical connection can be achieved by establishing an electrical path between each output and each electrode. For example, each output can be connected to a corresponding electrode by one or more wires or suitable electrical connectors. Thus, in some embodiments, an electrical path can include at least one wire. In some embodiments, the electrical path can further include an electrical connector and at least a second wire. Thus, electrodes 33 can be selectively activated and deactivated with the switches to receive radiofrequency energy separately from each of the other electrodes.

FIG. 2 illustrate catheter 24, which has a usable length of approximately 110 cm (though other dimensions are intended to be within the scope of the claimed invention as needed or required). Catheter 24 can have three major sections: handle 42, shaft portion 82 and distal tip 22. The shaft 82 can measure 10.5 F (French) with a 13.5 F maximum outer diameter around the balloon 80 when the balloon is in its fully collapsed state. The catheter 24 can have a high-torque shaft 82, with a uni-directional braided deflectable tip section. The shaft allows the plane of the curved tip with balloon 80 to be rotated to facilitate accurate positioning of the catheter tip 22 to the desired site (ostia of the pulmonary veins). The compliance of the balloon 80 allows for its flexible surface electrodes 33 to conform to the anatomy when pressed against the tissue.

The handle section 42 can incorporate a deflection thumb knob allowing for unidirectional deflection, a balloon advancement mechanism, and a luer fitting for balloon inflation and irrigation. An additional luer fitting can be included and located proximally to the ejector and serve as an entry port for a guidewire as well as distal irrigation and/or contrast injection. The catheter 24 can be used with an irrigation pump to control irrigation to the balloon. Heparinized normal saline can be delivered through the luer fitting of the handle 42.

Figure 3:
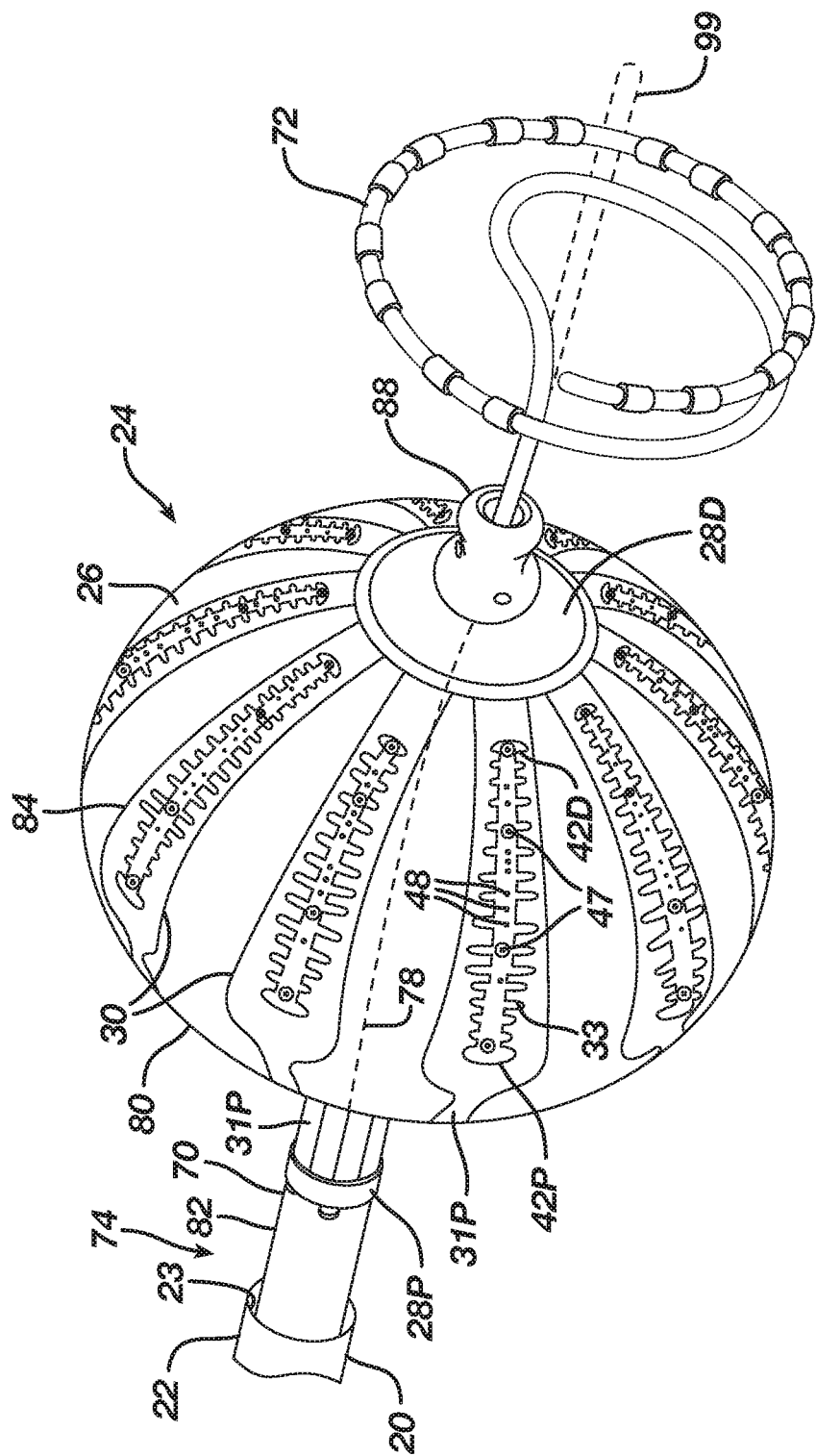
FIG. 3 is a perspective view of a multi-electrode ablation balloon catheter along with the lasso catheter that can be used in the clinical study.

FIG. 3 is a schematic perspective view of an example multi-electrode radiofrequency balloon catheter 24 in an expandable configuration in the form of a balloon in its expanded configuration, according to an embodiment used in the study. In a disclosed embodiment, where the multi-electrode radiofrequency balloon catheter 24 is used to ablate an ostium 11 of a lumen, such as a pulmonary vein 13, the multi-electrode radiofrequency balloon catheter 24 is supported by a tubular shaft 70 having a proximal shaft portion 82 and a distal shaft end 88. The shaft 70 includes a hollow central tube 74, which permits a catheter to pass therethrough and past the distal shaft end 88. The catheter can be a lasso catheter 72, as illustrated, or a diagnostic catheter (i.e., for recording ECG signals on propagating through heart tissues). It is also intended that the catheter can have a relatively small diameter (e.g., 3 mm) through which a similarly small diameter catheter, such as a focal linear catheter or the like, could be used. The lasso catheter 72 can be inserted into the pulmonary vein to position the multi-electrode radiofrequency balloon catheter 24 correctly with respect to the ostium prior to ablation of the ostium. The distal lasso portion of the catheter 72 is typically formed of shape-memory retentive material such as nitinol. It is understood that the multi-electrode radiofrequency balloon catheter 24 can also be used with a linear or focal catheter 99 (as shown in broken lines in FIG. 3) in the PV or elsewhere in the heart. Any catheter used in conjunction with the multi-electrode radiofrequency balloon catheter 24 can have features and functions, including, for example, pressure sensing, ablation, diagnostic, e.g., navigation and pacing.

The balloon 80 of the multi-electrode radiofrequency balloon catheter 24 can have an exterior wall or membrane 26 of a bio-compatible material, for example, formed from a plastic such as polyethylene terephthalate (PET), polyurethane or PEBAX®. The shaft 70 and the distal shaft end 88 define a longitudinal axis 78 of the balloon 80. The balloon 80 is deployed, in a collapsed configuration, via the lumen 23 of the probe 20, and can be expanded after exiting from the distal end 22. The membrane 26 of the balloon 80 is formed with irrigation pores or apertures 27 through which the fluid (e.g., saline) can exit from the interior of the balloon 80 to outside the balloon for cooling the tissue ablation site at the ostium. It is understood that the fluid can exit the balloon 80 with any desired flow rate or pressure, including a rate where the fluid is seeping out of the balloon 80.

Figure 4A:
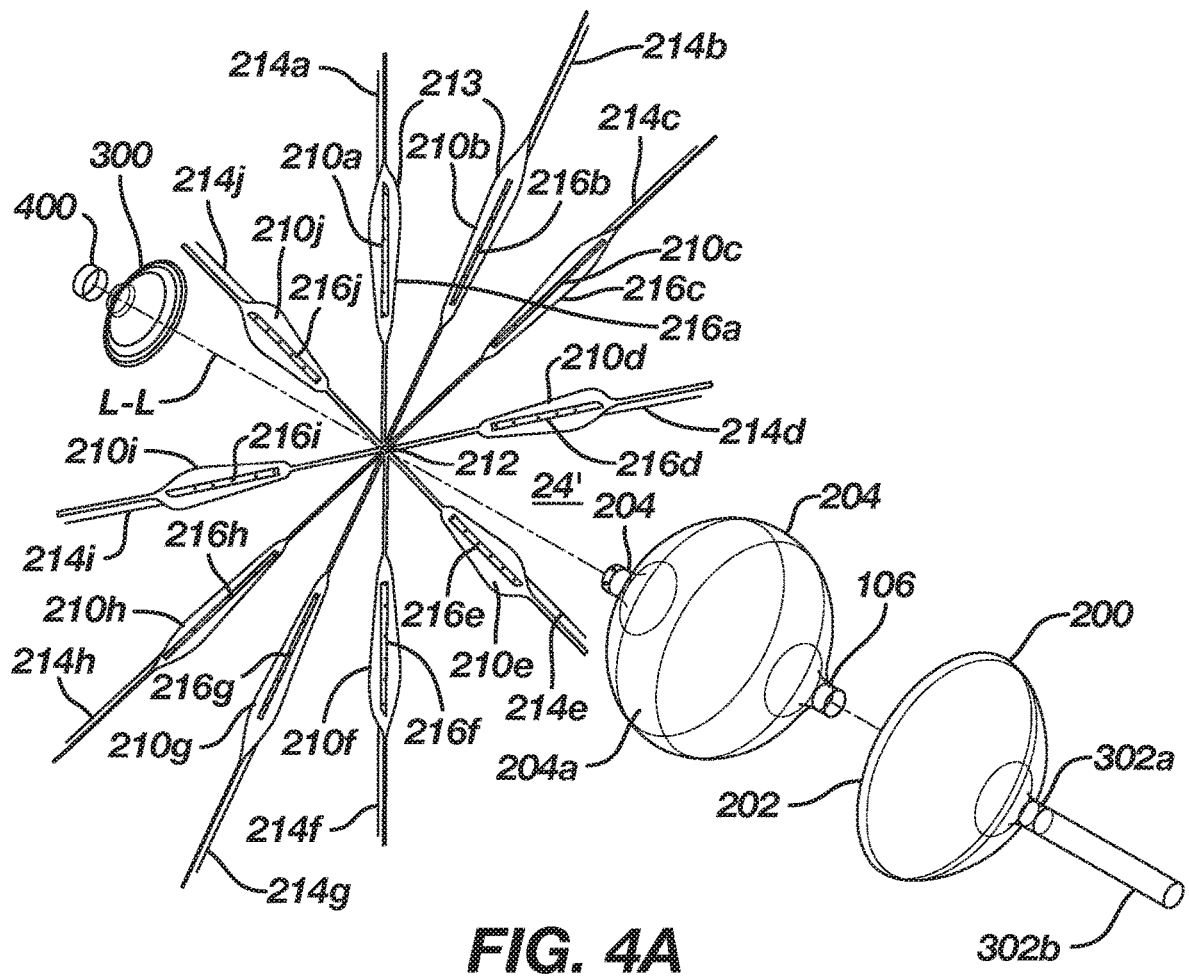
FIG. 4A is an exploded perspective view of the yet another embodiment of the balloon ablation catheter from FIG. 3, which shows a base balloon or first expandable membrane with radiating electrode assemblies that are partially covered by respective second and third expandable membranes.

Yet another embodiment of the catheter can be utilized, referenced here as probe 24'. FIG. 4A illustrates an exploded perspective view of the electrophysiology probe 24' that includes a tubular member 302 extending along a longitudinal axis L-L from a first (proximal) end 302b to a second (or distal) end 302a. A first expandable membrane 204 is attached to the tubular member 302 near the distal end 302b. The membrane 204 has an outer surface 204a and an inner surface 204b disposed about the longitudinal axis L-L. The outer surface 204a is exposed to the ambient environment while the inner surface 204b is exposed to the internal volume of the balloon defined by the membrane 204. The first expandable membrane 204 has a first expandable distal membrane portion 208 being coupled to the second end 302a of the tubular member 302 and second expandable distal membrane portion 206 spaced apart from the first expandable distal membrane portion 208 along the longitudinal axis L-L.

It is noted that first expandable membrane 204 is configured to be expanded from a compressed shape (generally tubular configuration) to a balloon (or generally spheroidal) shaped member. A plurality of electrodes 210a, 210b, 210c, 210d, 210e, 210f, 210g, 210h, 210i and 210j, (which may be referred to singularly or collectively as "electrode 210") are disposed on the outer surface 204a of the first expandable membrane 204. The electrodes 210 are arranged so that they radiate from a generally common center or centroid substrate 212 near the second expandable distal membrane portion 208 which is distal to the tubular member 302. The electrodes 210a-210j may have one or more wires, i.e., bifilar 214a-214j, respectively, connected to each of the plurality of electrodes 210a-210j via a connection junction 216a-216j. Each of the wires 214a-214j (which may be singular in form "wire" or plural "wires" will be collectively referred to as "wire 214") is connected to the connection point at the "underside" surface of the electrode 210. The underside surface of each electrode 210 is the electrode surface that is not exposed to the ambient environment and is typically bonded to the outer surface 204a of the membrane 204. As the connection point 216 (typically a solder point) is generally at the center of the electrode, the wire is covered by the underside surface of each electrode. However, as each wire or bifilar 214a-214j extends toward the tubular member 302, the electrode surface or the substrate on which the electrode is bonded thereto becomes smaller thereby leaving the wire or bifilars 214a-214j exposed.

Figure 4B:
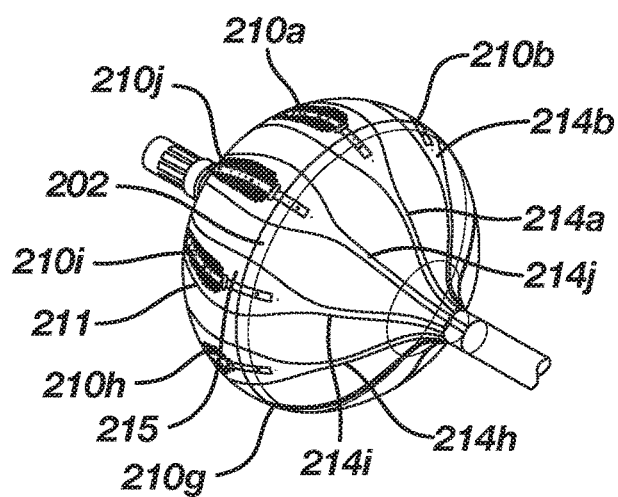
FIG. 4B illustrates an embodiment of an assembled balloon ablation catheter of FIG. 4A.
Figure 5:
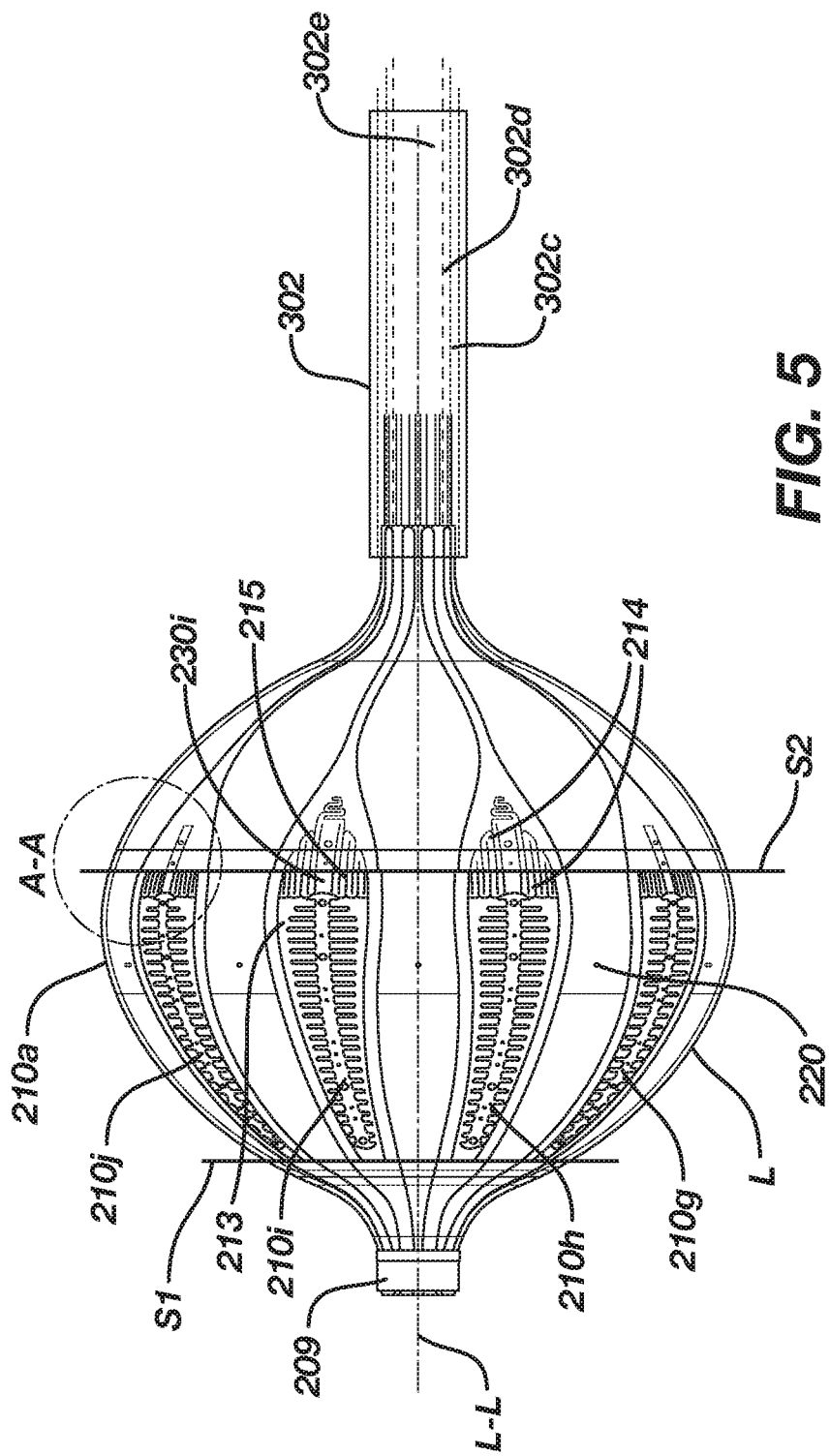
FIG. 5 is a side view of the balloon ablation catheter of FIG. 4B.
Figure 7:
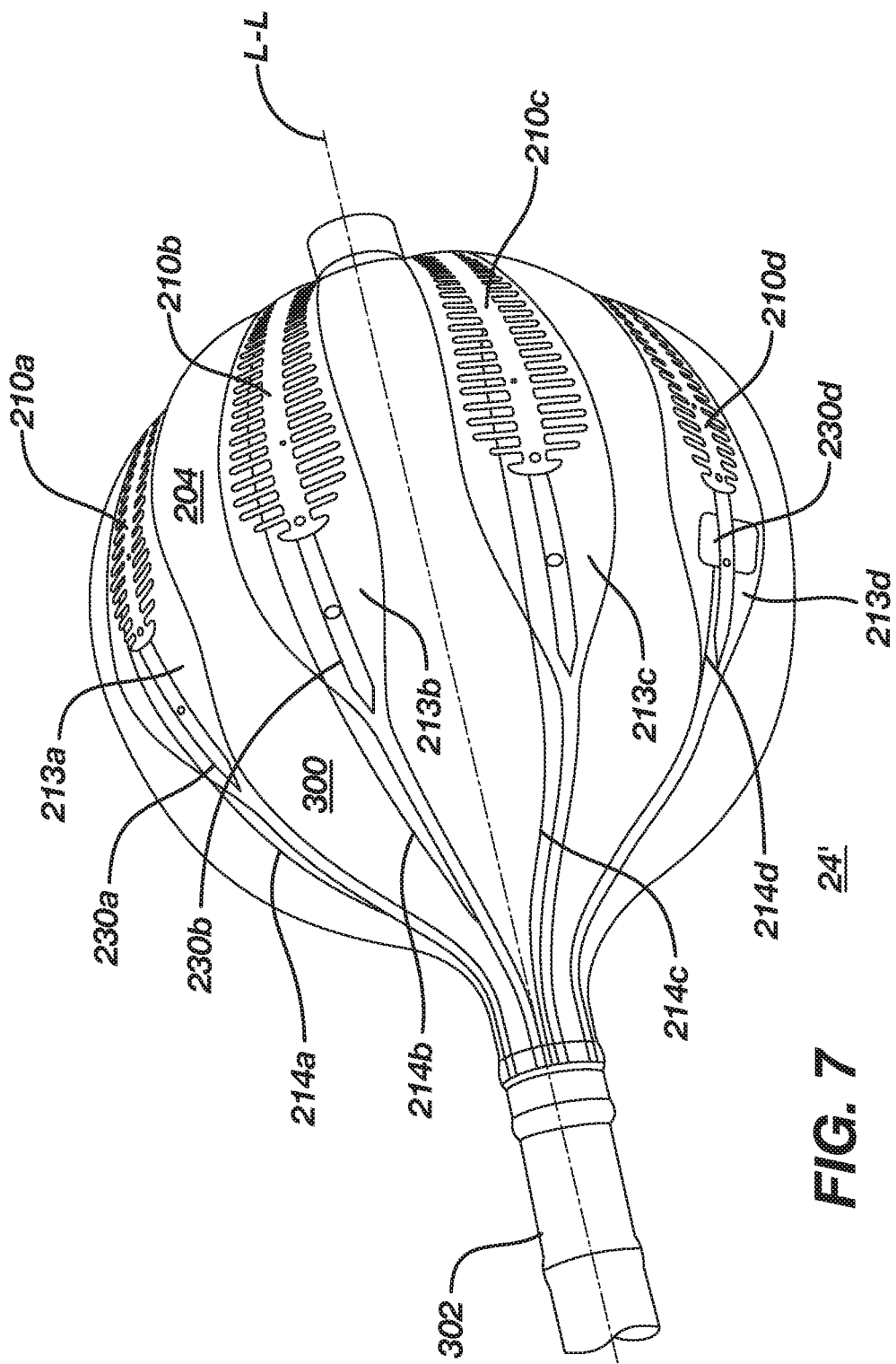
FIG. 7 is a photograph of an actual prototype according to an embodiment described and illustrated herein.

As can be seen in FIG. 4B, when group of wires 214a-214j are mounted on the membrane 204, each wire 214 is configured to extend from the tubular member 302 to the respective electrode 210 such that each wire follows the topographic outer surface 204a of membrane 204. In extending the wires 214 toward the tubular member 302, the wires 214 become exposed to the ambient environment (e.g., biological tissues or blood) as each wire 214 leaves the underside surface of each electrode or the underside surface of the substrate 213 (FIG. 5). As each wire 214 may be used to conduct or transmit electrical energy or signals, it would be detrimental to expose the wires 214 to the ambient biological tissue environment. As such, we have devised a second expandable membrane 200 that encapsulates the one or more wires (214a-214j) between the second expandable membrane 200 and the first expandable membrane 204 so that the wires 214a-214j are constrained between the first and second expandable membrane (FIG. 7). Such configuration eliminates the exposure of the wires to the ambient environment yet still allowing the electrodes/thermocouples to be exposed to biological tissues so that the electrodes and thermocouples to work for their intended purposes. Moreover, as the wires 214 are constrained or captured between the first and second membranes, there is virtually no likelihood of the wires being entangled or mis-connected to the wrong electrode or thermocouple during assembly. In the preferred embodiment, each wire of the bifilar is coupled to a temperature sensor in the form of a thermocouple 216 disposed on or near each electrode 210.

It is noted that tubular member 302 defines a first internal passageway in the form of a lumen 302c, shown here as dashed lines in FIG. 5, that extends from the first end 302a to the second end 302b of tubular member 302 so that the one or more wires are disposed in the first lumen 302c. To allow other instruments (e.g., guide wires, optical sensor etc.,) to be delivered through the balloon 204 (and outside of the distal-most portion 209 of balloon) the tubular member 302 can be provided with a second lumen 302d that extends through the membrane portions 206 and 208 to allow for another instrument to pass through the second lumen 302d. Additionally, the tubular member 302 can be provided with yet another internal passageway in the form of a third lumen 302e. Irrigation fluid can be provided in either of the second lumen 302d or third lumen 302e so that the irrigation fluid flows into the internal volume of the membrane 204, through openings or pores 220 provided through the membrane inner surface 204b and outer surface 204a to outside of the membrane 204 to the ambient environment (e.g., biological tissues or organ). Each electrode may have four irrigation openings formed on the electrode such that the electrode irrigation openings are aligned with the pores 220 of the membrane. In the preferred embodiment, lumen 302c, lumen 302d and 302e are configured or extruded as concentric passageways, in the form of a tube 302e within tube 302d within a tube 302c with outer tubular member 302. Tubular member 302 can be a suitable biocompatible polymer as is known to those skilled in the art.

Referring to FIG. 4B, the plurality of electrodes 210a-210j extend from a substrate centroid 212 equiangularly about the longitudinal axis L-L from the first expandable distal membrane portion 208 towards the second expandable distal membrane portion 206 such that the second expandable membrane 200 encapsulates a portion of each of the electrodes (210a-210j) proximate the second expandable membrane portion 206. The second expandable membrane 200 has a border 202 (FIG. 4A) that extends over a proximal portion (i.e., fish-head 115) of the electrode 210 outer surface (FIG. 4B) while allowing the electrode fish-bone pattern 210 to be exposed to the ambient environment.

That is, each of the plurality of electrodes 210a-210j defines a fishbone pattern not covered by the second expandable membrane 200 to allow the fishbone electrodes to be exposed to the ambient environment. Each electrode (210a-210j) is coupled to the outer surface of the first expandable membrane 204 via a substrate 213 which itself is connected to or bonded to the outer surface 204a of the first expandable membrane 204. The electrode 210a-210j can have a portion of its perimeter bonded directly to membrane 204. A suitable seal 211 can be formed so that the seal 211 runs along the outer perimeter of the substrate 213 of each electrode (210a-210j). In a preferred embodiment, the seal 211 can be provided in the form of a polyurethane seal.

Referring to FIG. 5, a radiopaque marker 230 is defined by a proximal fish-head portion of each electrode such that there can be respective radiopaque markers 230a, 230b, 230c, 230d, 230e, 230f, 230g, 230h, 230i and 230j for corresponding electrodes 210a-210j. To ensure that the location of each electrode can be determined while inside a body organ with x-rays, each electrode 210 may have a radiopaque marker (230a-230j) with each marker having a configuration different from other radiopaque markers on the other electrodes.

Referring back to FIG. 4A, a third expandable membrane 300 can be disposed proximate the first expandable distal membrane portion 208 so that the third expandable membrane 300 encircles an outer surface portion of the first expandable membrane 204 about the longitudinal axis L-L proximate the distal portion 209 of the membrane 204. The third expandable membrane encapsulates a portion of the substrate 213 (FIG. 5) for each of the plurality of electrodes near distal portion 209 of membrane 204. Preferably, the third expandable membrane 300 allows for encapsulation of the substrates 213 of each electrode (210a-210j) as the substrates 213 converge to centroid 212 near the distal portion 209 of the membrane 204. A retaining ring 209 is disposed about the third expandable membrane 300 (near distal portion 208 of membrane 204) to hold the third expandable membrane 300 as well as the substrates 213 to the first expandable membrane 204. The third expandable membrane 300 can be bonded to the first expandable membrane 204 thereby capturing the substrate 213 therebetween the two membranes (204 and 300).

Figure 6A:
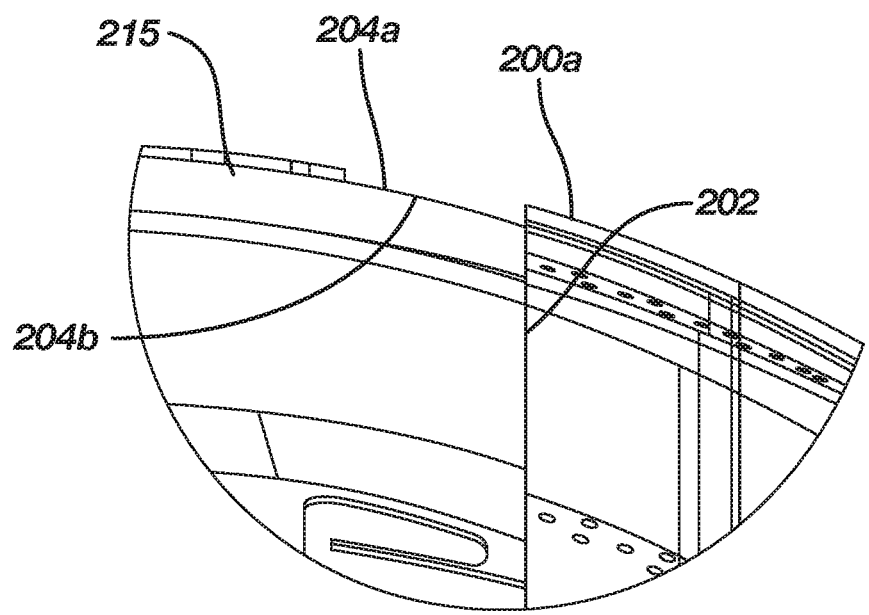
FIG. 6A is a blown-up side view of a portion of the membrane of FIG. 4A.
Figure 6B:
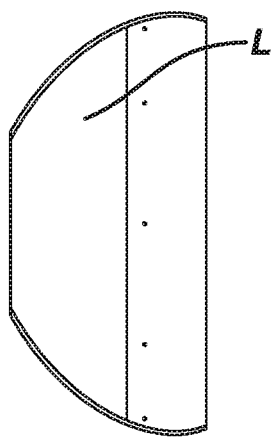
FIG. 6B illustrates a lateral or circumferential surface area not covered by the hemispherical second and third expandable membranes of FIG. 4B

Referring to FIG. 6A, a blown-up side view of a portion of the membrane of FIG. 4A is shown. FIG. 6B shows a lateral or circumferential surface area that is not covered. In particular, the surface area of the membrane 204 that is exposed (i.e., not covered) by second expandable membrane 200 and third expandable membrane has a circumferential surface area L delineated between a virtual slice S1 (defined by the intersection of third expandable membrane 300 with first expandable membrane 204) orthogonal to axis L-L and virtual slice S2 orthogonal to the longitudinal axis L-L whereby slice S2 is defined by the intersection of the second expandable membrane 200 to the first expandable membrane 204. For clarity, it can be seen in FIG. 6B that if the first expandable membrane 204 approximates a sphere (when membrane 204 is expanded to its service characteristic) then the circumferential surface area L can be determined once the parameters of the spheroid body is known. In the preferred embodiment, shown in FIG. 7, the first expandable membrane 204 includes a circumferential surface area L (FIGS. 5 and 6B) of approximately 52% of a total surface area of the first expandable membrane 204. That is, the circumferential surface area L is the exposed surface area (without any electrode or substrate) of first expandable membrane 204 or outer circumferential area of first expandable membrane 204 that is also not covered by the second expandable membrane 200 and third expandable membrane 300. Further, it is noted that each substrate 213 for each electrode 210 includes a substrate surface area approximately 8% of the exposed outer circumferential surface area L of the first expandable membrane 204. In the preferred embodiments, the second expandable membrane 200 and third expandable membrane 300 cover approximately half of the outer surface area of the first expandable membrane 204.

In the preferred embodiments, the first expandable membrane includes a generally spheroidal member with a diameter as referenced to the longitudinal axis L-L of about 30 millimeters and the second expandable membrane and the third expandable membrane each includes a hemi-spherical member with the respective major diameter of each hemi-spherical member being less than 30 mm. In the preferred embodiments, the total surface area of membrane 204 is about 4500 squared-mm while the circumferential surface area L is about 2400 squared-mm and each flexible substrate 213 is about 200 squared-mm when the membrane 204 is at its fully expanded (i.e., designed) configuration, shown exemplarily in FIG. 7.

The balloon 204 of the diagnostic/therapeutic catheter has an exterior wall or membrane 204a of a bio-compatible material, for example, formed from a plastic such as polyethylene terephthalate (PET), polyurethane or PEBAX®. The tubular shaft 302 and the distal shaft end 302a define a longitudinal axis L-L of the balloon 204. The balloon 204 is deployed, in a collapsed configuration as described in commonly-owned U.S. patent application Ser. No. 15/939,154 filed on Mar. 28, 2018 (via the lumen 23 of the probe 20 in this prior application, which is incorporated by reference herein to this present application). The membrane 204a of the balloon 204 is formed with irrigation pores or apertures 220 (shown in FIG. 5) through which the fluid (e.g., saline) can exit from the interior of the balloon 204 to outside the balloon for cooling the tissue ablation site at the ostium.

As described earlier in relation to FIG. 4B, membrane 24 supports and carries a combined electrode and temperature sensing member which is constructed as a multi-layer flexible circuit electrode assembly 210a-210j. The "flex circuit electrode assembly" 210a-210j may have many different geometric configurations than as shown here. In the illustrated embodiment, the flex circuit electrode assembly 210a-210j has a plurality of radiating substrates or strips 213a-213j, as best seen in FIG. 2. The substrates 213a-213j are evenly distributed about the distal end 209 and the balloon 204. Each substrate 213a-213j has wider proximal portion that gradually tapers to a narrower distal portion as referenced to the longitudinal axis.

For simplicity, the flex circuit electrode assembly 210 is described with respect to one of its substrate 213 as shown in FIG. 5, although it is understood that following description may apply to each substrate 213 of the assembly 210. The flex circuit electrode assembly 210 includes a flexible and resilient sheet substrate material 213, constructed of suitable bio-compatible materials, for example, polyimide. In some embodiments, the sheet substrate material 213 has a greater heat resistance (or a higher melting temperature) compared to that of the balloon membrane 204. In some embodiments, the substrate material 213 is constructed of a thermoset material having a decomposition temperature that is higher than the melting temperature of the balloon membrane 204 by approximately 24 degrees Celsius or more.

The substrate material 213 is formed with one or more irrigation pores or apertures (not labeled) that are in alignment with the irrigation apertures 220 of the balloon member 204 so that fluid passing through the irrigation apertures 220 and (not labeled) can pass to the ablation site on the ostium.

The substrate material 213 has a first or outer surface facing away from the balloon membrane 204, and a second or inner surface facing the balloon membrane 204. On its outer surface, the substrate material 213 supports and carries the contact electrodes 210. The configuration or trace of the contact electrode 210 may resemble a "fishbone" but it should be noted that the invention is not limited to such configuration. In contrast to an area or "patch" ablation electrode, the fingers of the contact electrode 210 advantageously increase the circumferential or equatorial contact surface of the contact electrode 210 with the ostium while void regions between adjacent fingers advantageously allow the balloon 204 to collapse inwardly or expand radially as needed at locations along its equator. In the illustrated embodiment, the fingers have different lengths, some being longer, others being shorter. For example, the plurality of fingers includes a distal finger, a proximal finger and fingers therebetween, where each of the fingers in between has a shorter adjacent finger. For example, each finger has a length different from its distal or proximal immediately adjacent neighboring finger(s) such that the length of each finger generally follows the tapered configuration of each substrate 213. In the illustrated embodiment, there are 22 fingers extending across (past each lateral side of) the elongated portion. In some embodiments, the contact electrode 210 includes gold with a seed layer between the gold and the membrane 204. The seed layer may include titanium, tungsten, palladium, silver, or combinations thereof.

Figure 8:
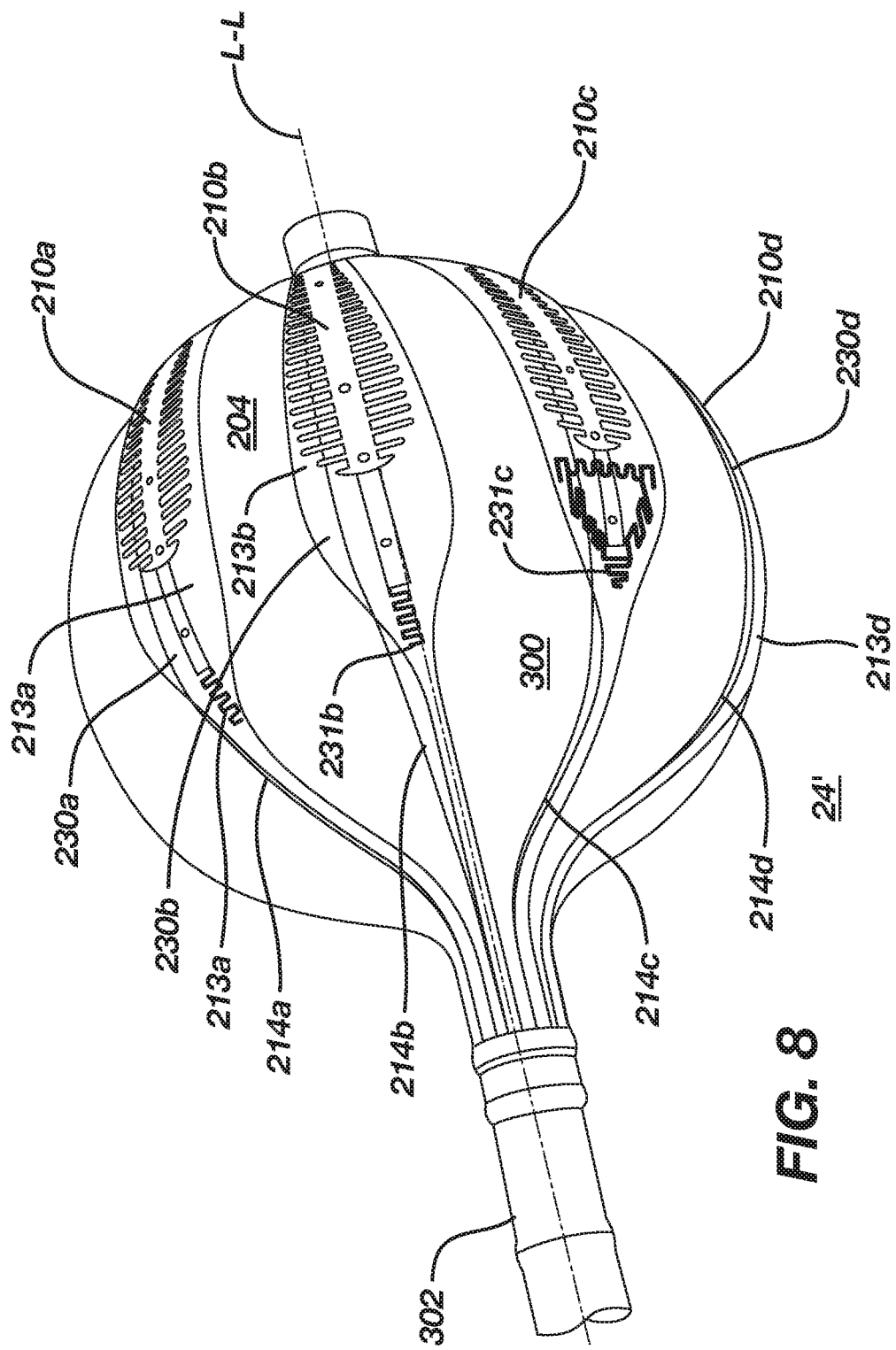
FIG. 8 is a photograph of yet another prototype of the embodiments described and illustrated herein.

As shown in FIG. 8, the flexible electrode may have its radiopaque marker in the variation identified as 231a, 231b, 231c and so on to assist in the identification of the electrode being energized. The markers 231a-231j have various serpentine configurations (as compared to FIG. 7) to allow for increased flexibility due to the presence of the second membrane 200 which tend to reduce the flexibility of the device near the markers 231a-231j.

Figure 9:
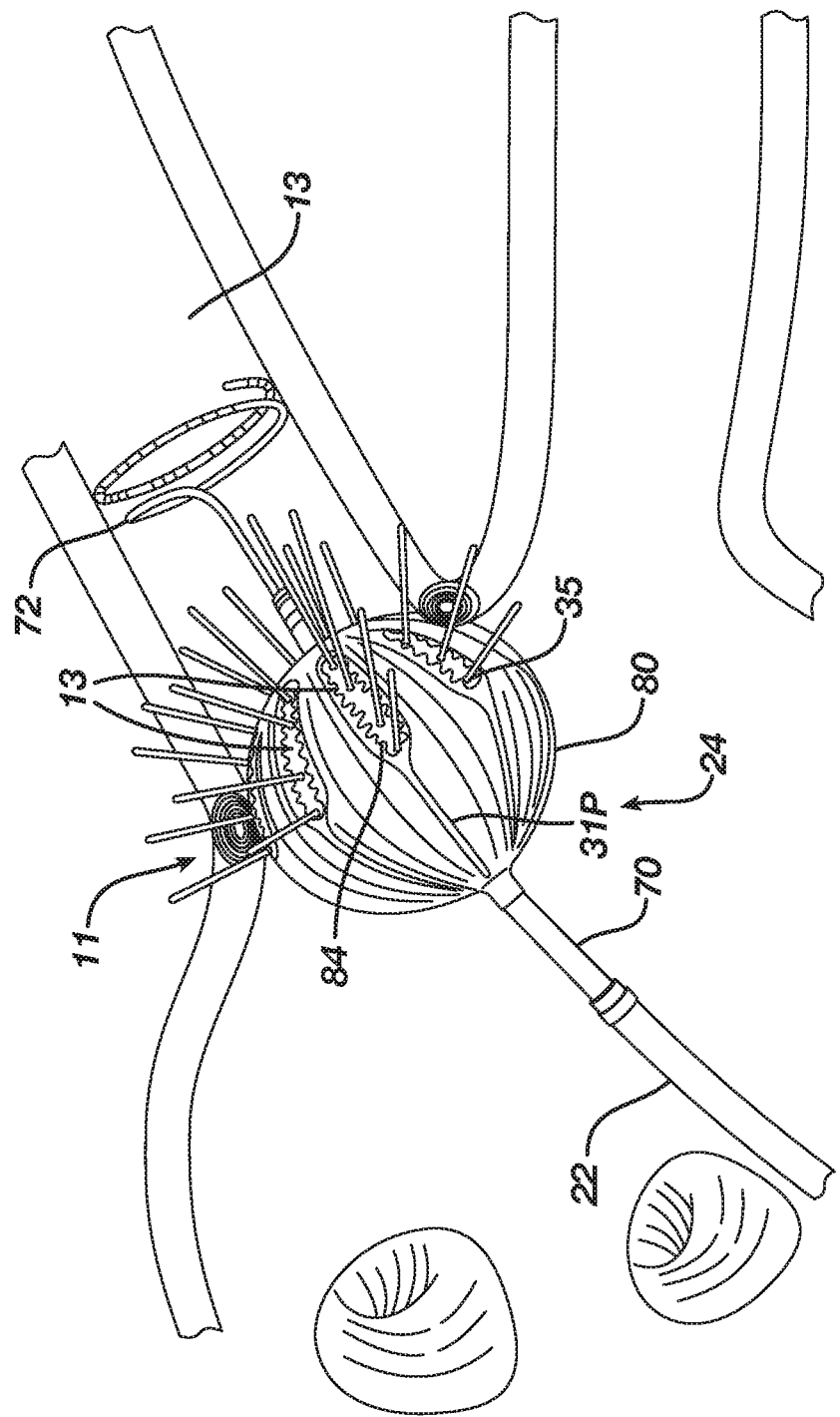
FIG. 9 is a side view of a distal end of the catheter of FIG. 2 deployed in the region of a pulmonary vein and its ostium.

FIG. 9 is a side view of a distal end of the catheter of FIG. 2 deployed in the region of a pulmonary vein and its ostium.

Figure 10:
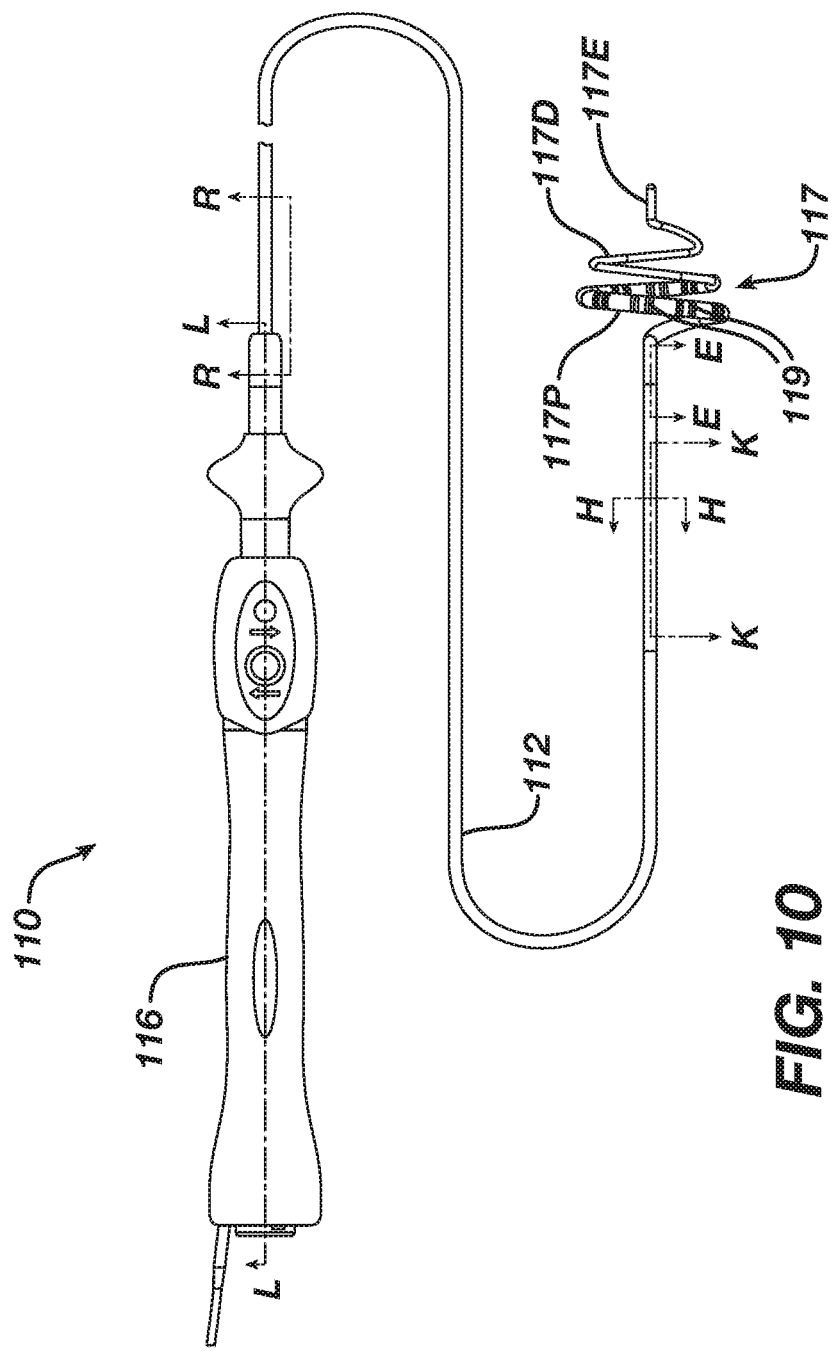
FIG. 10 is a top plan view of an example diagnostic catheter of the present disclosure.
Figure 11:
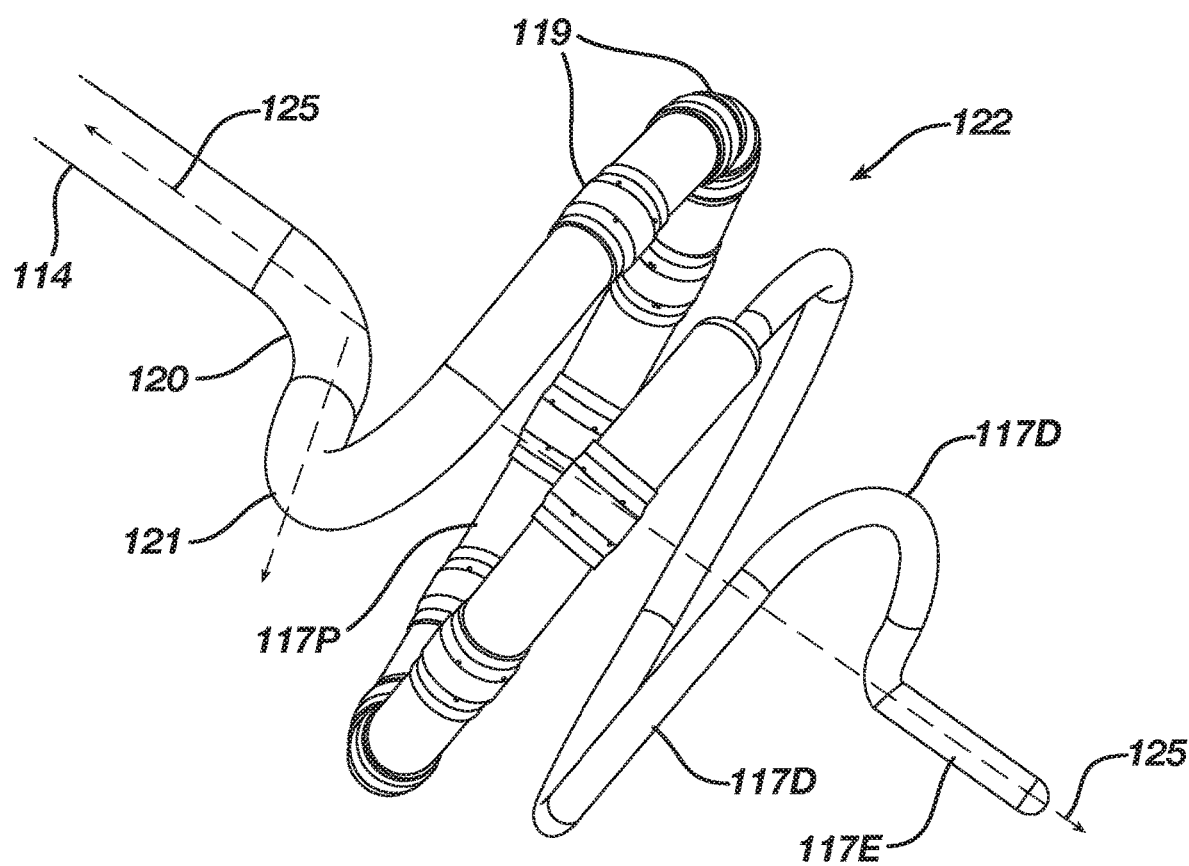
FIG. 11 is a detailed view of a distal assembly of the diagnostic catheter of FIG. 10.

FIG. 10 is a top plan view of an example diagnostic catheter of the present disclosure. FIG. 11 is a detailed view of a distal assembly of the diagnostic catheter of FIG. 5.

The membrane 26 supports and carries a combined electrode and temperature sensing member which is constructed as a multi-layer flexible circuit electrode assembly 84. The "flex circuit electrode assembly" 84 can have many different geometric configurations. In the illustrated embodiment, the flex circuit electrode assembly 84 has a plurality of radiating substrates or strips 30. One or more electrodes 33 on each substrate come into galvanic contract with the ostium 11 during an ablation procedure, during which electrical current flows from the electrodes 33 to the ostium 11, as shown in FIG. 4.

The circuit which contains the electrodes 33 can be made of a very flexible and resilient polyimide substrate (e.g., about 0.001-inch-thick) with a layer of gold on the top (exterior surface) and a layer of gold-plated copper on the back side (between the circuit and the balloon 80). In order to deliver current to the electrodes 33, a bifilar wire can be connected to each electrode 33, routed through the catheter 24, and terminated in the connector in the handle 42. The bifilar wire can be made of one copper and one constantan wire. The copper wire can be used for RF delivery. In order to fit the catheter 24 into the sheath, it is necessary to first collapse the balloon 80 with its flexible electrodes 33 to a smaller diameter by moving the distal end of the balloon 80 forward a specific distance to provide the elongation necessary to decrease the balloon's outer diameter (OD).

One example of diagnostic catheter 110 used in this disclosure is shown in FIGS. 10-11 and includes lasso-type structures to facilitate maneuvering and positioning in the heart. Catheter 110 can be understood as including features more clearly described in Appendix 2 as incorporated by reference in its entirety from the U.S. Provisional applications from which this application claims priority which includes U.S. Provisional Patent Application Ser. No. 62/769,424 (filed Nov. 19, 2019); 62/692,439 (filed Jun. 29, 2018); U.S. Pat. Nos. 5,718,241; 6,198,974; 6,484,118; 6,987,995; 7,142,903; 7,274,957; 7,377,906; 7,591,799; 7,593,760; 7,720,517; 7,853,302; 8,000,765; 8,021,327; 8,275,440; and 8,348,888, each of which are incorporated by reference in their entirety as if set forth verbatim herein. Such catheters 110 can be used to produce curved, circular, looped or otherwise closed ablation paths, as well as sensing electrical activity along a curve, circle, loop or closed pattern for electrical potential and anatomical mapping.

Catheter 110 can therefore be an electrophysiological recording and stimulation of the atrial region of the heart and can be used in conjunction with catheter 24, as well as other ancillary equipment. Catheter 110's distal end can be a circular spine with ring electrodes located circularly and are used for stimulation and recording within the atria. The looped distal end is available in multiple diameters (15 mm, 20 mm and 25 mm) to achieve an optimal contact in variably sized pulmonary veins. In some examples, the loop tip can be a circular spine with ten electrodes bonded to its surface, a straight distal tip section and a hypotube shaft. The ten electrodes can be used for stimulation and recording within the atria of the heart and oriented circularly on the loop to achieve appropriate circumferential contact with the inside of the PV. Nominal electrode spacing can include 4.5 mm for the 15 mm loop, 6 mm for the 20 mm loop, and 8 mm for the 25 mm loop.

Catheter 110 according to the disclosed example can include an elongated body that can include an insertion shaft or catheter body 112 having a longitudinal axis, and an intermediate section 114 distal of the catheter body that can be uni- or bi-directionally deflected off axis from the catheter body longitudinal axis. A resilient three-dimensional distal assembly 117, with ring electrodes 119 disposed along a nonlinear or curved distal portion, extends from the elongated body 112 or the intermediate section 114. The helical form is oriented obliquely relative to a longitudinal axis 125 of the catheter 110 extending from the intermediate section 114. The term "obliquely", in this respect means that the plane P in space that best fits the helical form is angled relative to the longitudinal axis 125. An angle θ between the plane P and the axis 125 ranges between about 45 to 105 degrees, preferably between about 75 to 105 degrees, and more preferably about 90 degrees. Moreover, the helical form 122 of the distal assembly 117 spirals or subtends in a predetermined manner.

The distal assembly 117 can have an electrode-carrying proximal loop 117P, and a soft "pigtail" that includes a distal loop 117D and a distal straight end section 117E, wherein the distal' loop 117D and the distal straight end section 117E have a greater resiliency than the resiliency of the electrode-carrying proximal loop 117P. The pitch of the helical form 122 of the distal assembly 117 is selected to provide a gentle pressure for ensuring contact of all of ring electrodes 119 with tissue. It is understood that tapering of the helical form 122 ensures that the smaller distal loop 117D can fit into the tubular region or pulmonary vein which ensures placement of accuracy of the larger proximal loop 117P and the ring electrodes 119 carried thereon at an ostium 111 of the tubular region 113, e.g., a pulmonary vein. The greater flexibility of the distal loop 117D and the distal straight end section 117E provides an atraumatic leading element that guides distal assembly 117 into the tubular region or pulmonary vein and ensures placement accuracy of the distal assembly.

The catheter 110 enters a patient's body through a guiding sheath that has been inserted in a body cavity, such as a heart chamber. Due to the flexible construction of the distal assembly 117, the helical form 122 readily straightens for insertion into the guiding sheath. When exposed and unconstrained, the distal assembly 117 reassumes the helical form 122 which is maneuvered to engage the tissue surface frontally with some or all of the ring electrodes 119 on the proximal loop 117P contacting the tissue surface simultaneously.

Figure 12:
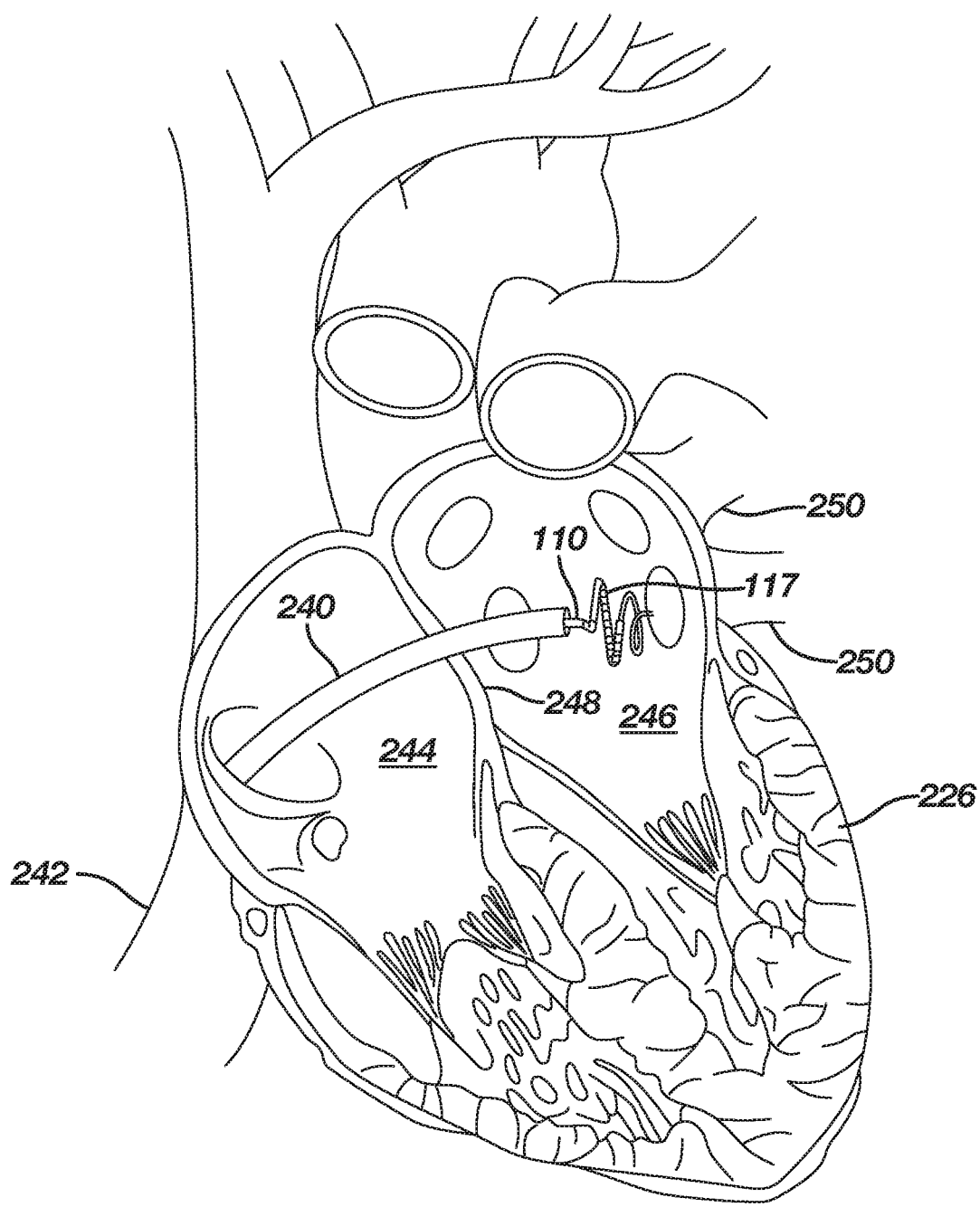
FIG. 12 is a schematic sectional view of a heart showing insertion of a diagnostic catheter according to FIGS. 10 and 11 and into the left atrium.

FIG. 12 is a schematic sectional view of heart 226, showing insertion of catheter 110 into the heart. To insert catheter 110, the user first passes a guiding sheath 240 percutaneously through the vascular system and into right atrium 244 of the heart through ascending vena cava 242. The sheath penetrates through interatrial septum 248, typically via the fossa ovalis, into left atrium 246. Alternatively, other approach paths can be used. Catheter 110 is then inserted through the guiding sheath until the distal assembly 117 of the catheter 110 extends past the distal end of the guiding sheath 240 into the left atrium 246.

Continuing on with the procedure, the operator aligns the longitudinal axis of guiding sheath 240 (and of catheter 110) inside left atrium 246 with the axis of one of pulmonary veins. Alignment can be performed under fluoroscopic or other means of visualization. The user advances the catheter 110 distally toward the pulmonary vein so that the soft distal end 117E first enters the pulmonary vein, followed by the soft distal loop 117D, both of which guide the positioning and placement of the electrode-carrying proximal loop 117P onto the ostium. The user can apply a force F in the axial direction to press the proximal loop 117P onto the ostium to ensure contact between the ring electrodes 119 and the tissue.

The operator can rotate the catheter 110 about its axis within the guiding sheath 240 so that the proximal loop 117P traces an annular path around the inner circumference of the vein. Meanwhile, the user can actuate an RF generator to ablate the tissue in contact with the AR electrodes along the path. Simultaneously, impedance and/or PV potential recordings can be made with the IR and/or RR electrodes. After completing this procedure around one pulmonary vein, the user can shift the sheath 240 and catheter 110 and repeat the procedure around one or more of the other pulmonary veins.

Study Overview

Figure 13:
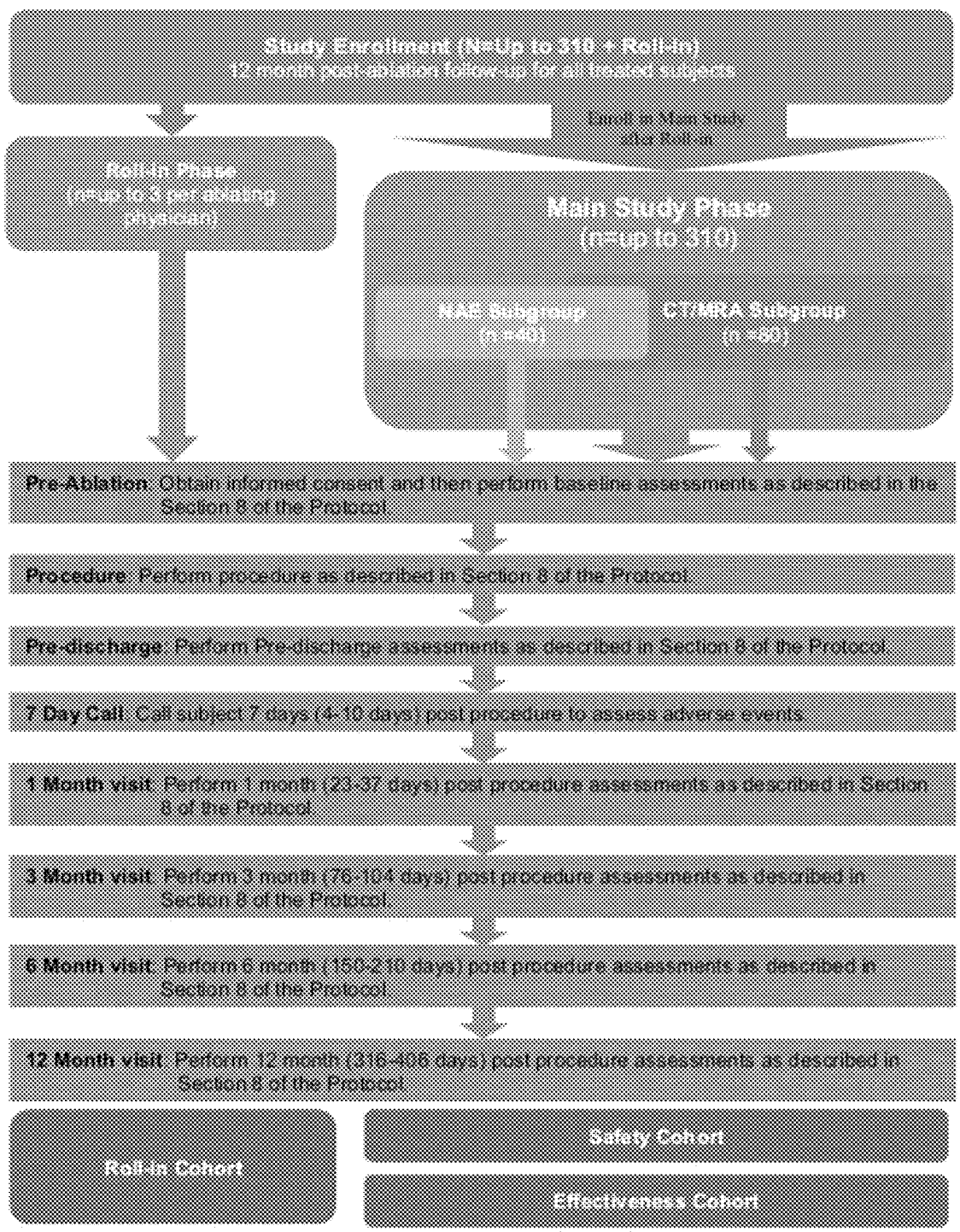
FIG. 13 shows a schematic overview of the study of this disclosure.

This disclosure is more clearly understood with a corresponding study discussed more particularly below with respect to treatment of PAF. FIG. 13 in particular provides a schematic overview of the subject study protocol of this disclosure as Appendix 3 and Appendix 4, each of which are incorporated by reference in their entirety as if set forth verbatim herein. The purpose of this study is to prove that the use of the catheter 24, as depicted graphically in FIG. 3, in conjunction with the catheter 110, for the isolation of the atrial pulmonary veins in treatment of subjects with drug refractory, symptomatic, paroxysmal atrial fibrillation is clinically safe and clinically effective.

The study was a prospective, multicenter, single arm clinical evaluation utilizing catheters 24 and 110. The sample size for the study is primarily driven by the safety endpoint. An adaptive Bayesian design can be used to determine the sample size based on the safety endpoint alone. Sample size selection interim analyses can be performed when 80, 130, 180, and 230 evaluable subjects are enrolled in the main study (e.g., mITT Population). Safety outcome at 30 days will be used as a proxy for the primary safety endpoint at each interim. The final safety analysis is on complete follow-up for the primary safety endpoint for all evaluable patients in the main study. Predictive probabilities of success are used to determine whether the sample size at each interim analysis will be sufficient or if the trial enrollment will continue. Sample size simulations were performed using performance goals of 15% and 80% respectively for the safety and effectiveness endpoint rates.

At the time of each interim analysis, predictive probabilities of success are estimated using the available data from all evaluable subjects in the mITT population, assuming a non-informative uniform prior distribution for the primary safety rate. Enrollment is stopped if the predictive probability of trial success at any interim is greater than 90%, or if the predictive probability of trial success with the maximum sample size is less than a futility bound of 6.5%. Otherwise, enrollment continues until the next interim or the final sample size. Analysis of the effectiveness endpoint is performed at the final sample size determined for the safety endpoint. Power for the effectiveness endpoint assessment is >80% at all sample sizes N30 subjects.

The primary safety and effectiveness endpoints are evaluated using exact tests for binomial proportions at a one-sided 5% significance level.

In order to control for operational bias, the timing and results of the interim analyses are not revealed to study investigators unless an interim analysis results in a decision to stop enrollment. The interim analyses are conducted seamlessly with no interruption to study enrollment unless indicated by an interim analysis. The predicted probability of study success or summary results which are calculated at the time of the interim analysis is not disseminated by the statistician performing the interim analysis until the time of the final database lock for the CSR.

Analyses for primary effectiveness endpoint included null and alternative hypotheses, including Ho: PE<0.80 and Ha: PE>0.80. It is understood that primary effectiveness (PE) can mean proportion of patients with acute procedural success defined as confirmation of entrance block in treated PVs after adenosine and/or isoproterenol challenge (with or without the use of a focal catheter). The per-protocol population is used as the primary analysis population. Subjects with missing effectiveness endpoints data will be excluded in the primary analysis. Sensitivity analyses for missing data is performed using the PP and population to assess the impact of missing data on the primary effectiveness outcome and are described in the Statistical Analysis Plan (SAP).

With respect ablation parameters of the study, electrodes 33 of catheter 24 can make contact with the tissue due to the balloon 80 and length of the electrodes, which each helps in accommodating variable anatomy. The power needed to create a circumferential contiguous lesion in the ostium to the pulmonary vein is therefore less than that of other RF catheters. Power delivery from each electrode is regulated by the generator and is determined by user input and by the temperature read by the thermocouple located on the electrode.

When used with the catheter 24, the irrigation pump of the study delivered a continuous infusion of 5 mL/minute of room temperature heparinized saline (1$u$ heparin/1 mL saline) when not delivering RF current. To inflate the balloon and during ablation, the high flow setting was used to deliver 35 mL/minute. The recommended operating parameters for the catheter 24 are presented in FIG. 14.

The study duration is approximately 21 months for the enrollment phase and follow-up. It is understood that data is presented herein for purposes of illustration and should not be construed as limiting the scope of the disclosed technology in any way or excluding any alternative or additional embodiments.

The study can demonstrate the clinical safety and acute effectiveness of the balloon catheter 24 when used with catheter 110 in the isolation of the atrial pulmonary veins in treatment of subjects with Paroxysmal Atrial Fibrillation (PAF). Specifically, the study can demonstrate the clinical safety based on the incidence of early-onset (within 7 days of the mapping and ablation procedure) primary adverse events (PAE). FIG. 15 shows a table summarizing intensity or severity of each AE assessed according to classifications. For purposes of this disclosure, an AE can be any undesirable experience (sign, symptom, illness, abnormal laboratory value, or other medical event) occurring to a subject during the course of the study, whether or not it is related to the device or procedure. Physical findings (including vital signs) observed at follow-up, or preexisting physical findings that worsen compared to baseline, are adverse events if the investigator determines they are clinically significant. As to the study, any medical condition present at the time that the subject is screened is considered as baseline and not reported as an AE. Such conditions should be added to background medical history, if not previously reported. However, if the study subject's condition deteriorates at any time during the study, it can be recorded as an AE. To demonstrate the acute and/or long-term effectiveness based on the proportion of acute procedural success, whereby success in this context can be defined as confirmation of entrance block in treated pulmonary veins after adenosine and/or isoproterenol challenge, including with or without the use of a focal ablation catheter.

Subjects with drug symptomatic PAF were enrolled and the patient population size included a maximum of 230 evaluable subjects (though fewer or more subjects could be investigated as needed or required, including populations such as 80, 130, and 180). Subjects can be evaluated prior to the procedure, prior to discharge, and post procedure at 7 days (4-10 days), 1 month (23-37 days), 3 months (76-104 days), and 6 months (150-210 days).

The primary objective of study was demonstrating the clinical safety and acute effectiveness of catheter 24 in conjunction with catheter 110, in the isolation of the atrial pulmonary veins in treatment of subjects with paroxysmal atrial fibrillation. Specifically, the study sought to demonstrate the clinical safety based on the proportion of early-onset primary adverse events (within 7 days of ablation procedure) and demonstrate the acute effectiveness based on the proportion of acute procedural success defined as confirmation of entrance block in treated PVs after adenosine and/or isoproterenol challenge, including with or without the use of a focal ablation catheter.

Primary endpoints of the study include acute effectiveness and acute safety. Acute safety can include incidence of early onset Primary Adverse Events (PAE) (within 7 days of an initial mapping and ablation procedure which used one or more of the investigational devices). Throughout this disclosure, it is understood that an adverse event (AE) is any untoward medical occurrence in a subject whether or not related to the investigational medical device.

In contrast, the following clinical events were not considered an adverse event for this study: minor pericarditis attributable to the ablation procedure defined as pleuritic chest discomfort with or without pericardial rub and ECG changes, AF/AFL/AT recurrence requiring pharmacological or synchronized electrical cardioversion during the hospitalization for the index ablation procedure, or throughout the duration of the study. However, new onset of left atrial flutter occurring post-ablation is an AE, and re-ablation for AF or pre-existing AFL/AT itself is not an AE, however any procedural complication is considered an AE and shall be reported within the applicable timelines.

A serious adverse event (SAE) in this disclosure is any event that meets one or more of the following criteria: leads to a death, leads to a serious deterioration in the health of a subject that resulted in a life-threatening illness or injury, a permanent impairment of a body structure or a body function, in-patient hospitalization or prolongation of an existing hospitalization, medical or surgical intervention to prevent life-threatening illness or injury or permanent impairment to body structure or a body function, leads to fetal distress, fetal death or a congenital abnormality or birth defect. It is understood that planned hospitalization for a condition present prior to the subject's enrollment in the study cannot meet the definition of an SAE. An AE would meet the criterion of "hospitalization" if the event necessitated an admission to a health care facility (e.g., an overnight stay). Emergency room visits that do not result in admission to the hospital were evaluated for one of the other serious outcomes. For further reference, FIG. 16 is provided summarizing classifications for the intensity or severity of each AE.

In the study, PAEs included the following AEs: device or procedure related death, Atrio-Esophageal Fistula, Myocardial Infarction, Cardiac Tamponade/Perforation, Thromboembolism, Stroke/Cerebrovascular Accident (CVA), Transient Ischemic Attach (TIA), Phrenic Nerve Paralysis, Pulmonary Vein Stenosis, Pericarditis, Pulmonary Edema, Major Vascular Access Complication/Bleeding, and Hospitalization (initial or prolonged). In the study, events were considered as primary AEs even if they occur greater than one week (7 days) post-procedure. Events related to hospitalization were excluded solely due to arrhythmia recurrence or non-medically urgent cardioversion.

Secondary endpoints of the study as to safety included incidence of individual PAEs from the primary composite, incidence of Serious Adverse Device Effects (SADEs), incidence of Serious Adverse Events (SAEs) within 7 days (early-onset), >7-30 days (peri-procedural), and >30 days (late onset) of initial ablation procedure, incidence of non-serious adverse events, acute procedural success defined as confirmation of entrance block in treated pulmonary veins (PVs) after adenosine challenge (with or without the use of a focal catheter), pulmonary vein isolation (PVI) touch-up by focal catheter among all targeted veins and by subject during the index procedure, use of focal catheter ablation for non-PV triggers during the index procedure, freedom from documented AF/AT/Atypical (left-side) AFL episodes based on electrocardiographic data through the effectiveness evaluation period (day 91-365 post index procedure) off Class I and III AADs, average number of RF applications, and RF time, required to isolate common pulmonary veins, incidence of hospitalization for cardiovascular events (with hospitalization defined as prolonged stay ≥2 nights post standard index procedure or in-patient stay not concurrent with index procedure ≥1 calendar day), Health Economics data including but not limited to index procedure workflow costs, quality of life (QoL), and hospital cost, incidence of pre-procedure and post-ablation asymptomatic and symptomatic cerebral emboli as determined by MRI evaluations, frequency, anatomic location, and size (diameter and volume) of cerebral emboli by MRI evaluations at baseline, post-ablation and during follow-up, incidence of new or worsening neurologic deficits at baseline, post-ablation and follow-up compared to baseline summary of NIHSS scores at baseline, post-ablation and during follow-up, summary of MoCA scores at baseline, 1 month follow-up and during further follow-up, and hospitalization for cardiovascular events (hospitalization defined as prolonged stay nights post index procedure or in-patient stay not concurrent with index procedure 1 calendar day.

Secondary endpoints of the study as to effectiveness included percentage (%) of PVI touch-up by focal catheter among all targeted veins and by subject; percentage (%) of subjects with use of focal catheter ablation for non-PV triggers; percentage (%) of subjects with freedom from documented, symptomatic atrial fibrillation (AF), atrial tachycardia (AT), or atypical (left side) atrial flutter (AFL) episodes (episodes >30 seconds on arrhythmia monitoring device from day 91 to 180); and percentage (%) of subjects with freedom from documented, atrial fibrillation (AF), atrial tachycardia (AT), or atypical (left side) atrial flutter (AFL) episodes (episodes >30 seconds on arrhythmia monitoring device from day 91 to 180).

Secondary endpoints of the study as to additional analyses on procedural characteristics, including but not limited to total procedure time, ablation time, RF application time, balloon dwell time, time to effect PVI, number and time of RF applications per PV location, and fluoroscopy time and dose.

Secondary endpoints of the study as to health economic assessments included index procedural workflow costs, hospital costs, and quality of life.

Subjects enrolled in a NAE (Neurological Assessment Evaluable) subgroup are assessed for incidences of symptomatic and asymptomatic pre-ablation and post-ablation cerebral emboli, with either an absence of neurological symptoms (asymptomatic) or with emboli-associated neurological symptoms (symptomatic). The NAE subgroup is a prospective design with consecutive enrollment. Roll-in subjects can NOT be eligible for the NAE subgroup. This approach minimizes the confounding influence of a learning curve during early use of a medical device. Enrollment in the NAE subgroup can be terminated prior to achieving the target 40 subjects if study enrollment ends early after a planned interim look.

Subjects enrolled in the Modified Intent-To-Treat (mITT) population included enrolled subjects meeting eligibility criteria and had the study catheter inserted. The safety population (SP) included all enrolled subjects who have undergone insertion of the study catheter. The Per Protocol (PP) Population was a subset of the mITT population and included subjects enrolled and meet all eligibility criteria, had undergone RF ablation with the study catheter, and had been treated for the study-related arrhythmia.

Primary effectiveness endpoints as to clinical effectiveness in the study was determined by those events where there was freedom from documented AF, atrial tachycardia (AT), or Atypical (left-side) atrial flutter (AFL) episodes (e.g., >30 seconds on arrhythmia monitoring device) based on electrocardiographic data through the effectiveness evaluation period (day 91-365 post index procedure). Additionally, if a subject met any one of the following criteria, then the subject was considered as chronic effectiveness failure: Acute procedural failure (i.e., failure to confirm entrance block in clinically relevant pulmonary veins post-procedure), repeat ablation or surgical treatment for AF/AT/Atypical (left-side) AFL after the blanking period (after day 90 post index procedure), DC cardioversion for AF/AT/Atypical (left-side) AFL after the blanking period (after day 90 post index procedure), continuous AF/AT/AFL on a standard 12-lead ECG even if the recording is less than 30 seconds in duration (after day 90 post index procedure), a new Class I and/or Class III AAD is prescribed for AF during effectiveness evaluation period (e.g., day 91-365 post index procedure) or prescribed during the blanking period and continued past 90 days, a previously failed Class I and/or Class III AAD (failed at or before screening) was taken for AF at a greater dose than the highest ineffective historical dose during the effectiveness evaluation period (e.g., day 91-365 post index procedure), and amiodarone was prescribed post index ablation procedure.

During this study, current AF management guidelines and the institution's standard of care practices are followed as closely as possible for AAD therapy. FIG. 16 shows a table illustrating classifications based on AAD therapy administered in the blanking and post-blanking periods in the study.

It is understood that prior to the procedure, uninterrupted anticoagulation therapy was in place at least 1 month prior to the ablation procedure. If receiving warfarin/coumadin therapy, subjects had an international normalized ratio (INR) ≥2 for at least 3 weeks prior to treatment and the subject's must be confirmed to be ≥2 within 48 hours pre-procedure. Any INR <2 within 3 weeks prior to ablation was understood to lead to exclusion of the subject or postponement of the study procedure until the INR is ≥2 for at least 3 weeks prior to treatment. Anticoagulation therapy was not interrupted or stopped prior to the procedure (e.g., no doses should be missed or omitted) and daily regimen was continued.

During the procedure, a heparin bolus was administered prior to transseptal puncture an ACT of 350-400 was targeted seconds prior to inserting the balloon 80 and throughout the procedure. ACT levels were checked every 15-30 minutes during the procedure to ensure an ACT target of 350-400 seconds. All recordings (ACT level, timing of heparin administration and dose) were documented in the medical records as source documentation. All tubing and sheath were continuously flushed with heparinized saline.

After the procedure, anticoagulation therapy was strongly recommended for at least 2 months following ablation. Additional medications needed to treat clinical indications were at the discretion of the clinical investigation physician AAD management during the study was at the discretion of the investigator.

Secondary effectiveness endpoints included acute procedural success defined as confirmation of entrance block in treated PVs after adenosine challenge (with or without the use of a focal catheter), PVI touch-up by focal catheter among all targeted veins and by subject during the index procedure, use of focal catheter ablation for non-PV triggers during the index procedure, freedom from documented symptomatic AF/AT/Atypical (left-side) AFL episodes based on electrocardiographic data through the effectiveness evaluation period (day 91-365 post index procedure) off Type I and III antiarrhythmic drugs (AADs), and average number of RF applications, and RF time, required to isolate common pulmonary veins.

Patient Selection

The criteria for patient selection, method or uses, personnel, facilities, and training specified in this study were intended to minimize the risk to subjects undergoing this procedure.

Patients were prescreened carefully prior to enrollment in the study to ensure compliance with the inclusion and exclusion criteria. The risk of phrenic nerve paralysis (PNP) was minimized by monitoring the PN with pacing maneuvers before the ablation. Ablation was stopped immediately if evidence of PN impairment is observed, and the balloon can be repositioned. The risk of PV stenosis can be minimized by not positioning the balloon within the tubular portion of the target PV. The balloon should not be inflated while the catheter is positioned inside the pulmonary vein; rather, it is always to be inflated in the atrium, then positioned at the PV ostium.

The risk of asymptomatic cerebral emboli (ACE) can be minimized by implementing an anti-coagulation regimen prior to balloon introduction into the left atrium and during procedure to avoid thrombi/emboli during procedure. Investigators are instructed to remove air bubbles and to minimize catheter exchange during procedure to mitigate the risk of air introduction. A single transseptal technique, with administration of heparin bolus prior to transseptal puncture, is also implemented. In order to help prevent esophageal injury, intraluminal esophageal temperature monitoring is required for the study.

Following procedures, all subjects are maintained on systemic oral anticoagulation therapy for at least two months post-procedure, beginning within 6 hours post-procedure. After two-months post-procedure, a decision regarding continuation of systemic anti-coagulation agents is made based on the subject's risk for thromboembolism. Systemic oral anticoagulation can be continued beyond two-months post-ablation in subjects with Congestive heart failure Hypertension Age 75 years or older Diabetes mellitus Stroke, TIA, or TE Vascular disease Age 65 to 74 years Sex category (female) (hereafter "$CHA_2DS_2$-VASc") score≥2.

For each included patient, age, gender and cardiovascular risk factors (e.g., diabetes mellitus, obesity, smoking, high blood pressure, hyperlipidemia) were recorded. Initial imaging was brain CT with cervical and intracranial angiography or brain MRI with time of flight angiography, depending on hospital protocol. The ASPECT (Alberta Stroke Program Early CT) score was evaluated by experienced neuroradiologists on either modality, and the NIHSS score by neurologists. Patients were treated up to 12 hours from time of stroke onset or time last known well in case of wake-up stroke.

Inclusion criteria for the study included the following:

Diagnosed with Symptomatic PAF, including at least three (3) symptomatic episodes of AF with attacks lasting ≥1 minute) within six (6) months prior to enrollment, and at least one (1) AF episode must be electrocardiographically documented within twelve (12) months prior to enrollment. Electrocardiographic documentation can include, but is not limited to, electrocardiogram (ECG), Holter monitor, or telemetry strip;

Selected for AF ablation procedure for pulmonary vein isolation; Able and willing to comply with uninterrupted per-protocol;

Failing at least one (1) Class I or Class III AAD as evidenced by recurrent symptomatic AF or intolerable side effects to the AAD;

Willingness to comply with anticoagulation requirements (e.g., warfarin, rivaroxaban, dabigatran, apixaban);

Age 18-75 years; and

Able and willing to comply with all pre-procedure, post-procedure, and follow-up testing and visit requirements.

Exclusion criteria for the study included the following:

AF secondary to electrolyte imbalance, thyroid disease, or reversible or non-cardiac cause;

Previous surgical or catheter ablation for AF;

Anticipated to receive ablation outside the PV ostia and CTI region (e.g. AVRT, AVNRT, atrial tachycardia, VT and WPW);

Previously diagnosed with persistent or long-standing persistent AF and/or Continuous AF >7 days, or >48 hrs terminated by cardioversion;

Any percutaneous coronary intervention within the past 2 months;

Valve repair or replacement or presence of a prosthetic valve;

Any carotid stenting or endarterectomy;

Any carotid stenting or endarterectomy.

Coronary artery bypass grafting (CABG), cardiac surgery (e.g. ventriculotomy, atriotomy), or valvular cardiac surgical or percutaneous procedure within the past 6 months.

Documented left atrium (LA) thrombus on baseline/pre-procedure imaging.

LA antero posterior diameter >50 mm

Any PV with a diameter 26 mm

Left Ventricular Ejection Fraction (LVEF) <40%.

Contraindication to anticoagulation (e.g. heparin).

History of blood clotting or bleeding abnormalities.

Myocardial infarction within the past 2 months.

Documented thromboembolic event (including transient ischemic attack [TIA]) within the past 12 months.

Rheumatic Heart Disease.

Uncontrolled heart failure or New York Heart Association (NYHA) function class III or IV.

Awaiting cardiac transplantation or other cardiac surgery within the next 12 months.

Unstable angina.

Acute illness or active systemic infection or sepsis.

Diagnosed atrial myxoma or interatrial baffle or patch.

Presence of implanted pacemaker or, implantable cardioverter defibrillator (ICD), or tissue-embedded, iron-containing metal fragments.

Significant pulmonary disease, (e.g. restrictive pulmonary disease, constrictive or chronic obstructive pulmonary disease) or any other disease or malfunction of the lungs or respiratory system that produces chronic symptoms.

Significant congenital anomaly or medical problem that, in the opinion of the investigator, would preclude enrollment in this study.

Women who are pregnant (as evidenced by pregnancy test if pre-menopausal), lactating, or who are of child bearing age and plan on becoming pregnant during the course of the clinical investigation.

Enrollment in an investigational study evaluating another device, biologic, or drug.

Has known pulmonary vein stenosis.

Presence of intramural thrombus, tumor or other abnormality that precludes vascular access, or manipulation of the catheter.

Presence of an IVC filter

Presence of a condition that precludes vascular access.

Life expectancy or other disease processes likely to limit survival to less than 12 months.

Presenting contra-indication for the devices (e.g. TTE, CT, etc.) used in the study, as indicated in the respective instructions for use.

Categorized as a vulnerable population and requires special treatment with respect to safeguards of well-being Additional exclusion criteria for Neurological Assessment Evaluable (NAE) subjects include contraindication Patient on amiodarone at any time during the past 3 months prior to enrollment;

Contraindication to use of contrast agents for MRI such as advanced renal disease, etc. (at PI discretion), presence of iron-containing metal fragments in the body, and Unresolved pre-existing neurological deficit.

Results of the Study

During the study, investigators collected the following data: RF ablation parameters per PV, number of RF application(s) per target PV, number of RF application(s) required with a focal catheter (if applicable), total RF duration per target PV, total time of RF application with the balloon catheter 24 until PV isolation of targeted vein was achieved (TTI ~time to isolate), total time of RF application with the focal catheter (if applicable), PV acute reconnection, RF ablation parameters per application, Targeted vein, Ablation number of the generator, Total Duration of RF energy per application, Balloon Inflation Index prior to target PV application, pacing electrodes, ablation parameters (impedance, temperature, power, number of active electrodes per application, and total duration of RF application. Also, RF duration of posterior/anterior electrode, etc.) can be collected during the ablation procedure via the generator log files, ablation parameters, including but not limited to percentage of targeted PV isolated on first shot and percentage of targeted PV with acute reconnections, procedural parameters, including but not limited to: Duration of time in mapping (LA and PVs), Total RF duration (consecutive time of RF energy delivered by multi-electrode RF balloon catheter and focal catheter (if applicable)), Total PVI time with balloon catheter (Duration of time from 1$^{st}$ RF application to final RF application), Total PVI time with focal catheter (if applicable), Total procedure time (from first femoral puncture to catheter removal), Total fluoroscopy time and dose, Total Balloon dwell time (from first RF balloon insertion until RF balloon removal), ECG data, Total fluid delivered via ablation catheter, Total fluid delivered via intravenous line (if captured), Fluid output (if captured), Net Fluid input, ACT level and timepoint of heparin administration, Strategy to evaluate the proximity to the phrenic nerve, Strategy used to minimize risk of esophageal injury, Type of temperature probe, cut-off temperature and any abnormal increases in temperature observed.

FIG. 17 depicts a method or use 1700 for administering a procedure for treating atrial fibrillation. The method or use 1700 can include 1710 delivering a multi-electrode radiofrequency balloon catheter to one or more targeted pulmonary veins; 1720 ablating tissue of the pulmonary vein using the multi-electrode radiofrequency balloon catheter; and 1730 achieving a predetermined effectiveness rate of pulmonary vein isolation.

FIG. 18 depicts a method or use 1800 for administering a procedure for treating atrial fibrillation. The method or use 1800 can include 1810 delivering a multi-electrode radiofrequency balloon catheter to a pulmonary vein; 1820 ablating tissue of the pulmonary vein using the multi-electrode radiofrequency balloon catheter; and 1830 achieving a predetermined effectiveness rate of pulmonary vein isolation.

FIG. 19 depicts a method or use 1900 for administering a procedure for treating atrial fibrillation. The method or use 1900 can include 1910 delivering a multi-electrode radiofrequency balloon catheter to a pulmonary vein; 1920 ablating tissue of the pulmonary vein using the multi-electrode radiofrequency balloon catheter; and 1930 achieving pulmonary vein isolation and at least a 97% safety endpoint within seven (7) days of successful pulmonary vein isolation.

FIG. 20 depicts a method or use 2000 for administering a procedure for treating atrial fibrillation. The method or use 2000 can include 2010 delivering a multi-electrode radiofrequency balloon catheter to a pulmonary vein; 2020 ablating tissue of the pulmonary vein using the multi-electrode radiofrequency balloon catheter; and 2030 achieving pulmonary vein isolation and at least a 90% safety endpoint within seven (7) days of successful pulmonary vein isolation FIG. 21 depicts a method or use 2100 for administering a procedure for treating atrial fibrillation. The method or use 2100 can include 2110 delivering a multi-electrode radiofrequency balloon catheter having a plurality of independently controllable electrodes for radiofrequency ablation and a multi-electrode diagnostic catheter to one or more targeted pulmonary veins; 2120 ablating tissue of the one or more targeted pulmonary veins with one or more of the plurality of the electrodes independently controlled multi-electrode radiofrequency balloon catheter; 2130 diagnosing the one or more targeted pulmonary veins using the multi-electrode diagnostic catheter; and 2140 achieving at least one of a predetermined clinical effectiveness and acute effectiveness of the method or use based on use of the multi-electrode radiofrequency balloon catheter and the multi-electrode diagnostic catheter in the isolation of the one or more targeted pulmonary vein.

FIG. 22 depicts a method or use 2200 to treat a plurality of patients for paroxysmal atrial fibrillation. The method or use 2200 can include 2210 delivering a multi-electrode radiofrequency balloon catheter having a plurality of independently controllable electrodes for radiofrequency ablation and a multi-electrode diagnostic catheter to one or more targeted pulmonary veins; 2220 ablating tissue of one or more targeted pulmonary veins with one or more of the plurality of the electrodes independently controlled multi-electrode radiofrequency balloon catheter; 2230 diagnosing all targeted pulmonary veins using the multi-electrode diagnostic catheter; and 2240 achieving a predetermined rate of adverse events based on use of the multi-electrode radiofrequency balloon catheter and the multi-electrode diagnostic catheter in the isolation of all targeted pulmonary veins, during and approximately 6 months after the method or use.

Figure 23:
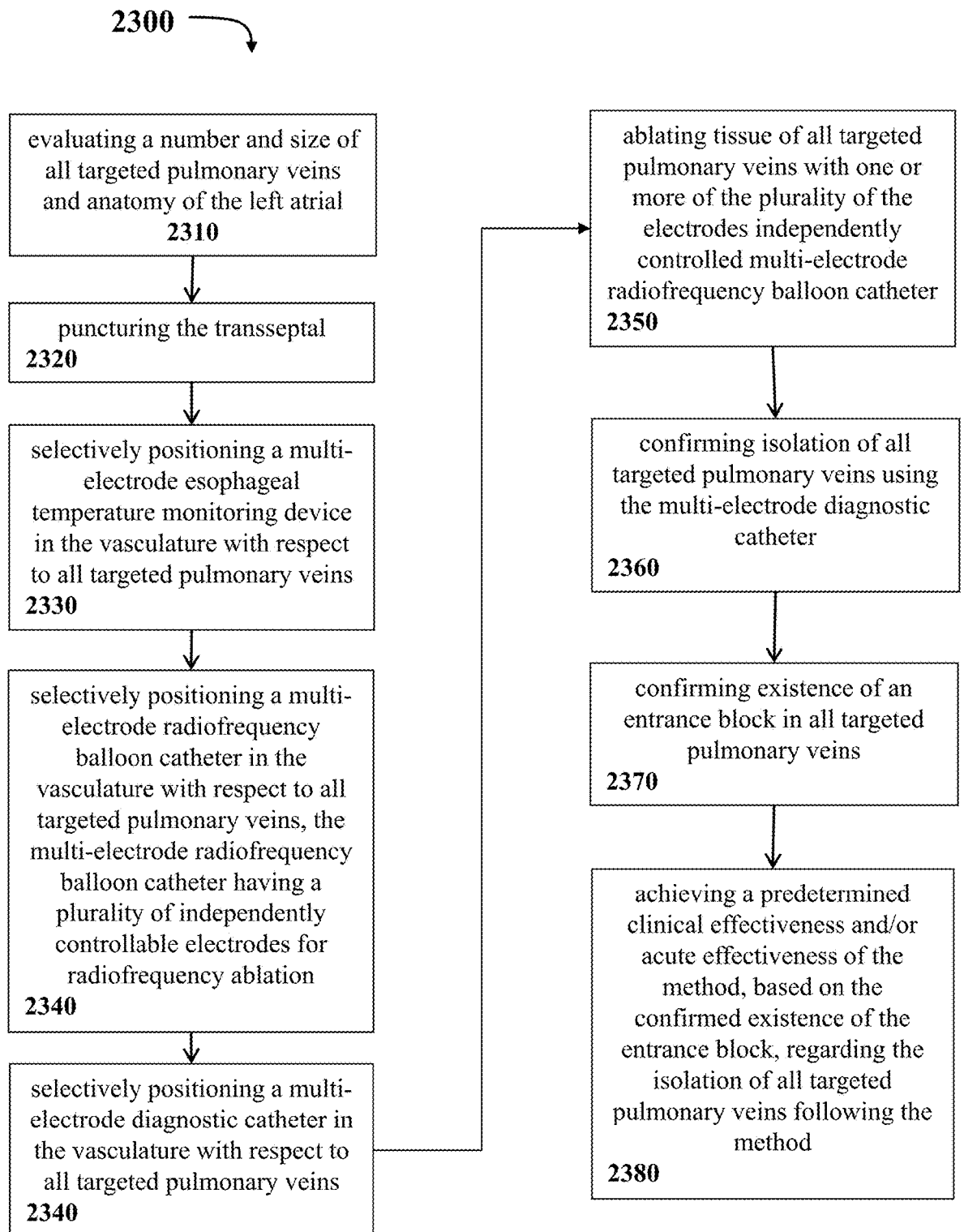
FIG. 23 depicts a graphical overview of one method or use according to this disclosure.

FIG. 23 depicts a method or use 2300 to treat a plurality of patients for paroxysmal atrial fibrillation. The method or use 2300 can include 2310 evaluating a number and size of all targeted pulmonary veins and anatomy of the left atrial; 2320 puncturing the transseptal; 2330 selectively positioning a multi-electrode esophageal temperature monitoring device in the vasculature with respect to all targeted pulmonary veins; 2340 selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation; 2350 ablating tissue of all targeted pulmonary veins with one or more of the plurality of the electrodes independently controlled multi-electrode radiofrequency balloon catheter; 2360 confirming isolation of all targeted pulmonary veins using the multi-electrode diagnostic catheter; 2370 confirming existence of an entrance block in all targeted pulmonary veins; and 2380 achieving a predetermined clinical effectiveness and/or acute effectiveness of the method or use, based on the confirmed existence of the entrance block, regarding the isolation of all targeted pulmonary veins following the method or use.

FIG. 24 shows a table summarizing single shot isolation versus non-isolation according to the study of this disclosure. In particular, FIG. 24 summarizes single shot isolation versus non-isolation according to ablation location, number of electrode ablations, initial impedance, impedance drop, maximum temperature, and temperature rise. With respect to the number of electrode ablations, only first ablation with full circle and full duration ablations were included for analysis. With this in mind, the study investigated certain endpoints of the study as potential predictors for successful isolation. One endpoint investigated included duration and energy, whereby longer duration and higher energy were evaluated as to inducing to higher rate of single shot PVI as shown and discussed herein.

Another endpoint included time to isolation, but no noticeable impact on success of ablations was observed. Another endpoint included inflation index but no noticeable impact on success of ablations was observed. Another endpoint included initial impedance, whereby higher initial impedance variation among the full-circle electrodes was evaluated as to leading to lower rate of single-shot PVI (e.g., <30Ω), as shown and discussed herein. Another endpoint included impedance drop, whereby a difference of the impedance drop between anterior and posterior wall was evaluated as to being a possible indicator for the success of ablation, as shown and discussed herein. Another endpoint included max temperature, but no noticeable impact on success of ablations was observed.

Figure 25:
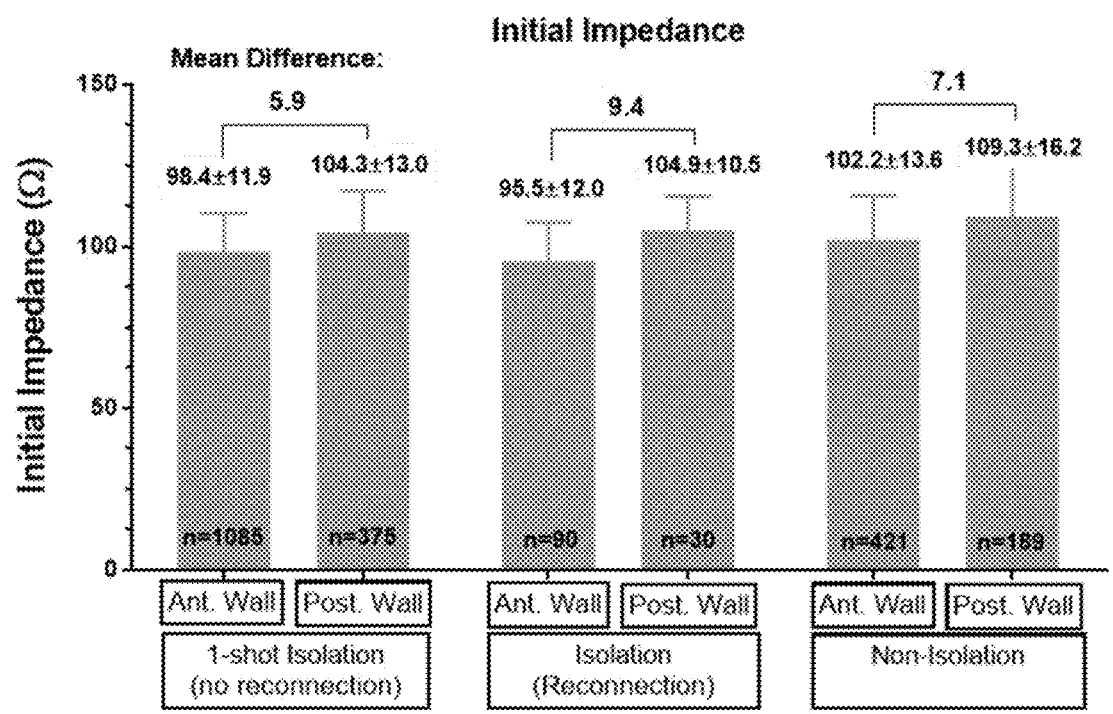
FIG. 25 shows a graph summarizing initial impedance according to the study of this disclosure.

FIG. 25 shows a graph summarizing initial impedance according to the study of this disclosure. In particular, FIG. 25 shows mean difference of initial impedance between anterior and posterior wall as to single shot isolation (no reconnection), isolation (reconnection), and non-isolation for patients evaluated in the study of this disclosure.

Figure 26:
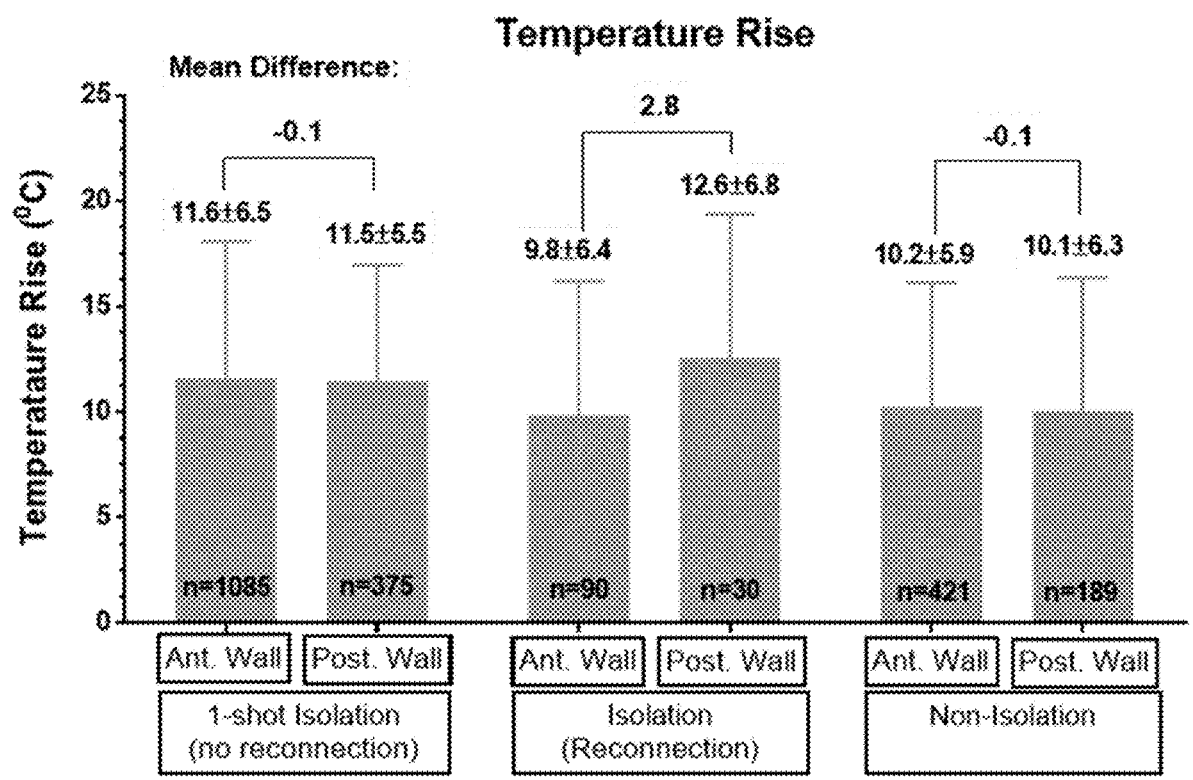
FIG. 26 shows a graph summarizing temperature rise according to the study of this disclosure.

FIG. 26 shows a graph summarizing temperature rise according to the study of this disclosure. In particular, FIG. 26 shows mean difference of temperature rise between anterior and posterior wall as to single shot isolation (no reconnection), isolation (reconnection), and non-isolation for patients evaluated in the study of this disclosure.

Figure 27:
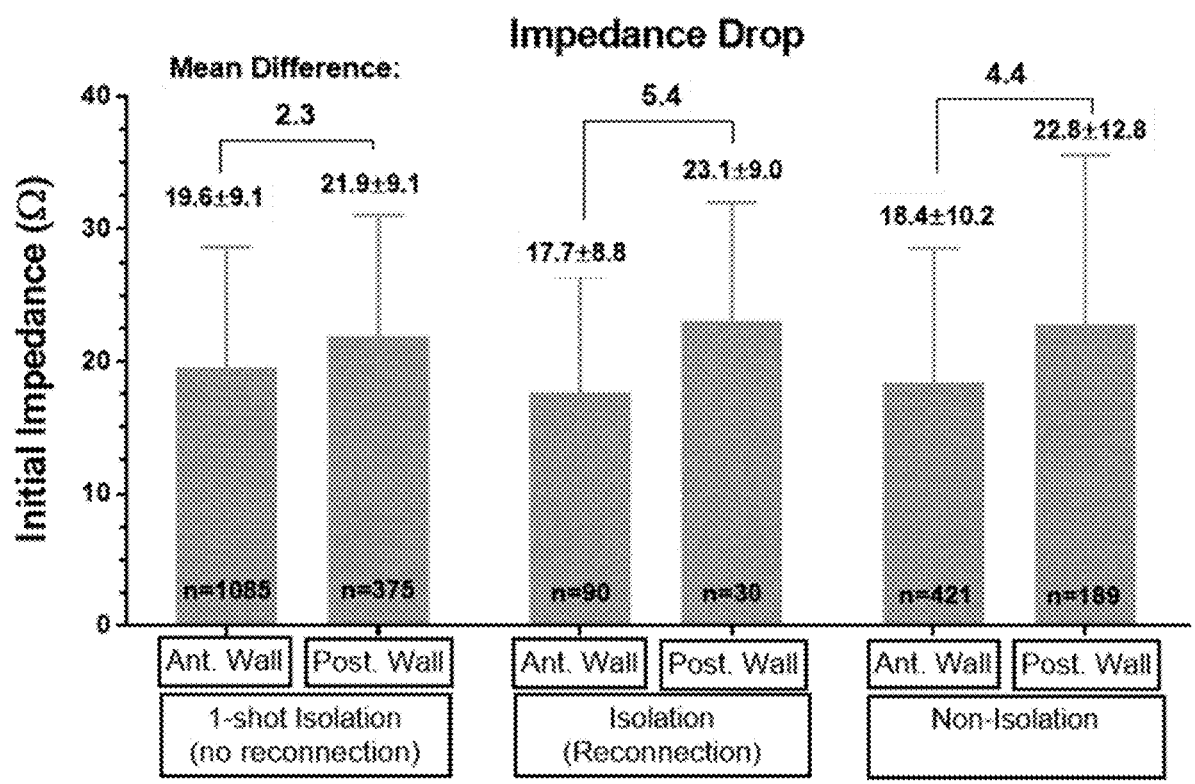
FIG. 27 shows a graph summarizing impedance drop according to the study of this disclosure.

FIG. 27 shows a graph summarizing impedance drop according to the study of this disclosure. In particular, FIG. 27 shows mean difference of impedance drop between anterior and posterior wall as to single shot isolation (no reconnection), isolation (reconnection), and non-isolation for patients evaluated in the study of this disclosure. In the study, the difference of the impedance drop between anterior and posterior wall was determined to be a possible indicator for the success of ablation.

Figure 28:
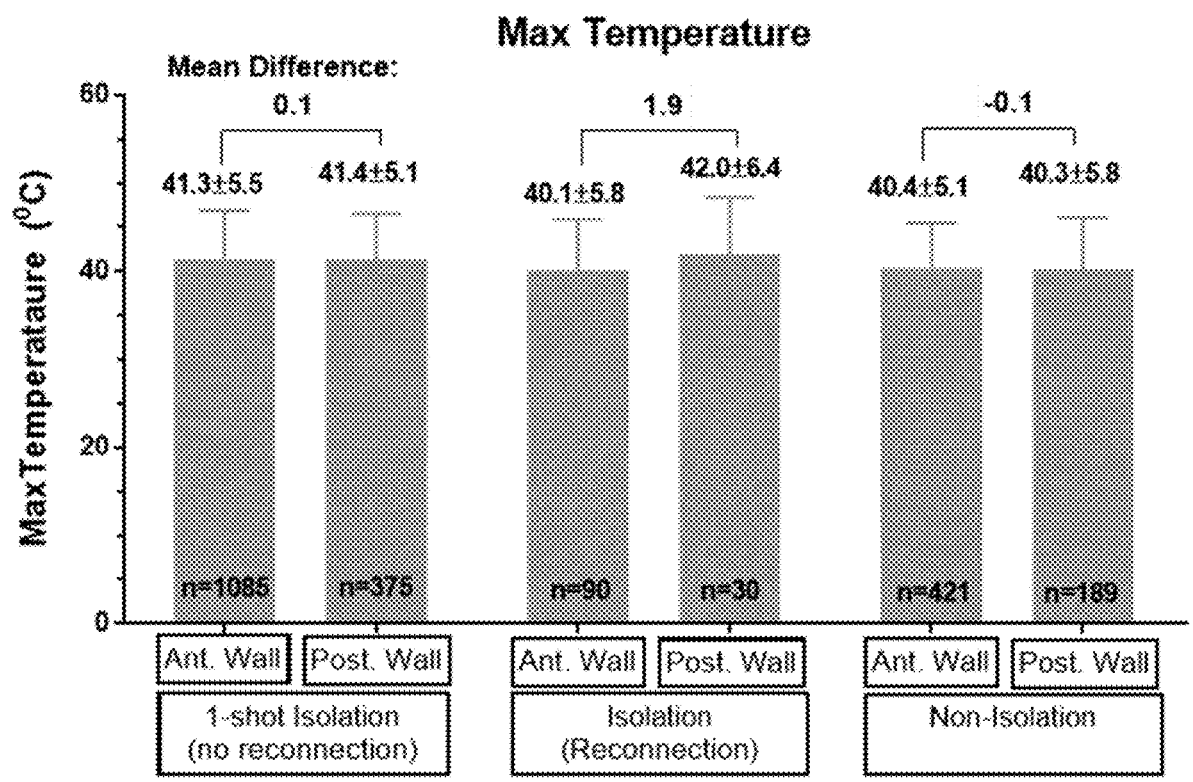
FIG. 28 shows a graph summarizing maximum temperature according to the study of this disclosure.

FIG. 28 shows a graph summarizing maximum temperature according to the study of this disclosure. In particular, FIG. 28 shows mean difference of maximum temperature between anterior and posterior wall as to single shot isolation (no reconnection), isolation (reconnection), and non-isolation for patients evaluated in the study of this disclosure.

Figures 29A, 29B:
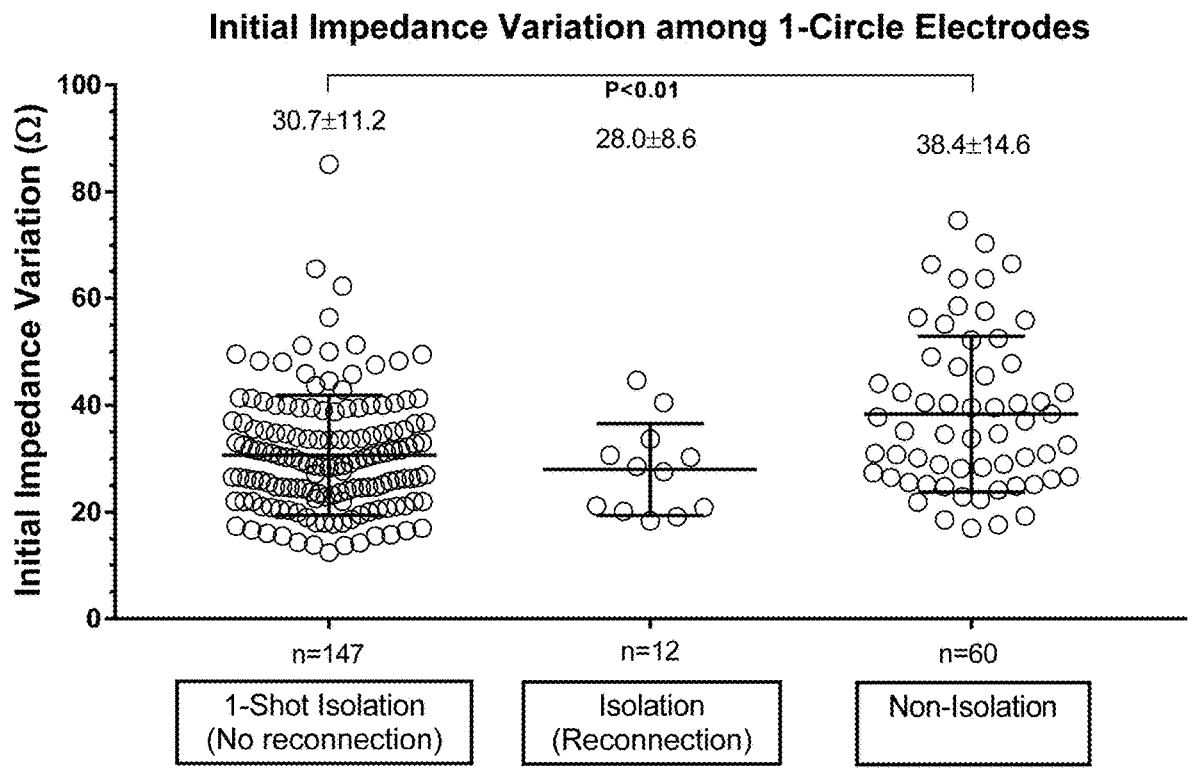
FIG. 29A shows a graph summarizing initial impedance variation among 1-circle electrodes in the study of this disclosure.
FIG. 29B shows a table summarizing initial impedance variation among 1-circle electrodes in the study of this disclosure.

FIG. 29A shows a graph summarizing initial impedance variation among 1-circle electrodes in the study of this disclosure. In particular, FIG. 29A summarizes mean initial impedance variation among 1-circle electrodes for single shot isolation (no reconnection), isolation (reconnection), and non-isolation for patients evaluated in the study of this disclosure. It is noted that only first ablation with full circle and full duration ablations were included for analysis. FIG. 29B shows a table summarizing initial impedance variation among 1-circle electrodes in the study of this disclosure.

Figure 30:
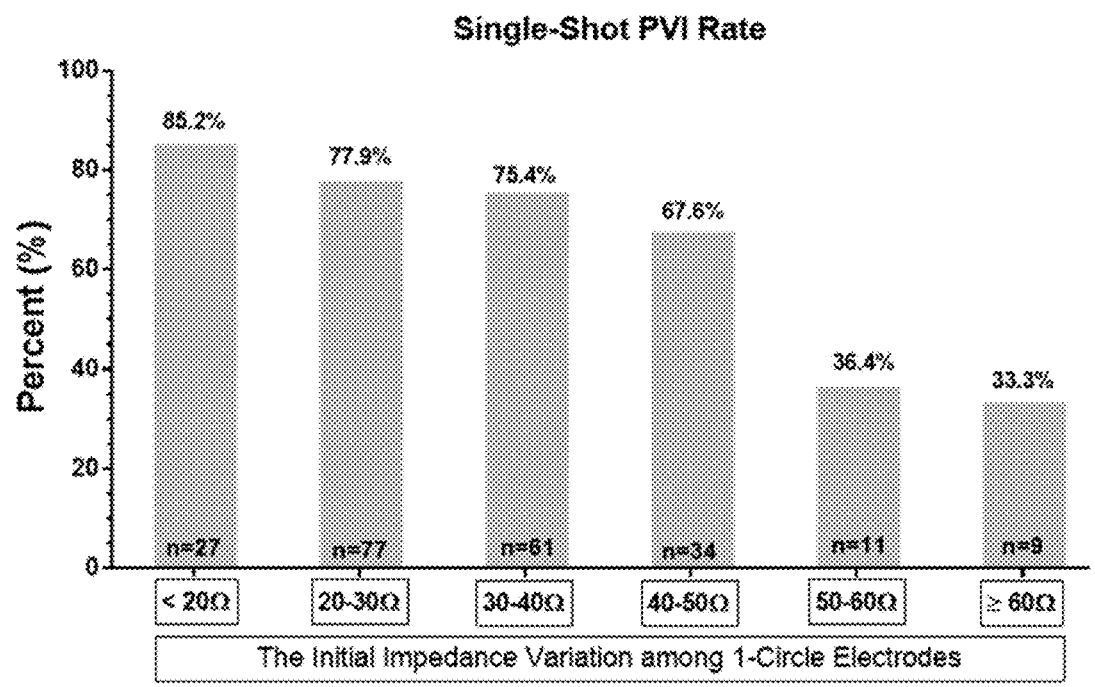
FIG. 30 shows a graph summarizing single-shot PVI rate in the study of this disclosure.

FIG. 30 shows a graph summarizing single-shot PVI rate in the study of this disclosure according to the initial impedance variation among 1-circle electrodes. For 27 patients evaluated less than approximately about 20Ω, single-shot PVI was observed at about 85.2%. For 77 patients evaluated and approximately between 20 to 30Ω, single-shot PVI was observed at about 77.9%. For 61 patients evaluated and approximately between 30 to 40Ω, single-shot PVI was observed at about 75.4%. For 34 patients evaluated and approximately between about 40 to 50Ω, single-shot PVI was observed at about 67.6%. For 11 patients evaluated and approximately between about 50 to 60Ω, single-shot PVI was observed at about 36.4%. For 9 patients evaluated and approximately greater than about 60Ω, single-shot PVI was observed at about 33.3%.

Figure 31:
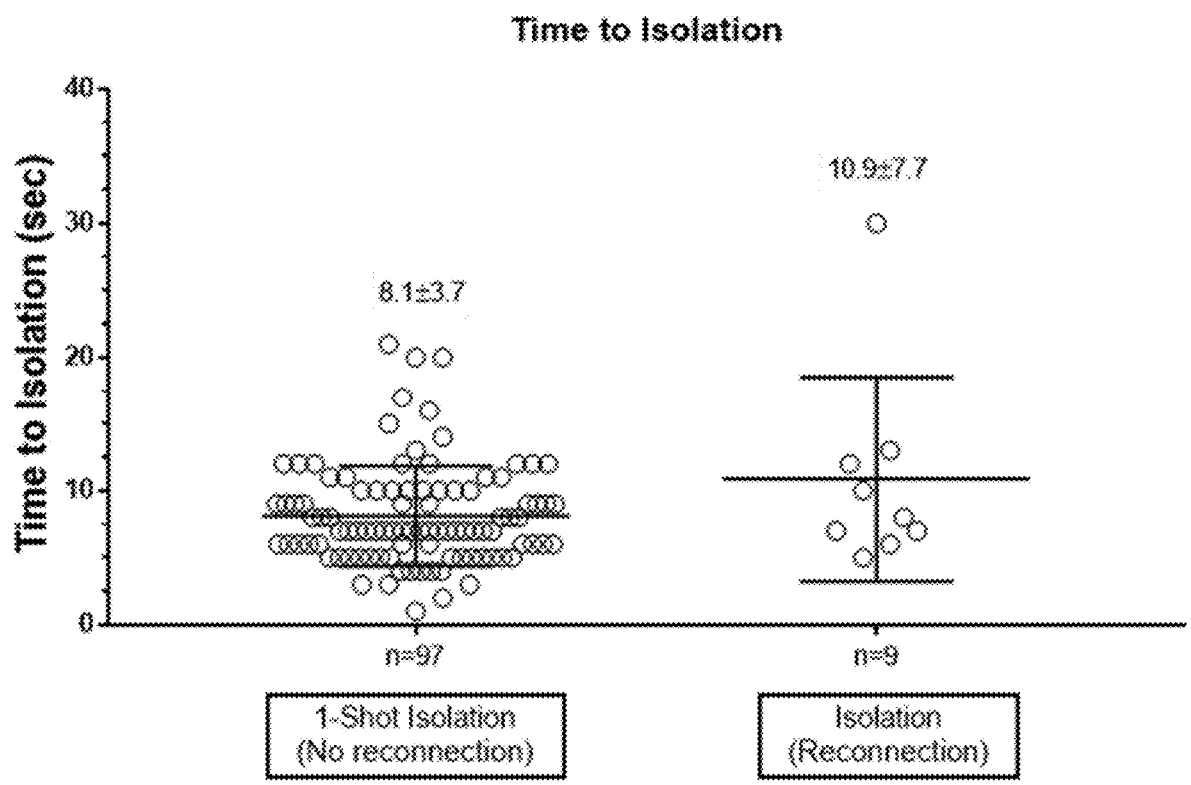
FIG. 31 shows a graph summarizing time to isolation in the study of this disclosure.

FIG. 31 shows a graph summarizing time to isolation in the study of this disclosure including single shot isolation (no reconnection) at approximately about 8.1 seconds and isolation (reconnection) at approximately about 10.9 for patients evaluated in the study of this disclosure.

Figure 32:
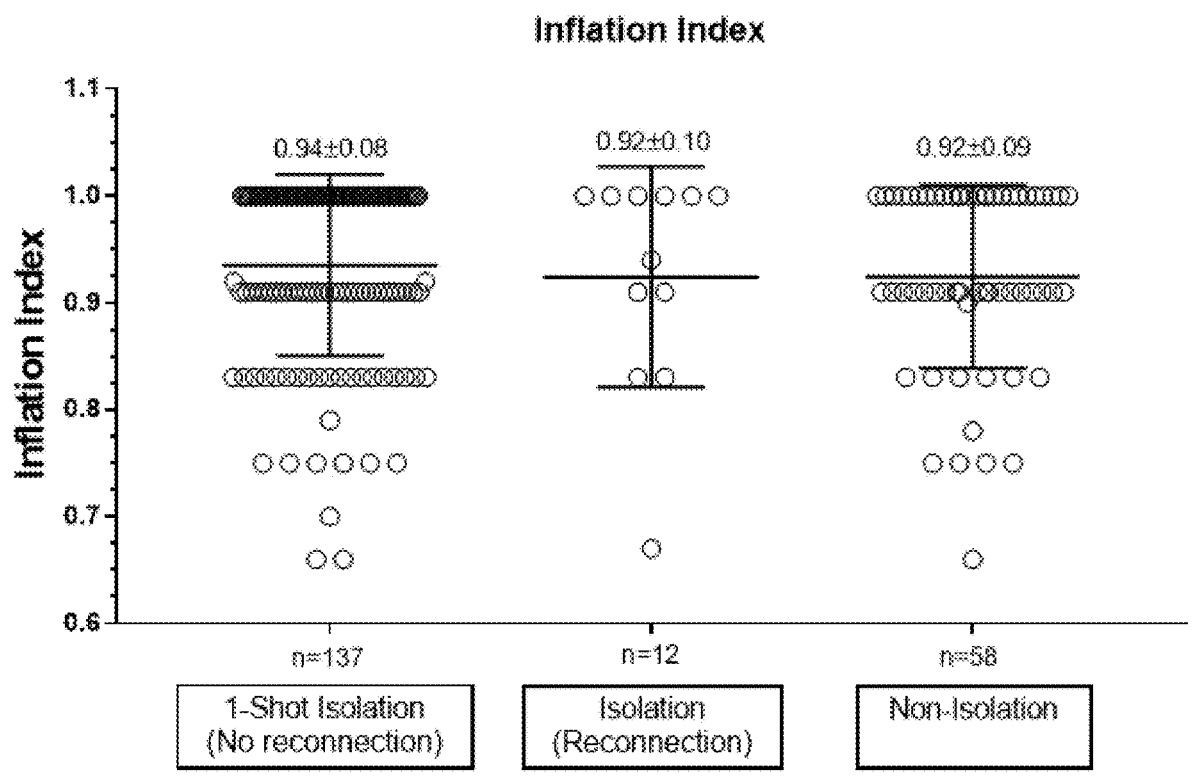
FIG. 32 shows a graph summarizing inflation index in the study of this disclosure.

FIG. 32 shows a graph summarizing inflation index in the study of this disclosure as to single shot isolation (no reconnection), isolation (reconnection), and non-isolation for patients evaluated in the study of this disclosure.

FIG. 33 shows a table summarizing pre- and post-ablation parameters in the study of this disclosure as to impedance, impedance variation, lowest initial impedance, mean initial impedance, initial impedance variation, lowest maximum temperature, lowest impedance drop, mean impedance drop, and impedance drop variation. Excluding roll-in cases, only first shot for each PV with full-circle (e.g., all electrode burning) and full duration (e.g., 60 sec) were evaluated for analysis, including a total of 219 ablations with 158 single shot isolation. Minitabe Pearson correlations and binary logistic regression models were used to evaluate each parameter as a potential predictor of single shot isolation (including LCPV and RMPV). It was understood that larger coefficient and lower P-value of the table in FIG. 33, the better predictor. In this analysis, the pre-ablation parameters of mean initial impedance and initial impedance variation were deemed as predictors of single shot isolation. As for post-ablation parameters, lowest impedance drop and impedance drop variation were similarly deemed as predictors of single shot isolation.

FIG. 34 shows a table summarizing pre-ablation parameters in the study of this disclosure as to initial temperature, initial impedance, and initial anterior wall impedance. Predictors of single shot isolation were those observed with correlation P-value <0.01, including maximum initial temperature, initial temperature variation, mean initial impedance, maximum initial impedance, initial impedance variation, mean initial anterior wall impedance, lowest anterior wall impedance, maximum anterior wall impedance, and anterior wall impedance variation. It is understood that anterior wall impedance values were among the anterior wall electrodes. Minitabe Pearson correlations and binary logistic regression models were used to evaluate each parameter as a potential predictor of single shot isolation (including LCPV and RMPV).

FIG. 35 shows a table summarizing post-ablation parameters in the study of this disclosure as to temperature slope, temperature rise, maximum temperature, impedance drop, and impedance drop percentage (e.g., impedance drop/initial impedance). Predictors of single shot isolation were those observed with correlation P-value <0.01, including mean temperature slope, lowest temperature slope, mean temperature rise, lowest temperature rise, lowest impedance drop, impedance drop variation, lowest impedance drop percentage, and variation of impedance drop percentage. Minitabe Pearson correlations and binary logistic regression models were used to evaluate each parameter as a potential predictor of single shot isolation (including LCPV and RMPV). As can be seen, in FIGS. 34-35 the mean and highest value of initial impedance and anterior wall initial impedance had high correlation with single shot isolation rate (P value <0.0005). The optimal range (>90% single shot isolate rate) was <95Ω for mean initial impedance and <110Ω for highest initial impedance.

Based on the data from the SHINE study (with a copy in Appendix 4), it is believed that there are six (6) single-parameter predictor of single-shot-isolation ("SSI") and eight (8) single-parameter evaluator for SSI. The "predictor" allows for a determination of whether the relevant parameters observed or measured (with the study device as described herein) before ablation (i.e., pre-ablation parameters) would likely lead to a success rate of 90% or higher based on the data gleaned from the study. The "evaluator" on the other hand, allows for a determination of whether the actual ablation performed would likely lead to a success rate of 90% or greater for SSI. The "predictor" and "evaluator" are summarized in Table 1 below:

TABLE 1

SINGLE PARAMETER PREDICTORS AND EVALUATORS

| | Potential Predictors or evaluators (P value < 0.01) | Implication |
|---|---|---|
| Predictor (Pre-ablation parameters) | Initial Imp - Variation | Initial Impedance variation <20 Ω, single shot isolation (SSI) rate of nearly 90%. Lower variation, higher SSI rate. |
| | Initial Imp - Highest | When the highest initial impedance <<110 Ω, SSI rate >90% |
| | Initial Imp - Mean | When the mean initial impedance <95 Ω, SSI rate >90% |
| | Initial Temp - Highest | Highest Initial temp <31° C., SSI rate >90% |
| | Initial Temp - Variation | Initial temp variation <3° C., SSI rate >90% |
| | # of electrodes with initial impedance deviation from mean value ≥10 Ω | # of electrode with initial impedance deviation from mean value is zero, the single shot isolation rate is 92.3% (n~13). |
| Evaluator (Post-Ablation Parameters) | Imp drop - Variation | Impedance drop Variation <20 Ω, SSI rate >85% |
| | Temp Rise - Lowest | Lowest Temp rise ≥6° C., SSI rate >90% |
| | Imp drop - Lowest | Lowest Impedance drop ≥12 Ω, SSI rate >90% |
| | Imp drop percent-Lowest | Lowest Impedance drop Percent ≥12%, single shot isolation rate >90% |
| | Temp Slope - Lowest | Lowest Temp slope ≥0.75° C./sec, SSI rate >90% |
| | Temp Slope - Mean | Higher mean temp slope, higher SSI isolation rate |
| | Imp drop percent-variation | larger Imp drop percent variation, higher SSI isolation rate |
| | Temp Rise - Mean | Mean Temp rise ≥14° C., SSI rate >90% |

FIG. 36 shows a table summarizing what is believed to be potential rankings of pre- and post-ablation parameters from Table 1 above that were single shot predictors observed in the study of this disclosure. Regarding pre-ablation parameters, rankings of single shot predictors from first to fifth were initial impedance variation, highest initial temperature, variation of initial temperature, anterior impedance variation, and anterior lowest impedance, respectively. Regarding post-ablation parameters, rankings of single shot predictors from first to sixth were initial impedance drop variation, lowest temperature rise, lowest impedance drop, lowest temperature slope, mean temperature slope, and mean temperature rise, respectively. Stated differently, the most accurate predictor of single shot isolation rate before ablation was (a) achieving small variation in the impedance (e.g., <20Ω) and temperature (<3° C.) among 10 electrodes, (b) limiting the highest initial temp (e.g., <31° C.) of 10 electrodes, and (c) permitting the lowest anterior wall impedance to range between approximately about 80-90Ω.

Figure 37:
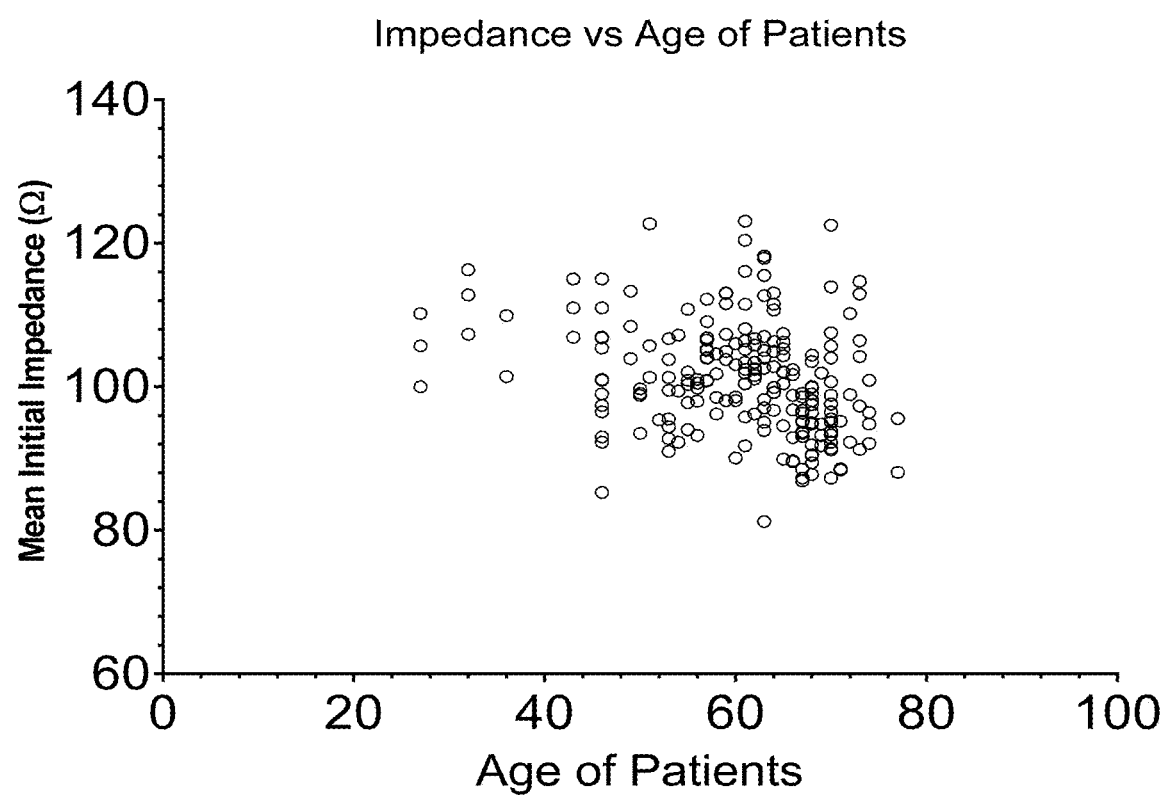
FIG. 37 shows a graph summarizing correlations between mean initial impedance and age of patients in the study of this disclosure.
Figure 38:
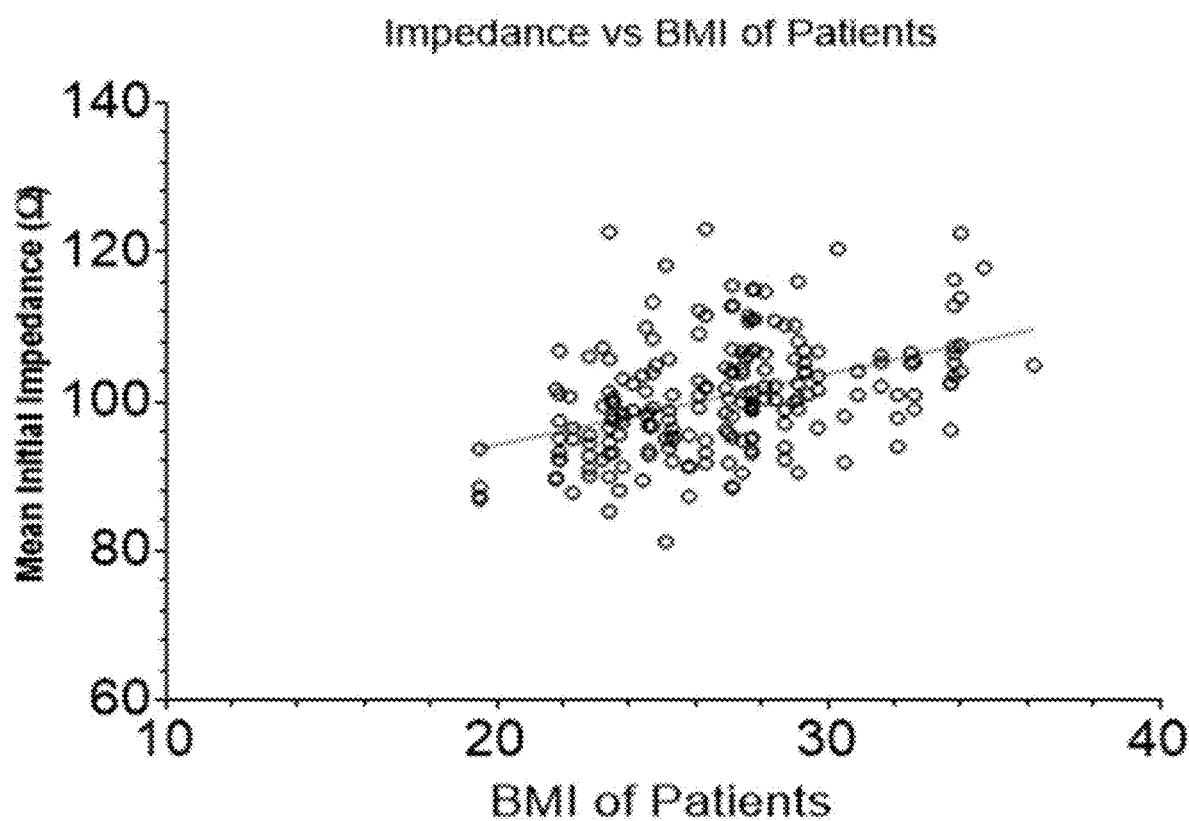
FIG. 38 shows a graph summarizing correlations between mean initial impedance and body mass index (BMI) of patients in the study of this disclosure.
Figure 39:
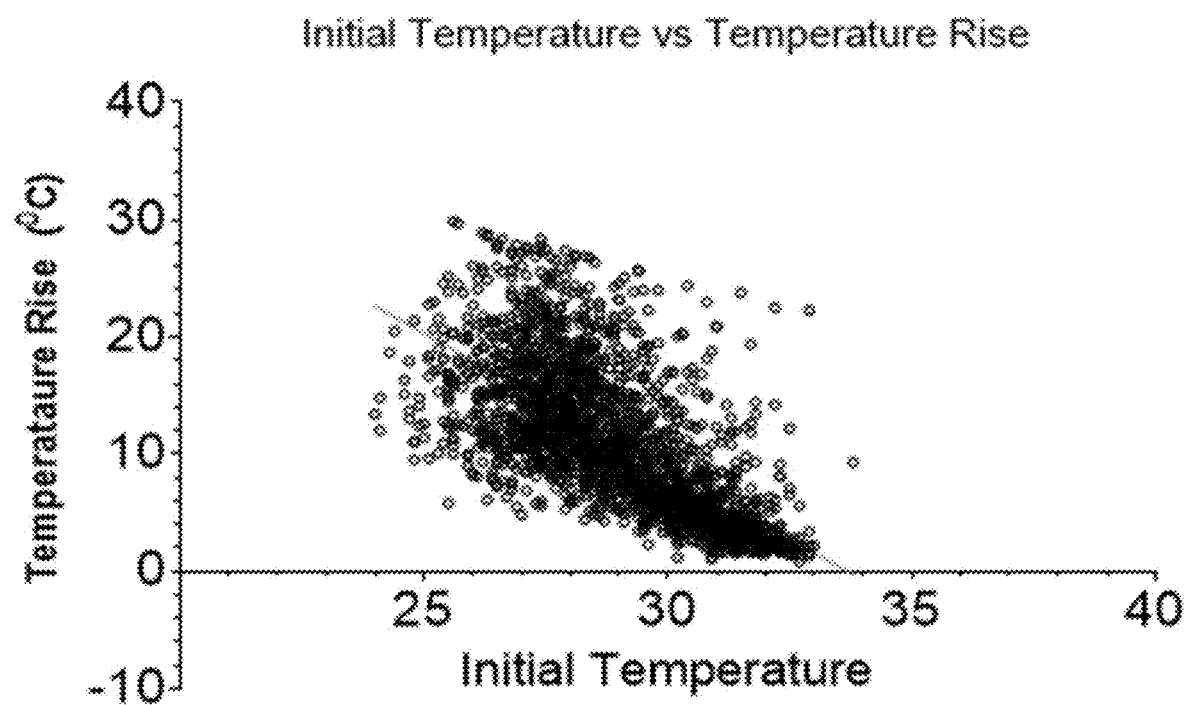
FIG. 39 shows a graph summarizing correlations between initial temperature and temperature rise in the study of this disclosure.
Figure 40:
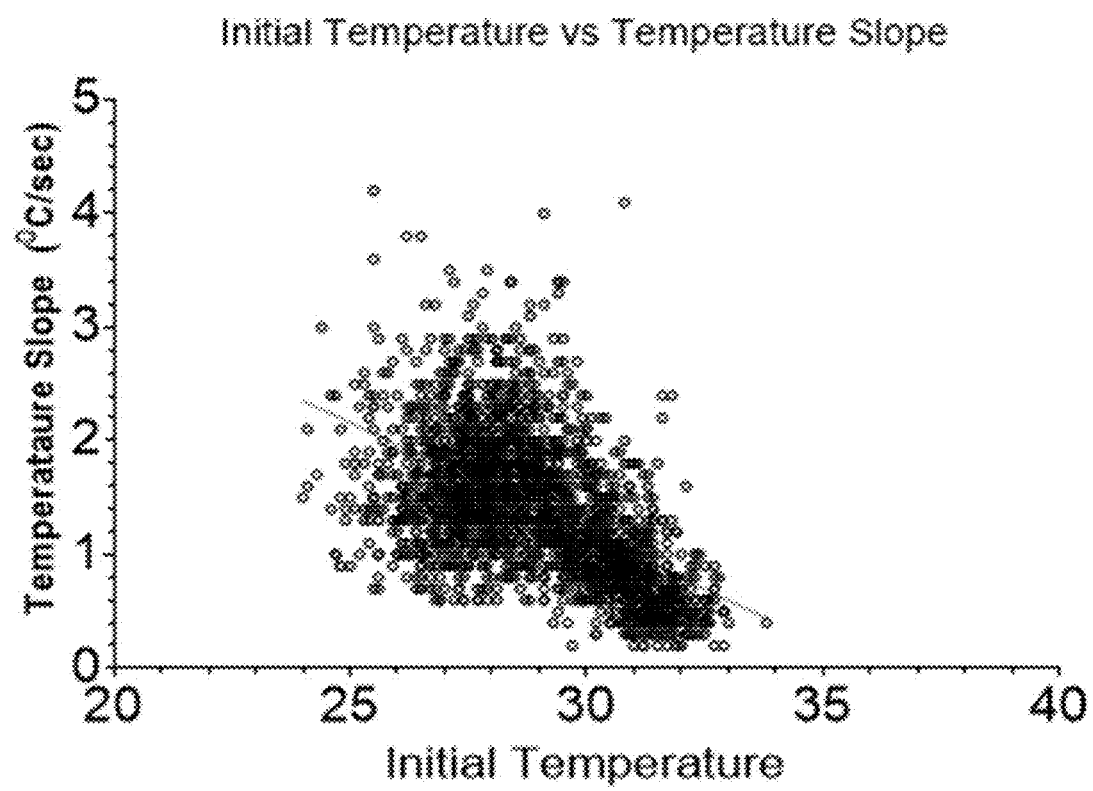
FIG. 40 shows a graph summarizing correlations between initial temperature and temperature slope in the study of this disclosure.
Figure 41:
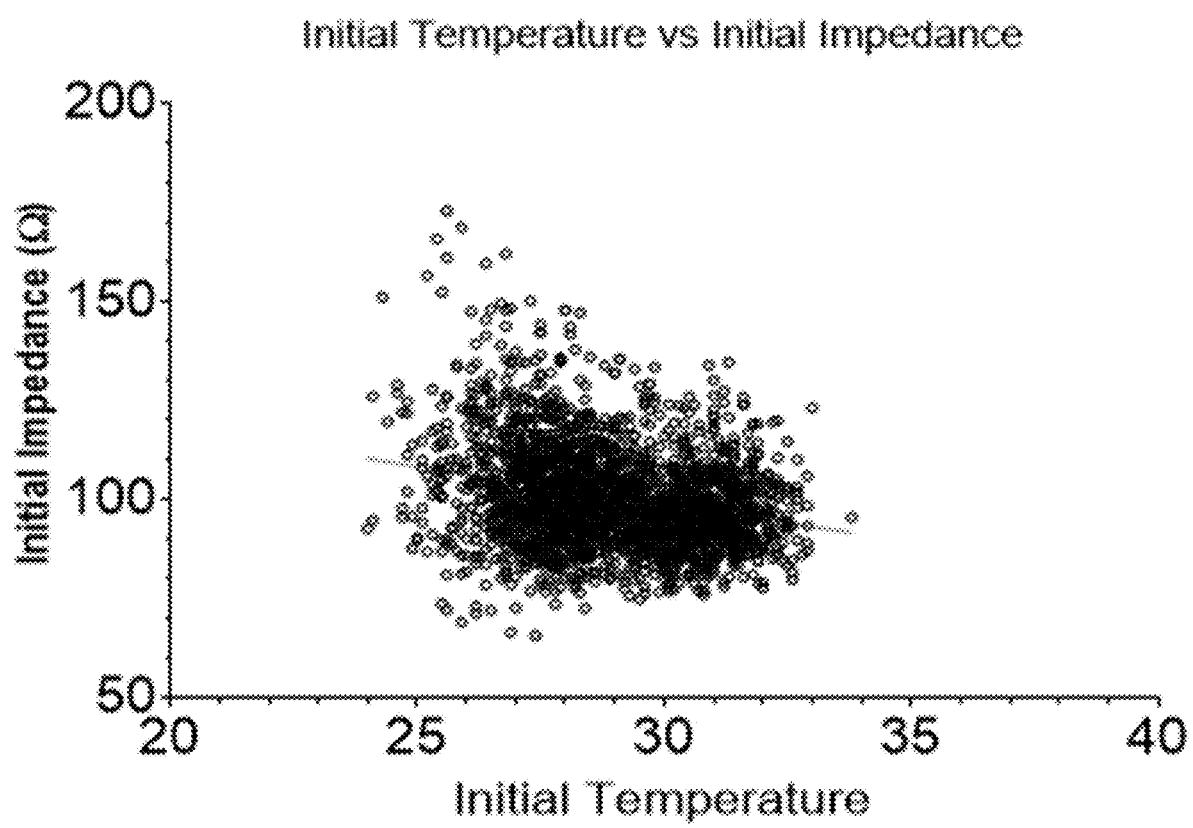
FIG. 41 shows a graph summarizing correlations between initial temperature and initial impedance in the study of this disclosure.
Figure 42:
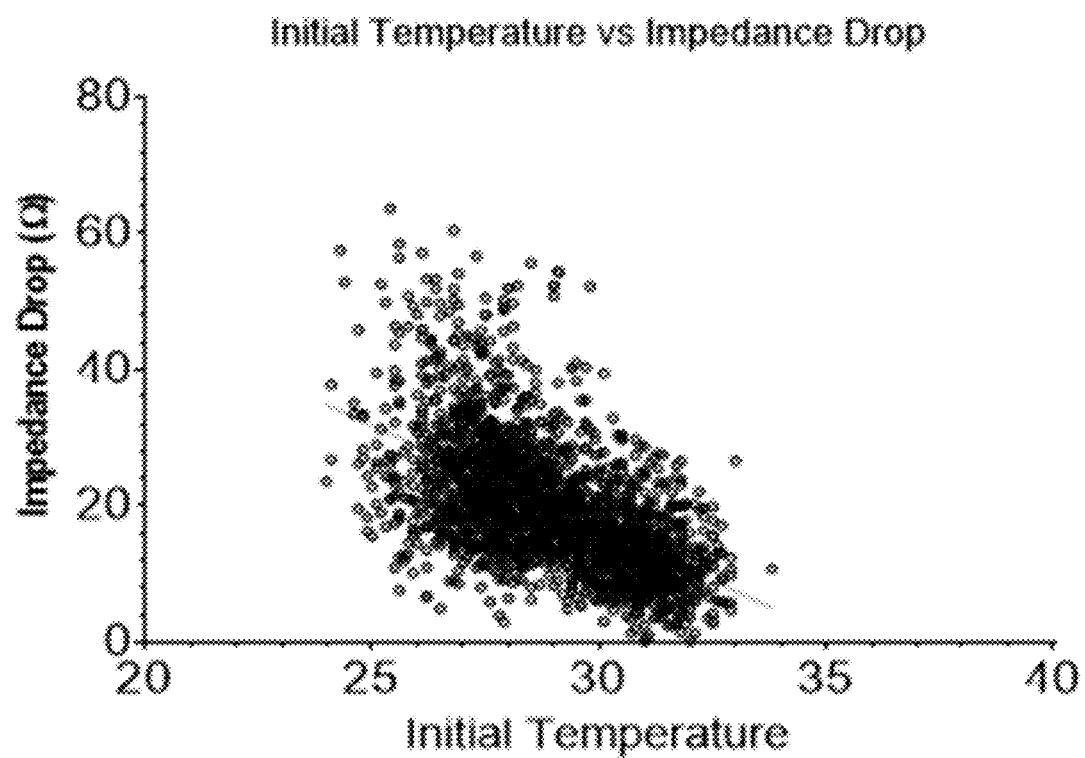
FIG. 42 shows a graph summarizing correlations between initial temperature and impedance drop in the study of this disclosure.
Figure 43:
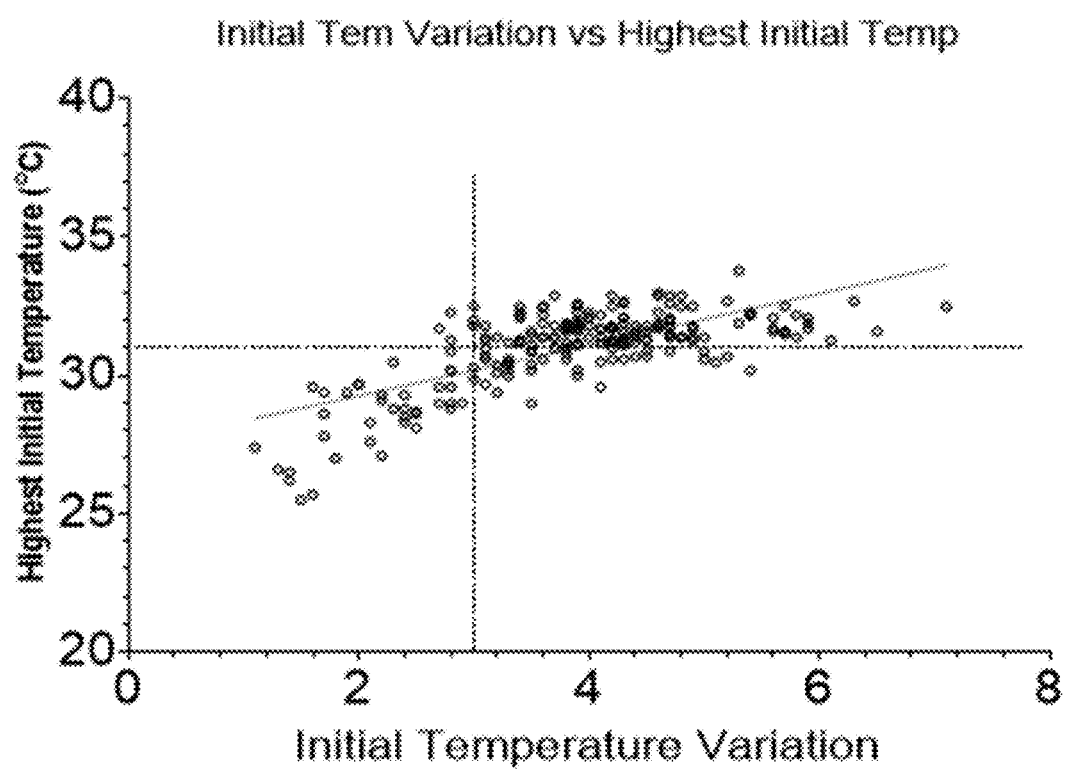
FIG. 43 shows a graph summarizing correlations between initial temperature variation and highest initial temperature in the study of this disclosure.
Figure 44:
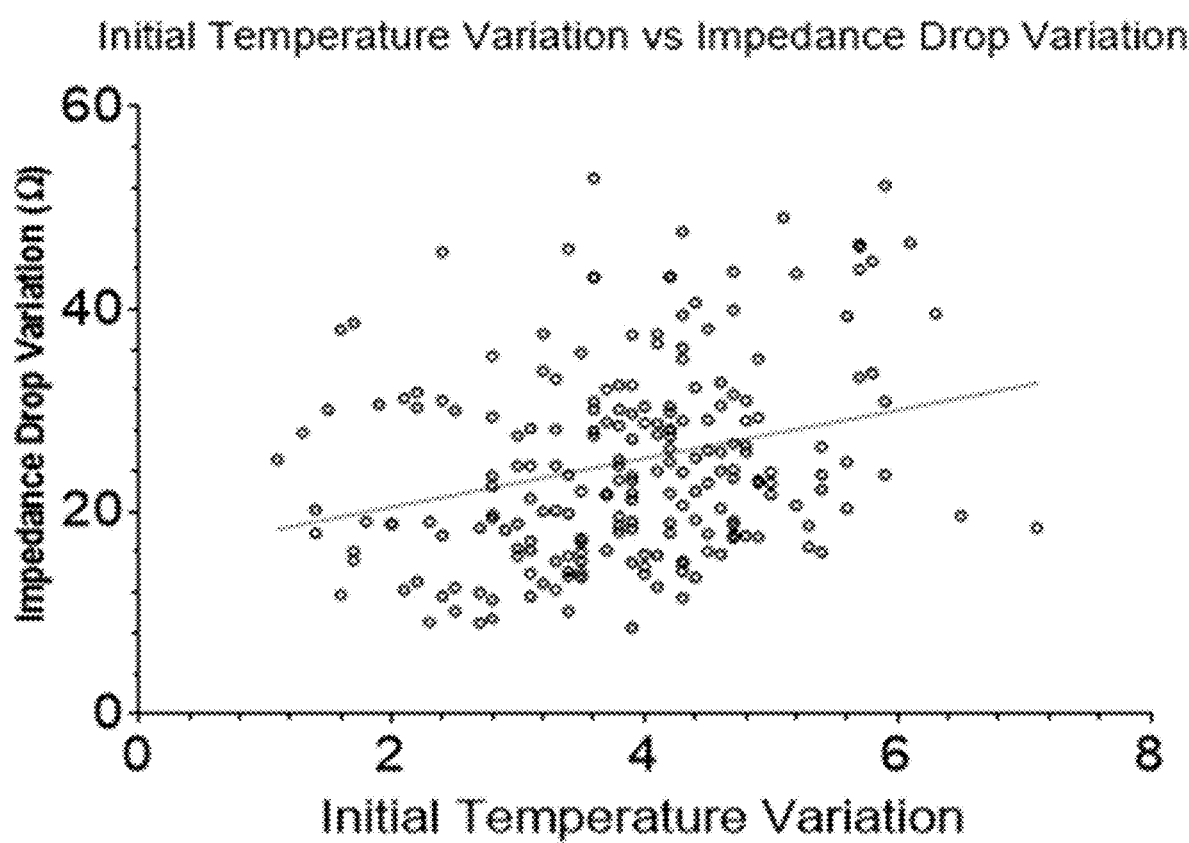
FIG. 44 shows a graph summarizing correlations between initial temperature variation and impedance drop variation in the study of this disclosure.
Figure 45:
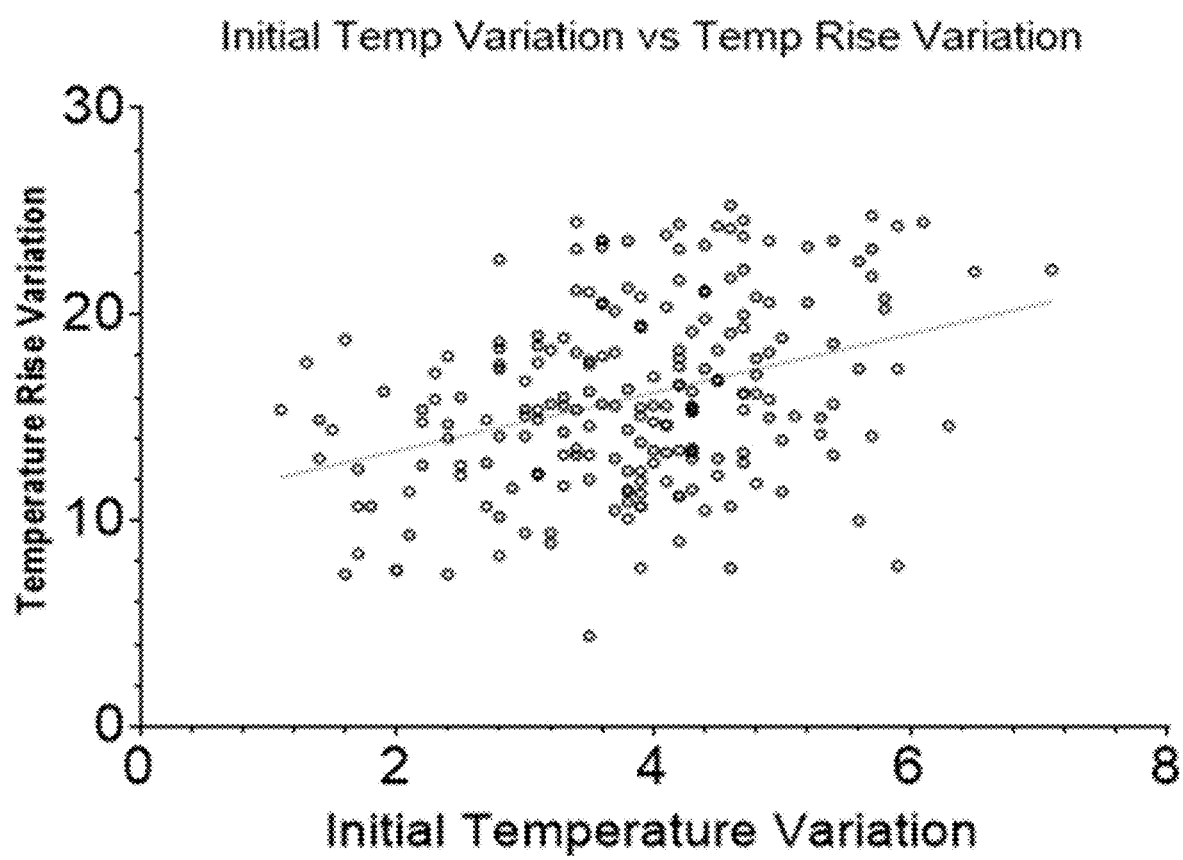
FIG. 45 shows a graph summarizing correlations between initial temperature variation and temperature rise variation in the study of this disclosure.

FIG. 37 shows a graph summarizing correlations between mean initial impedance and age of patients in the study of this disclosure. FIG. 38 shows a graph summarizing correlations between mean initial impedance and BMI of patients in the study of this disclosure. FIG. 39 shows a graph summarizing correlations between initial temperature and temperature rise in the study of this disclosure. FIG. 40 shows a graph summarizing correlations between initial temperature and temperature slope in the study of this disclosure. FIG. 41 shows a graph summarizing correlations between initial temperature and initial impedance in the study of this disclosure. FIG. 42 shows a graph summarizing correlations between initial temperature and impedance drop in the study of this disclosure. FIG. 43 shows a graph summarizing correlations between initial temperature variation and highest initial temperature in the study of this disclosure. FIG. 44 shows a graph summarizing correlations between initial temperature variation and impedance drop variation in the study of this disclosure. FIG. 45 shows a graph summarizing correlations between initial temperature variation and temperature rise variation in the study of this disclosure.

Figure 46:
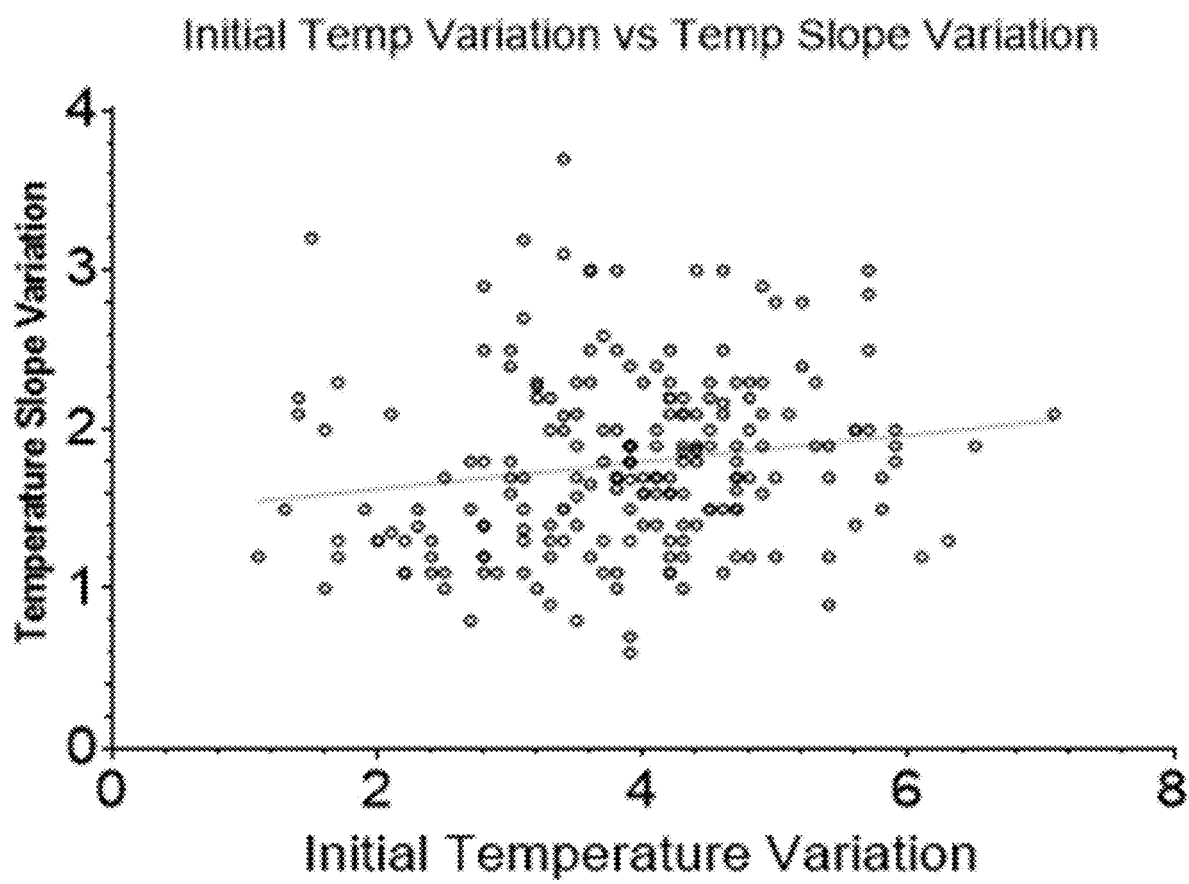
FIG. 46 shows a graph summarizing correlations between initial temperature variation and temperature slope variation in the study of this disclosure.
Figure 47:
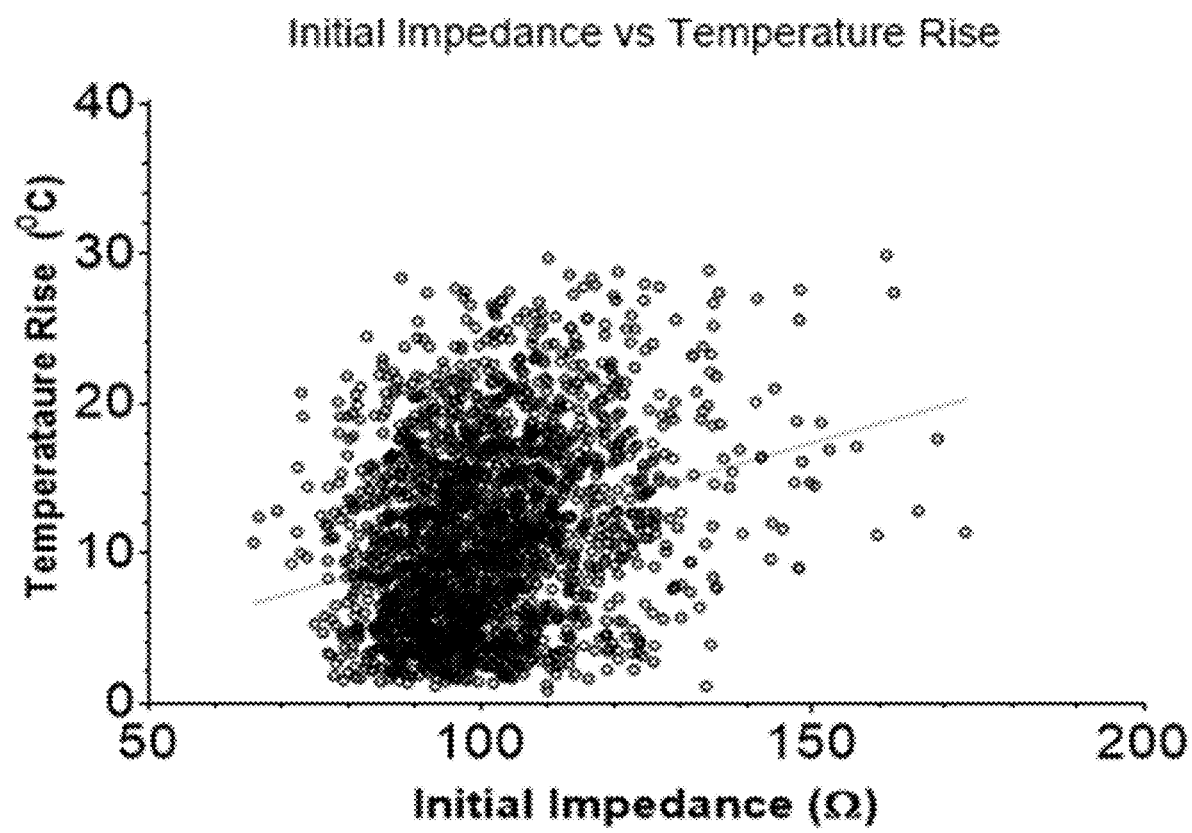
FIG. 47 shows a graph summarizing correlations between initial impedance and temperature rise in the study of this disclosure.
Figure 48:
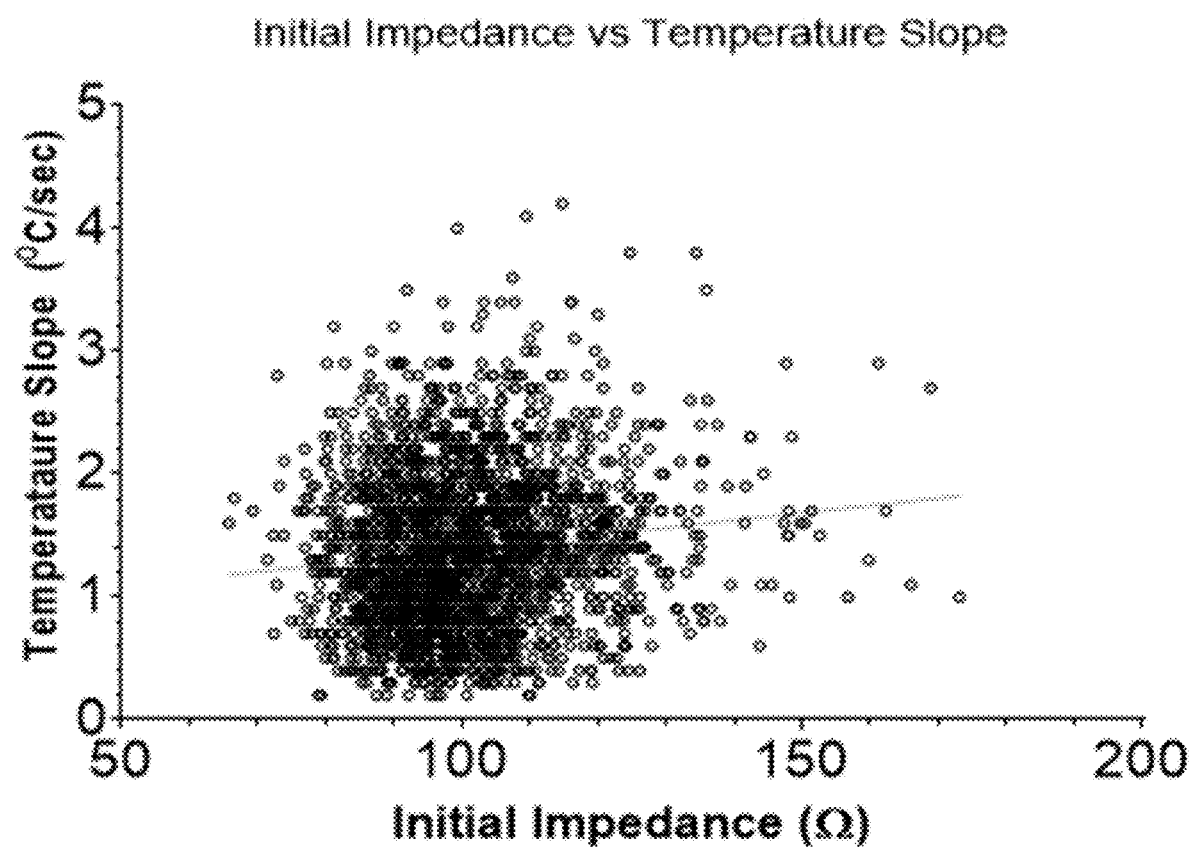
FIG. 48 shows a graph summarizing correlations between initial impedance and temperature slope in the study of this disclosure.
Figure 49:
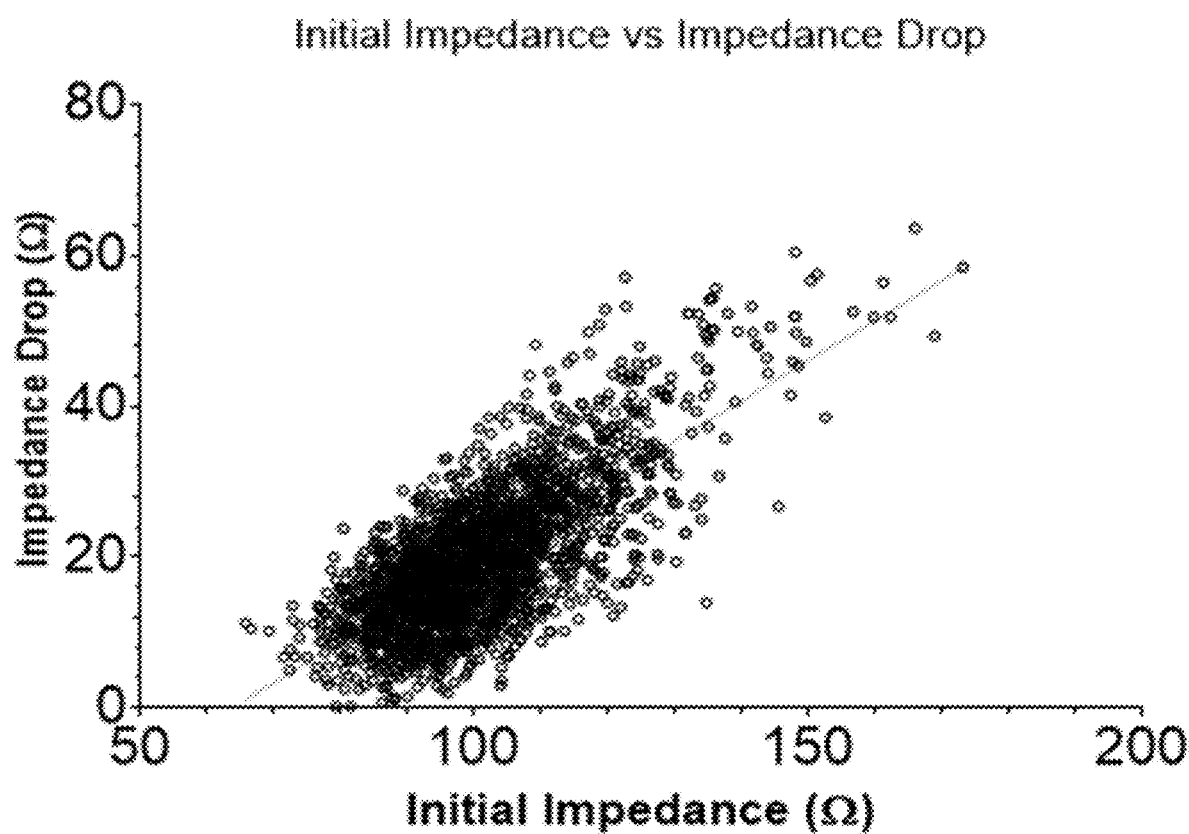
FIG. 49 shows a graph summarizing correlations between initial impedance and impedance drop in the study of this disclosure.
Figure 50:
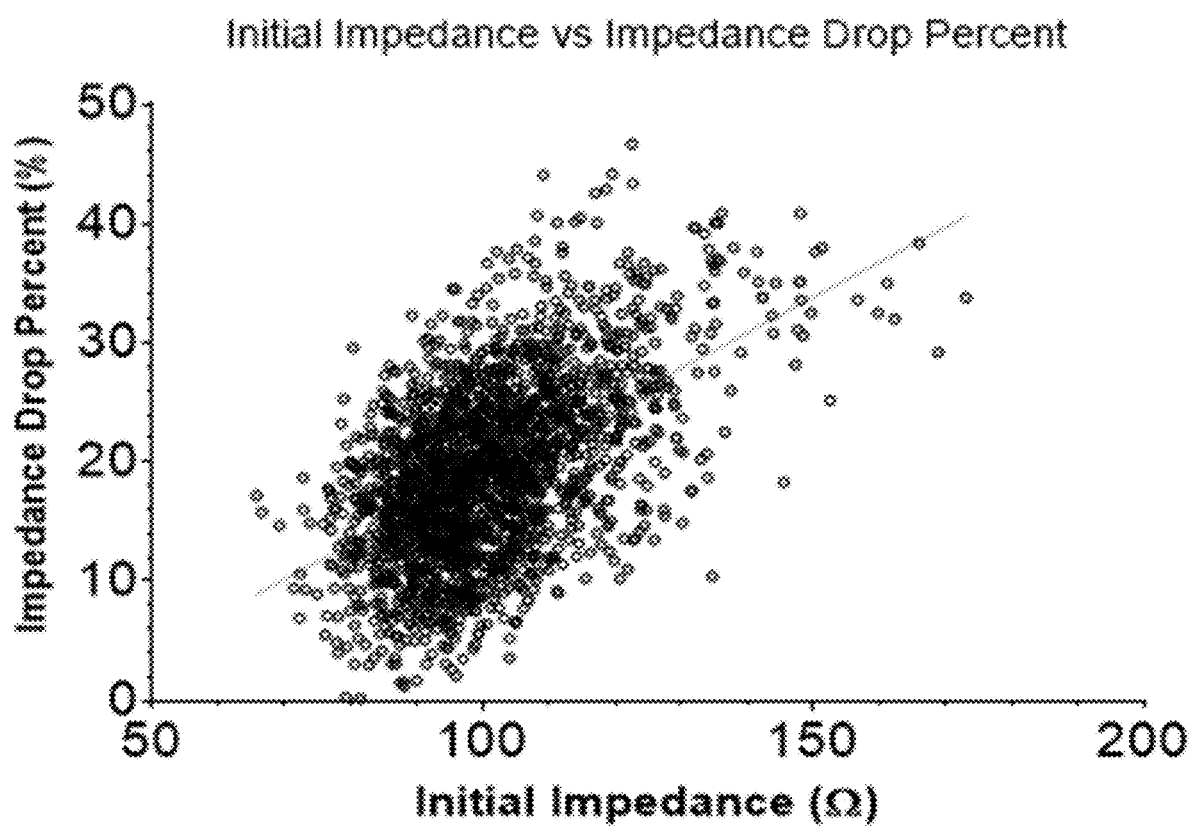
FIG. 50 shows a graph summarizing correlations between initial impedance and impedance drop percent in the study of this disclosure.
Figure 51:
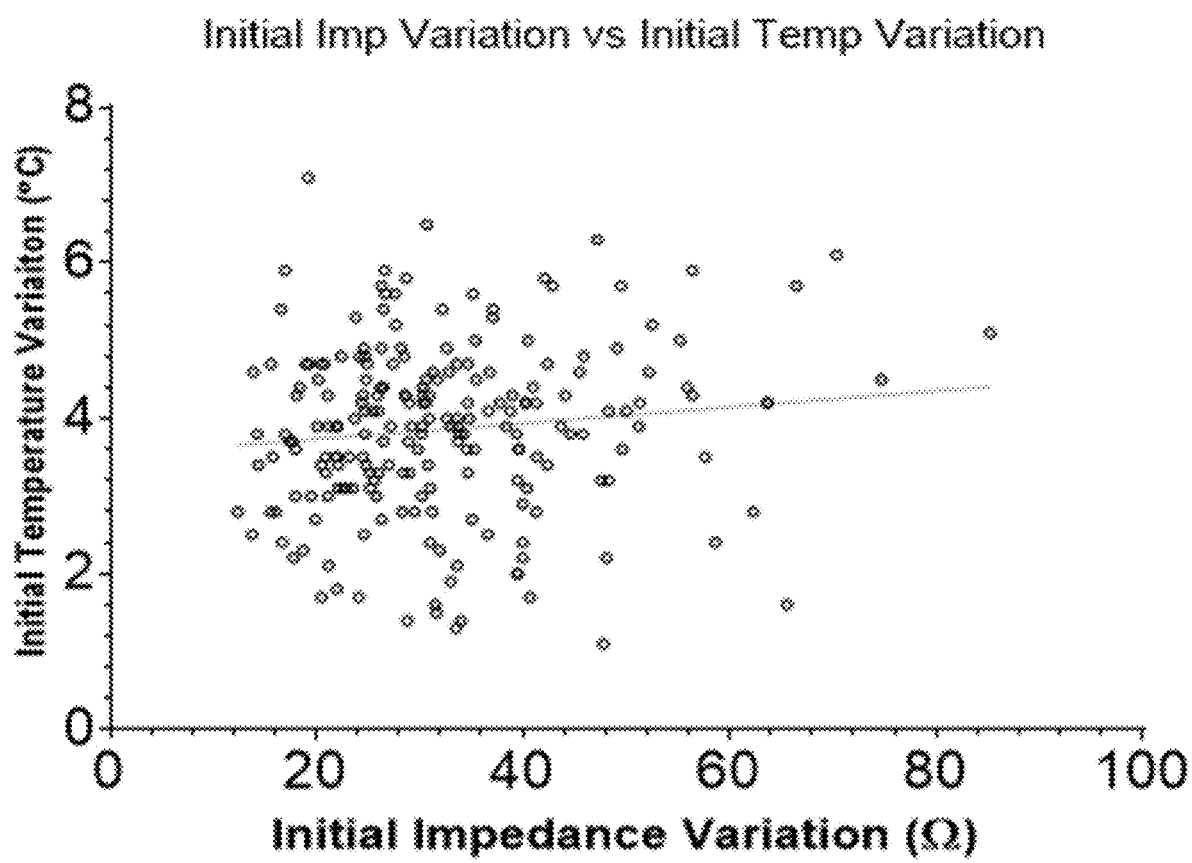
FIG. 51 shows a graph summarizing correlations between initial impedance variation and initial temperature variation in the study of this disclosure.
Figure 52:
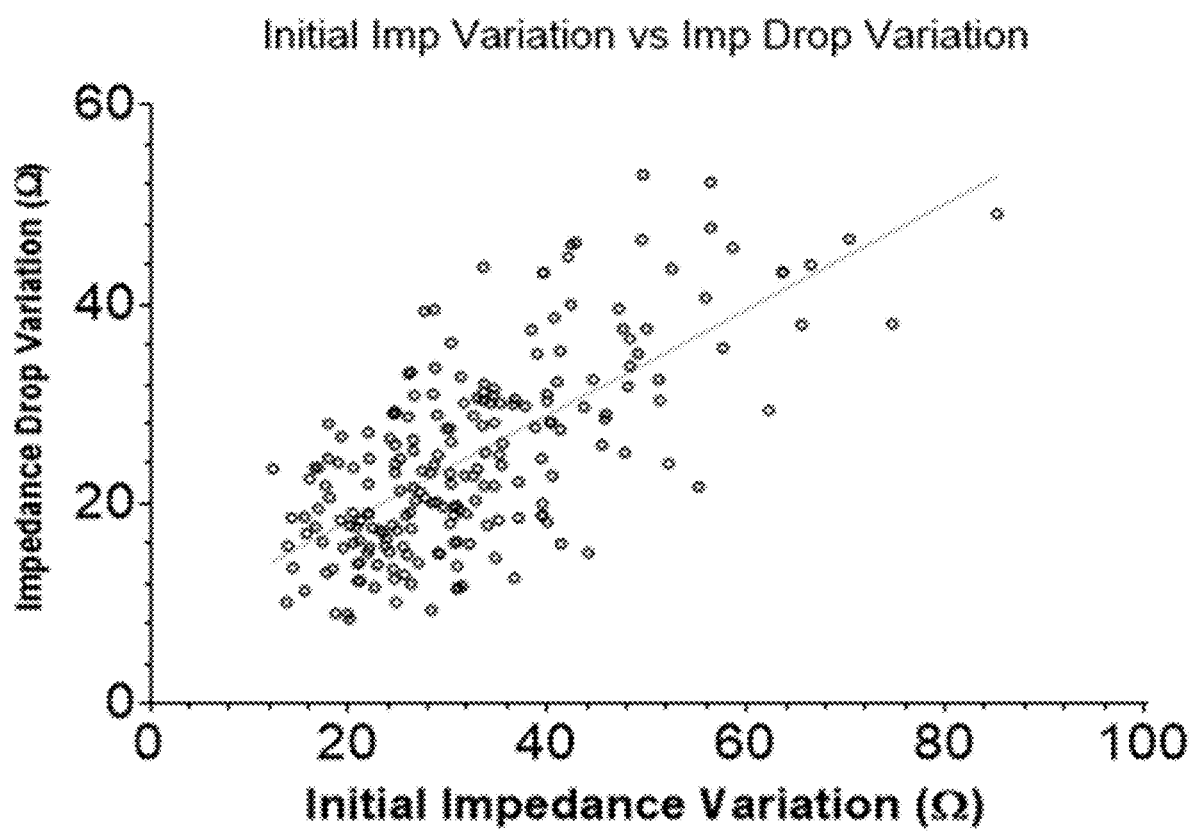
FIG. 52 shows a graph summarizing correlations between initial impedance variation and impedance drop variation in the study of this disclosure.
Figure 53:
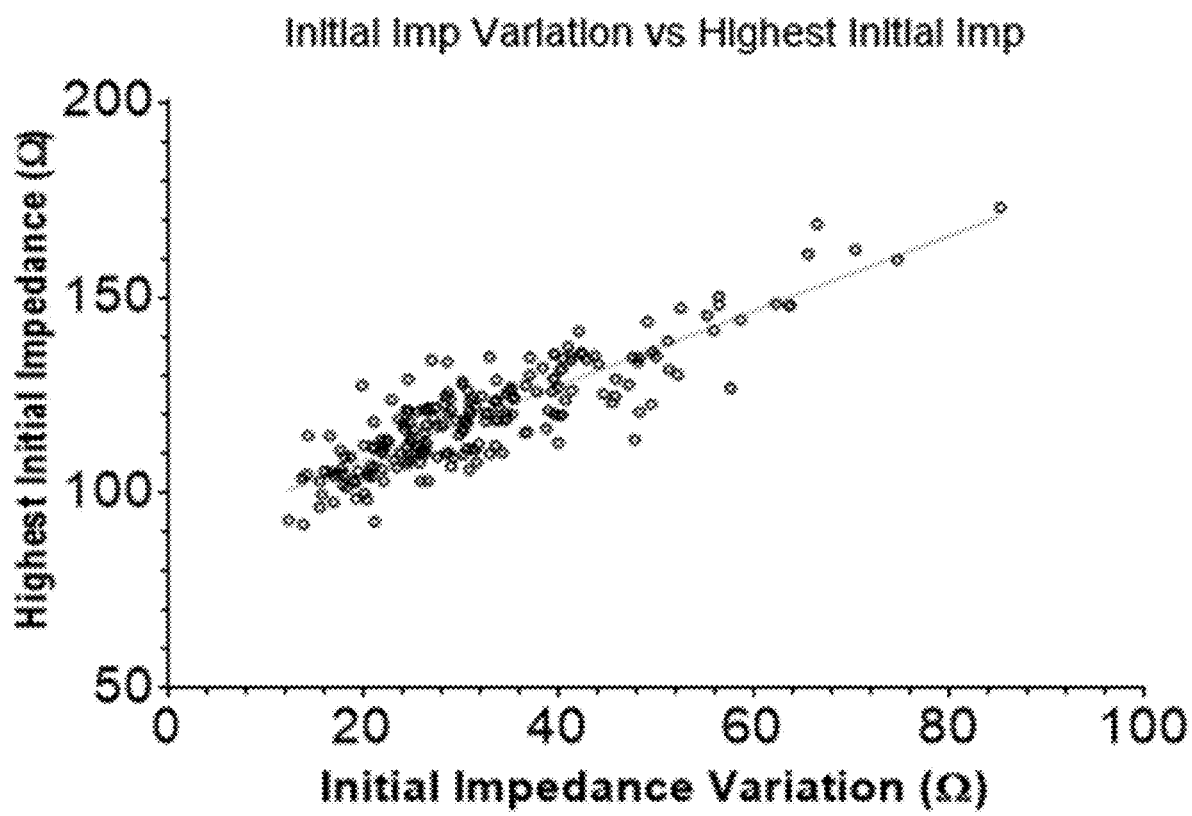
FIG. 53 shows a graph summarizing correlations between initial impedance variation and highest initial impedance in the study of this disclosure.
Figure 54:
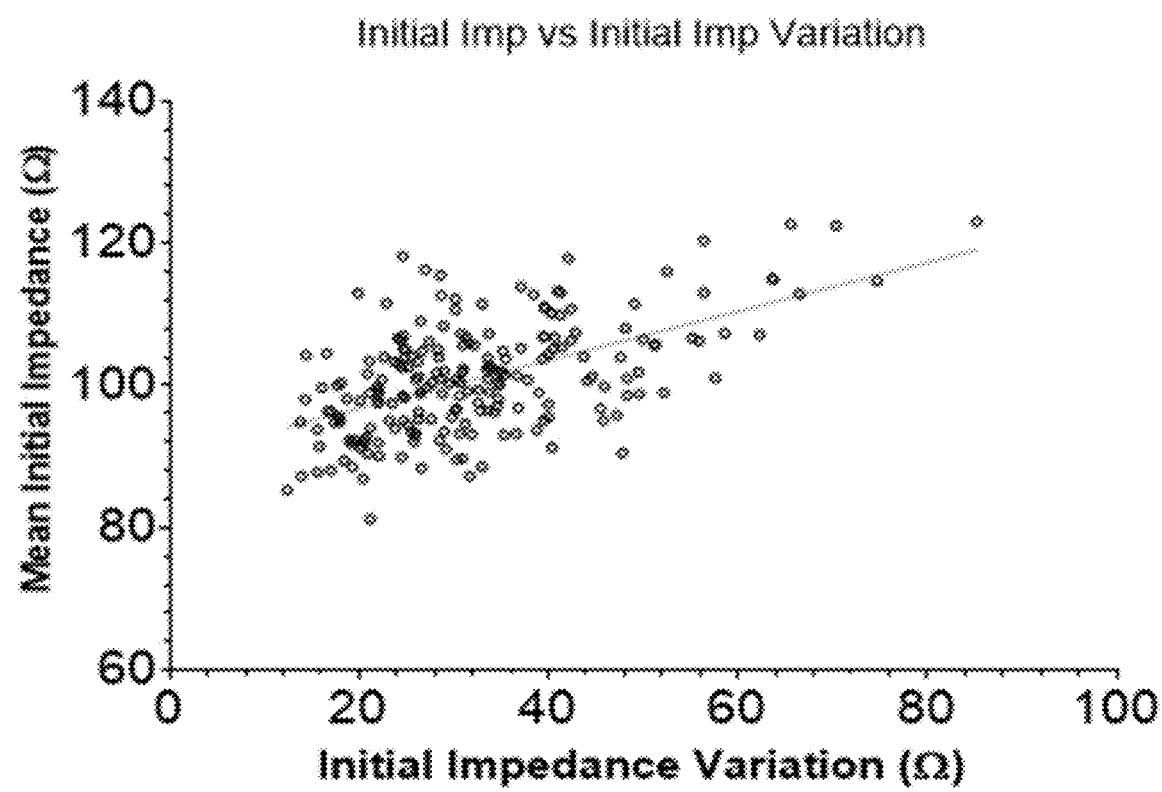
FIG. 54 shows a graph summarizing correlations between initial impedance variation and mean initial impedance in the study of this disclosure.

FIG. 46 shows a graph summarizing correlations between initial temperature variation and temperature slope variation in the study of this disclosure. FIG. 47 shows a graph summarizing correlations between initial impedance and temperature rise in the study of this disclosure. FIG. 48 shows a graph summarizing correlations between initial impedance and temperature slope in the study of this disclosure. FIG. 49 shows a graph summarizing correlations between initial impedance and impedance drop in the study of this disclosure. FIG. 50 shows a graph summarizing correlations between initial impedance and impedance drop percent in the study of this disclosure. FIG. 51 shows a graph summarizing correlations between initial impedance variation and initial temperature variation in the study of this disclosure. FIG. 52 shows a graph summarizing correlations between initial impedance variation and impedance drop variation in the study of this disclosure. FIG. 53 shows a graph summarizing correlations between initial impedance variation and highest initial impedance in the study of this disclosure. FIG. 54 shows a graph summarizing correlations between initial impedance variation and mean initial impedance in the study of this disclosure.

Figure 55:
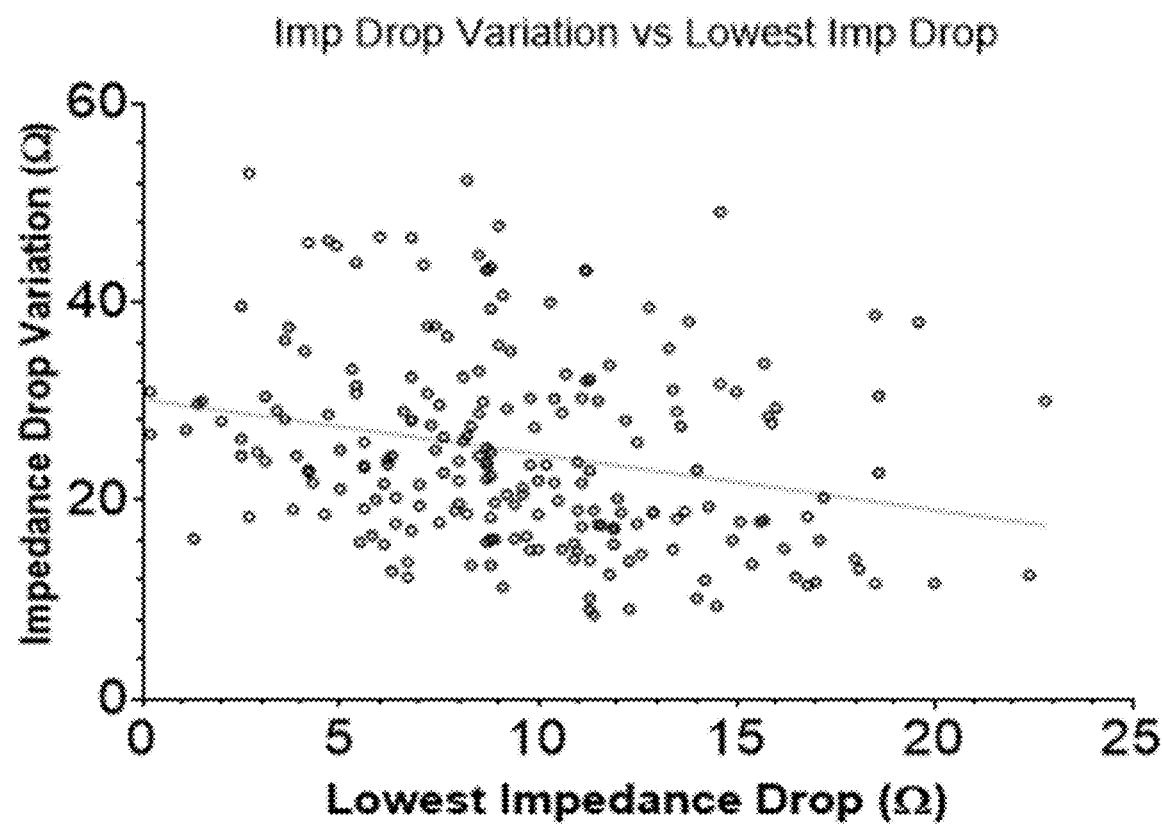
FIG. 55 shows a graph summarizing correlations between initial impedance variation and lowest impedance drop in the study of this disclosure.
Figure 56:
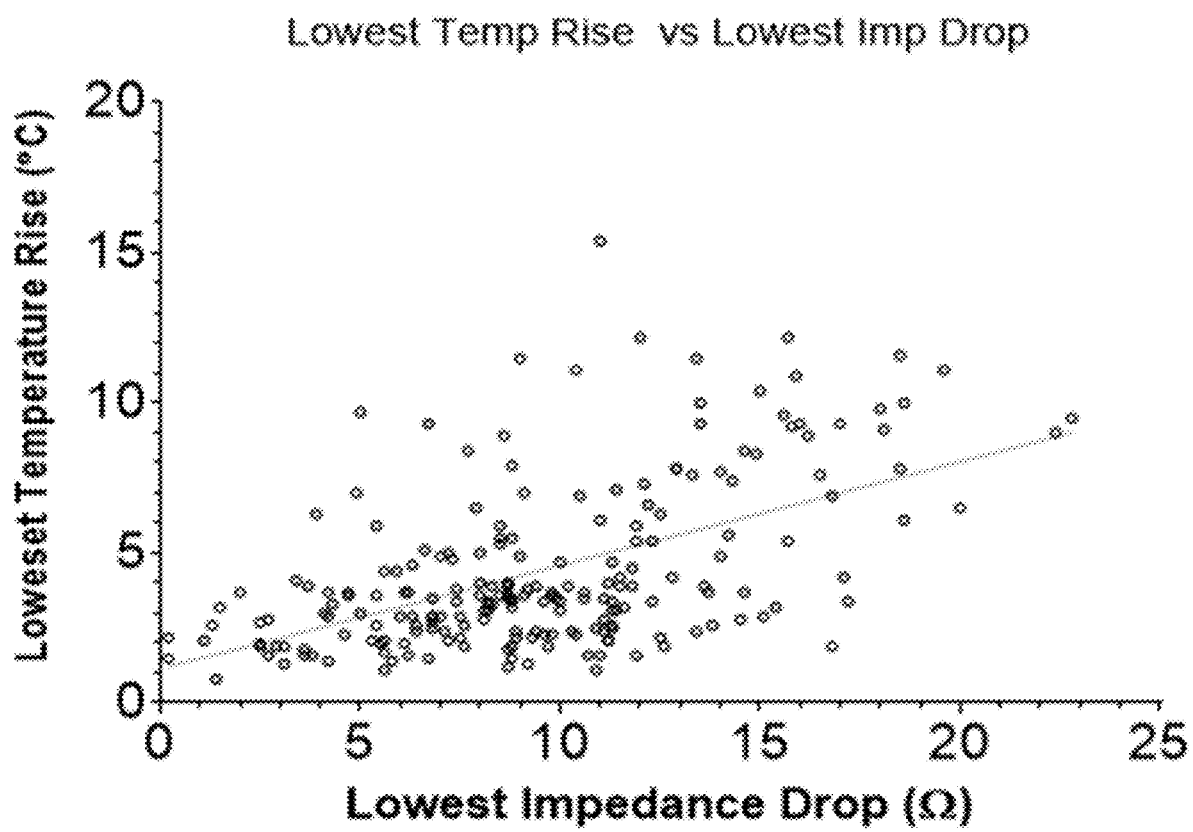
FIG. 56 shows a graph summarizing correlations between lowest temperature rise and lowest impedance drop in the study of this disclosure.
Figure 57:
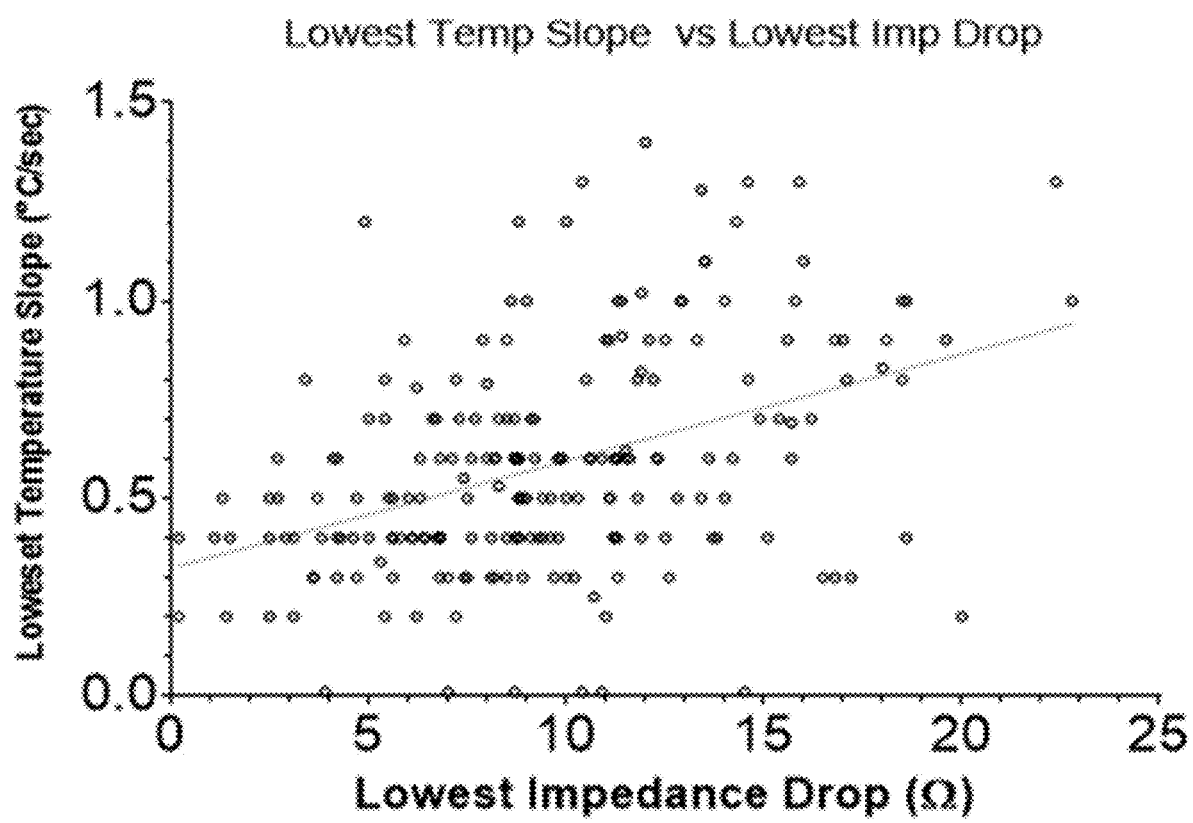
FIG. 57 shows a graph summarizing correlations between lowest impedance drop and lowest temperature slope in the study of this disclosure.
Figure 58:
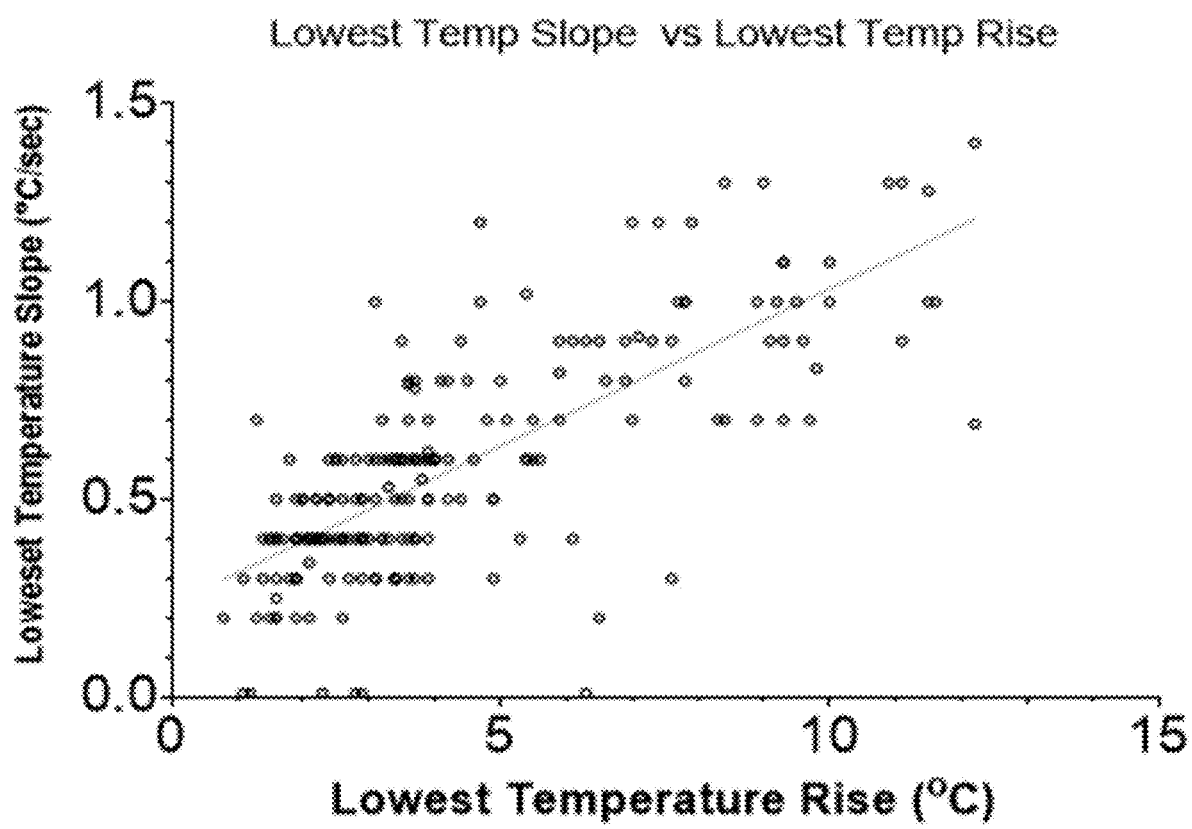
FIG. 58 shows a graph summarizing correlations between lowest temperature rise and lowest temperature slope in the study of this disclosure.

FIG. 55 shows a graph summarizing correlations between initial impedance variation and lowest impedance drop in the study of this disclosure. FIG. 56 shows a graph summarizing correlations between lowest temperature rise and lowest impedance drop in the study of this disclosure. FIG. 57 shows a graph summarizing correlations between lowest impedance drop and lowest temperature slope in the study of this disclosure. FIG. 58 shows a graph summarizing correlations between lowest temperature rise and lowest temperature slope in the study of this disclosure.

Figure 59:
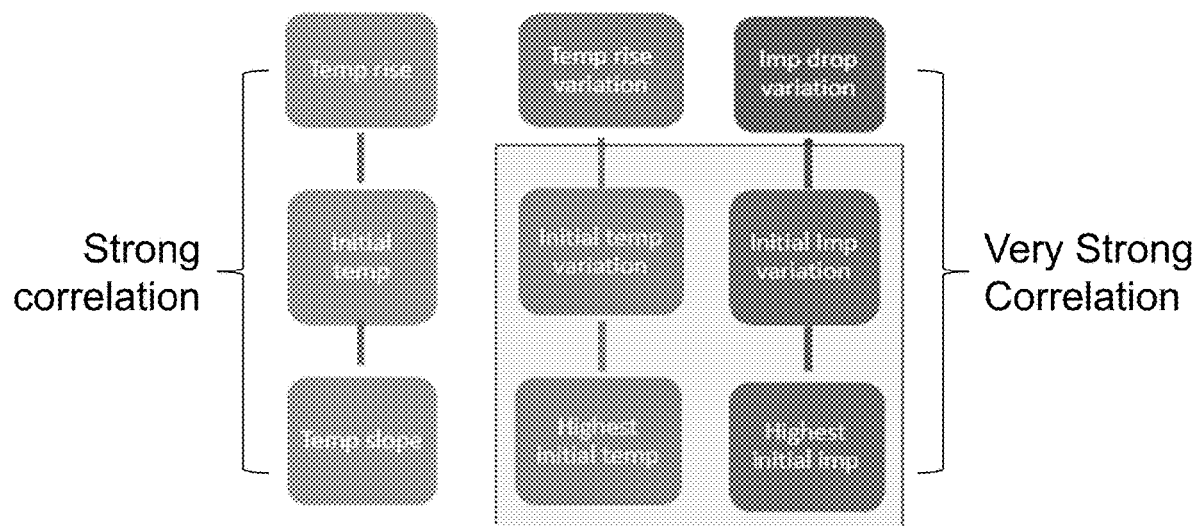
FIG. 59 shows a schematic summarizing correlative data sets for single-shot isolation predictors according to the study of this disclosure.

FIG. 59 shows a schematic summarizing correlative data sets for single-shot isolation predictors according to the study of this disclosure. In particularly, FIG. 59 demonstrates that pre-ablation parameter data sets such as temperature rise, initial temperature, and temperature slope were deemed to have strong correlations to single-shot isolation predictors for single-shot isolation. Similarly, FIG. 59 demonstrates that pre-ablation parameter data sets such as impedance drop variation, initial impedance variation, and highest initial impedance were deemed to have very strong correlations to single-shot isolation predictors for single-shot isolation. It is contemplated that the solution of this disclosure may use multiple parameters (as opposed to a single-parameter for predictor and evaluator referenced in the Table) such as, for example, initial temperature variation, highest initial temperature, initial impedance variation, and highest initial impedance as pre-ablation predictors of single-shot isolation. Table 2 summarizes the parameters utilized for the multi-parameter predictors and evaluators.

TABLE 2

MULTIPLE-PARAMETERS PREDICTORS AND EVALUATORS

| | | Combination of multiple parameters | |
|---|---|---|---|
| | | Temperature parameter | Impedance parameter |
| Predictor | Predictor-1 | Initial temperature variation | Initial impedance variation |
| | Predictor-2 | | Highest initial impedance |
| | Predictor-3 | | Mean initial impedance |
| | Predictor-4 | Highest initial temperature | Initial impedance variation |
| | Predictor-5 | | Highest initial impedance |
| | Predictor-6 | | Mean initial impedance |
| | Predictor-7 | Initial temperature variation & Highest initial temperature | initial impedance variation & Highest initial impedance |
| Evaluator | Evaluator-1 | Lowest Temperature rise | Impedance drop variation |
| | Evaluator-2 | | Lowest impedance drop |
| | Evaluator-3 | | Lowest impedance drop & impedance drop variation |
| | Evaluator-4 | | impedance drop percent variation |
| | Evaluator-5 | | Lowest impedance drop percent |
| | Evaluator-6 | | Lowest impedance drop percent & impedance drop percent variation |

Figure 60:
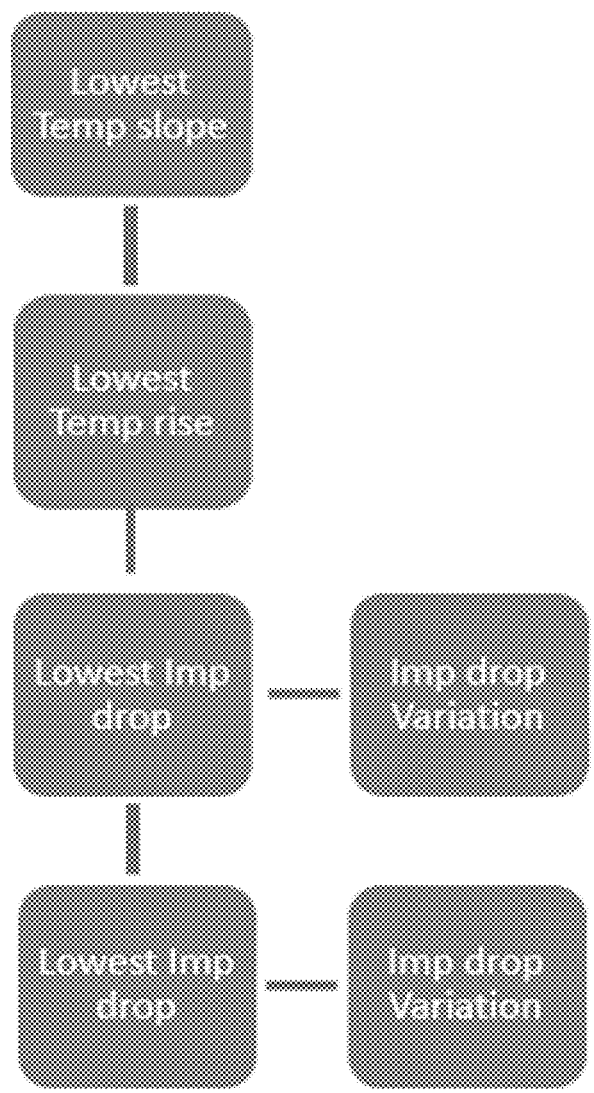
FIG. 60 shows a schematic summarizing correlative data sets for single-shot isolation evaluators according to the study of this disclosure.

FIG. 60 shows a schematic summarizing correlative data sets for single-shot isolation evaluators according to the study of this disclosure. FIG. 60 demonstrates that post-ablation parameter data sets such as lowest temperature slope, lowest temperature rise, lowest impedance drop, impedance drop variation, lowest impedance drop, and impedance drop variation were deemed to have strong correlations to single-shot isolation evaluators for single-shot isolation. It is contemplated that the solution of this disclosure may use one or more of these parameters as post-ablation evaluators of single-shot isolation. Taking into account the foregoing, one example algorithm that is contemplated for use as a predictor of single shot isolation includes the following:

$$\text{Probability} \sim \frac{e^Y}{(1+e^Y)}$$

$$Y \sim 4.367 - 0.420\Delta T_0 - 0.0486\Delta Z_0$$

Where single shot isolation probability is a function of two parameters: initial impedance variation ($\Delta T_0$) and initial temperature variation ($\Delta Z_0$).

Figures 61A, 61B, 61C:
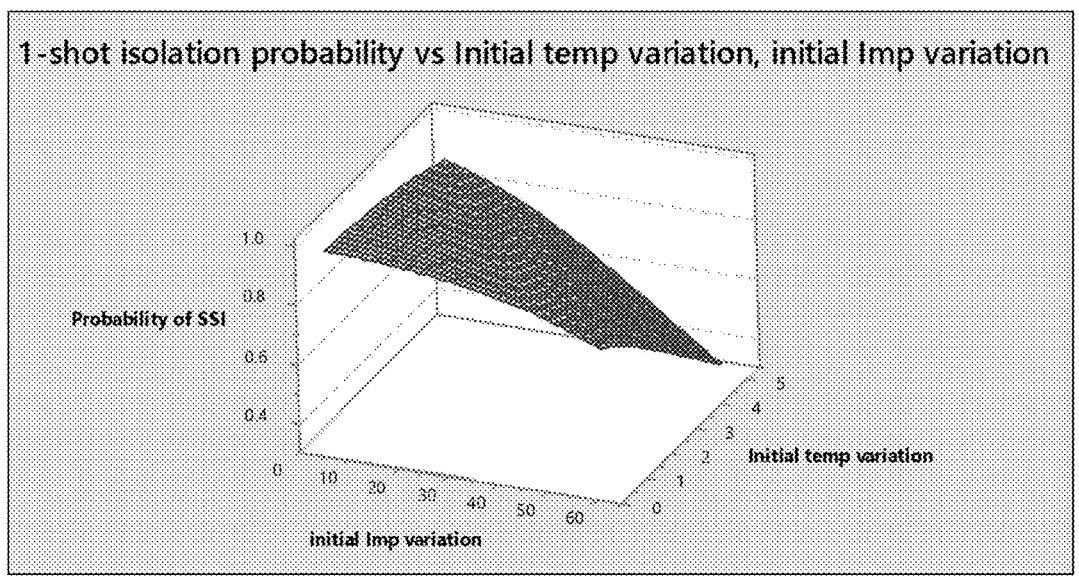
FIG. 61A shows a computer simulation model executing one example predictor function.
FIG. 61B shows a table summarizing data associated with the simulation of FIG. 61A.
FIG. 61C shows a table summarizing data associated with the simulation of FIG. 61A.

FIG. 61A shows a computer simulation model executing the aforementioned single shot isolation probability algorithm while FIGS. 61B-61C show tables summarizing data associated with the simulation of FIG. 61A.

Figures 62A, 62B, 62C:
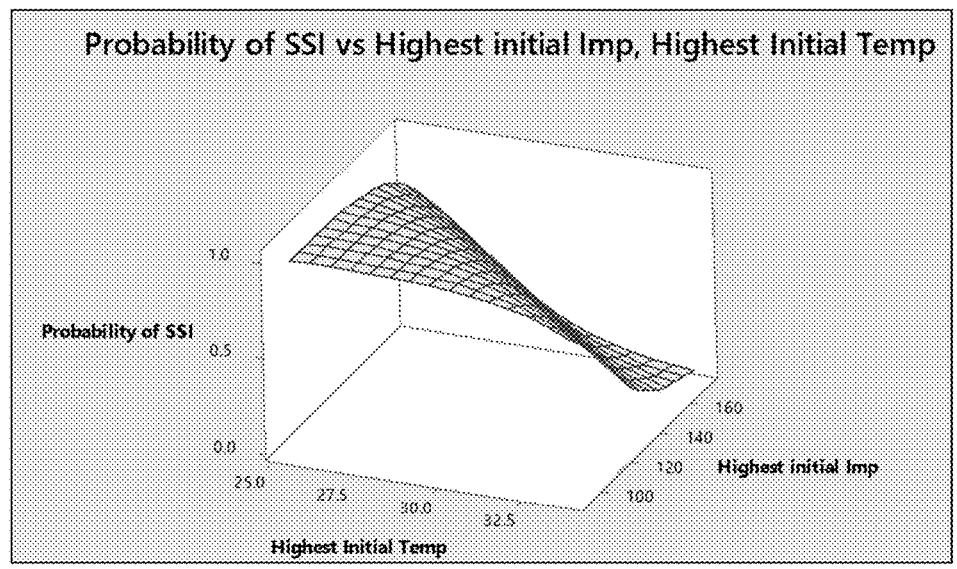
FIG. 62A shows a computer simulation model executing one example predictor function.
FIG. 62B shows a table summarizing data associated with the simulation of FIG. 62A.
FIG. 62C shows a table summarizing data associated with the simulation of FIG. 62A.

Another example algorithm contemplated for use as a predictor of single shot isolation includes the following:

$$Prob \sim \frac{e^Y}{(1+e^Y)}$$

$$Y \sim 26.78 - 0.576 T_{0max} - 0.0632 Z_{0max}$$

Where the predictor algorithm includes two parameters: highest initial temperature ($T_{0max}$) and highest initial impedance ($Z_{0max}$). FIG. 62A shows a computer simulation model executing the aforementioned example algorithm while FIGS. 62B-62C show tables summarizing data associated with the simulation of FIG. 62A.

Figures 63A, 63B, 63C:
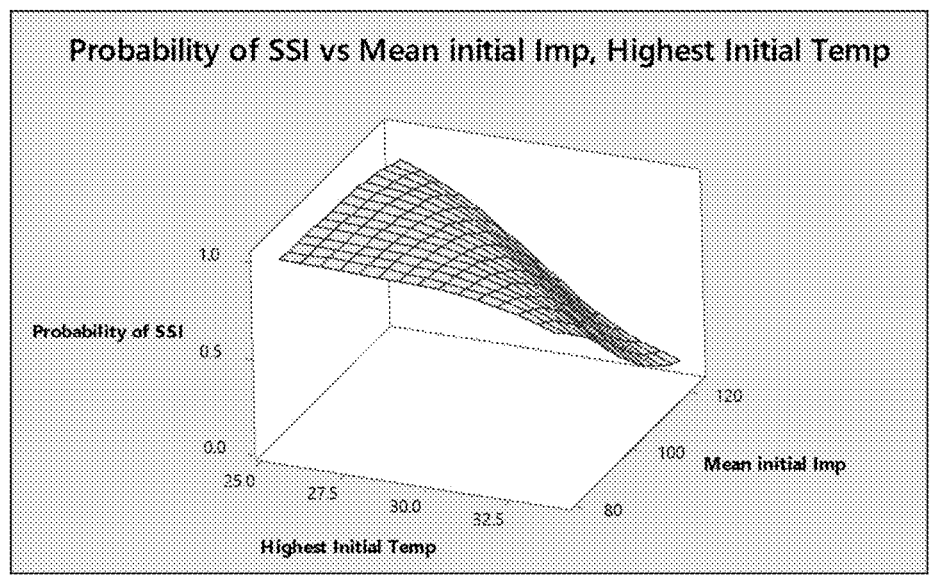
FIG. 63A shows a computer simulation model executing one example predictor function.
FIG. 63B shows a table summarizing data associated with the simulation of FIG. 63A.
FIG. 63C shows a table summarizing data associated with the simulation of FIG. 63A.

Another example algorithm contemplated for use as a predictor of single shot isolation includes the following:

$$Prob \sim \frac{e^Y}{(1+e^Y)}$$

$$Y \sim 27.70 - 0.540 T_{0max} - 0.0959 Z_{0max}$$

Where the predictor algorithm includes two parameters: highest initial temperature ($T_{0max}$) and highest initial impedance ($Z_{0max}$). FIG. 63A shows a computer simulation model executing the aforementioned example algorithm while FIGS. 63B-63C show tables summarizing data associated with the simulation of FIG. 63A.

Figures 64A, 64B, 64C:
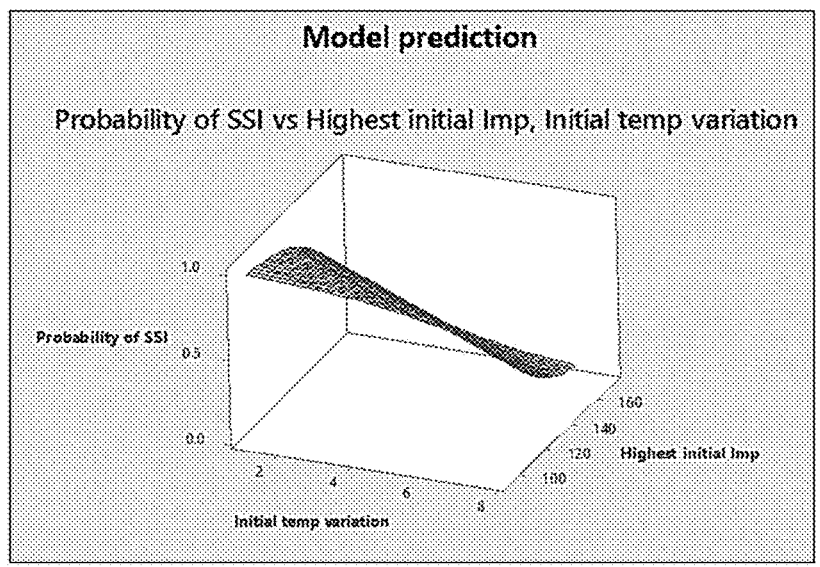
FIG. 64A shows a computer simulation model executing one example predictor function.
FIG. 64B shows a table summarizing data associated with the simulation of FIG. 64A.
FIG. 64C shows a table summarizing data associated with the simulation of FIG. 64A.

Another example algorithm contemplated for use as a predictor of single shot isolation includes the following:

$$Prob \sim \frac{e^Y}{(1+e^Y)}$$

$$Y \sim 9.31 - 0.408 \Delta T_0 - 0.0544 Z_{0max}$$

Where the predictor algorithm includes two parameters: initial temperature variation ($\Delta T_0$) and highest initial impedance ($Z_{0max}$). FIG. 64A shows a computer simulation model executing the aforementioned example algorithm while FIGS. 64B-64C show tables summarizing data associated with the simulation of FIG. 64A.

Figures 65A, 65B, 65C:
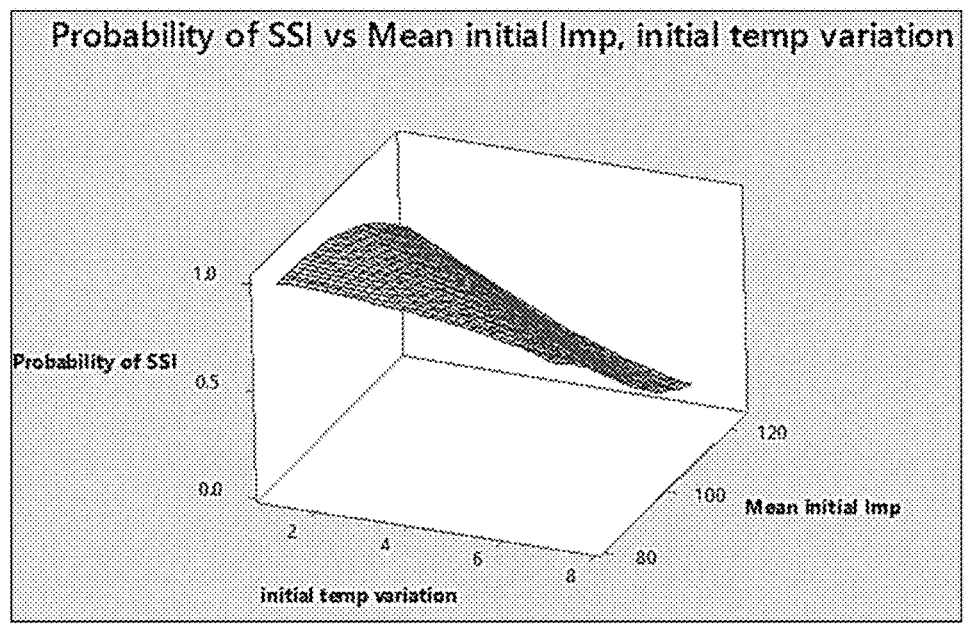
FIG. 65A shows a computer simulation model executing one example predictor function.
FIG. 65B shows a table summarizing data associated with the simulation of FIG. 65A.
FIG. 65C shows a table summarizing data associated with the simulation of FIG. 65A.

Another example algorithm contemplated for use as a predictor of single shot isolation includes the following:

$$Prob \sim \frac{e^Y}{(1+e^Y)}$$

$$Y \sim 11.53 - 0.439 \Delta T_0 - 0.0856 Z_{0mean}$$

Where the predictor algorithm includes two parameters: initial temperature variation ($\Delta T_0$) and mean initial impedance ($Z_{0mean}$). FIG. 65A shows a computer simulation model executing the aforementioned example algorithm while FIGS. 65B-65C show tables summarizing data associated with the simulation of FIG. 65A.

Figures 66A, 66B, 66C:
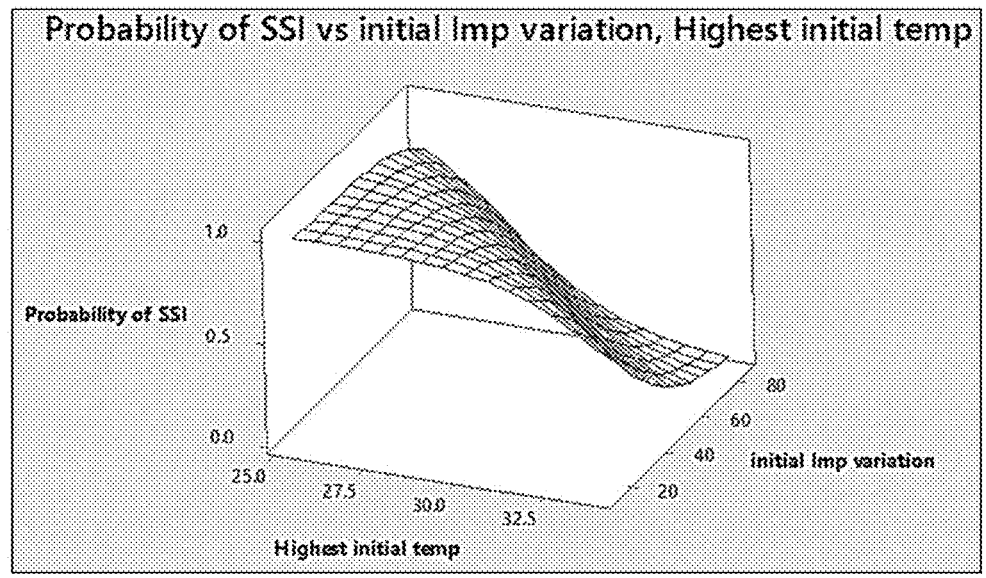
FIG. 66A shows a computer simulation model executing one example predictor function.
FIG. 66B shows a table summarizing data associated with the simulation of FIG. 66A.
FIG. 66C shows a table summarizing data associated with the simulation of FIG. 66A.

Another example algorithm contemplated for use as a predictor of single shot isolation includes the following:

$$Prob \sim \frac{e^Y}{(1+e^Y)}$$

$$Y \sim 22.61 - 0.622 T_{0max} - 0.0626 \Delta Z_0$$

Where the predictor algorithm includes two parameters: highest initial temperature ($T_{0max}$) and initial impedance variation ($\Delta Z_0$). FIG. 66A shows a computer simulation model executing the aforementioned example algorithm while FIGS. 66B-66C show tables summarizing data associated with the simulation of FIG. 66A.

Another example algorithm contemplated for use as a predictor of single shot isolation includes the following:

$$Prob \sim \frac{e^Y}{(1+e^Y)}$$

$$Y \sim 26.52 + 0.013 \Delta T_0 - 0.594 T_{0max} - 0.0122 \Delta Z_0 - 0.0535 Z_{0max}$$

Where the predictor algorithm includes four parameters: initial temperature variation ($\Delta T_0$), highest initial temperature ($T_{0max}$), initial impedance variation ($\Delta Z_0$) and highest initial impedance ($Z_{0max}$). FIG. 67 shows a table summarizing data associated with a simulation of this example algorithm.

Figures 68A, 68B, 68C:
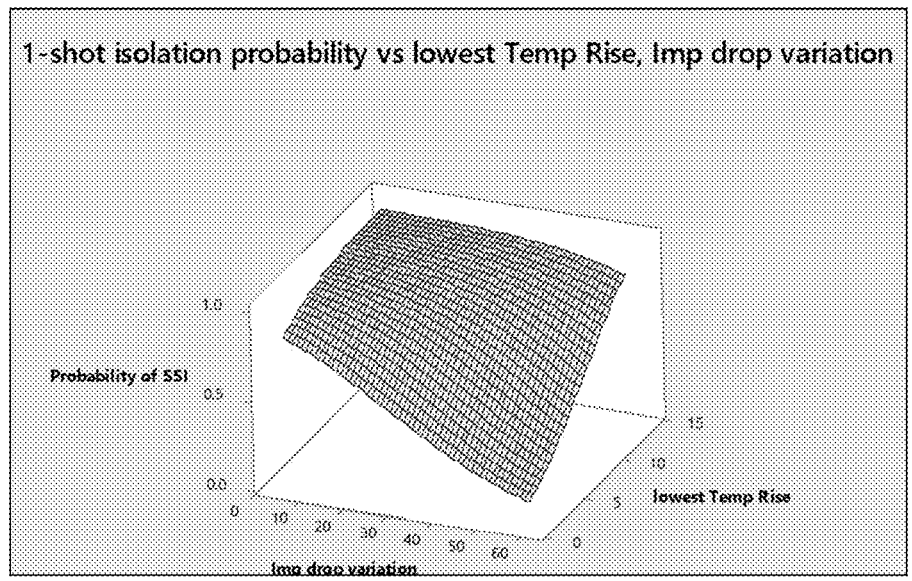
FIG. 68A shows a computer simulation model executing one example evaluator function.
FIG. 68B shows a table summarizing data associated with the simulation of FIG. 68A.
FIG. 68C shows a table summarizing data associated with the simulation of FIG. 68A.

Another example algorithm contemplated for use as an evaluator of single shot isolation includes the following:

$$Prob \sim \frac{e^Y}{(1+e^Y)}$$

$$Y \sim 1.562 + 0.2856 \Delta T_{min} - 0.0629 \Delta Z_{drop}$$

Where the evaluator algorithm includes two parameters: lowest temperature rise ($\Delta T_{min}$) and impedance drop variation ($\Delta Z_{drop}$). FIG. 68A shows a computer simulation model executing the aforementioned example algorithm while FIGS. 68B-68C show tables summarizing data associated with the simulation of FIG. 68A.

Figures 69A, 69B, 69C:
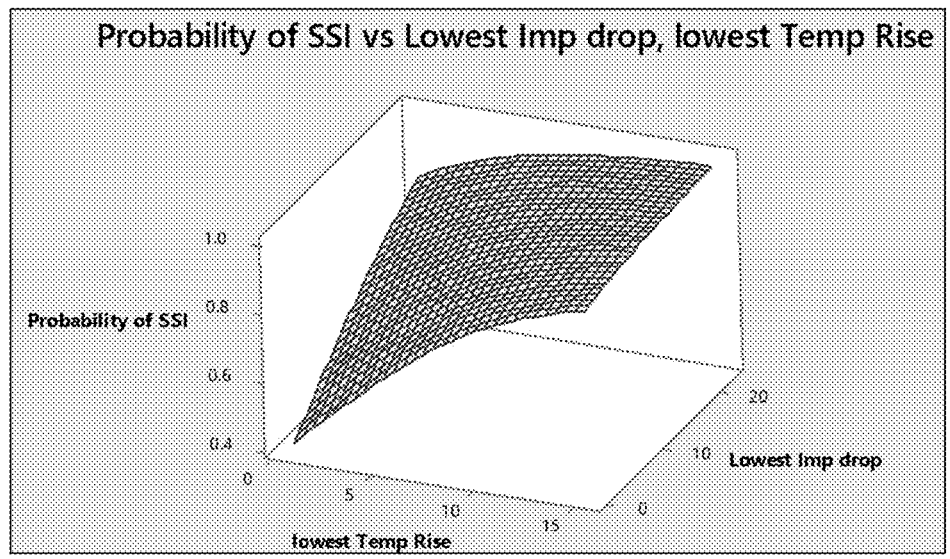
FIG. 69A shows a computer simulation model executing one example evaluator function.
FIG. 69B shows a table summarizing data associated with the simulation of FIG. 69A.
FIG. 69C shows a table summarizing data associated with the simulation of FIG. 69A.

Another example algorithm contemplated for use as an evaluator of single shot isolation includes the following:

$$P \sim \frac{e^Y}{(1+e^Y)}$$

$$Y \sim -0.507 + 0.206 \Delta T_{min} + 0.083 Z_{dropmin}$$

Where the evaluator algorithm includes two parameters: lowest temperature rise ($\Delta T_{min}$) and minimum impedance drop ($Z_{dropmin}$). FIG. 69A shows a computer simulation model executing the aforementioned example algorithm while FIGS. 69B-69C show tables summarizing data associated with the simulation of FIG. 69A.

Another example algorithm contemplated for use as an evaluator of single shot isolation includes the following:

$$P \sim \frac{e^Y}{(1+e^Y)}$$

$$Y \sim 1.248 + 0.2486\Delta T_{min} - 0.0594\Delta Z_{drop} + 0.0419\, Z_{dropmin}$$

Where the evaluator algorithm includes three parameters: lowest temperature rise ($\Delta T_{min}$), impedance drop variation ($\Delta Z_{drop}$) and lowest impedance drop ($Z_{dropmin}$). FIG. 70A-FIG. 70B show tables summarizing data associated with a simulation of above-referenced example algorithm.

Figures 71A, 71B, 71C:
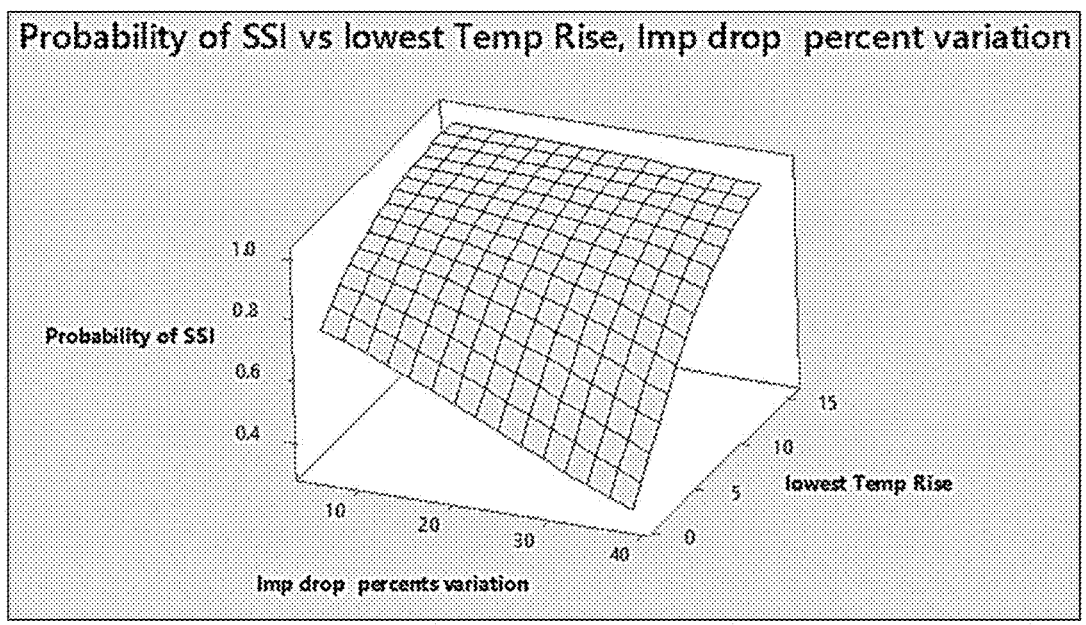
FIG. 71A shows a computer simulation model executing one example evaluator function.
FIG. 71B shows a table summarizing data associated with the simulation of FIG. 71A.
FIG. 71C shows a table summarizing data associated with the simulation of FIG. 71A.

Another example algorithm contemplated for use as an evaluator of single shot isolation includes the following:

$$P \sim \frac{e^Y}{(1+e^Y)}$$

$$Y \sim 1.174 + 0.2515\Delta T_{min} - 0.0564\Delta Z_{drop}\,\%$$

Where the evaluator algorithm includes two parameters: lowest temperature rise ($\Delta T_{min}$), and impedance drop percent variation ($\Delta Z_{drop}\%$). FIG. 71A shows a computer simulation model executing the aforementioned example algorithm while FIGS. 71B-71C show tables summarizing data associated with the simulation of FIG. 71A.

Figures 72A, 72B, 72C:
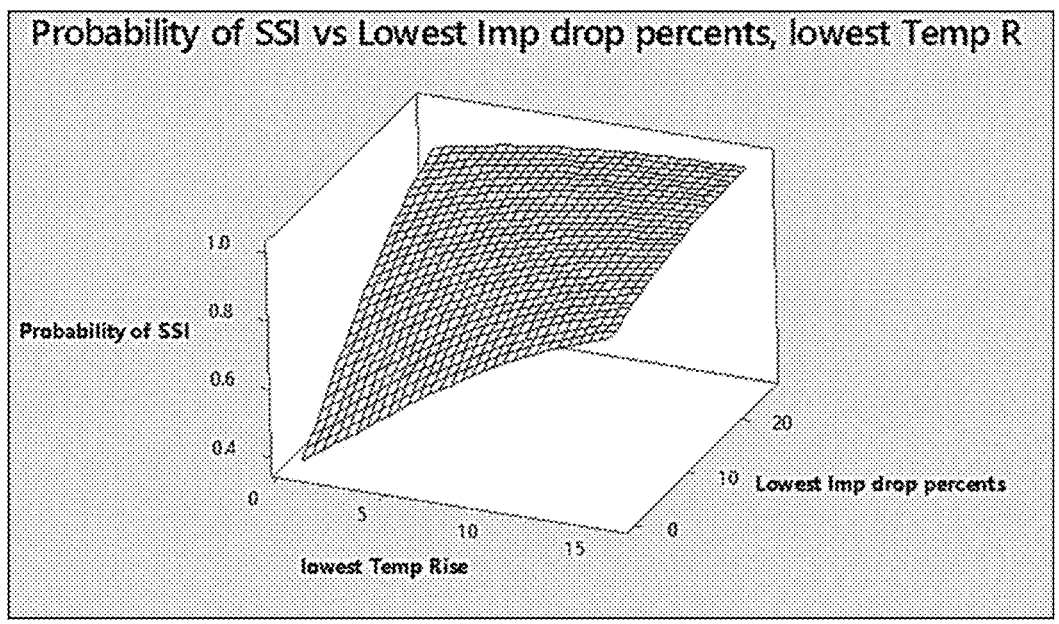
FIG. 72A shows a computer simulation model executing one example evaluator function.
FIG. 72B shows a table summarizing data associated with a simulation of an example evaluator algorithm.
FIG. 72C shows a table summarizing data associated with a simulation of an example evaluator algorithm.

Another example algorithm contemplated for use as an evaluator of single shot isolation includes the following:

$$P \sim \frac{e^Y}{(1+e^Y)}$$

$$Y \sim -0.644 + 0.170\Delta T_{min} + 0.107 Z_{drop}\,\%_{min}$$

Where the evaluator algorithm includes two parameters: lowest temperature rise ($\Delta T_{min}$), and lowest impedance drop percent ($Z_{drop}\%_{min}$). FIG. 72A shows a computer simulation model executing the aforementioned example algorithm while FIGS. 72B-72C show tables summarizing data associated with the simulation of FIG. 72A.

Another example algorithm contemplated for use as an evaluator of single shot isolation includes the following:

$$P \sim \frac{e^Y}{(1+e^Y)}$$

$$Y \sim 0.339 + 0.187\Delta T_{min} + 0.0737 Z_{drop}\,\%_{min} - 0.0368\Delta Z_{drop}\,\%$$

Where the evaluator algorithm includes three parameters: lowest temperature rise ($\Delta T_{min}$), lowest impedance drop Percent ($Z_{drop}\%_{min}$) and impedance drop percent variation ($\Delta Z_{drop}\%$). FIG. 73A-FIG. 73B show tables summarizing data associated with a simulation of above-referenced example algorithm.

Another example algorithm contemplated for use as an evaluator of single shot isolation includes the following:

$$P \sim \frac{e^Y}{(1+e^Y)}$$

$$Y \sim 1.043 + 0.777 T'_{min} + 0.171\Delta T_{min} + 0.0479\, Z_{drop-min} - 0.0589\Delta Z_{drop}$$

Where the evaluator algorithm includes four parameters: lowest temperature slope ($T'_{min}$), lowest temperature rise ($\Delta T_{min}$), lowest impedance drop ($Z_{drop-min}$) and impedance drop variation ($\Delta Z_{drop}$). FIG. 74 shows a table summarizing data associated with the simulation of the referenced evaluator algorithm.

Figure 75A:
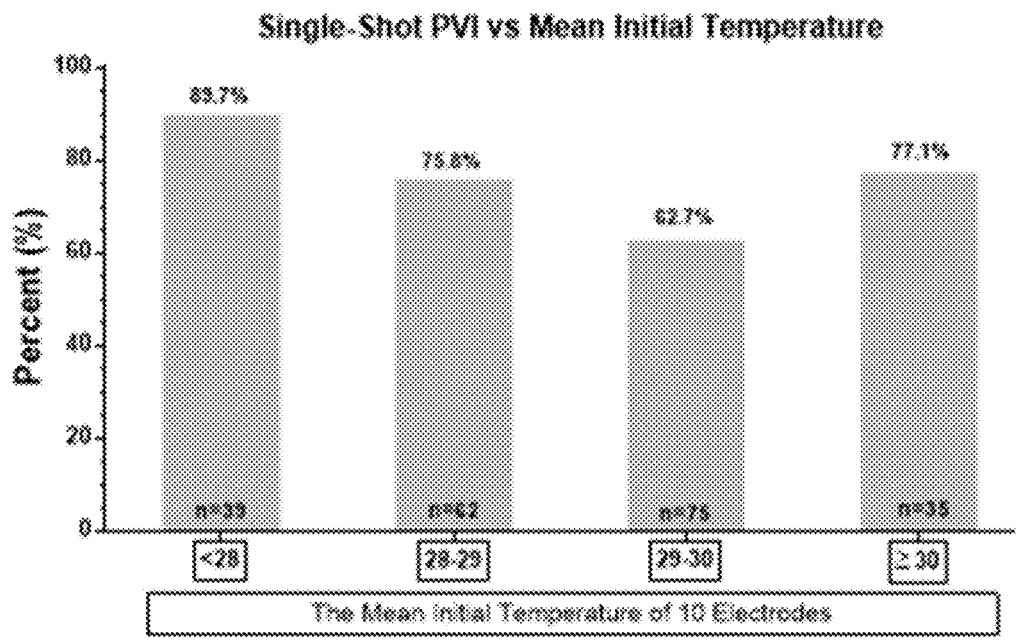
FIG. 75A shows a bar graph summarizing single shot isolation probability versus pre-ablation mean initial temperature in the study of this disclosure.
Figure 75B:
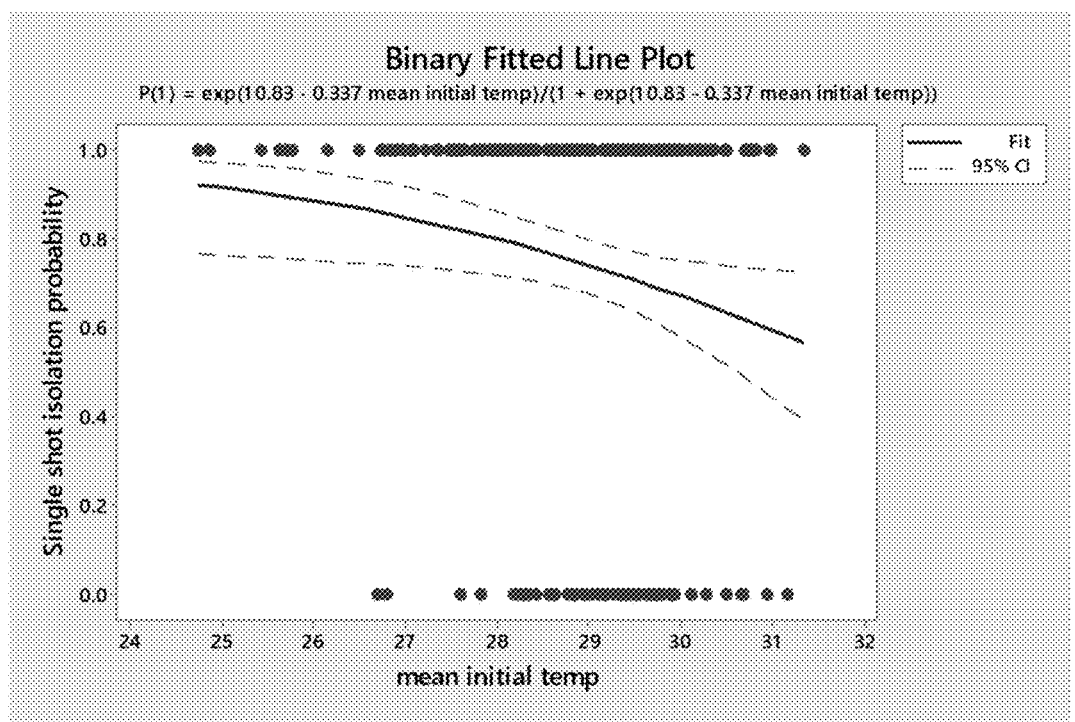
FIG. 75B shows a binary fitted line plot of single shot isolation probability versus pre-ablation mean initial temperature in the study of this disclosure.

FIG. 75A shows a bar graph summarizing single shot isolation probability versus pre-ablation mean initial temperature while FIG. 75B shows a binary fitted line plot of single shot isolation probability versus pre-ablation mean initial temperature in the study of this disclosure. As can be seen, at a mean initial temperature of approximately less than about 28° C., the single shot isolation rate was approximately about 90%. The P-value of FIG. 75B was 0.016 with an odds ratio (95% CI) of 0.714 (0.536-0.951).

Figure 76A:
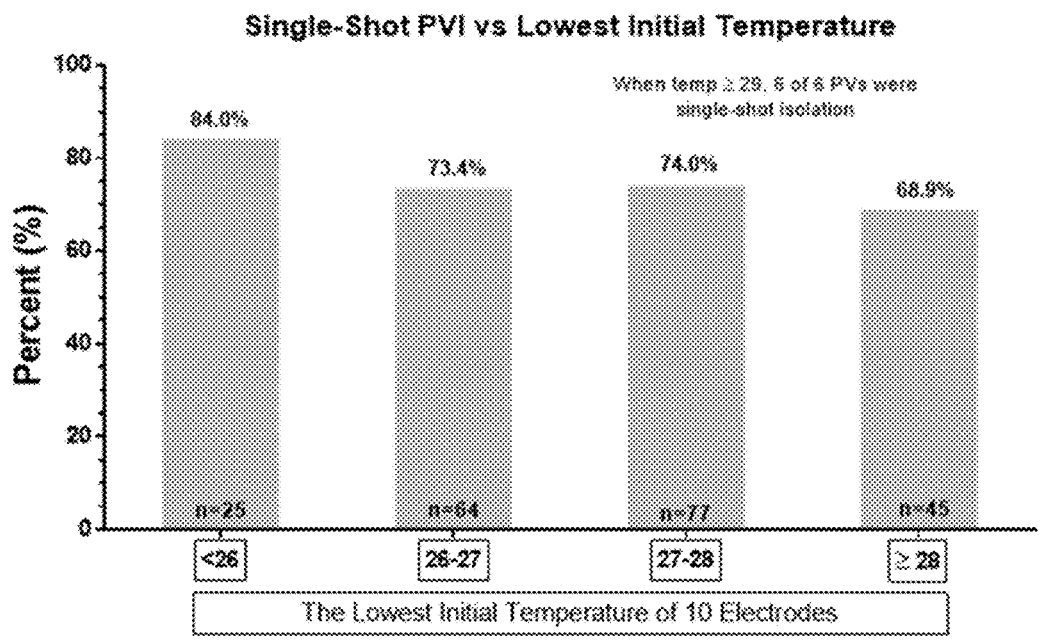
FIG. 76A shows a bar graph summarizing single shot isolation probability versus pre-ablation lowest initial temperature in the study of this disclosure.
Figure 76B:
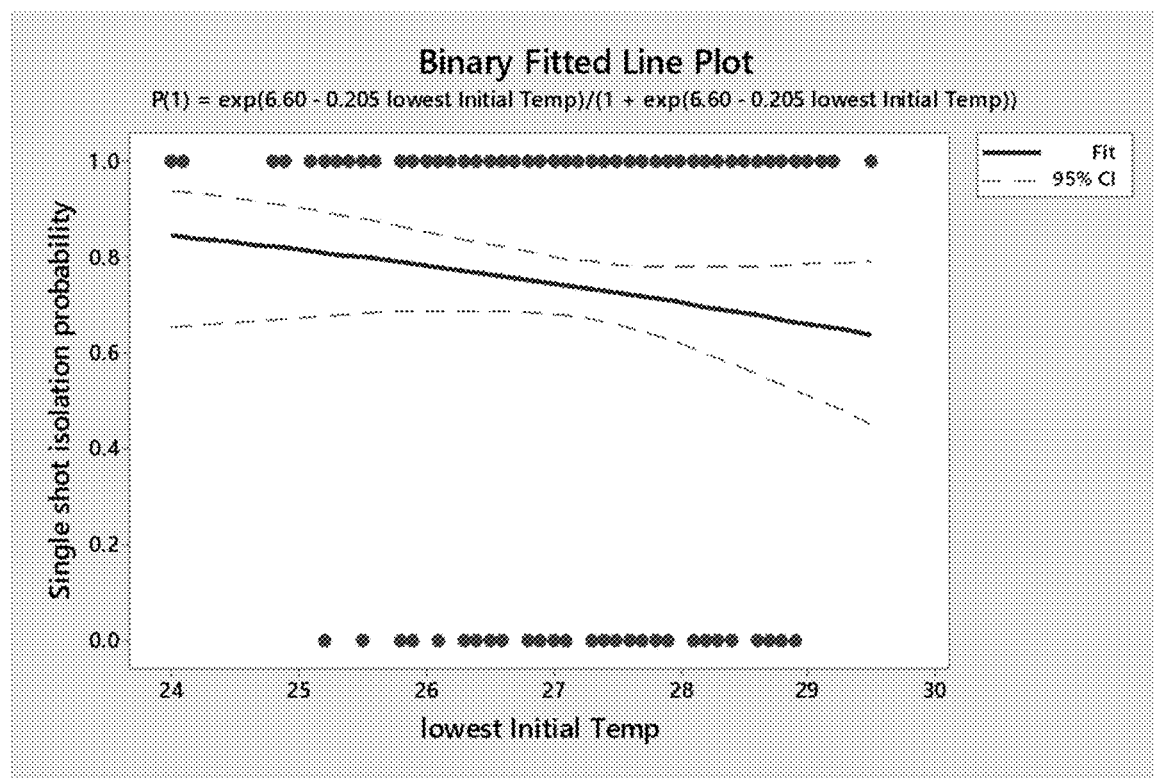
FIG. 76B shows a binary fitted line plot of single shot isolation probability versus pre-ablation lowest initial temperature in the study of this disclosure.

FIG. 76A shows a bar graph summarizing single shot isolation probability versus pre-ablation lowest initial temperature while FIG. 76B shows a binary fitted line plot of single shot isolation probability versus pre-ablation lowest initial temperature in the study of this disclosure. The single shot isolation rate was approximately about 90%. The P-value of FIG. 76B was 0.191 with an odds ratio (95% CI) of 0.815 (0.580-1.111).

Figure 77A:
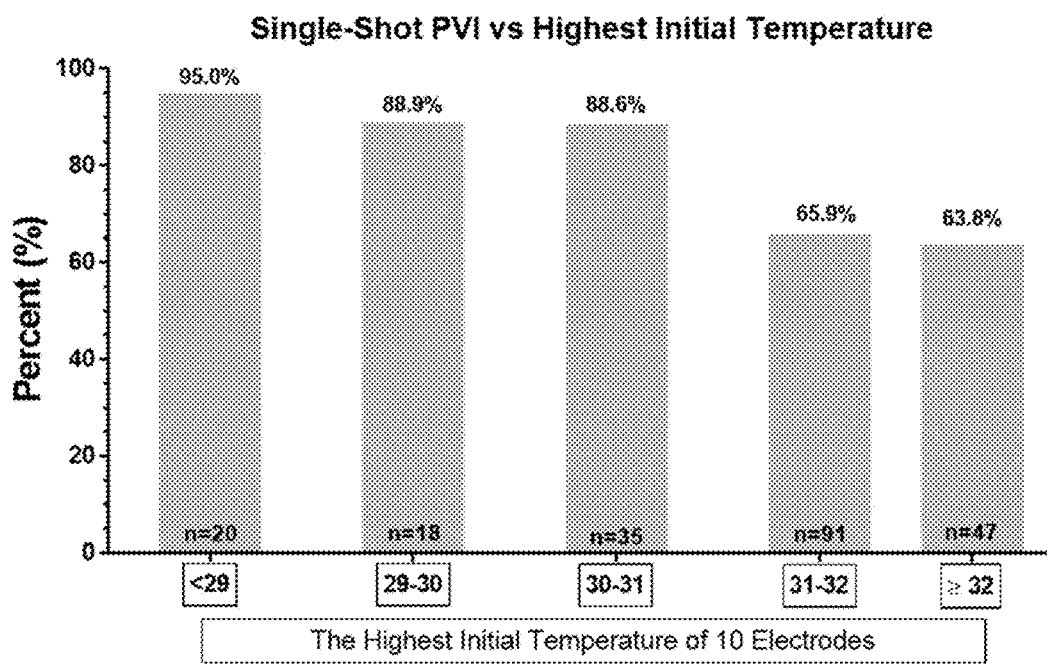
FIG. 77A shows a bar graph summarizing single shot isolation probability versus pre-ablation highest initial temperature in the study of this disclosure.
Figure 77B:
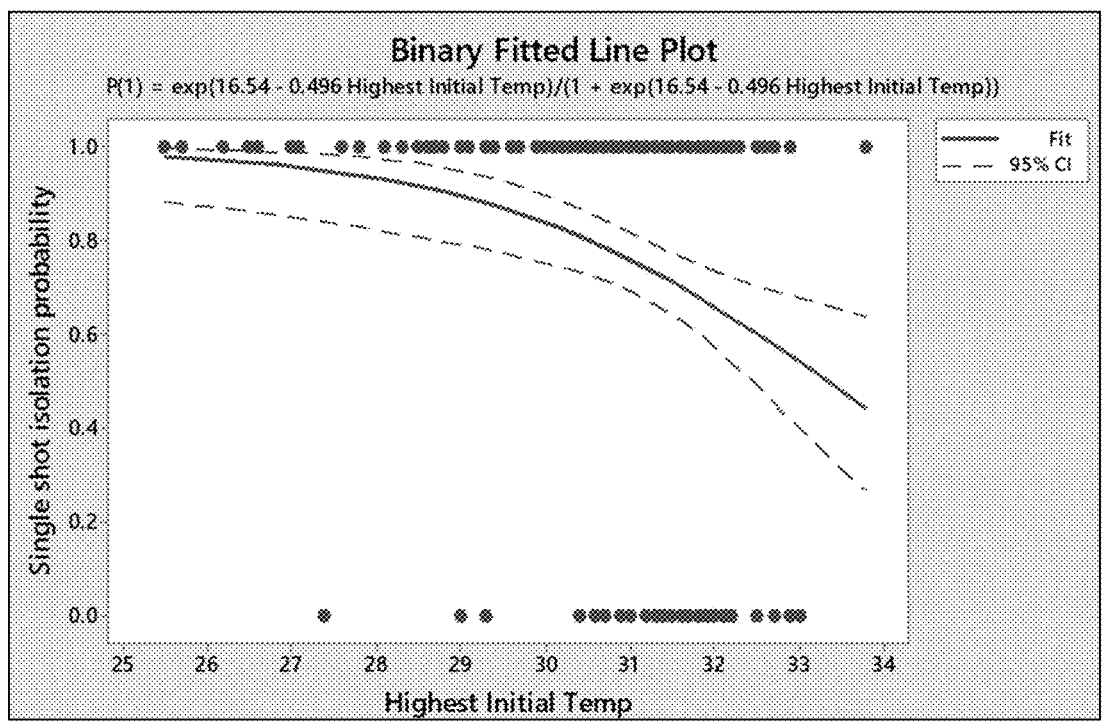
FIG. 77B shows a binary fitted line plot of single shot isolation probability versus pre-ablation highest initial temperature in the study of this disclosure.

FIG. 77A shows a bar graph summarizing single shot isolation probability versus pre-ablation highest initial temperature while FIG. 77B shows a binary fitted line plot of single shot isolation probability versus pre-ablation highest initial temperature in the study of this disclosure. The single shot isolation rate was approximately about 90% when the highest initial temperature was less than approximately 31° C. The P-value of FIG. 77B was 0.000 with an odds ratio (95% CI) of 0.609 (0.448-0.828).

Figure 78A:
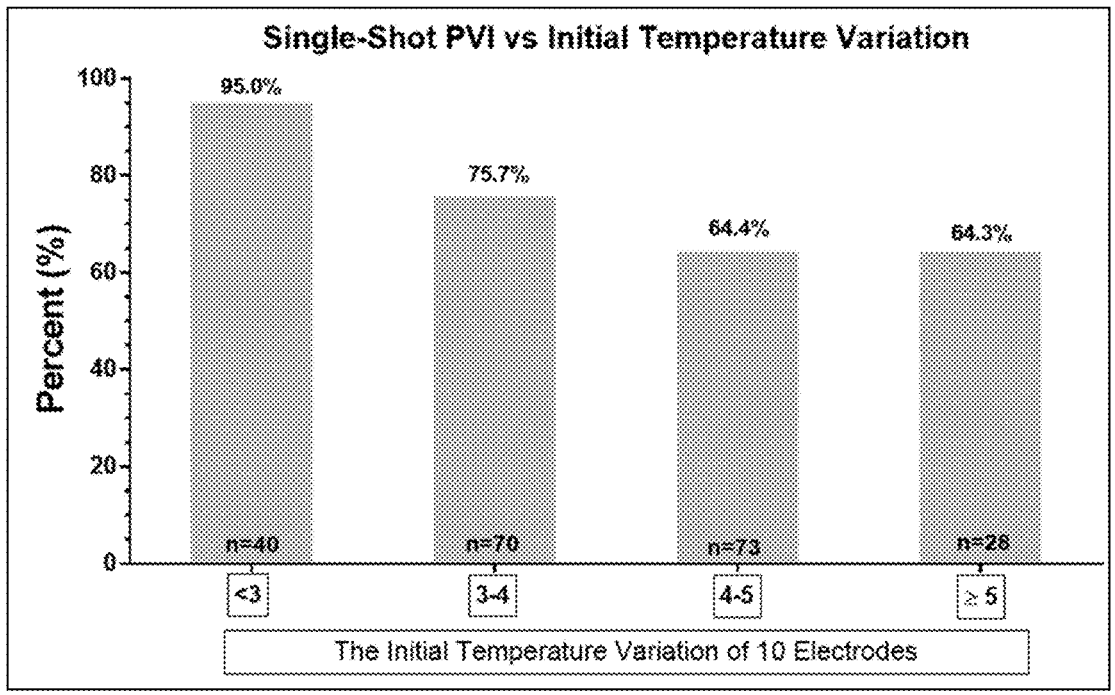
FIG. 78A shows a bar graph summarizing single shot isolation probability versus pre-ablation initial temperature variation in the study of this disclosure.
Figure 78B:
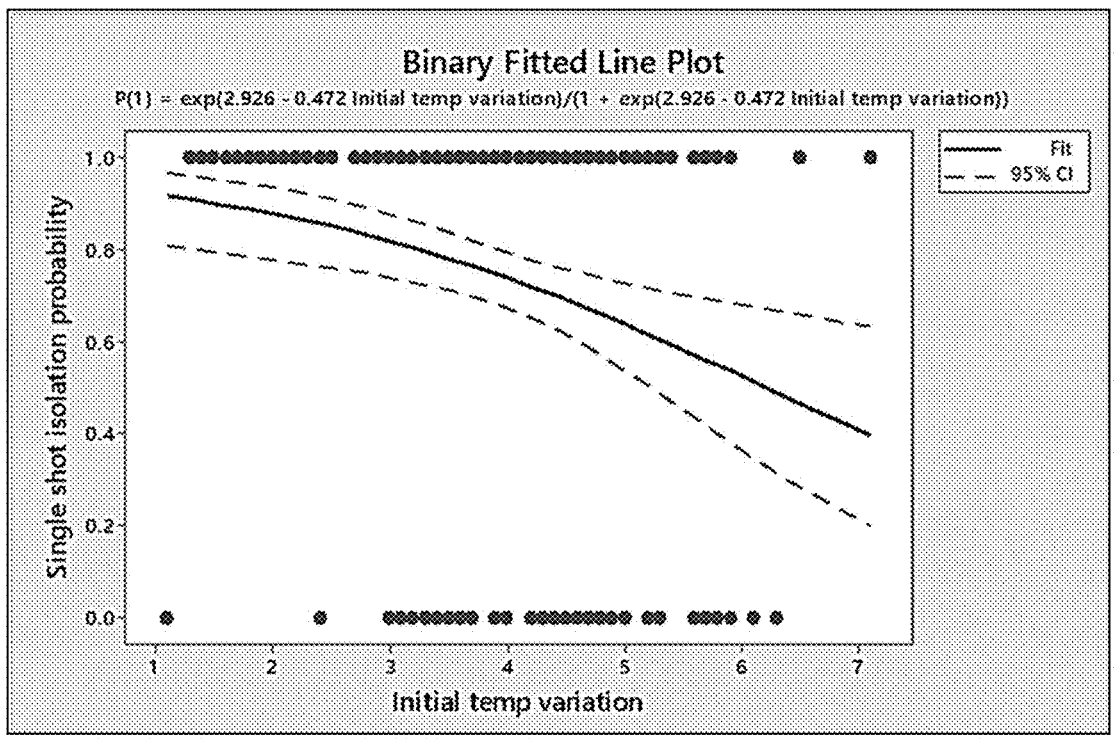
FIG. 78B shows a binary fitted line plot of single shot isolation probability versus pre-ablation initial temperature variation in the study of this disclosure.

FIG. 78A shows a bar graph summarizing single shot isolation probability versus pre-ablation initial temperature variation while FIG. 78B shows a binary fitted line plot of single shot isolation probability versus pre-ablation initial temperature variation in the study of this disclosure. The single shot isolation rate was greater than approximately about 95% when the initial temperature variation was less than approximately 3° C. The P-value of FIG. 78B was 0.002 with an odds ratio (95% CI) of 0.624 (0.460-0.847).

Figure 79A:
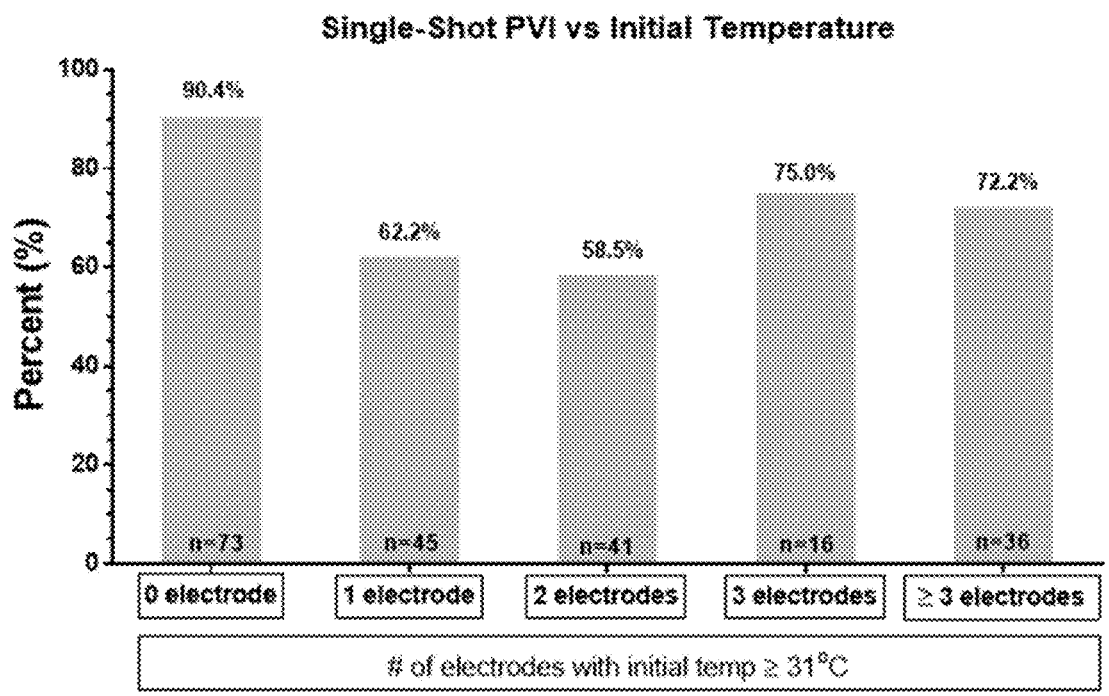
FIG. 79A shows a bar graph summarizing single shot isolation probability versus pre-ablation distributed initial temperature in the study of this disclosure.
Figure 79B:
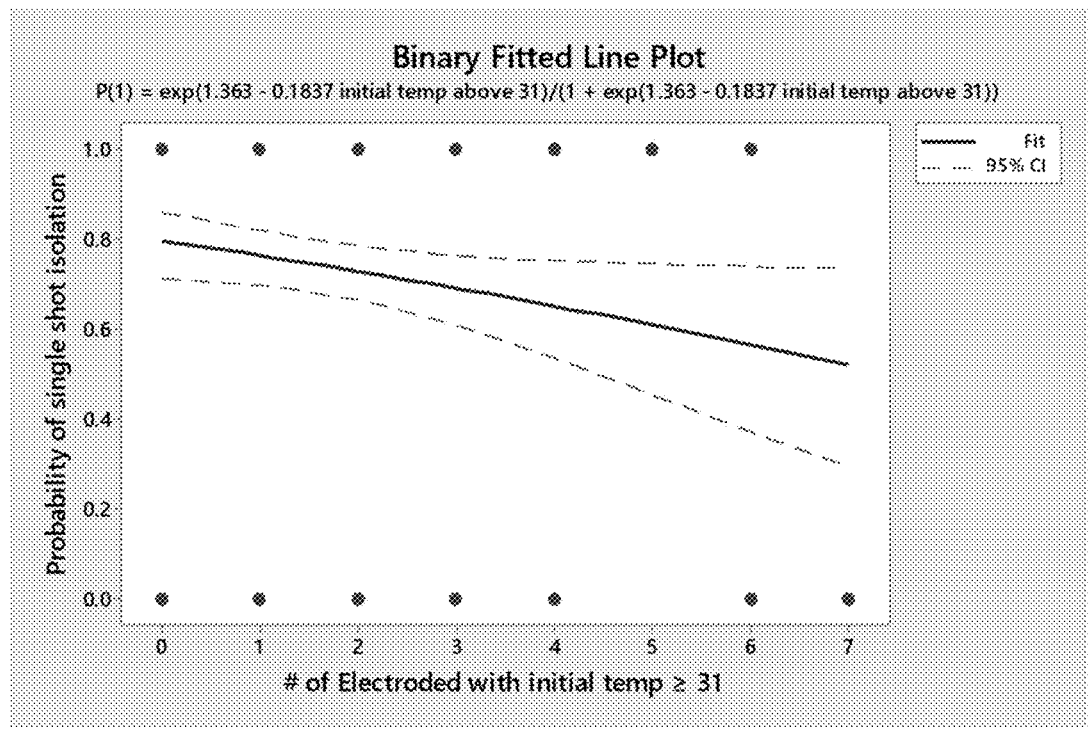
FIG. 79B shows a binary fitted line plot of single shot isolation probability versus pre-ablation distributed initial temperature in the study of this disclosure.

FIG. 79A shows a bar graph summarizing single shot isolation probability versus pre-ablation distributed initial temperature while FIG. 79B shows a binary fitted line plot of single shot isolation probability versus pre-ablation distributed initial temperature in the study of this disclosure. As can be seen, at a distributed initial temperature of approximately greater than about 31° C., the single shot isolation rate was greater than approximately about 90%. The P-value of FIG. 59B was 0.040 with an odds ratio (95% CI) of 0.832 (0.699-0.991).

Figure 80A:
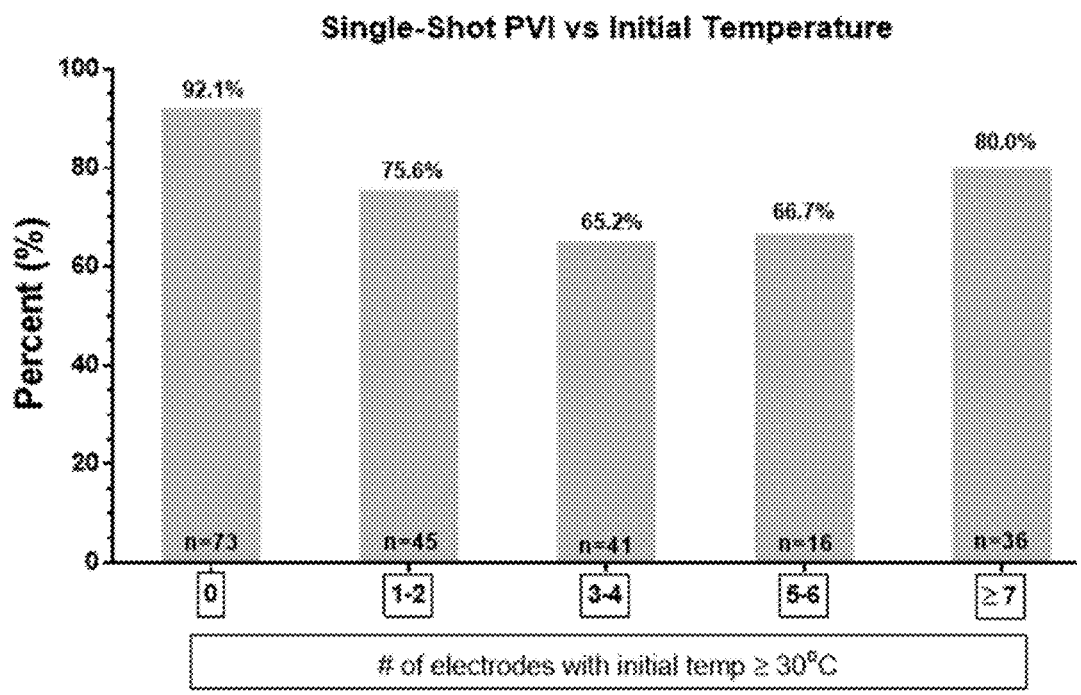
FIG. 80A shows a bar graph summarizing single shot isolation probability versus pre-ablation distributed initial temperature in the study of this disclosure.
Figure 80B:
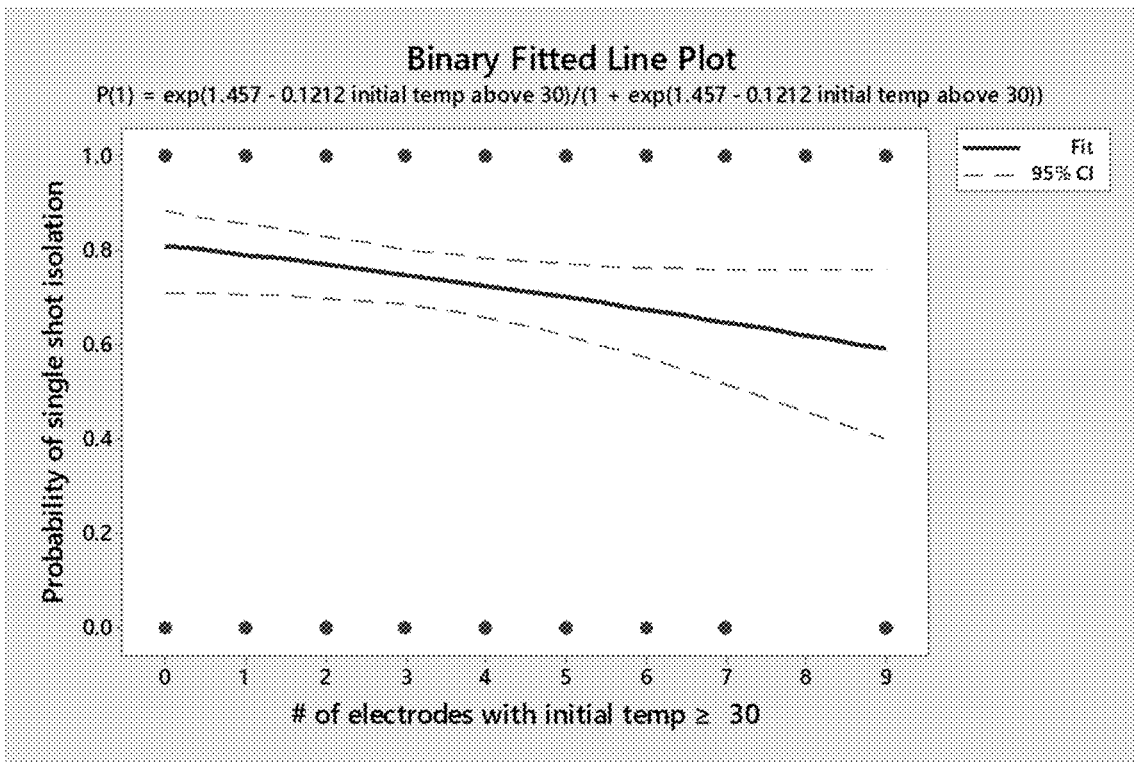
FIG. 80B shows a binary fitted line plot of single shot isolation probability versus pre-ablation distributed initial temperature in the study of this disclosure.

FIG. 80A shows a bar graph summarizing single shot isolation probability versus pre-ablation distributed initial temperature while FIG. 79B shows a binary fitted line plot of single shot isolation probability versus pre-ablation distributed initial temperature in the study of this disclosure. As can be seen, at a distributed initial temperature of approximately greater than about 30° C., the single shot isolation rate was greater than approximately about 90%. The P-value of FIG. 60B was 0.068 with an odds ratio (95% CI) of 0.886 (0.777-1.010).

Figure 81A:
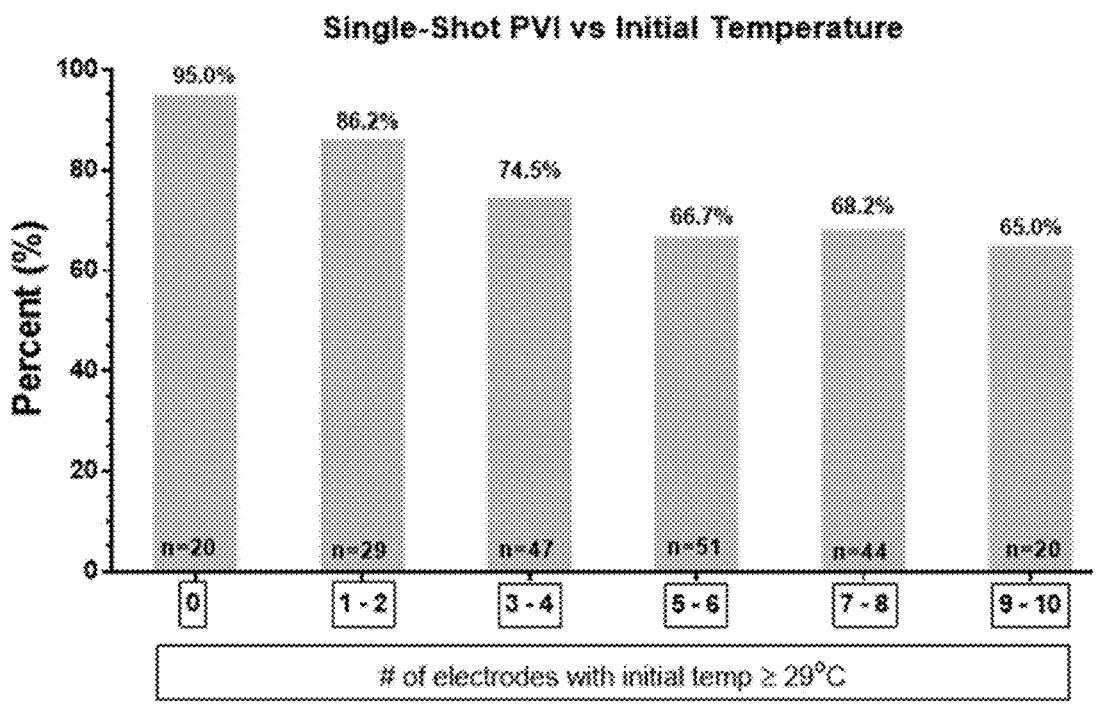
FIG. 81A shows a bar graph summarizing single shot isolation probability versus pre-ablation distributed initial temperature in the study of this disclosure.
Figure 81B:
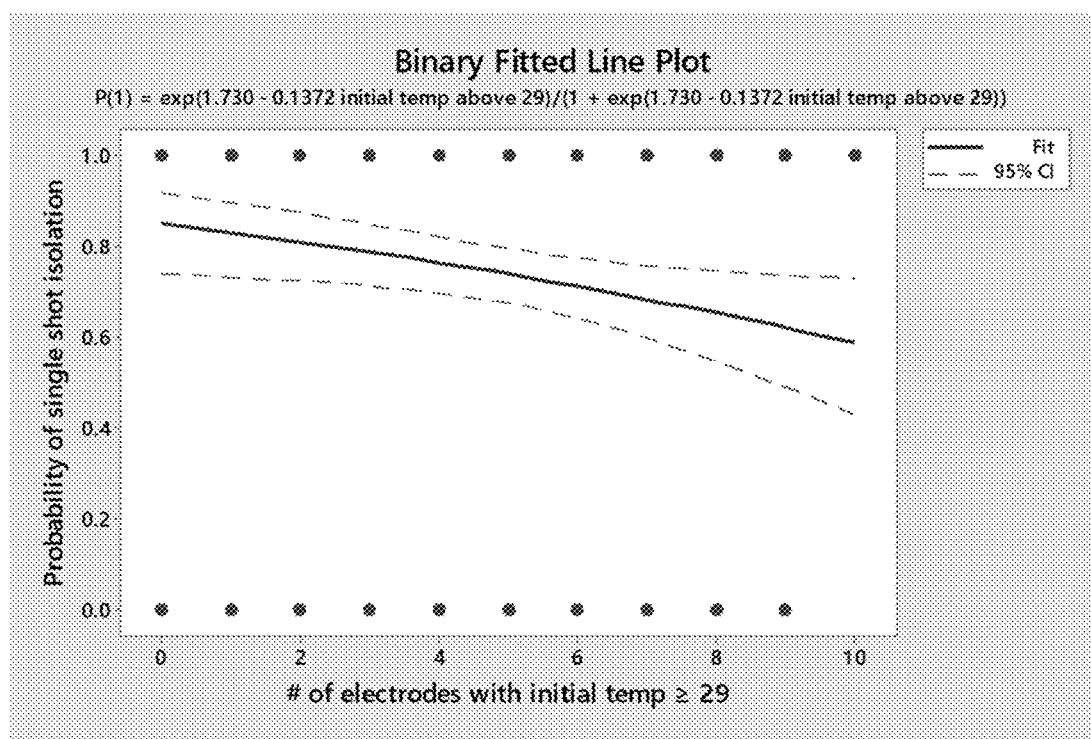
FIG. 81B shows a binary fitted line plot of single shot isolation probability versus pre-ablation distributed initial temperature in the study of this disclosure.

FIG. 81A shows a bar graph summarizing single shot isolation probability versus pre-ablation distributed initial temperature while FIG. 81B shows a binary fitted line plot of single shot isolation probability versus pre-ablation distributed initial temperature in the study of this disclosure. As can be seen, at a distributed initial temperature of approximately greater than about 29° C., the single shot isolation rate was approximately about 90%. The P-value of FIG. 81B was 0.019 with an odds ratio (95% CI) of 0.872 (0.776-0.980).

Figure 82A:
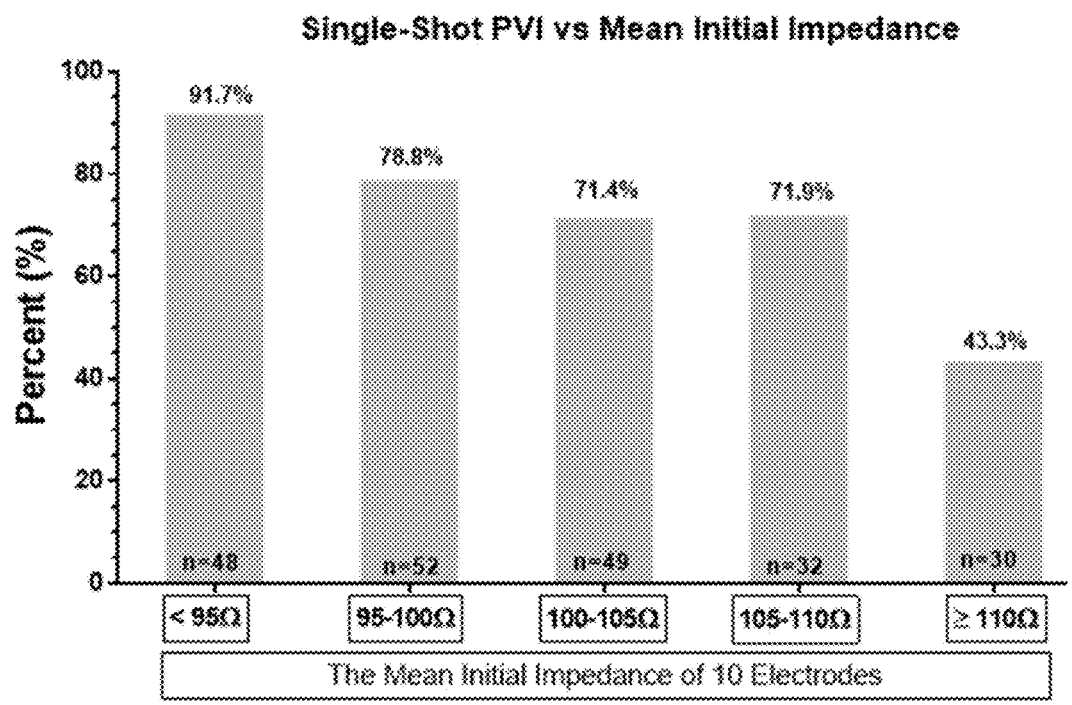
FIG. 82A shows a bar graph summarizing single shot isolation probability versus pre-ablation mean initial impedance in the study of this disclosure.
Figure 82B:
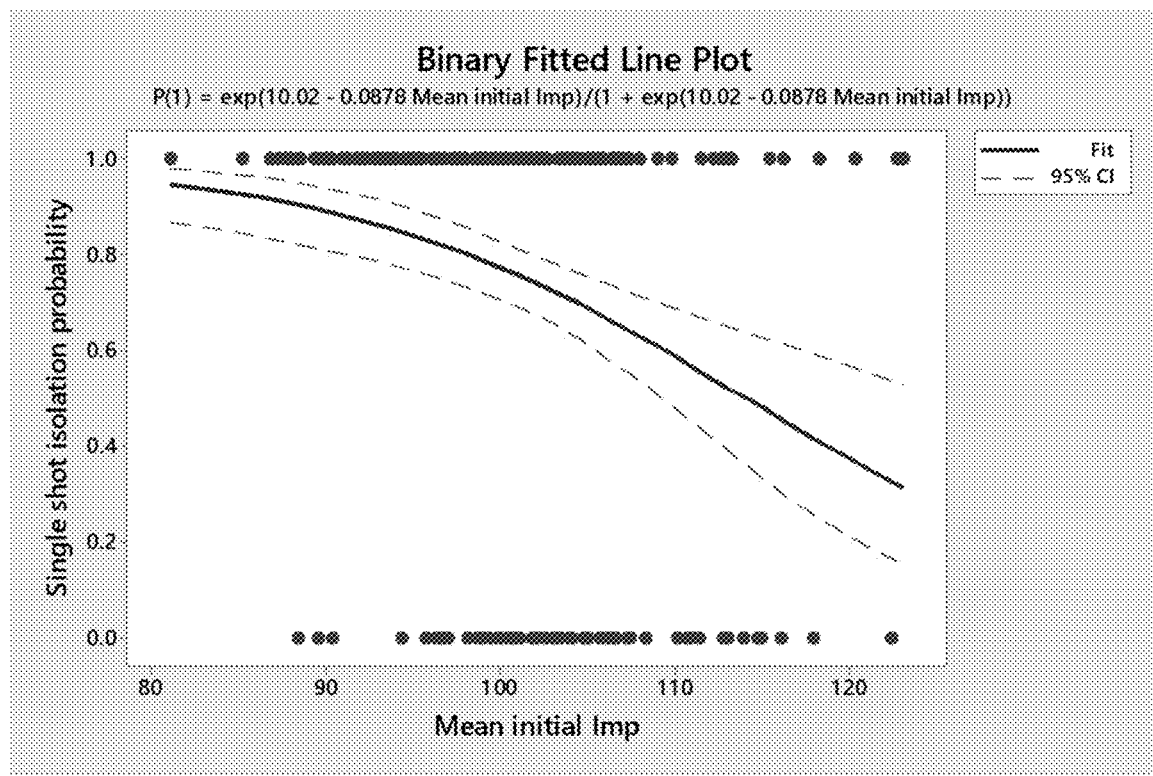
FIG. 82B shows a binary fitted line plot of single shot isolation probability versus pre-ablation mean initial impedance in the study of this disclosure.

FIG. 82A shows a bar graph summarizing single shot isolation probability versus pre-ablation mean initial impedance while FIG. 82B shows a binary fitted line plot of single shot isolation probability versus pre-ablation mean initial impedance in the study of this disclosure. As can be seen, at an optimal range of approximately less than about 95Ω, the single shot isolation rate was greater than approximately about 91.7%. The P-value of FIG. 82B was 0.000 with an odds ratio (95% CI) of 0.916 (0.877-0.956).

Figure 83A:
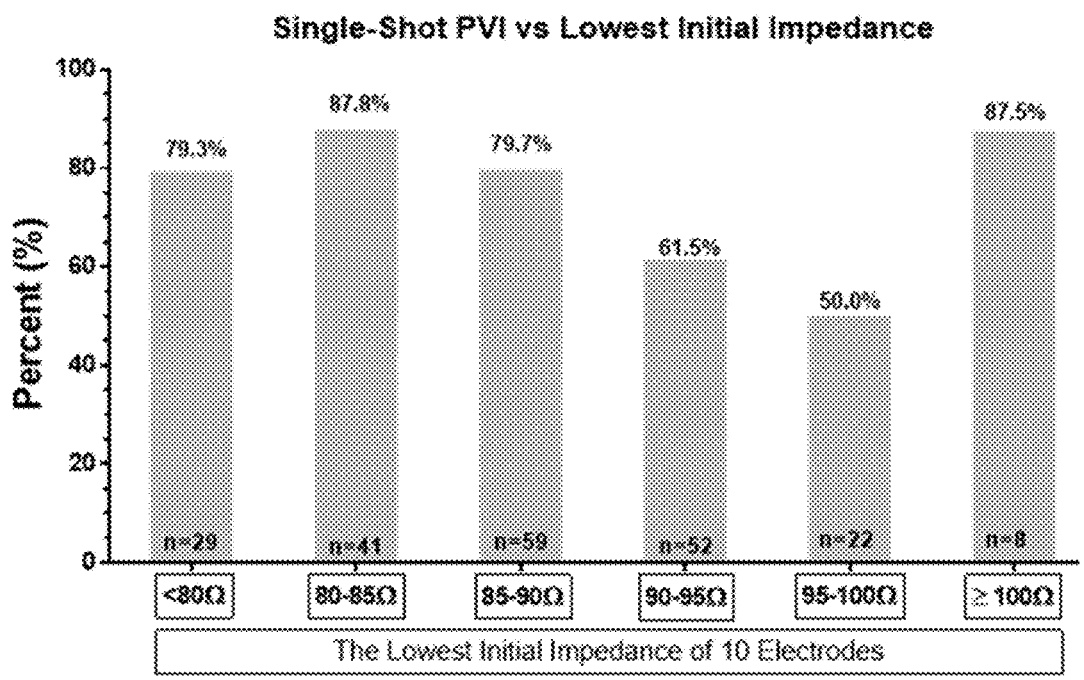
FIG. 83A shows a bar graph summarizing single shot isolation probability versus pre-ablation lowest initial impedance in the study of this disclosure.
Figure 83B:
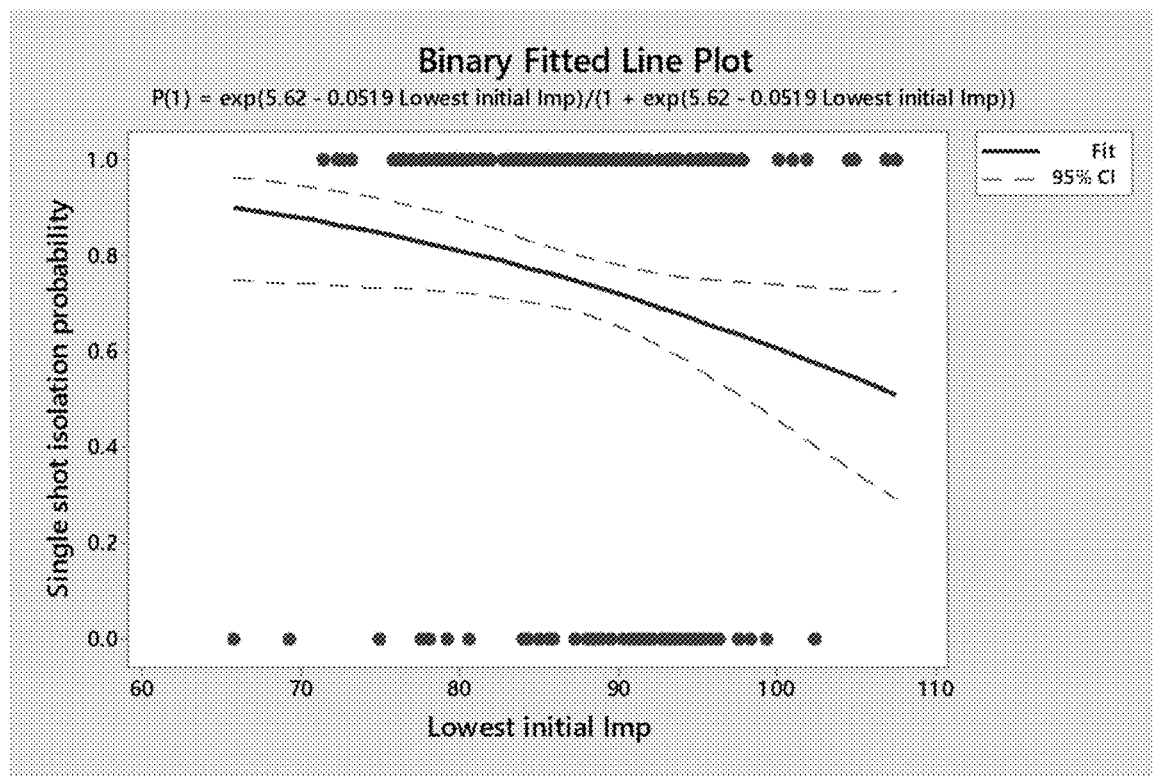
FIG. 83B shows a binary fitted line plot of single shot isolation probability versus pre-ablation lowest initial impedance in the study of this disclosure.

FIG. 83A shows a bar graph summarizing single shot isolation probability versus pre-ablation lowest initial impedance while FIG. 83B shows a binary fitted line plot of single shot isolation probability versus pre-ablation lowest initial impedance in the study of this disclosure. The P-value of FIG. 83B was 0.026 with an odds ratio (95% CI) of 0.950 (0.906-0.995).

Figure 84A:
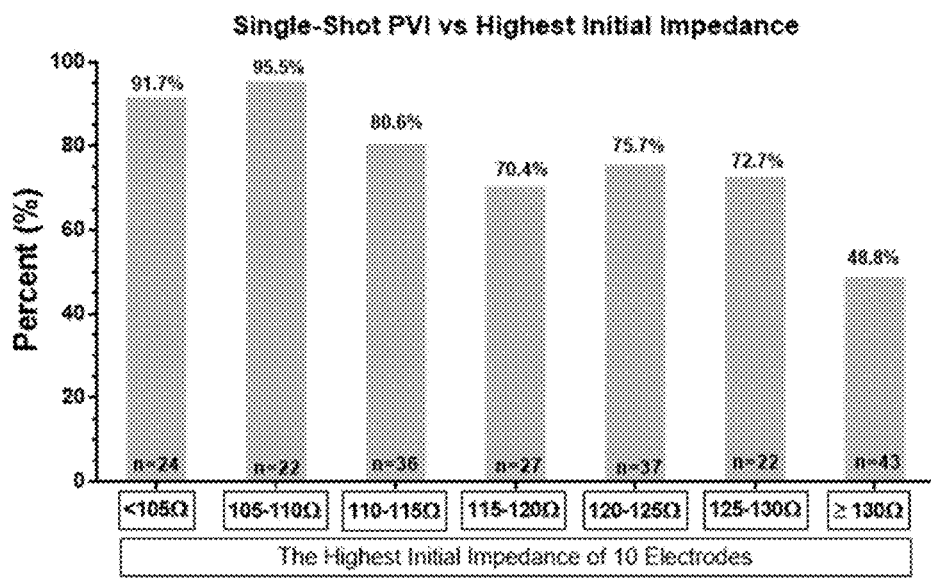
FIG. 84A shows a bar graph summarizing single shot isolation probability versus pre-ablation highest initial impedance in the study of this disclosure.
Figure 84B:
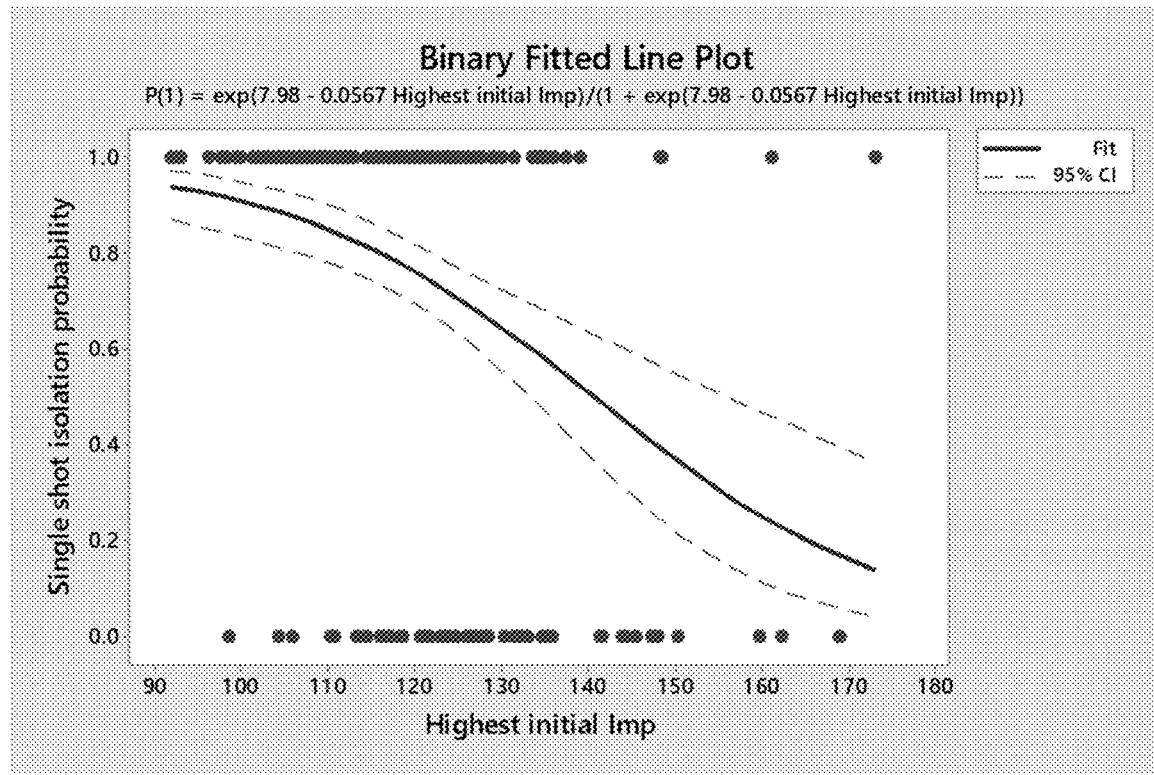
FIG. 84B shows a binary fitted line plot of single shot isolation probability versus pre-ablation highest initial impedance in the study of this disclosure.

FIG. 84A shows a bar graph summarizing single shot isolation probability versus pre-ablation highest initial impedance while FIG. 84B shows a binary fitted line plot of single shot isolation probability versus pre-ablation highest initial impedance in the study of this disclosure. As can be seen, at an optimal range of approximately less than about 110Ω, the single shot isolation rate was greater than approximately about 91.7%. The P-value of FIG. 84B was 0.000 with an odds ratio (95% CI) of 0.945 (0.922-0.969).

Figure 85A:
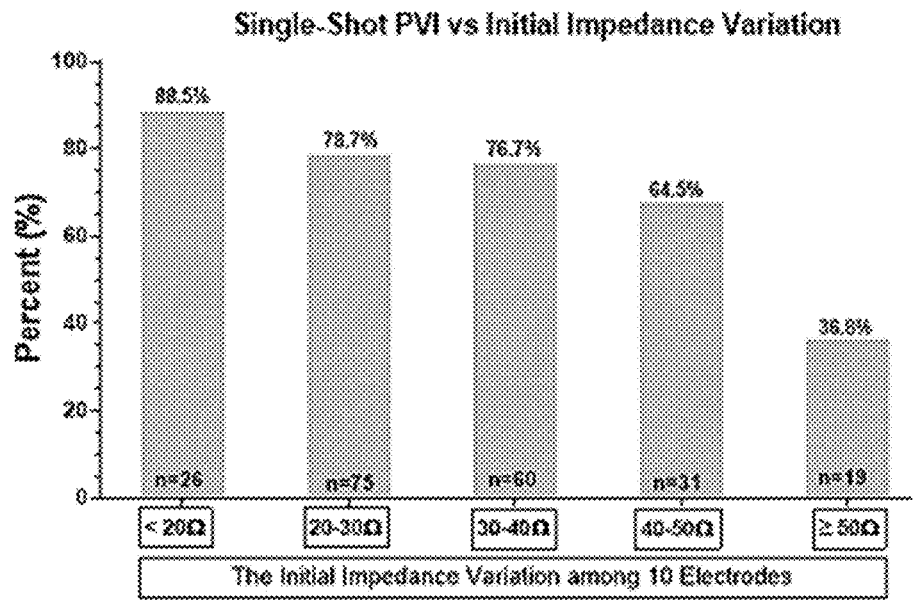
Figure 85B:
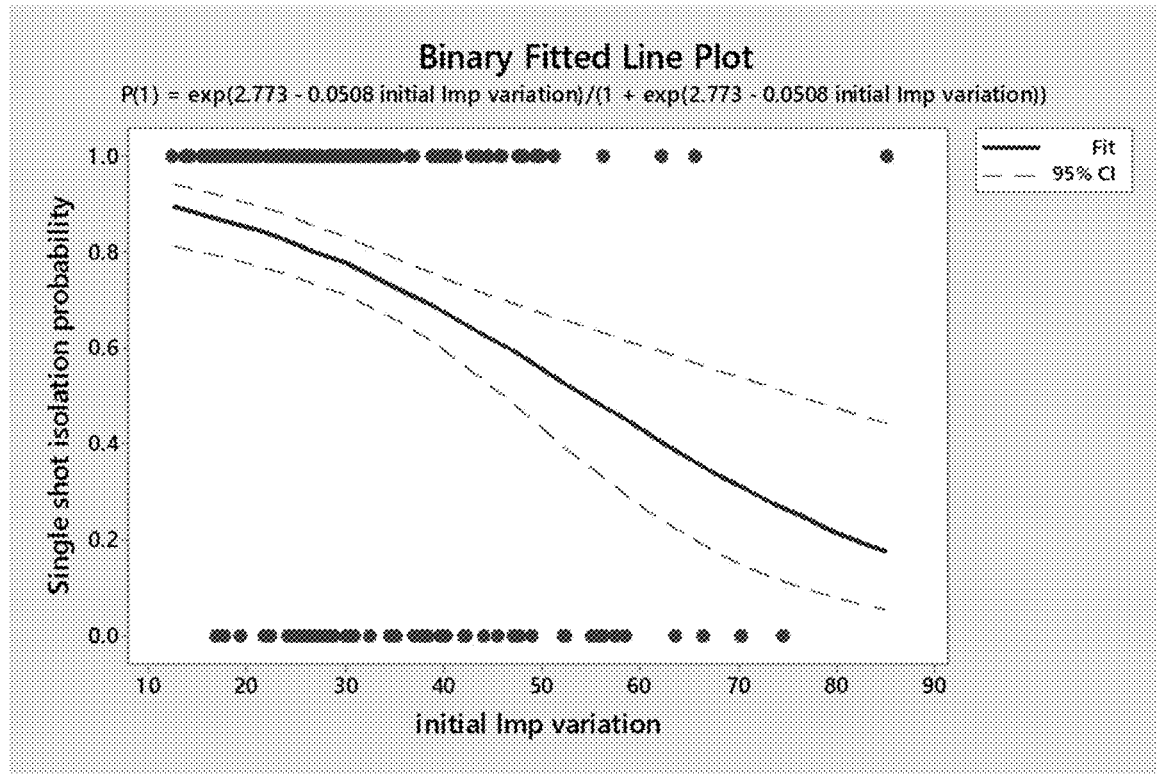

FIG. 85A shows a bar graph summarizing single shot isolation probability versus pre-ablation initial impedance variation while FIG. 85B shows a binary fitted line plot of single shot isolation probability versus pre-ablation initial impedance variation in the study of this disclosure. As can be seen, at an optimal range of approximately less than about 20Ω, the single shot isolation rate was greater than approximately about 88.5%. The P-value of FIG. 85B was 0.000 with an odds ratio (95% CI) of 0.950 (0.927-0.975).

Figure 86A:
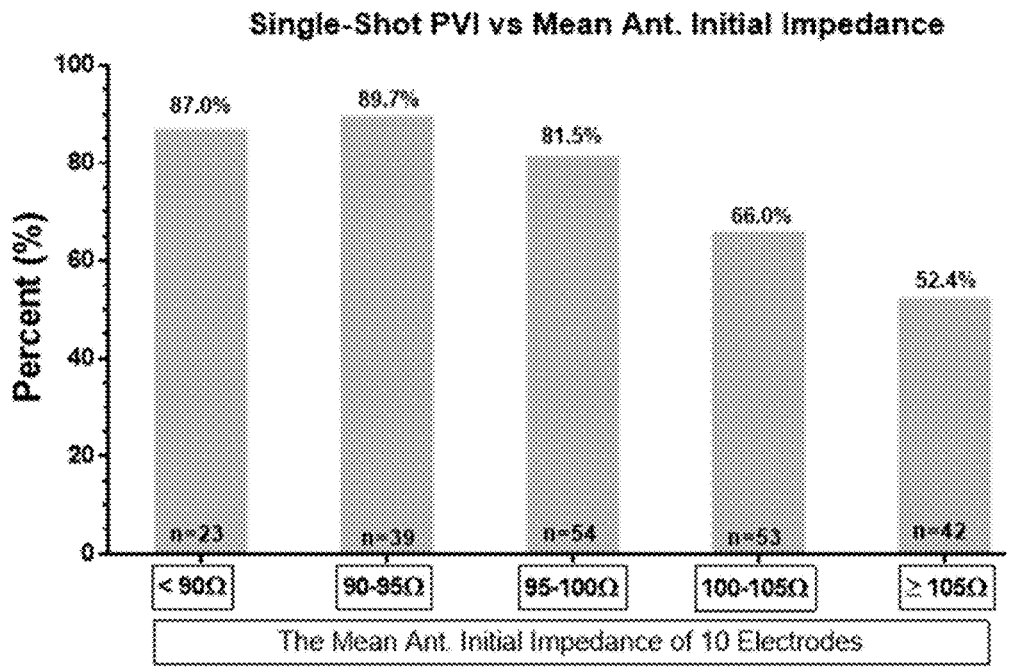
Figure 86B:
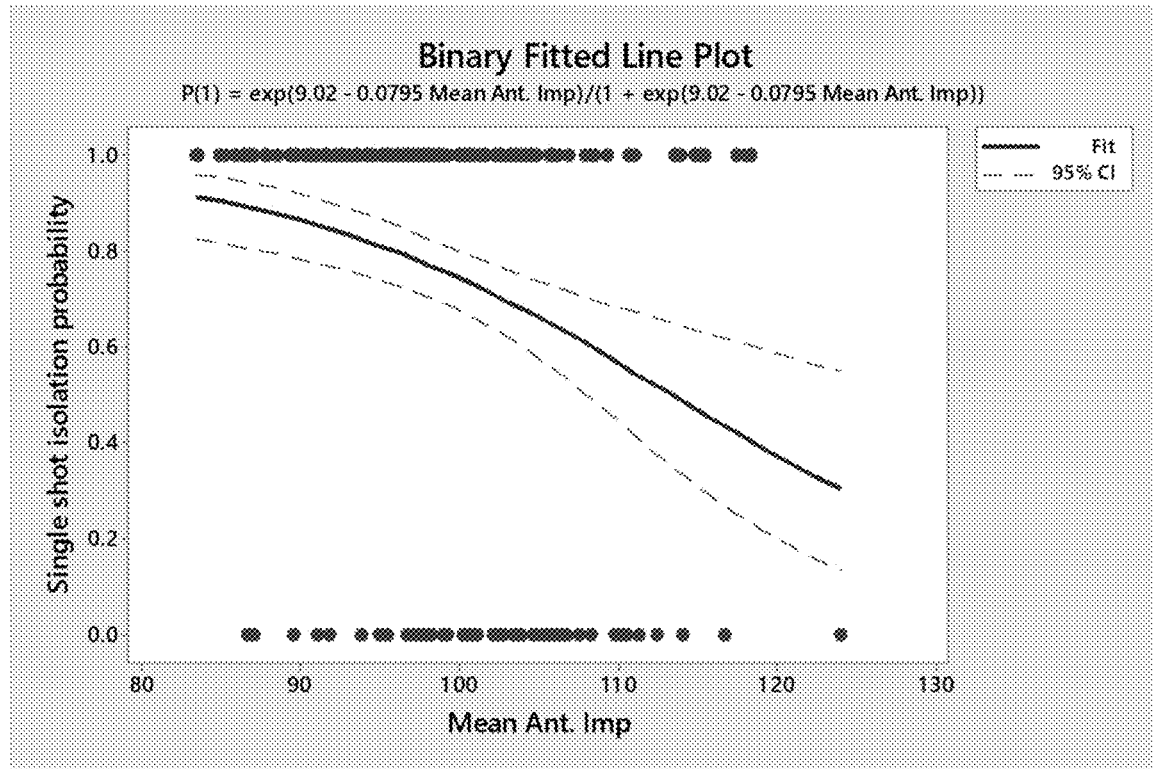

FIG. 86A shows a bar graph summarizing single shot isolation probability versus pre-ablation initial anterior wall impedance while FIG. 86B shows a binary fitted line plot of single shot isolation probability versus pre-ablation initial anterior wall impedance in the study of this disclosure. As can be seen, at an optimal range of approximately less than about 95Ω, the single shot isolation rate was nearly approximately between 87 to 89.7%. The P-value of FIG. 86B was 0.000 with an odds ratio (95% CI) of 0.924 (0.885-0.964).

Figure 87A:
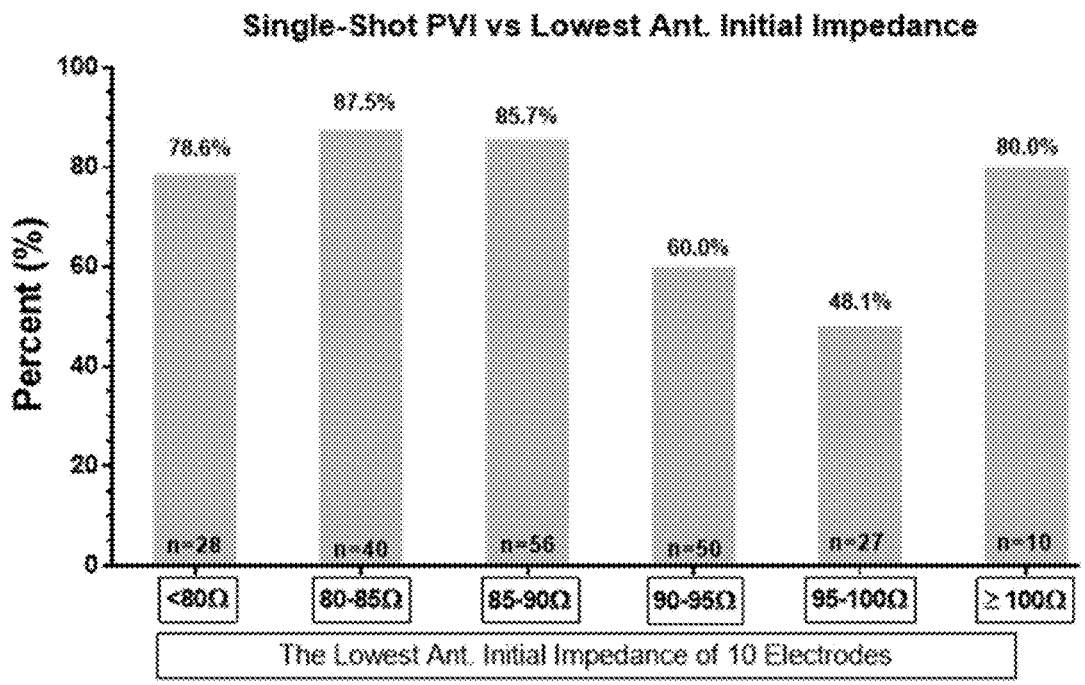
Figure 87B:
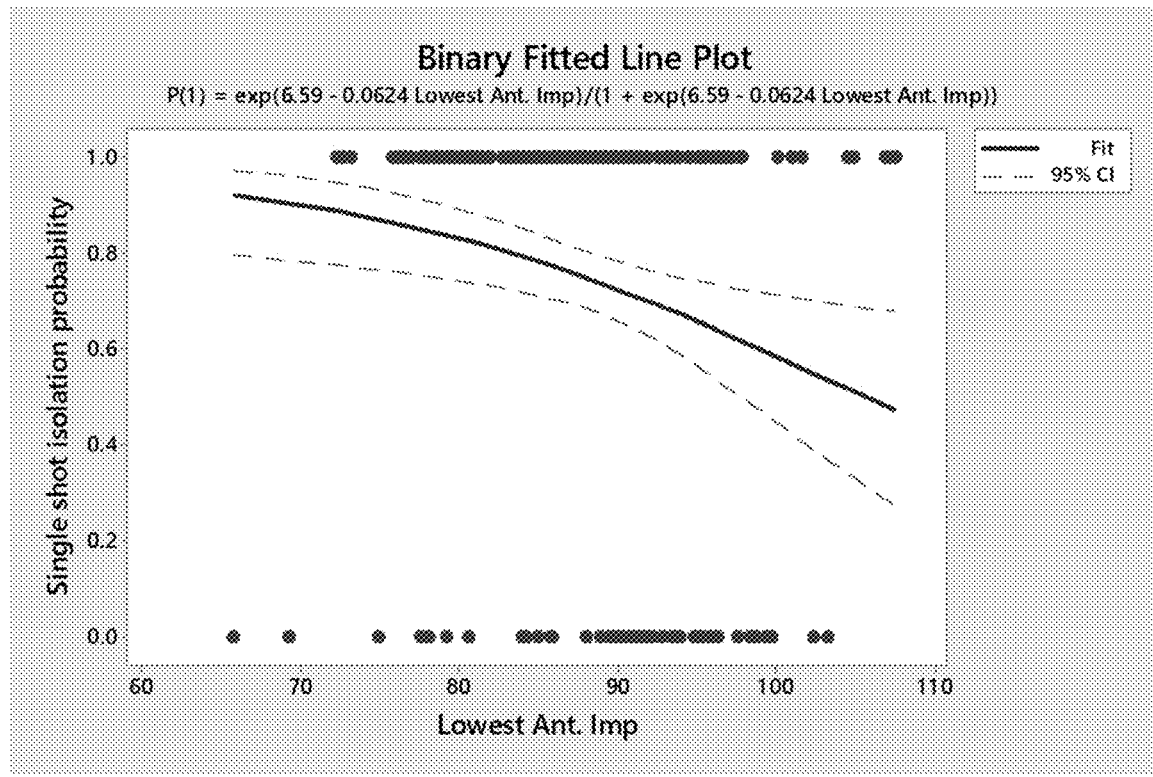

FIG. 87A shows a bar graph summarizing single shot isolation probability versus pre-ablation lowest initial anterior wall impedance while FIG. 87B shows a binary fitted line plot of single shot isolation probability versus pre-ablation lowest initial anterior wall impedance in the study of this disclosure. As can be seen, at an optimal range of about 80-90Ω, the single shot isolation rate was nearly approximately between 85.7 to 87.5%. The P-value of FIG. 87B was 0.005 with an odds ratio (95% CI) of 0.940 (0.898-0.983).

Figure 88A:
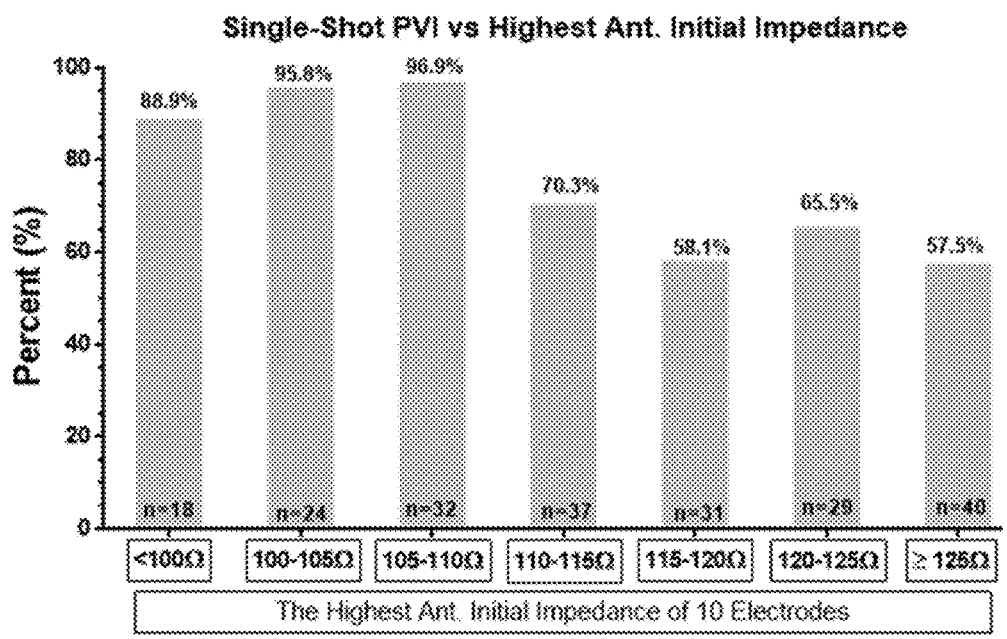
Figure 88B:
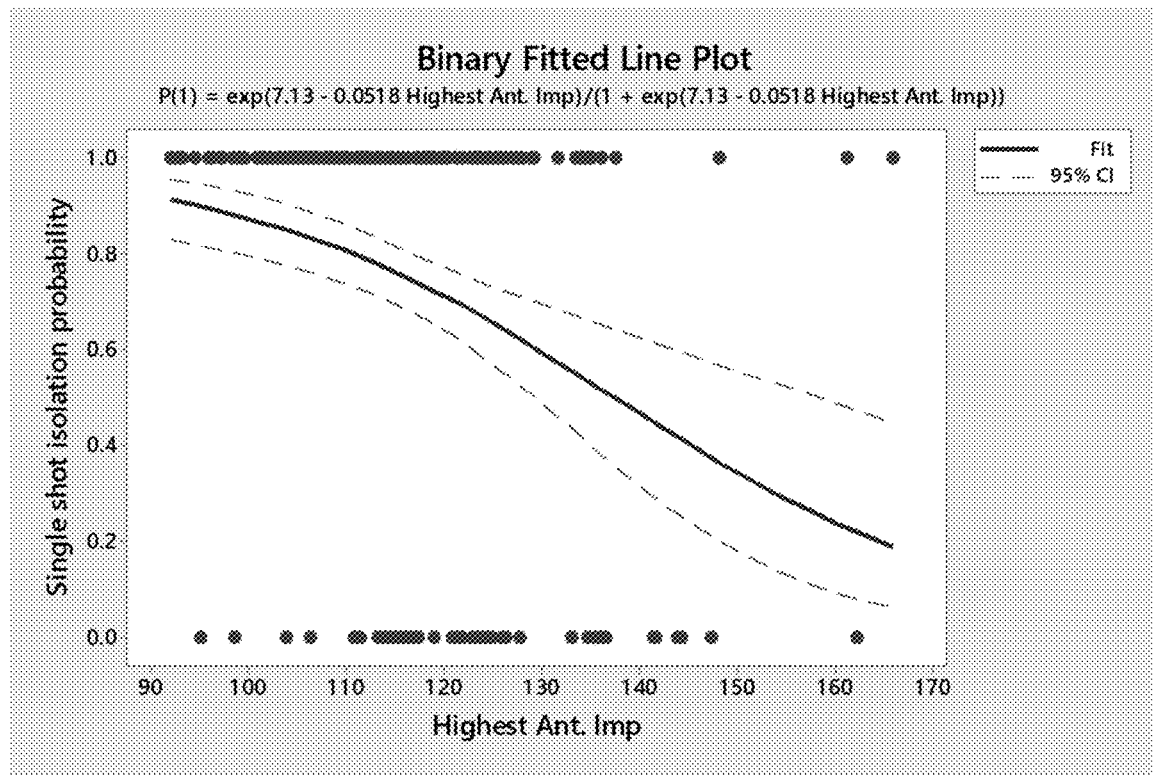

FIG. 88A shows a bar graph summarizing single shot isolation probability versus pre-ablation highest initial anterior wall impedance while FIG. 88B shows a binary fitted line plot of single shot isolation probability versus pre-ablation highest initial anterior wall impedance in the study of this disclosure. As can be seen, at an optimal range of about 110Ω, the single shot isolation rate was nearly approximately between 88.9 to 96.9%. The P-value of FIG. 67B was 0.000 with an odds ratio (95% CI) of 0.950 (0.926-0.974).

Figure 89A:
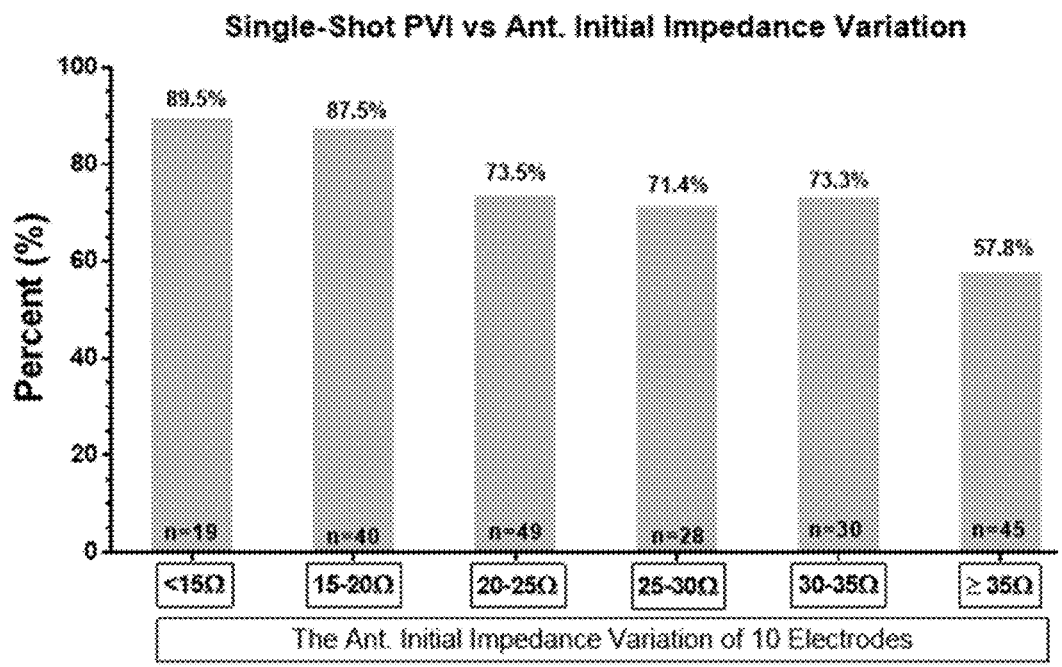
Figure 89B:
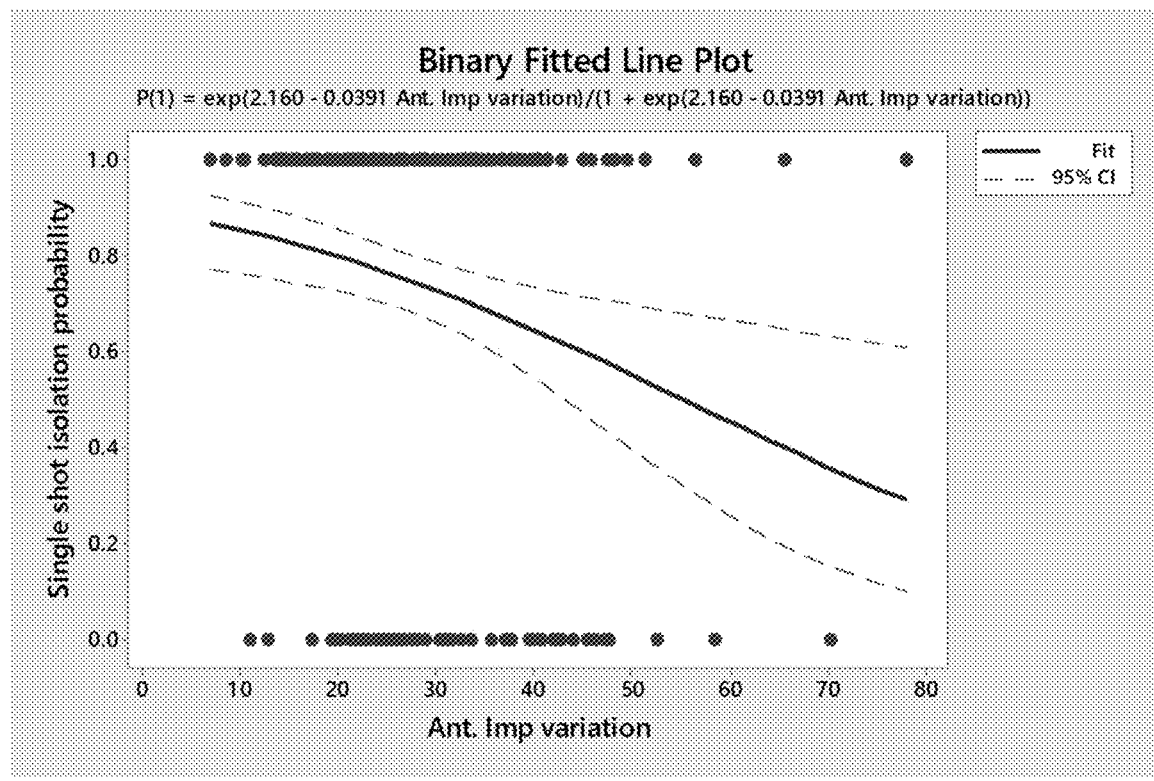

FIG. 89A shows a bar graph summarizing single shot isolation probability versus pre-ablation initial anterior wall impedance variation while FIG. 89B shows a binary fitted line plot of single shot isolation probability versus pre-ablation initial anterior wall impedance variation in the study of this disclosure. As can be seen, at a range of less than about 20Ω, the single shot isolation rate was nearly approximately between 87.5 to 89.5%. The P-value of FIG. 89B was 0.003 with an odds ratio (95% CI) of 0.962 (0.936-0.988).

Figure 90A:
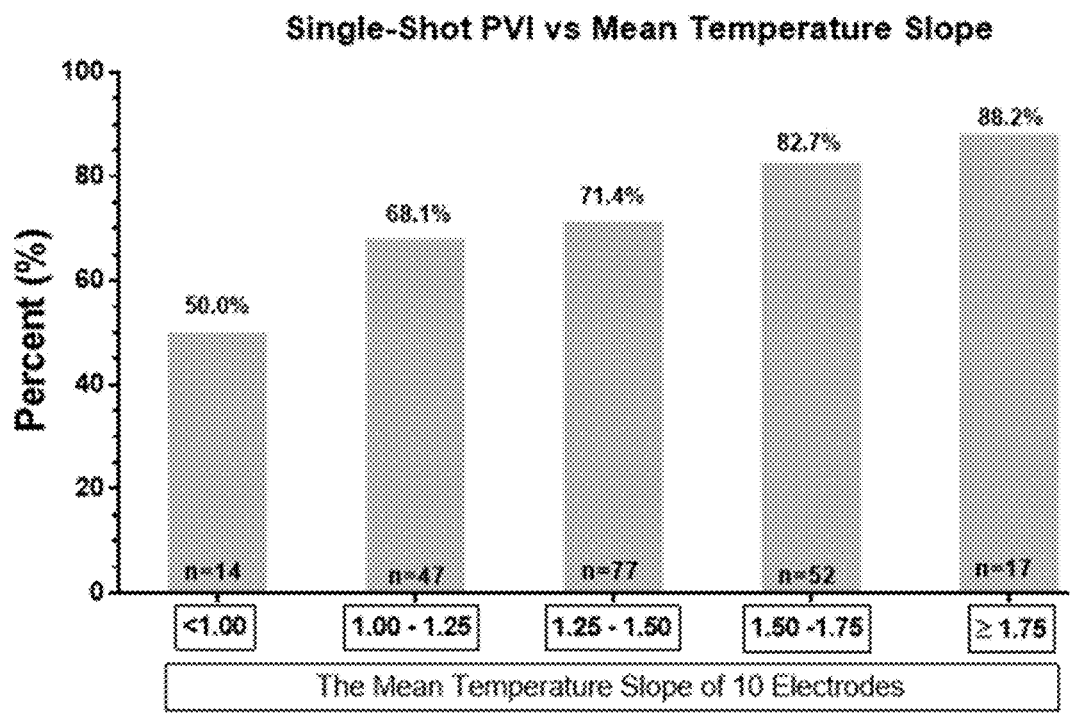
Figure 90B:
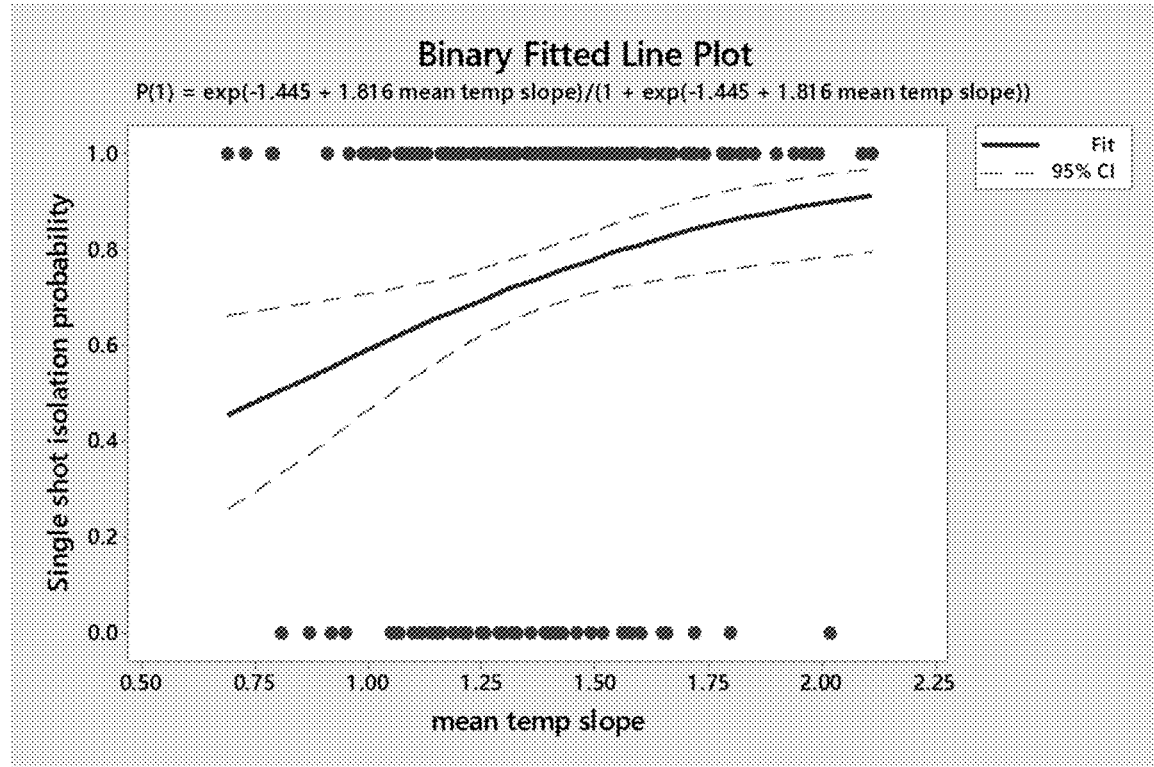

FIG. 90A shows a bar graph summarizing single shot isolation probability versus pre-ablation mean temperature slope while FIG. 90B shows a binary fitted line plot of single shot isolation probability versus pre-ablation mean temperature slope in the study of this disclosure. The P-value of FIG. 90B was 0.003 with an odds ratio (95% CI) of 6.145 (1.754-21.529).

FIG. 91A shows a bar graph summarizing single shot isolation probability versus pre-ablation lowest temperature slope while FIG. 91B shows a binary fitted line plot of single shot isolation probability versus pre-ablation lowest temperature slope in the study of this disclosure. As can be seen, at a range of greater or equal than about 0.75° C./sec, the single shot isolation rate was greater than approximately 90%. The P-value of FIG. 91B was 0.001 with an odds ratio (95% CI) of 7.251 (2.023-25.983).

FIG. 92A shows a bar graph summarizing single shot isolation probability versus pre-ablation highest temperature slope while FIG. 92B shows a binary fitted line plot of single shot isolation probability versus pre-ablation highest temperature slope in the study of this disclosure. The P-value of FIG. 92B was 0.129 with an odds ratio (95% CI) of 1.614 (0.860-3.029).

FIG. 93A shows a bar graph summarizing single shot isolation probability versus pre-ablation temperature slope variation while FIG. 93B shows a binary fitted line plot of single shot isolation probability versus pre-ablation temperature slope variation in the study of this disclosure. The P-value of FIG. 93B was 0.837 with an odds ratio (95% CI) of 0.943 (0.541-1.644).

FIG. 94A shows a bar graph summarizing single shot isolation probability versus pre-ablation mean temperature rise while FIG. 94B shows a binary fitted line plot of single shot isolation probability versus pre-ablation mean temperature rise in the study of this disclosure. As can be seen, for a mean temperature rise of equal to or greater than about 14° C., the single shot isolation rate was greater than approximately 90%. The P-value of FIG. 94B was 0.003 with an odds ratio (95% CI) of 1.170 (1.050-1.304).

FIG. 95A shows a bar graph summarizing single shot isolation probability versus pre-ablation lowest value temperature rise while FIG. 95B shows a binary fitted line plot of single shot isolation probability versus pre-ablation lowest value temperature rise in the study of this disclosure. As can be seen, for a lowest temperature rise of equal to or greater than about 6° C., the single shot isolation rate was greater than approximately 90%. The P-value of FIG. 95B was 0.000 with an odds ratio (95% CI) of 1.320 (1.122-1.553).

FIG. 96A shows a bar graph summarizing single shot isolation probability versus pre-ablation highest value temperature rise while FIG. 96B shows a binary fitted line plot of single shot isolation probability versus pre-ablation highest value temperature rise in the study of this disclosure. The P-value of FIG. 96B was 0.126 with an odds ratio (95% CI) of 1.053 (0.985-1.125).

FIG. 97A shows a bar graph summarizing single shot isolation probability versus pre-ablation temperature rise variation while FIG. 97B shows a binary fitted line plot of single shot isolation probability versus pre-ablation temperature rise variation in the study of this disclosure. The P-value of FIG. 97B was 0.546 with an odds ratio (95% CI) of 0.979 (0.914-1.049).

FIG. 98A shows a bar graph summarizing single shot isolation probability versus pre-ablation maximum mean temperature while FIG. 98B shows a binary fitted line plot of single shot isolation probability versus pre-ablation maximum mean temperature in the study of this disclosure. The P-value of FIG. 98B was 0.010 with an odds ratio (95% CI) of 1.189 (1.039-1.359).

FIG. 99A shows a bar graph summarizing single shot isolation probability versus pre-ablation lowest value maximum temperature while FIG. 99B shows a binary fitted line plot of single shot isolation probability versus pre-ablation lowest value maximum temperature in the study of this disclosure. The P-value of FIG. 99B was 0.022 with an odds ratio (95% CI) of 1.250 (1.022-1.528).

FIG. 100A shows a bar graph summarizing single shot isolation probability versus pre-ablation highest value maximum temperature while FIG. 100B shows a binary fitted line plot of single shot isolation probability versus pre-ablation highest value maximum temperature in the study of this disclosure. The P-value of FIG. 100B was 0.162 with an odds ratio (95% CI) of 1.050 (0.980-1.125).

FIG. 101A shows a bar graph summarizing single shot isolation probability versus pre-ablation maximum temperature variation while FIG. 101B shows a binary fitted line plot of single shot isolation probability versus pre-ablation maximum temperature variation in the study of this disclosure. The P-value of FIG. 101B was 0.576 with an odds ratio (95% CI) of 1.021 (0.950-1.097).

FIG. 102A shows a bar graph summarizing single shot isolation probability versus pre-ablation mean impedance drop while FIG. 102B shows a binary fitted line plot of single shot isolation probability versus pre-ablation mean impedance drop in the study of this disclosure. The P-value of FIG. 102B was 0.805 with an odds ratio (95% CI) of 1.008 (0.944-1.077).

FIG. 103A shows a bar graph summarizing single shot isolation probability versus pre-ablation lowest value impedance drop while FIG. 103B shows a binary fitted line plot of single shot isolation probability versus pre-ablation lowest value impedance drop in the study of this disclosure. As can be seen, when the impedance drop is at a range of greater than or equal to approximately about 12Ω, the single shot isolation rate was greater than approximately 90%. The P-value of FIG. 103B was 0.000 with an odds ratio (95% CI) of 1.146 (1.057-1.243).

FIG. 104A shows a bar graph summarizing single shot isolation probability versus pre-ablation highest value impedance drop while FIG. 104B shows a binary fitted line plot of single shot isolation probability versus pre-ablation highest value impedance drop in the study of this disclosure. The P-value of FIG. 104B was 0.022 with an odds ratio (95% CI) of 0.964 (0.934-0.995).

FIG. 105A shows a bar graph summarizing single shot isolation probability versus pre-ablation impedance drop variation while FIG. 105B shows a binary fitted line plot of single shot isolation probability versus pre-ablation impedance drop variation in the study of this disclosure. As can be seen, when the impedance drop variation is at a range of less than approximately about 20Ω, the single shot isolation rate was greater than approximately 85%. The P-value of FIG. 105B was 0.000 with an odds ratio (95% CI) of 0.941 (0.911-0.972).

FIG. 106A shows a bar graph summarizing single shot isolation probability versus pre-ablation lowest value impedance drop percent while FIG. 106B shows a binary fitted line plot of single shot isolation probability versus pre-ablation lowest value impedance drop percent in the study of this disclosure. As can be seen, when the lowest impedance drop percent is at a range of greater than or equal to approximately about 12%, the single shot isolation rate was greater than approximately 90%. The P-value of FIG. 106B was 0.000 with an odds ratio (95% CI) of 1.166 (1.077-1.263).

FIG. 107A shows a bar graph summarizing single shot isolation probability versus pre-ablation impedance drop percent variation while FIG. 107B shows a binary fitted line plot of single shot isolation probability versus pre-ablation impedance drop percent variation in the study of this disclosure. As can be seen, at an impedance drop variation range of less than 20Ω, the single shot isolation rate was greater than approximately 85%. The P-value of FIG. 107B was 0.004 with an odds ratio (95% CI) of 0.931 (0.887-0.978).

FIG. 108A shows a bar graph summarizing single shot isolation probability versus pre-ablation initial impedance deviation from mean value while FIG. 108B shows a binary fitted line plot of single shot isolation probability versus pre-ablation initial impedance deviation from mean value in the study of this disclosure. As can be seen, when the number of electrodes with initial impedance deviation from mean value is zero, the single shot isolation rate is approximately about 92.3% (n~13). The P-value of FIG. 108B was 0.009 with an odds ratio (95% CI) of 0.821 (0.708-0.953).

FIG. 109 shows a table summarizing predictors associated with corresponding Pearson correlation and binary logistic regression values in the study of this disclosure. In particular, the table shows that among ten electrodes that predictors of the study included (a) the number of electrodes with initial impedance at least 10Ω higher than mean value, (b) the number of electrodes with initial impedance at least 10Ω lower than mean value, and (c) the number of electrodes with initial impedance at least 10Ω higher or lower than mean value.

FIG. 110 shows a table summarizing pre- and post-ablation parameters in the study of this disclosure as to impedance, impedance variation, lowest initial impedance, mean initial impedance, initial impedance variation, lowest maximum temperature, lowest impedance drop, mean impedance drop, and impedance drop variation. Excluding roll-in cases in the SHINE clinical study, there were 95 cases (including 8 roll-in), only first shot for each PV with full-circle (e.g., all electrode burning) and full duration (e.g., 60 sec) were evaluated for analysis (with Minitab tool), including a total of 211 ablations with 156 single shot isolation (excluding left-common-pulmonary-vein ("LCPV") and right-middle-pulmonary-vein ("RMPV")). Minitabe Pearson correlations and binary logistic regression models were used to evaluate each parameter as a potential predictor of single shot isolation (including LCPV and RMPV). It was understood that larger coefficient and lower P-value of the table in FIG. 110, the better predictor. In this analysis, the pre-ablation parameters of mean initial impedance and initial impedance variation were deemed as predictors of single shot isolation, similar to FIG. 109. As for post-ablation parameters, lowest impedance drop and impedance drop variation were similarly deemed as predictors of single shot isolation, also similar to FIG. 109.

FIG. 111 shows a binary fitted line plot of probability of single shot isolation versus pre-ablation lowest anterior impedance in the study of this disclosure. FIG. 112 shows a binary fitted line plot of probability of single shot isolation versus pre-ablation anterior impedance variation in the study of this disclosure. FIG. 113 shows a binary fitted line plot of probability of single shot isolation versus pre-ablation lowest impedance in the study of this disclosure. FIG. 114 shows a binary fitted line plot of probability of single shot isolation versus pre-ablation mean impedance in the study of this disclosure. FIG. 115 shows a binary fitted line plot of probability of single shot isolation versus pre-ablation impedance variation in the study of this disclosure. FIG. 116 shows a binary fitted line plot of probability of single shot isolation versus post-ablation lowest maximum temperature in the study of this disclosure. FIG. 117 shows a binary fitted line plot of probability of single shot isolation versus post-ablation lowest impedance drop in the study of this disclosure. FIG. 118 shows a binary fitted line plot of probability of single shot isolation versus post-ablation mean impedance drop in the study of this disclosure. FIG. 119 shows a binary fitted line plot of probability of single shot isolation versus post-ablation impedance drop variation in the study of this disclosure.

FIG. 120A shows a graph summarizing single shot electrode temperature versus time for of electrodes of the balloon catheter used in the study of this disclosure, while FIG. 120B shows a graph summarizing single shot electrode impedance versus time for electrodes of the balloon catheter used in the study of this disclosure. FIG. 121 shows a table summarizing impedance and temperature values from the graphs of FIGS. 120A-120B. In the summarized example data, the balloon catheter was placed at the lesion site and initial temperature and impedance measurements were taken to determine as a predictor of PVI success rate.

Initial temperature values of FIGS. 120A-120B were observed as having relatively low values with a relatively narrow range determined to be desireable for being an predictor of PVI success rate more so than the absolute values of temperature readings being within a predetermined range. Absolute temperature of electrodes of the balloon catheter analyzed depended on tissue-touch, blood temperature, and/or irrigation temperature. Generally, temperature was observed as being less influenced by patient and tissue type, and was not usually subject to RF generation artifacts.

In FIGS. 120A-120B, it was further observed that initial impedance values having relatively high values with a relatively narrow range were effective as a predictor of PVI success rate, more so than the absolute values of impedance readings being within a predetermined range. Absolute impedance can depend on patient, tissue type and the degree of contact and generally speaking, impedance can be influenced by RF generation artifacts (e.g., interference, calibration, leakage). In certain examples, an extreme impedance drop can be a predictor of poor contact.

FIG. 122 shows a table demonstrating temperature and impedance trends in electrodes of the balloon catheter as to single shot versus non-isolation comparison for cases of the study of this disclosure. By monitoring the temperature of the balloon catheter before and during ablation, PVI success can be predicted. The information summarized in this table was observed as being particularly useful in predicting PVI success by using temperature and impedance in tandem, pre-ablation and/or during ablation, since both parameters can provide feedback in a complimentary manner.

FIG. 123A shows a graph summarizing electrode temperature versus time in the study of this disclosure, while FIG. 123B shows a graph summarizing electrode impedance versus time in the study of this disclosure. FIG. 124 shows a graph summarizing electrode impedance phase versus time in the study of this disclosure.

During the ablation of FIG. 123B to FIG. 124, the temperature and impedance measurements may be taken to provide an indication of the ultimate success of the ablation procedure. An impedance drop was expected and the impedance drop of FIG. 123B to FIG. 124 was observed as similar for each electrode and significant. Observing the data of FIG. 123B to FIG. 124, using temperature, impedance, and/or impedance phase change parameters during ablation was an indicator of PVI success rate when using the balloon catheter of this disclosure.

FIG. 125 depicts a method or use 12500 to treat a predetermined patient population for paroxysmal atrial fibrillation. The method or use 12510 can include ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently controllable; 12520 determining a characteristic, based on ablation parameters of the balloon catheter, of single shot pulmonary vein isolation (PVI) success rate; 12530 achieving, based on the characteristic and step of ablating tissue, a single shot isolation PVI success rate in the isolation of all targeted pulmonary veins for the predetermined patient population; and 12540 displaying the characteristic and the electrodes energized during the ablating.

FIG. 126 depicts a method or use 12600 to treat a predetermined patient population for paroxysmal atrial fibrillation. The method or use 12610 can include ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently controllable; 12620 determining a characteristic, based on ablation parameters of the balloon catheter, of single shot pulmonary vein isolation (PVI) success rate; and 12630 achieving, based on the characteristic and step of ablating tissue, a single shot isolation PVI success rate in the isolation of all targeted pulmonary veins for the predetermined patient population. The method or use can include 12640 displaying the characteristic and identity of electrodes that were energized during the ablating. Additionally, or optionally, a graphical representation of the characteristic (e.g., predictor or evaluator) and the identity of the electrodes energized during the ablating in a graphical display such as, for example, that shown in FIG. 128.

FIG. 127 illustrates an exemplary flow chart of the subroutine to determine a probability of success P from either the single-parameter predictor/evaluator (Table 1) or the multi-parameter predictor/evaluator (Table 2). The subroutine starts with step 1270 whereby the processor initiates a low current signal to be sent from the generator to each of the ten electrodes and the body patch (also known as the indifferent electrode). The processor also collects measurement of temperatures at step 1272 from the thermocouple or temperature sensor proximate each of the electrode. The temperature values are logged into the memory of the processor for analysis in step 1274. The processor retrieves the measured temperature values and derives the (a) initial temperature variation $\Delta T_0$; (b) highest initial temperature $T_{0max}$; (c) lowest temperature rise $\Delta T_{min}$. At step 1282, the processor retrieves the data logged impedance measurements and derive (a) initial impedance variation $\Delta Z_0$; (b) highest initial impedance $Z_{0max}$; (c) mean initial impedance $Z_{0mean}$; (d) impedance drop variation $\Delta Z_{drop}$; (e) lowest impedance drop $Z_{dropmin}$; (f) impedance drop percent variation $\Delta Z_{drop}\%$; and (g) lowest impedance drop percent $Z_{drop}\%_{min}$.

If the ablation is not completed at step 1284, the processor continues to collect temperature and impedance values in steps 1272-1282. On the other hand, if the first ablation has been completed then a decision moves to step 1286 which references a look-up table (e.g., Table 1) which is used to determine in step 1288 a probability of success using a single parameter (either temperature or impedance). The processor moves to step 1290 to calculate a probability of success using more than a single parameter based on the data from the SHINE study. The processor may use one or more of the Y term derived in data storage 1290 for the equation in step 1292. At step 1294, an output of either the single parameter probability of success in Step 1288 or the multi-parameter probability of success in step 1292. The system may display both the single-parameter probability of step 1288 and the multi-parameter probability of success of step 1292 as a form of cross-checking for accuracy.

An exemplary graphical-user-interface and display 1300 is reflected in FIG. 128. GUI display 1300 provides summary information or statistics of the ablation procedure for an electrode that a physician may find useful in making determinations of further therapy. As shown, electrode icon 1320 is highlighted such that the information provided corresponds to a first electrode. A visual indicator 1322 of the probability P of success can be provided before the actual ablation or as well after the ablation on the GUI display 1300. The visual indicator 1322 can be provided before, during or after the first ablation for consideration by the physician as to whether to continue with one or more subsequent ablations. Subsequent ablations are sometimes needed to ensure that all the tissues giving rise to erratic signals are fully ablated and that any unablated or partially ablated tissues will not form reconnect as to propagate erratic rhythm signals. By giving such indications to the physician (of which indicator 1322 is one example), the physician can decide whether the first ablation was sufficient or continue with subsequent ablations.

The following clauses list non-limiting embodiments of the disclosure:

1. A method or use to treat a predetermined patient population for paroxysmal atrial fibrillation, the method or use comprising:

ablating tissue of one or more targeted pulmonary veins with one or more of a plurality of the electrodes of an independently controlled multi-electrode radiofrequency balloon catheter, the balloon catheter comprising the plurality of electrodes for radiofrequency ablation that are independently controllable;

determining a characteristic, based on ablation parameters of the balloon catheter, of single shot pulmonary vein isolation (PVI) success rate; and achieving, based on the characteristic and step of ablating tissue, a single shot isolation PVI success rate in the isolation of all targeted pulmonary veins for the predetermined patient population.

2. The method or use of clause 1, wherein the step of achieving the single shot isolation PVI success rate further comprises further ablating tissue of one or more targeted pulmonary veins, based on the characteristic, with one or more of a plurality of the electrodes.

3. The method or use of clause 1, wherein the step of achieving the single shot isolation PVI success rate further comprises ceasing further tissue ablation with the multi-electrode radiofrequency balloon catheter, based on the characteristic.

4. The method or use of clause 1, wherein the step of achieving the single shot isolation PVI success rate further comprises achieving at least about a 91.7% success rate by ablating with a pre-ablation mean initial impedance of less than about 95Ω.

5. The method or use of clause 1, wherein the step of achieving the single shot isolation PVI success rate further comprises achieving at least about a 91.7% success rate by ablating with a pre-ablation highest initial impedance of less than about 100Ω.

6. The method or use of clause 1, wherein the step of achieving the single shot isolation PVI success rate further comprises achieving at least about 87% success rate by ablating with a pre-ablation initial anterior wall impedance of less than about 95Ω.

7. The method or use of clause 1, wherein the step of achieving the single shot isolation PVI success rate further comprises achieving at least about 85% success rate by ablating with a pre-ablation lowest initial anterior wall impedance of between about 80-90Ω.

8. The method or use of clause 1, wherein the step of achieving the single shot isolation PVI success rate further comprises achieving at least about 88% success rate by ablating with a pre-ablation highest initial anterior wall impedance of about 110Ω.

9. The method or use of clause 1, wherein the step of achieving the single shot isolation PVI success rate further comprises achieving at least about 87.5% success rate by ablating with a pre-ablation initial anterior wall impedance variation impedance range of less than about 20Ω.

10. The method or use of clause 1, wherein the characteristic is a predictor of the single shot isolation PVI success rate before ablation was limiting a highest initial temperature to less than about 31° C. among the electrodes of the balloon catheter.

11. The method or use of clause 1, wherein the characteristic is a predictor of the single shot isolation PVI success rate before ablation was permitting a lowest anterior wall impedance between approximately about 80-90Ω.

12. The method or use of clause 1, wherein the step of achieving the single shot isolation PVI success rate further comprises achieving at least about a 90% success rate by ablating with a mean initial impedance of less than about 95Ω for and a highest initial impedance of less than about 110Ω.

13. The method or use of clause 1, wherein the characteristic is a predictor is of the single shot isolation PVI success rate before ablation, the predictor being initial temperature and impedance at a lesion site just before the step of ablating.

14. The method or use of clause 1, wherein the characteristic is a predictor is of the single shot isolation PVI success rate before ablation, the predictor being relatively low initial temperature and impedance at a lesion site just before the step of ablating.

15. The method or use of clause 1, wherein the characteristic is a predictor is of the single shot isolation PVI success rate before ablation, the predictor being initial temperature in a relatively low range and impedance at a lesion site just before the step of ablating.

16. The method or use of clause 1, wherein the characteristic is a predictor is of the single shot isolation PVI success rate before ablation, the predictor being initial impedance impedance having relatively high values with a relatively narrow range.

17. The method or use of clause 1, wherein the characteristic is a predictor is of the single shot isolation PVI success rate before ablation, the predictor being absolute values of impedance readings within a predetermined range.

18. The method or use of clause 1, wherein the characteristic is a predictor is of the single shot isolation PVI success rate before and during ablation, the predictor being electrode temperature before and during ablation.

19. The method or use of clause 1, wherein the characteristic is a predictor is of the single shot isolation PVI success rate before ablation, the predictor being mean initial temperature, and wherein the mean initial temperature is approximately less than about 28° C. and the single shot isolation PVI success rate is at least approximately about 90%.

20. The method or use of clause 1, wherein the characteristic is a predictor is of the single shot isolation PVI success rate before ablation, the predictor being a distributed initial temperature, and wherein the distributed initial temperature is approximately greater than about 31° C., and the single shot isolation PVI success rate is at least approximately about 90%.

21. The method or use of clause 1, wherein the characteristic is a predictor is of the single shot isolation PVI success rate before ablation, the predictor being a distributed initial temperature, and wherein the distributed initial temperature is approximately greater than about 30° C., and the single shot isolation PVI success rate is at least approximately about 90%.

22. The method or use of clause 1, wherein the characteristic is a predictor is of the single shot isolation PVI success rate before ablation, the predictor being a distributed initial temperature, and wherein the distributed initial temperature is approximately greater than about 29° C., and the single shot isolation PVI success rate is at least approximately about 90%.

23. The method or use of clause 1, wherein the characteristic is a predictor is of the single shot isolation PVI success rate before ablation, the predictor being a pre-ablation lowest temperature slope, and wherein the pre-ablation lowest temperature slope is approximately greater than about 0.75° C./sec, and the single shot isolation PVI success rate is at least approximately about 90%.

24. The method or use of clause 1, wherein the characteristic is a predictor is of the single shot isolation PVI success rate before ablation, the predictor being a pre-ablation lowest value temperature, and wherein the pre-ablation lowest value temperature is approximately greater than about 6° C., and the single shot isolation PVI success rate is at least approximately about 90%.

25. The method or use of clause 1, wherein the characteristic is a predictor is of the single shot isolation PVI success rate before ablation, the predictor being a pre-ablation highest initial temperature, and wherein the pre-ablation highest initial temperature is approximately less than about 31° C., and the single shot isolation PVI success rate is at least approximately about 90%.

26. The method or use of clause 1, wherein the characteristic is a predictor is of the single shot isolation PVI success rate before ablation, the predictor being a pre-ablation initial temperature variation, and wherein the pre-ablation initial temperature variation is approximately less than about 3° C., and the single shot isolation PVI success rate is at least approximately about 95%.

27. The method or use of clause 1, wherein the characteristic is a predictor is of the single shot isolation PVI success rate before ablation, the predictor being a pre-ablation initial impedance variation, and wherein the pre-ablation initial impedance variation comprises an optimal range of approximately less than about 20Ω, and the single shot isolation PVI success rate is at least approximately about 88.5%.

28. The method or use of clause 1, wherein the characteristic is a predictor is of the single shot isolation PVI success rate before ablation, the predictor being a pre-ablation lowest value impedance drop, and wherein the pre-ablation lowest value impedance drop is approximately greater than about 12Ω, and the single shot isolation PVI success rate is at least approximately about 90%.

29. The method or use of clause 1, wherein the characteristic is a predictor is of the single shot isolation PVI success rate before ablation, the predictor being a pre-ablation impedance drop variation, and wherein the pre-ablation impedance drop variation is approximately greater than about 20Ω, and the single shot isolation PVI success rate is at least approximately about 85%.

30. The method or use of clause 1, wherein the characteristic is a predictor is of the single shot isolation PVI success rate before ablation, the predictor being a pre-ablation lowest value impedance drop percent, and wherein the pre-ablation lowest value impedance drop percent is greater than or equal to approximately about 12%, and the single shot isolation PVI success rate is at least approximately about 90%.

31. The method or use of clause 1, wherein the characteristic is a predictor is of the single shot isolation PVI success rate before ablation, the predictor being a pre-ablation impedance drop percent variation, and wherein the pre-ablation impedance drop percent variation is less than about 20Ω, and the single shot isolation PVI success rate is at least approximately about 85%.

32. The method or use of clause 1, wherein when a number of electrodes with initial impedance deviation from mean value is zero, the single shot isolation PVI success rate is approximately about 92%.

33. The method or use of clause 1, wherein the characteristic is a predictor is of the single shot isolation PVI success rate before ablation, the predictor being a difference of impedance between anterior and posterior wall.

34. The method or use of clause 33, wherein the difference is less than approximately about 20Ω and the single-shot PVI success rate is at least approximately about 85% for the predetermined patient population.

35. The method or use of clause 33, wherein the difference is less than approximately about 20Ω and the single-shot PVI success rate is at least approximately about 85% for the predetermined patient population of at least 25 patients.

36. The method or use of clause 33, wherein the difference is approximately between 20 to 30Ω and the single-shot PVI success rate is at least approximately about 78% for the predetermined patient population.

37. The method or use of clause 33, wherein the difference is approximately between 20 to 30Ω and the single-shot PVI success rate is at least approximately about 78% for the predetermined patient population of at least 75 patients.

38. The method or use of clause 33, wherein the difference is approximately between 30 to 40Ω and the single-shot PVI success rate is at least approximately about 75% for the predetermined patient population.

39. The method or use of clause 33, wherein the difference is approximately between 30 to 40Ω and the single-shot PVI success rate is at least approximately about 75% for the predetermined patient population of at least 60 patients.

40. The method or use of clause 33, wherein the difference is approximately between 40 to 50Ω and the single-shot PVI success rate is at least approximately about 67% for the predetermined patient population.

41. The method or use of clause 33, wherein the difference is approximately between 40 to 50Ω and the single-shot PVI success rate is at least approximately about 67% for a predetermined patient population of at least 34 patients.

42. The method or use of clause 33, wherein the difference is approximately between 50 to 60Ω and the single-shot PVI success rate is at least approximately about 35% for the predetermined patient population.

43. The method or use of clause 33, wherein the difference is approximately between 50 to 60Ω and the single-shot PVI success rate is at least approximately about 35% for the predetermined patient population of at least 11 patients.

44. The method or use of clause 33, wherein the difference is greater than approximately about 60Ω and the single-shot PVI success rate is at least approximately about 33% for the pre-determined patient population.

45. The method or use of clause 33, wherein the difference is greater than approximately about 60Ω and the single-shot PVI success rate is at least approximately about 33% for the pre-determined patient population of at least 9 patients.

46. The method or use of clause 33, wherein the balloon catheter is a full-circle all electrode burning ablation catheter.

47. The method or use of clause 33, wherein the step of ablating tissue is for a duration of 60 seconds.

48. The method or use of clause 1, wherein the characteristic is a predictor is of the single shot isolation PVI success rate before ablation, and wherein pre-ablation mean initial impedance is the predictor.

49. The method or use of clause 1, wherein the characteristic is a predictor is of the single shot isolation PVI success rate before ablation, and wherein pre-ablation initial impedance variation is the predictor.

50. The method or use of clause 1, wherein the characteristic is an evaluator of the single shot isolation PVI success rate post ablation, and wherein post-ablation lowest impedance drop is the evaluator.

51. The method or use of clause 1, wherein the characteristic is an evaluator of the single shot isolation PVI success rate post ablation, and wherein post-ablation impedance drop variation is the evaluator.

52. The method or use of clause 1, wherein the characteristic is a predictor is of the single shot isolation PVI success rate before ablation, and wherein post-ablation mean temperature slope is the evaluator.

53. The method or use of clause 1, wherein the characteristic is an evaluator of the single shot isolation PVI success rate post ablation, and wherein post-ablation lowest temperature slope is the predictor.

54. The method or use of clause 1, wherein the characteristic is an evaluator of the single shot isolation PVI success rate post ablation, and wherein post-ablation mean temperature rise is the evaluator.

55. The method or use of clause 1, wherein the characteristic is an evaluator of the single shot isolation PVI success rate post ablation, and wherein post-ablation lowest temperature rise is the evaluator.

56. The method or use of clause 1, wherein the characteristic is an evaluator of the single shot isolation PVI success rate post ablation, and wherein post-ablation lowest impedance drop percentage is the evaluator.

57. The method or use of clause 1, wherein the characteristic is an evaluator of the single shot isolation PVI success rate post ablation, and wherein post-ablation variation of impedance drop percentage is the evaluator.

58. The method or use of clause 1, wherein the characteristic is a predictor is of the single shot isolation PVI success rate before ablation, and wherein pre-ablation lowest impedance drop is the predictor.

59. The method or use of clause 1, wherein the characteristic is a predictor is of the single shot isolation PVI success rate before ablation, and wherein pre-ablation initial temperature variation is the predictor.

60. The method or use of clause 1, wherein the characteristic is a predictor is of the single shot isolation PVI success rate before ablation, and wherein pre-ablation maximum initial impedance is the predictor.

61. The method or use of clause 1, wherein the characteristic is a predictor is of the single shot isolation PVI success rate before ablation, and wherein pre-ablation mean initial anterior wall impedance is the predictor.

62. The method or use of clause 1, wherein the characteristic is a predictor is of the single shot isolation PVI success rate before ablation, and wherein pre-ablation lowest anterior wall impedance is the predictor.

63. The method or use of clause 1, wherein the characteristic is a predictor is of the single shot isolation PVI success rate before ablation, and wherein pre-ablation maximum anterior wall impedance is the predictor.

64. The method or use of clause 1, wherein the characteristic is a predictor is of the single shot isolation PVI success rate before ablation, and wherein pre-ablation anterior wall impedance variation is the predictor.

65. The method or use of any preceding clause, wherein impedance values were among the electrodes of an anterior wall.

66. The method or use of any preceding clause, wherein the characteristic is a predictor is of the single shot isolation PVI success rate before ablation, and wherein the predictor is determined by:

$$\text{Probability} \sim \frac{e^Y}{(1+e^Y)}$$

$$Y \sim 4.367 - 0.420\Delta T_0 - 0.0486\Delta Z_0$$

wherein $\Delta T_0$ is initial impedance variation and $\Delta Z_0$ is initial temperature variation.

67. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 26.78 - 0.576 T_{0max} - 0.0632 Z_{0max}$$

wherein $T_{0max}$ is highest initial temperature and $Z_{0max}$ is highest initial impedance.

68. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 27.70 - 0.540 T_{0max} - 0.0959 Z_{0max}$$

wherein $T_{0max}$ is highest initial temperature and $Z_{0max}$ is highest initial impedance.

69. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 9.31 - 0.408 \Delta T_0 - 0.0544 Z_{0max}$$

wherein $\Delta T_0$ is initial temperature variation and $Z_{0max}$ is highest initial impedance.

70. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 22.61 - 0.622 T_{0max} - 0.0626 \Delta Z_0$$

wherein $T_{0max}$ is highest initial temperature and $\Delta Z_0$ is initial impedance variation.

71. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 11.53 - 0.439 \Delta T_0 - 0.0856 Z_{0mean}$$

wherein $\Delta T_0$ is initial temperature variation and $Z_{0max}$ is mean initial impedance.

72. The method or use of any preceding clause, wherein the characteristic is a predictor is of the single shot isolation PVI success rate before ablation, and wherein the predictor is determined by:

$$Prob \sim \frac{e^Y}{(1+e^Y)}$$

$$Y \sim 26.52 + 0.013 \Delta T_0 - 0.594 T_{0max} - 0.0122 \Delta Z_0 - 0.053 Z_{0max}$$

wherein $\Delta T_0$ is initial temperature variation, $T_{0max}$ is highest initial temperature, $\Delta Z_0$ is initial impedance variation, and $Z_{0max}$ is highest initial impedance.

73. The method or use of any preceding clause, wherein the characteristic is an evaluator of the single shot isolation PVI success rate post ablation, and wherein the evaluator is determined by:

$$Prob \sim \frac{e^Y}{(1+e^Y)}$$

$$Y \sim 1.562 + 0.2856 \Delta T_{min} - 0.0629 \Delta Z_{drop}$$

wherein $\Delta T_{min}$ is lowest temperature rise and $\Delta Z_{drop}$ is impedance drop variation.

74. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim -0.507 + 0.206 \Delta T_{min} + 0.083 Z_{dropmin}$$

wherein $\Delta T_{min}$ is lowest temperature rise and $Z_{dropmin}$ is minimum impedance drop.

75. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim 1.248 + 0.2486 \Delta T_{min} - 0.0594 \Delta Z_{drop} + 0.0419 Z_{dropmin}$$

wherein $\Delta T_{min}$ is lowest temperature rise and $Z_{dropmin}$ is minimum impedance drop.

76. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim 1.174 + 0.2515 \Delta T_{min} - 0.0564 \Delta Z_{drop} \%$$

wherein $\Delta T_{min}$ is lowest temperature rise and $\Delta Z_{drop}$ is impedance drop percent variation.

77. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim -0.644 + 0.170 \Delta T_{min} + 0.107 Z_{drop} \%_{min}$$

wherein $\Delta T_{min}$ is lowest temperature rise and $Z_{drop}\%_{min}$ is lowest impedance drop percent.

78. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim 0.339 + 0.187\Delta T_{min} + 0.0737 Z_{drop}\%_{min} - 0.0368\Delta Z_{drop}\%$$

wherein $\Delta T_{min}$ is lowest temperature rise, $Z_{drop}\%_{min}$ is lowest impedance drop percent, and $\Delta Z_{drop}\%$) is impedance drop percent variation.

79. The method or use of any preceding clause, wherein the characteristic is an evaluator of the single shot isolation PVI success rate post ablation, and wherein the evaluator is determined by:

$$P \sim \frac{e^Y}{(1+e^Y)}$$

$$Y \sim 1.043 + 0.777 T'_{min} + 0.171\Delta T_{min} + 0.0479 Z_{drop-min} - 0.0589\Delta Z_{drop}$$

wherein $T'_{min}$ is lowest temperature slope, $\Delta T_{min}$ is lowest temperature rise, $Z_{drop}$-min is lowest impedance drop and $\Delta Z_{drop}$ is impedance drop variation.

80. The method or use of claim 1, further comprising the step of displaying a graphical representation of the independently controllable electrodes and the ablation parameters.

81. The method or use of clause 74, wherein one ablation parameter comprises impedance measured proximate each electrode.

82. The method or use of clause 75, wherein the measured impedance comprises impedance measured before ablation.

83. The method or use of clause 75, wherein the measured impedance comprises impedance measured after ablation.

84. The method or use of clause 75, wherein the measured impedance comprises impedance measured before and impedance measured after ablation.

85. The method or use of clause 74, wherein one ablation parameter comprises temperature measured proximate each electrode.

86. The method or use of clause 74, wherein one ablation parameter comprises a maximum temperature measured proximate each electrode during the ablating.

87. The method or use of clause 74, wherein one ablation parameter comprises a measured temperature rise from a beginning of ablating to an end of the ablating.

88. A method or use to treat a plurality of patients for paroxysmal atrial fibrillation, the method or use comprising the steps of:
delivering a multi-electrode radiofrequency balloon catheter having a plurality of independently controllable electrodes for radiofrequency ablation and a multi-electrode diagnostic catheter to one or more targeted pulmonary veins;
ablating tissue of the one or more targeted pulmonary veins with one or more of the plurality of the electrodes independently controlled multi-electrode radiofrequency balloon catheter;
diagnosing the one or more targeted pulmonary veins using the multi-electrode diagnostic catheter; and
achieving at least one of a predetermined clinical effectiveness and acute effectiveness of the multi-electrode radiofrequency balloon catheter and the multi-electrode diagnostic catheter in the isolation of the one or more targeted pulmonary veins, during and approximately 3 months after the ablating step.

89. The method or use of clause 82, wherein acute effectiveness is defined by confirming if there is an entrance block in all targeted pulmonary veins after adenosine and/or isoproterenol challenge.

90. The method or use of clause 83, further comprising: determining the acute effectiveness determined at approximately 3 months after the ablating step; and generating an estimated acute effectiveness at approximately 12 months after the ablating step based on the acute effectiveness determined at approximately 3 months.

91. The method or use of clause 84, wherein the estimated acute effectiveness at approximately 12 months is substantially similar to the acute effectiveness determined at approximately 3 months.

92. The method or use of clause 83, wherein the acute effectiveness is further defined by success greater than 90% for the plurality of patients.

93. The method or use of clause 83, wherein the acute effectiveness is further defined by success greater than 95% for the plurality of patients.

94. The method or use of clause 83, wherein a Type-1 error rate for power the acute effectiveness and the clinical effectiveness of all targeted veins are controlled at approximately a 5% level, the method or use further comprising:
determining whether the ablating is clinically successful for the plurality of patients if both the acute effectiveness and the clinical effectiveness indications are controlled at approximately the 5% level.

95. The method or use of clause 83, wherein the acute effectiveness is at least 80% for the plurality of patients being at least 80 patients.

96. The method or use of clause 83, wherein the acute effectiveness is at least 80% for the plurality of patients being at least 130 patients.

97. The method or use of clause 83, wherein the acute effectiveness is at least 80% for the plurality of patients being at least 180 patients.

98. The method or use of clause 83, wherein the acute effectiveness is at least 80% for the plurality of patients being at least 230 patients.

99. The method or use of clause 83, wherein the acute effectiveness is further defined by confirming if there is an entrance block in all targeted pulmonary veins after adenosine and/or isoproterenol challenge using a focal ablation catheter.

100. The method or use of clause 83, wherein the acute effectiveness is further defined by confirming if there is an entrance block in all targeted pulmonary veins after adenosine and/or isoproterenol challenge without using a focal ablation catheter.

101. The method or use of clause 82, wherein the ablating is administered on the plurality of patients diagnosed with symptomatic paroxysmal atrial fibrillation.

102. The method or use of clause 82, wherein the step of diagnosing further comprises:
electrophysiological mapping of the heart.

103. The method or use of clause 82, wherein the multi-electrode diagnostic catheter further comprises a high torque shaft with a halo-shaped tip section containing a plurality of pairs of electrodes visible under fluoroscopy.

104. The method or use of clause 82, wherein the plurality of patients is at least 80.

105. The method or use of clause 82, wherein the plurality of patients is at least 130.

106. The method or use of clause 82, wherein the plurality of patients is at least 180.

107. The method or use of clause 82, wherein the plurality of patients is at least 230.

108. The method or use of clause 82, wherein the predetermined acute effectiveness is de-fined by ulceration being absent in the plurality of patients after the ablating.

109. The method or use of clause 82, wherein the predetermined acute effectiveness is de-fined by a complication rate of approximately 13% or fewer of the plurality of patients experiencing esophageal erythema after the ablating.

110. The method or use of clause 82, wherein the predetermined acute effectiveness is de-fined by a complication rate of approximately 25% or fewer of the plurality of patients experiencing new asymptomatic cerebral embolic lesions after the ablating.

111. The method or use of clause 82, wherein the predetermined acute effectiveness is de-fined by a complication rate of approximately 20% or fewer of the plurality of patients experiencing new asymptomatic cerebral embolic lesions after the ablating.

112. The method or use of clause 82, wherein the predetermined acute effectiveness is de-fined by a complication rate of approximately 5-9% or fewer of the plurality of patients experiencing a primary adverse event by approximately 7 or more days after the ablating.

113. The method or use of clause 82, wherein inclusion criteria for the plurality of patients comprises:
a diagnosis with symptomatic paroxysmal atrial fibrillation; and
a patient capability to comply with uninterrupted per-protocol anticoagulation requirements.

114. The method or use of clause 82, wherein the predetermined acute effectiveness is de-fined by a total procedure time.

115. The method or use of clause 82, wherein the predetermined acute effectiveness is de-fined by a total ablation time.

116. The method or use of clause 82, wherein the predetermined acute effectiveness is de-fined by a total RF application time.

117. The method or use of clause 82, wherein the predetermined acute effectiveness is de-fined by a total dwell time of the multi-electrode radiofrequency balloon catheter.

118. The method or use of clause 82, wherein the predetermined acute effectiveness is de-fined by a total time to isolate all targeted pulmonary veins.

119. The method or use of clause 82, wherein the predetermined acute effectiveness is de-fined by a number and a total time of applications by the multi-electrode radiofrequency balloon catheter per location of all targeted pulmonary veins.

120. The method or use of clause 82, wherein the predetermined acute effectiveness is de-fined by a number and a total time of applications by the multi-electrode radiofrequency balloon catheter per patient.

121. The method or use of clause 82, wherein the predetermined acute effectiveness is de-fined by a number and a total time of applications by the multi-electrode radiofrequency balloon catheter per targeted vein.

122. The method or use of any previous clause, wherein the multi-electrode radiofrequency balloon catheter comprises:
a compliant balloon with a plurality of electrodes bonded configured to deliver RF energy to tissue of the pulmonary vein and sense temperature at each electrode.

123. The method or use of clause 82, wherein clinical effectiveness is defined by an incidence of early onset of one or more adverse events within a predetermined time of the method or use being implemented.

124. The method or use of clause 117, wherein the predetermined time is at least 7 days.

125. The method or use of clause 117, wherein the one or more adverse events comprise: death, atrioesophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

126. The method or use of clause 117, wherein the one or more adverse events comprise: incidence of individual adverse events from a primary composite; incidence of serious adverse de-vice effect; incidence of serious adverse events within 7 days, at least 7¬30 days, and at least 30 days following the ablating; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

127. The method or use of clause 117, wherein the one or more adverse events for approximately 5-9% of the plurality of patients, the one or more adverse events comprising:
NIHSS (National Institute of Health Stroke Scale) scores at baseline, post-ablation and during follow-up;
a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins;
a percentage (%) of subjects with use of focal catheter ablations for non-PV triggers;
a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180);
a percentage (%) of subjects with freedom from documented atrial fibrillation (AF), atrial tachycardia (AT), or atypical (left side) atrial flutter (AFL);
one or more episodes that endure for 30 or more seconds on an arrhythmia monitoring device from day 91 to 180 following the ablating; and
one or more procedural parameters including total procedure and ablation time, balloon dwell time, RF application time, a number of RF applications, fluoroscopy time and dose.

128. The method or use of clause 82, wherein the acute safety rate includes complication rates of 10% or less and is defined by incidence of asymptomatic cerebral embolic lesions at a discharge magnetic resonance imaging (MRI).

129. The method or use of clause 82, wherein the acute effectiveness rate is 100% and is de-fined by electrically isolating all targeted pulmonary veins without use of a focal ablation catheter.

130. The method or use of clause 82, wherein the acute effectiveness rate is defined by a freedom from documented atrial fibrillation, atrial tachycardia, or atypical atrial flutter episodes based on electrocardiographic data through an effectiveness evaluation period (1 year).

131. The method or use of clause 82, wherein the acute effectiveness rate is defined by pulmonary vein isolation touch-up by a focal catheter among all targeted pulmonary veins.

132. The method or use of clause 82, wherein the predetermined clinical effectiveness rate is defined by 10% or less complication rates related to incidence of post-ablation symptomatic and asymptomatic cerebral emboli as compared to pre-ablation.

133. The method or use of clause 82, wherein the multi-electrode diagnostic catheter is con-figured for electrophysiological recording and stimulation of the atrial region of the heart and is used in conjunction with the multi-electrode radiofrequency balloon catheter.

134. A method or use to treat a plurality of patients for paroxysmal atrial fibrillation, the method or use comprising the steps of:
delivering a multi-electrode radiofrequency balloon catheter having a plurality of independently controllable electrodes for radiofrequency ablation and a multi-electrode diagnostic catheter to one or more targeted pulmonary veins; and
ablating tissue of one or more targeted pulmonary veins with one or more of the plurality of the electrodes independently controlled multi-electrode radiofrequency balloon catheter;
diagnosing all targeted pulmonary veins using the multi-electrode diagnostic catheter; and
achieving a predetermined rate of adverse events based on use of the multi-electrode radiofrequency balloon catheter and the multi-electrode diagnostic catheter in the isolation of all targeted pulmonary veins, during and approximately 6 months after the method or use.

135. A method or use to treat a plurality of patients for paroxysmal atrial fibrillation, the method or use comprising the steps of:
evaluating a number and size of all targeted pulmonary veins and anatomy of the left atrial;
puncturing the transseptal;
selectively positioning a multi-electrode esophageal temperature monitoring device in the vasculature with respect to all targeted pulmonary veins;
selectively positioning a multi-electrode radiofrequency balloon catheter in the vasculature with respect to all targeted pulmonary veins, the multi-electrode radiofrequency balloon catheter having a plurality of independently controllable electrodes for radiofrequency ablation;
selectively positioning a multi-electrode diagnostic catheter in the vasculature with respect to all targeted pulmonary veins;
ablating tissue of all targeted pulmonary veins with one or more of the plurality of the electrodes independently controlled multi-electrode radiofrequency balloon catheter;
confirming isolation of all targeted pulmonary veins using the multi-electrode diagnostic catheter;
confirming existence of an entrance block in all targeted pulmonary veins;
achieving a predetermined clinical effectiveness and/or acute effectiveness of the method or use, based on the confirmed existence of the entrance block, regarding the isolation of all targeted pulmonary veins following the method or use.

136. The method or use according to any of the preceding clauses, further comprising: map-ping all targeted pulmonary veins using the diagnostic catheter.

137. The method or use according to any of the preceding clauses, wherein exclusion criteria for the plurality of patients comprises at least one of the following:
atrial fibrillation secondary to electrolyte imbalance, thyroid disease, or reversible or non-cardiac cause;
previous surgical or catheter ablation for atrial fibrillation;
anticipated to receive ablation outside all targeted pulmonary veins ostia and CTI region;
previously diagnosed with persistent, longstanding atrial fibrillation and/or continuous atrial fibrillation >7 days, or >48 hrs terminated by cardioversion;
any percutaneous coronary intervention (PCI) within the past 2 months;
valve repair or replacement and presence of a prosthetic valve;
any carotid stenting or endarterectomy;
coronary artery bypass grafting, cardiac surgery, valvular cardiac surgical or percutaneous procedure within the past 6 months;
documented left atrium thrombus on baseline imaging;
LA antero posterior diameter greater than 50 mm;
any pulmonary vein with a diameter greater than or equal to 26 mm;
left ventricular ejection fraction less than 40%;
contraindication to anticoagulation;
history of blood clotting or bleeding abnormalities;
myocardial infarction within the past 2 months;
documented thromboembolic event within the past 12 months;
rheumatic heart disease;
awaiting cardiac transplantation or other cardiac surgery within the next 12 months;
unstable angina;
acute illness or active systemic infection or sepsis;
diagnosed atrial myxoma or interatrial baffle or patch;
presence of implanted pacemaker, implantable cardioverter defibrillator, tissue-embedded, or iron-containing metal fragments;
significant pulmonary disease or any other disease or malfunction of the lungs or respiratory system that produces chronic symptoms;
significant congenital anomaly;
pregnancy or lactating;
enrollment in an investigational study evaluating another device, biologic, or drug;
pulmonary vein stenosis;
presence of intramural thrombus, tumor or other abnormality that precludes vascular access, or manipulation of the catheter;
presence of an IVC filter;
presence of a condition that precludes vascular access;
life expectancy or other disease processes likely to limit survival to less than 12 months;
contraindication to use of contrast agents for MRI;
presence of iron-containing metal fragments in the patient; or
unresolved pre-existing neurological deficit.

138. The method or use of any previous clause, wherein the multi-electrode radiofrequency balloon catheter comprises:
a compliant balloon with a plurality of electrodes configured to deliver RF energy to tissue of all targeted pulmonary veins and sense temperature at each electrode.

139. The method or use of clause 132, wherein the plurality of electrodes is oriented circularly to circumferentially contact with an ostia of the pulmonary vein.

140. The method or use of clause 132, further comprising using the plurality of electrodes for visualization, stimulation, recording, and ablation.

141. The method or use of clause 132, wherein each electrode is configured so an amount of power delivered to each electrode is controlled independently.

142. The method or use of clause 132, wherein the multi-electrode radiofrequency balloon catheter further comprises a proximal handle, a distal tip, and a middle section disposed there-between.

143. The method or use of clause 136, wherein the proximal handle is a deflection thumb knob allowing for unidirectional deflection, a balloon advancement mechanism, and a luer fitting for balloon inflation and irrigation.

144. The method or use of clause 132, wherein the multi-electrode radiofrequency balloon catheter further comprises
a high-torque shaft configured to be rotated to facilitate accurate positioning of the catheter tip to a desired; and
a unidirectional braided deflectable tip section.

145. The method or use of any preceding clause, further comprising:
controlling irrigation to the multi-electrode radiofrequency balloon catheter with an irrigation pump.

146. The method or use of any preceding clause, further comprising:
administering uninterrupted anticoagulation therapy at least 1 month prior to the procedure.

147. The method or use of any preceding clause, wherein if the patient is receiving warfarin/coumadin therapy, the patient must have an international normalized ratio (INR)≥2 for at least 3 weeks prior to the procedure.

148. The method or use of any preceding clause, wherein if the patient is receiving warfarin/coumadin therapy, the patient must be confirmed to have an international normalized ratio (INR)≥2 within 48 hours pre-procedure.

149. The method or use of any preceding clause, further comprising: continuing anticoagulation therapy prior to the procedure.

150. The method or use of any preceding clause, further comprising:
administering a transseptal puncture;
confirming an activated clotting time target of ≥350 sec. prior to inserting the multi-electrode radiofrequency balloon catheter into the left atrium and maintaining throughout the procedure;
introducing the multi-electrode radiofrequency balloon catheter;
introducing of a multi-electrode circular diagnostic catheter;
ablating the pulmonary vein with the multi-electrode radiofrequency balloon catheter; determining in real time pulmonary vein isolation with the multi-electrode circular diagnostic catheter; and
confirming whether an entrance is blocked in the pulmonary vein.

151. The method or use of any preceding clause, wherein the multi-electrode circular diagnostic catheter comprises:
an elongated body having a longitudinal axis;
a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;
at least one irrigated ablation ring electrode mounted on the proximal loop;
a control handle proximal the elongated body; and
a contraction wire having a proximal end in the control handle and a distal end anchored in the proximal loop, the control handle including a first control member configured to actuate the contraction wire to contract the proximal loop, wherein the proximal loop has a first flexibility and the distal loop has a second flexibility, and the second flexibility is greater than the first flexibility.

152. A method or use of treating a plurality of patients for paroxysmal atrial fibrillation by applying energy to tissue of a subject's heart proximate to an esophagus, phrenic nerve, or lung, the method or use comprising the steps of:

achieving at least one of a predetermined clinical effectiveness and acute effectiveness of the procedure based on use of a multi-electrode radiofrequency balloon catheter and a multi-electrode diagnostic catheter in the isolation of the one or more targeted pulmonary veins by:
positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;
viewing an image of the expandable member as well as the first and second radiopaque markers in the left atrium;
determining an orientation of the first and second radiopaque markers with respect to a
portion of the left atrium closest to the esophagus, phrenic nerve, or lung, of the subject;
moving one of the first and second radiopaque markers to a portion of the left atrium closest to the esophagus, phrenic nerve or lung;
energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and
electrophysiologically recording and stimulating the atrial region of the tissue proximate to the esophagus, phrenic nerve, or lung using the multi-electrode diagnostic catheter.

153. A clinically effective device to treat atrial fibrillation in a group of patients, the device comprising an end probe coupled to a tubular member that extends along a longitudinal axis from a proximal portion to a distal portion, the end probe comprising:
a first expandable membrane coupled to the tubular member;
a plurality of electrodes disposed generally equiangularly about the longitudinal axis on an outer surface of the first expandable membrane;
at least one wire connected each of the plurality of electrodes, the at least one wire of each electrode extending from the first expandable membrane toward the tubular member; and
a second expandable membrane that encapsulates a portion of the at least one wire between the second expandable membrane and the first expandable membrane; and
wherein the device is configured to achieve a predetermined effectiveness rate of pulmonary vein isolation in the group of patients.

154. A clinically effective device to administer a procedure for cardiac electrophysiological ablation of pulmonary veins of the atria and treatment of drug refractory recurrent symptomatic pulmonary atrial fibrillation, the device comprising:
an end probe coupled to a tubular member that extends along a longitudinal axis from a proximal portion to a distal portion, the end probe comprising:
a first expandable membrane coupled to the tubular member;
a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve a predetermined effectiveness rate of pulmonary vein isolation.

155. A clinically effective device to administer a procedure for cardiac electrophysiological ablation of pulmonary veins of the atria and treatment of drug refractory recurrent symptomatic pulmonary atrial fibrillation, the device comprising:

an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 97% safety endpoint within seven (7) days of successful pulmonary vein isolation.

156. A clinically effective device to administer a procedure for cardiac electrophysiological ablation of pulmonary veins of the atria and treatment of drug refractory recurrent symptomatic pulmonary atrial fibrillation, the device comprising:

an end probe coupled to a tubular member that extends along a longitudinal axis from a proximal portion to a distal portion, the end probe comprising:

a first expandable membrane coupled to the tubular member;

a plurality of electrodes disposed generally equiangularly about the longitudinal axis on an outer surface of the first expandable membrane;

at least one wire connected each of the plurality of electrodes, the at least one wire of each electrode extending from the first expandable membrane toward the tubular member; and a second expandable membrane that encapsulates a portion of the at least one wire between the second expandable membrane and the first expandable membrane so that each of the plurality of electrodes is independently controlled to achieve pulmonary vein isolation and at least a 90% safety endpoint within seven (7) days of successful pulmonary vein isolation.

157. The device of one of the preceding clauses, wherein the predetermined effectiveness rate includes complication rates of 10% or less and is defined by existence or nonexistence of asymptomatic cerebral embolic lesions at a discharge magnetic resonance imaging (MRI).

158. The device of one of the preceding clauses, wherein the predetermined effectiveness rate includes complication rates of approximately 0% and is defined by existence or non-existence of esophageal injury erythema.

159. The device of one of the preceding clauses, wherein the predetermined effectiveness rate is approximately 100% and is defined by electrically isolating all targeted pulmonary veins without use of a focal ablation catheter.

160. The device of one of the preceding clauses, wherein the predetermined effectiveness rate is defined by a freedom from documented atrial fibrillation, atrial tachycardia, or atypical atrial flutter episodes based on electrocardiographic data through an effectiveness evaluation period.

161. The device of Clause 1, wherein the effectiveness evaluation period is approximately one year.

162. The device of one of the preceding clauses, wherein the predetermined effectiveness rate is defined by pulmonary vein isolation touch-up by a focal catheter among all targeted pulmonary veins.

163. The device of one of the preceding clauses, wherein the predetermined effectiveness rate is defined by using focal catheter ablation for non-PV triggers during the index procedure.

164. The device of one of the preceding clauses, wherein the predetermined effectiveness rate comprises a long-term effectiveness rate.

165. The device of one of the preceding clauses, wherein the predetermined effectiveness rate is defined by an average number of Radio-Frequency applications per patient and Radio-Frequency time required to isolate all pulmonary veins.

166. The device of one of the preceding clauses, wherein the predetermined effectiveness rate is defined by an average number of Radio-Frequency applications per vein and Radio-Frequency time required to isolate common pulmonary veins.

167. The device of one of the preceding clauses, wherein the predetermined effectiveness rate is defined by an average number of Radio-Frequency applications per patient and Radio-Frequency time required to isolate common pulmonary veins.

168. The device of one of the preceding clauses, wherein the predetermined effectiveness rate is defined by determining incidence of complication rates being 10% or less of post-ablation symptomatic and asymptomatic cerebral emboli as compared to pre-ablation.

169. The device of one of the preceding clauses, wherein the predetermined effectiveness rate is defined by evaluating a presence of emboli-associated neurological deficits by at least one of NIHSS and mRS assessments.

170. The device of any previous clause, wherein the end probe is configured for use in catheter-based cardiac electrophysiological mapping of the atria.

171. The device of any previous clause, wherein the end probe is configured for cardiac ablation.

172. The device of any previous clause, wherein the end probe comprises: the plurality of electrodes bonded to the first expandable membrane and configured to deliver Radio-Frequency energy to tissue of the pulmonary vein and sense temperature at each electrode.

173. The device of any previous clause, wherein the plurality of electrodes is oriented circularly to circumferentially contact with an ostia of the pulmonary vein.

174. The device of any previous clause, wherein the device is further configured for using the plurality of electrodes for visualization, stimulation, recording, and ablation.

175. The device of any previous clause, wherein each electrode is configured so an amount of power delivered to each electrode is controlled independently.

176. The device of any previous clause, wherein the end probe further comprises a proximal handle, a distal tip, and a middle section disposed therebetween.

177. The device of any previous clause, wherein the proximal handle is a deflection thumb knob allowing for unidirectional deflection, a balloon advancement mechanism, and a luer fitting for balloon inflation and irrigation.

178. The device of any previous clause, wherein the end probe further comprises a high-torque shaft configured to be rotated to facilitate accurate positioning of the catheter tip to a desired; and a unidirectional braided deflectable tip section.

179. The device of any previous clause, wherein the end probe further comprises:

a first substrate disposed on the membrane, the first substrate including a first radiopaque marker of a first form disposed thereon; and a second substrate disposed on the membrane, the second substrate including a second radiopaque marker of a second form disposed thereon, the second form being different from the first form.

180. The device of any previous clause, further comprising an irrigation pump to provide irrigation fluid to the first expandable membrane and out of the first expandable membrane.

181. The device of any preceding clause, wherein the effectiveness evaluation period is at least 91 days following a delivery of the end probe to the pulmonary vein; and ablation of tissue proximate the pulmonary vein with the end probe.

182. The device of any preceding clause, wherein the effectiveness evaluation period is less than or equal to one year following a delivery of the end probe to the pulmonary vein; and ablation of tissue proximate the pulmonary vein with the end probe.

183. The device of any previous clause, wherein the predetermined success rate is 60% for a population size of at least 40 patients.

184. The device of any previous clause, wherein a population size for the predetermined success rate is at least 300 patients.

185. The device of any previous clause, wherein a population size for the predetermined success rate is at least 200 patients.

186. The device of any previous clause, wherein a population size for the predetermined success rate is at least 100 patients.

187. The device of any previous clause, wherein a population size for the predetermined success rate is at least 50 patients.

188. The device of any previous clause, wherein the predetermined success rate is at least 60%.

189. The device of any previous clause, wherein the predetermined success rate is determined by evaluation of the patient 7 days following a delivery of the end probe to the pulmonary vein and ablation of tissue proximate the pulmonary vein with the end probe.

190. The device of any previous clause, wherein the predetermined success rate is determined by evaluation of the patient 1 month following a delivery of the end probe to the pulmonary vein; and ablation of tissue proximate the pulmonary vein with the end probe.

191. The device of any previous clause, wherein the predetermined success rate is determined by evaluation of the patient 6 months following a delivery of the end probe to the pulmonary vein; and ablation of tissue proximate the pulmonary vein with the end probe.

192. The device of any previous clause, wherein the predetermined success rate is determined by evaluation of the patient 12 months following a delivery of the end probe to the pulmonary vein; and ablation of tissue proximate the pulmonary vein with the end probe.

193. The device of any previous clause, wherein the predetermined success rate further comprises: confirmation of an entrance block in the pulmonary vein after at least one of adenosine and isoproterenol challenge.

194. The device of any previous clause, wherein the patient suffering at least one of the following events is deemed as unsuccessful pulmonary vein isolation, including:

device or procedure related death;

atrio-esophageal fistula, myocardial infarction;

cardiac Tamponade/Perforation;

thromboembolism;

stroke/Cerebrovascular Accident (CVA);

transient Ischemic Attach (TIA);

phrenic Nerve Paralysis, Pulmonary Vein Stenosis;

pericarditis;

pulmonary Edema;

major Vascular Access Complication/Bleeding; and hospitalization (initial or prolonged).

195. The device of any previous clause, wherein the patient suffering at least one of the following events is deemed as unsuccessful pulmonary vein isolation, comprising: acute procedural failure;

repeat ablation or surgical treatment for AF/AT/Atypical (left-side) AFL after the blanking period (after day 90 post index procedure);

DC cardioversion for AF/AT/Atypical (left-side) AFL, continuous AF/AT/AFL on a standard 12-lead ECG even if the recording is less than 30 seconds in duration (after day 90 post index procedure);

a new Class I and/or Class III AAD is prescribed for AF during effectiveness evaluation period (day 91-365 post index procedure) or prescribed during the blanking period and continued past 90 days;

a previously failed Class I and/or Class III AAD (failed at or before screening) is taken for AF at a greater dose than the highest ineffective historical dose during the effectiveness evaluation period; and amiodarone is prescribed post procedure.

196. The device any previous clause, wherein the safety endpoint is defined by a patient suffering a primary adverse event.

197. The device of any previous clause, wherein at least one risk factor for the patient is selected from the group consisting of:

at least three (3) symptomatic episodes of atrial fibrillation that last lasting ≥1 minute within six (6) months before the device;

at least one (1) atrial fibrillation episode electrocardiographically documented within twelve (12) months prior to enrollment, whereby electrocardiographic documentation can include, but is not limited to, electrocardiogram (ECG), Holter monitor, or telemetry strip;

failing at least one (1) Class I or Class III AAD as evidenced by recurrent symptomatic atrial fibrillation or intolerable side effects to the AAD;

age 18-75 years;
secondary to electrolyte imbalance;
thyroid disease;
reversible or non-cardiac cause; and
previous surgical or catheter ablation for atrial fibrillation.

198. The device of any previous clause, wherein the patient has at least one risk factor selected from the group consisting of:
Patients known to require ablation outside the PV ostia and CTI region;
Previously diagnosed with persistent or long-standing persistent atrial fibrillation and/or Continuous atrial fibrillation 7 days following the device procedure;
any percutaneous coronary intervention within the past 2 months;
repair or replacement or presence of a prosthetic valve;
any carotid stenting or endarterectomy within the past 6 months;
Coronary artery bypass grafting, cardiac surgery or valvular cardiac surgical procedure within the past 6 months;
Documented left atrium thrombus within 1 day prior to the device procedure;
left atrium antero posterior diameter >50 mm;
Left Ventricular Ejection Fraction <40%;
Contraindication to anticoagulation;
History of blood clotting or bleeding abnormalities;
Myocardial infarction within the past 2 months;
Documented thromboembolic event (including transient ischemic attack) within the past 12 months;
Rheumatic Heart Disease;
Uncontrolled heart failure or New York Heart Association (NYHA) function class III or IV;
Awaiting cardiac transplantation or other cardiac surgery within the next 12 months;
Unstable angina;
Acute illness or active systemic infection or sepsis;
Diagnosed atrial myxoma or presence of an interatrial baffle or patch;
Presence of implanted pacemaker or implantable cardioverter defibrillator (ICD);
Significant pulmonary disease or any other disease or malfunction of the lungs or respiratory system that produces chronic symptoms;
Significant congenital anomaly;
women who are pregnant;
enrollment in an investigational study evaluating another device, biologic, or drug;
known pulmonary vein stenosis;
presence of intramural thrombus, tumor or other abnormality that precludes vascular access, or manipulation of the catheter;
presence of an inferior vena cava filter;
presence of a condition that precludes vascular access;
life expectancy or other disease processes likely to limit survival to less than 12 months;
presenting contra-indication for the devices; and
patient on amiodarone at any time during the past 3 months prior to enrollment.

199. The device of any previous clause, wherein if the patient is receiving warfarin/coumadin therapy, the patient must have an international normalized ratio ≥2 for at least 3 weeks prior to the procedure.

200. The device of any previous clause, wherein if the patient is receiving warfarin/coumadin therapy, the patient must be confirmed to be ≥2 within 48 hours pre-procedure.

201. The device of any previous clause, wherein anticoagulation therapy is provided prior to the procedure.

202. The device of any previous clause, wherein an activated clotting time of 350-400 seconds is targeted prior to insertion of the catheter and throughout the procedure.

203. The device of any previous clause, wherein an activated clotting time levels are checked every 15-30 minutes during the procedure to ensure an activated clotting time target of 350-400 seconds.

204. The device of any previous clause, wherein the multi-electrode circular diagnostic catheter comprises:
an elongated body having a longitudinal axis;
a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;
at least one irrigated ablation ring electrode mounted on the proximal loop;
a control handle proximal the elongated body; and
a contraction wire having a proximal end in the control handle and a distal end anchored in the proximal loop, the control handle including a first control member configured to actuate the contraction wire to contract the proximal loop,
wherein the proximal loop has a first flexibility and the distal loop has a second flexibility, and the second flexibility is greater than the first flexibility.

205. Use of an independently controlled multi-electrode radiofrequency balloon catheter to treat a predetermined patient population for paroxysmal atrial fibrillation, comprising:
ablating tissue of one or more targeted pulmonary veins with one or more of a plurality of the electrodes of the independently controlled multi-electrode radiofrequency balloon catheter, the balloon catheter comprising the plurality of electrodes for radiofrequency ablation that are independently controllable;
determining a characteristic, based on ablation parameters of the balloon catheter, of single shot pulmonary vein isolation (PVI) success rate; and
achieving, based on the characteristic and step of ablating tissue, a single shot isolation PVI success rate in the isolation of all targeted pulmonary veins for the predetermined patient population.

206. Use according to Clause 205, wherein the step of achieving the single shot isolation PVI success rate further comprises further ablating tissue of one or more targeted pulmonary veins, based on the characteristic, with one or more of a plurality of the electrodes.

207. Use according to Clause 205, wherein the step of achieving the single shot isolation PVI success rate further comprises ceasing further tissue ablation with the multi-electrode radiofrequency balloon catheter, based on the characteristic.

208. Use according to Clause 205, wherein the step of achieving the single shot isolation PVI success rate further comprises achieving at least about a 91.7% success rate by ablating with a pre-ablation mean initial impedance of less than about 95Ω.

209. Use according to Clause 205, wherein the step of achieving the single shot isolation PVI success rate further comprises achieving at least about a 91.7% success rate by ablating with a pre-ablation highest initial impedance of less than about 100Ω.

210. Use according to Clause 205, wherein the step of achieving the single shot isolation PVI success rate further comprises achieving at least about 87% success rate by ablating with a pre-ablation initial anterior wall impedance of less than about 95Ω.

211. Use according to Clause 205, wherein the step of achieving the single shot isolation PVI success rate further comprises achieving at least about 85% success rate by ablating with a pre-ablation lowest initial anterior wall impedance of between about 80-90Ω.

212. Use according to Clause 205, wherein the step of achieving the single shot isolation PVI success rate further comprises achieving at least about 88% success rate by ablating with a pre-ablation highest initial anterior wall impedance of about 110Ω.

213. Use according to Clause 205, wherein the step of achieving the single shot isolation PVI success rate further comprises achieving at least about 87.5% success rate by ablating with a pre-ablation initial anterior wall impedance variation impedance range of less than about 20Ω.

214. Use according to Clause 205, wherein the characteristic is a predictor of the single shot isolation PVI success rate before ablation was limiting a highest initial temperature to less than about 31° C. among the electrodes of the balloon catheter.

215. Use according to Clause 205, wherein the characteristic is a predictor of the single shot isolation PVI success rate before ablation was permitting a lowest anterior wall impedance between approximately about 80-90Ω.

216. Use according to Clause 205, wherein the step of achieving the single shot isolation PVI success rate further comprises achieving at least about a 90% success rate by ablating with a mean initial impedance of less than about 95Ω for and a highest initial impedance of less than about 110Ω.

217. Use according to Clause 205, wherein the characteristic is a predictor is of the single shot isolation PVI success rate before ablation, the predictor being mean initial temperature, and wherein the mean initial temperature is approximately less than about 28° C. and the single shot isolation PVI success rate is at least approximately about 90%.

218. Use according to Clause 205, wherein the characteristic is a predictor is of the single shot isolation PVI success rate before ablation, the predictor being a distributed initial temperature, and wherein the distributed initial temperature is approximately greater than about 31° C., and the single shot isolation PVI success rate is at least approximately about 90%.

219. Use according to Clause 205, wherein the characteristic is a predictor is of the single shot isolation PVI success rate before ablation, the predictor being a distributed initial temperature, and wherein the distributed initial temperature is approximately greater than about 30° C., and the single shot isolation PVI success rate is at least approximately about 90%.

220. Use according to Clause 205, wherein the characteristic is a predictor is of the single shot isolation PVI success rate before ablation, the predictor being a distributed initial temperature, and wherein the distributed initial temperature is approximately greater than about 29° C., and the single shot isolation PVI success rate is at least approximately about 90%.

221. Use according to Clause 205, wherein the characteristic is a predictor is of the single shot isolation PVI success rate before ablation, the predictor being a pre-ablation lowest temperature slope, and wherein the pre-ablation lowest temperature slope is approximately greater than about 0.75° C./sec, and the single shot isolation PVI success rate is at least approximately about 90%.

222. Use according to Clause 205, wherein the characteristic is a predictor is of the single shot isolation PVI success rate before ablation, the predictor being a pre-ablation lowest value temperature, and wherein the pre-ablation lowest value temperature is approximately greater than about 6° C., and the single shot isolation PVI success rate is at least approximately about 90%.

223. Use according to Clause 205, wherein the characteristic is a predictor is of the single shot isolation PVI success rate before ablation, the predictor being a pre-ablation highest initial temperature, and wherein the pre-ablation highest initial temperature is approximately less than about 31° C., and the single shot isolation PVI success rate is at least approximately about 90%.

224. Use according to Clause 205, wherein the characteristic is a predictor is of the single shot isolation PVI success rate before ablation, the predictor being a pre-ablation initial temperature variation, and wherein the pre-ablation initial temperature variation is approximately less than about 3° C., and the single shot isolation PVI success rate is at least approximately about 95%.

225. Use according to Clause 205, wherein the characteristic is a predictor is of the single shot isolation PVI success rate before ablation, the predictor being a pre-ablation initial impedance variation, and wherein the pre-ablation initial impedance variation comprises an optimal range of approximately less than about 20Ω, and the single shot isolation PVI success rate is at least approximately about 88.5%.

226. Use according to Clause 205, wherein the characteristic is a predictor is of the single shot isolation PVI success rate before ablation, the predictor being a pre-ablation lowest value impedance drop, and wherein the pre-ablation lowest value impedance drop is approximately greater than about 12Ω, and the single shot isolation PVI success rate is at least approximately about 90%.

227. Use according to Clause 205, wherein the characteristic is a predictor is of the single shot isolation PVI success rate before ablation, the predictor being a pre-ablation impedance drop variation, and wherein the pre-ablation impedance drop variation is approximately greater than about 20Ω, and the single shot isolation PVI success rate is at least approximately about 85%.

228. Use according to Clause 205, wherein the characteristic is a predictor is of the single shot isolation PVI success rate before ablation, the predictor being a pre-ablation lowest value impedance drop percent, and wherein the pre-ablation lowest value impedance drop percent is greater than or equal to approximately about 12%, and the single shot isolation PVI success rate is at least approximately about 90%.

229. Use according to Clause 205, wherein the characteristic is a predictor is of the single shot isolation PVI success rate before ablation, the predictor being a pre-ablation impedance drop percent variation, and wherein the pre-ablation impedance drop percent variation is less than about 20Ω, and the single shot isolation PVI success rate is at least approximately about 85%.

230. Use according to Clause 205, wherein when a number of electrodes with initial impedance deviation from mean value is zero, the single shot isolation PVI success rate is approximately about 92%.

231. Use according to Clause 205, wherein the characteristic is a predictor is of the single shot isolation PVI success rate before ablation, the predictor being a difference of impedance between anterior and posterior wall.

232. Use according to Clause 231, wherein the difference is less than approximately about 20Ω and the single-shot PVI success rate is at least approximately about 85% for the predetermined patient population.

233. Use according to Clause 231, wherein the difference is less than approximately about 20Ω and the single-shot PVI success rate is at least approximately about 85% for the predetermined patient population of at least 25 patients.

234. Use according to Clause 231, wherein the difference is approximately between 20 to 30Ω and the single-shot PVI success rate is at least approximately about 78% for the predetermined patient population.

235. Use according to Clause 231, wherein the difference is approximately between 20 to 30Ω and the single-shot PVI success rate is at least approximately about 78% for the predetermined patient population of at least 75 patients.

236. Use according to Clause 231, wherein the difference is approximately between 30 to 40Ω and the single-shot PVI success rate is at least approximately about 75% for the predetermined patient population.

237. Use according to Clause 231, wherein the difference is approximately between 30 to 40Ω and the single-shot PVI success rate is at least approximately about 75% for the predetermined patient population of at least 60 patients.

238. Use according to Clause 231, wherein the difference is approximately between 40 to 50Ω and the single-shot PVI success rate is at least approximately about 67% for the predetermined patient population.

239. Use according to Clause 231, wherein the difference is approximately between 40 to 50Ω and the single-shot PVI success rate is at least approximately about 67% for a predetermined patient population of at least 34 patients.

240. Use according to Clause 231, wherein the difference is approximately between 50 to 60Ω and the single-shot PVI success rate is at least approximately about 35% for the predetermined patient population.

241. Use according to Clause 231, wherein the difference is approximately between 50 to 60Ω and the single-shot PVI success rate is at least approximately about 35% for the predetermined patient population of at least 11 patients.

242. Use according to Clause 231, wherein the difference is greater than approximately about 60Ω and the single-shot PVI success rate is at least approximately about 33% for the predetermined patient population.

243. Use according to Clause 231, wherein the difference is greater than approximately about 60Ω and the single-shot PVI success rate is at least approximately about 33% for the predetermined patient population of at least 9 patients.

244. Use according to Clause 231, wherein the balloon catheter is a full-circle all electrode burning ablation catheter.

245. Use according to Clause 231, wherein the step of ablating tissue is for a duration of 60 seconds.

246. Use according to Clause 205, wherein the characteristic is a predictor is of the single shot isolation PVI success rate before ablation, and wherein pre-ablation mean initial impedance is the predictor.

247. Use according to Clause 205, wherein the characteristic is a predictor is of the single shot isolation PVI success rate before ablation, and wherein pre-ablation initial impedance variation is the predictor.

248. Use according to Clause 205, wherein the characteristic is an evaluator of the single shot isolation PVI success rate post ablation, and wherein post-ablation lowest impedance drop is the evaluator.

249. Use according to Clause 205, wherein the characteristic is an evaluator of the single shot isolation PVI success rate post ablation, and wherein post-ablation impedance drop variation is the evaluator.

250. Use according to Clause 205, wherein the characteristic is a predictor is of the single shot isolation PVI success rate before ablation, and wherein post-ablation mean temperature slope is the evaluator.

251. Use according to Clause 205, wherein the characteristic is an evaluator of the single shot isolation PVI success rate post ablation, and wherein post-ablation lowest temperature slope is the predictor.

252. Use according to Clause 205, wherein the characteristic is an evaluator of the single shot isolation PVI success rate post ablation, and wherein post-ablation mean temperature rise is the evaluator.

253. Use according to Clause 205, wherein the characteristic is an evaluator of the single shot isolation PVI success rate post ablation, and wherein post-ablation lowest temperature rise is the evaluator.

254. Use according to Clause 205, wherein the characteristic is an evaluator of the single shot isolation PVI success rate post ablation, and wherein post-ablation lowest impedance drop percentage is the evaluator.

255. Use according to Clause 205, wherein the characteristic is an evaluator of the single shot isolation PVI success rate post ablation, and wherein post-ablation variation of impedance drop percentage is the evaluator.

256. Use according to Clause 205, wherein the characteristic is a predictor is of the single shot isolation PVI success rate before ablation, and wherein pre-ablation lowest impedance drop is the predictor.

257. Use according to Clause 205, wherein the characteristic is a predictor is of the single shot isolation PVI success rate before ablation, and wherein pre-ablation initial temperature variation is the predictor.

258. Use according to Clause 205, wherein the characteristic is a predictor is of the single shot isolation PVI success rate before ablation, and wherein pre-ablation maximum initial impedance is the predictor.

259. Use according to Clause 205, wherein the characteristic is a predictor is of the single shot isolation PVI success rate before ablation, and wherein pre-ablation mean initial anterior wall impedance is the predictor.

260. Use according to Clause 205, wherein the characteristic is a predictor is of the single shot isolation PVI success rate before ablation, and wherein pre-ablation lowest anterior wall impedance is the predictor.

261. Use according to Clause 205, wherein the characteristic is a predictor is of the single shot isolation PVI success rate before ablation, and wherein pre-ablation maximum anterior wall impedance is the predictor.

262. Use according to Clause 205, wherein the characteristic is a predictor is of the single shot isolation PVI success rate before ablation, and wherein pre-ablation anterior wall impedance variation is the predictor.

263. Use according to Clause 205, wherein impedance values were among the electrodes of an anterior wall.

264. Use according to Clause 205, wherein the characteristic is a predictor is of the single shot isolation PVI success rate before ablation, and wherein the predictor is determined by:

$$\text{Probability} \sim \frac{e^Y}{(1+e^Y)}$$
$$Y \sim 4.367 - 0.420\Delta T_0 - 0.0486\Delta Z_0$$

wherein $\Delta T_0$ is initial impedance variation and $\Delta Z_0$ is initial temperature variation.

265. Use according to Clause 205, wherein the characteristic is a predictor is of the single shot isolation PVI success rate before ablation, and wherein the predictor is determined by:

$$Prob \sim \frac{e^Y}{(1+e^Y)}$$
$$Y \sim 26.78 - 0.576 T_{0max} - 0.0632 Z_{0max}$$

wherein $T_{0max}$ is highest initial temperature and $Z_{0max}$ is highest initial impedance.

266. Use according to Clause 205, wherein the characteristic is a predictor is of the single shot isolation PVI success rate before ablation, and wherein the predictor is determined by:

$$Prob \sim \frac{e^Y}{(1+e^Y)}$$
$$Y \sim 27.70 - 0.540 T_{0max} - 0.0959 Z_{0max}$$

wherein $T_{0max}$ is highest initial temperature and $Z_{0max}$ is highest initial impedance.

267. Use according to Clause 205, wherein the characteristic is a predictor is of the single shot isolation PVI success rate before ablation, and wherein the predictor is determined by:

$$Prob \sim \frac{e^Y}{(1+e^Y)}$$
$$Y \sim 9.31 - 0.408\Delta T_0 - 0.0544 Z_{0max}$$

wherein $\Delta T_0$ is initial temperature variation and $Z_{0max}$ is highest initial impedance.

268. Use according to Clause 205, the characteristic is a predictor is of the single shot isolation PVI success rate before ablation, and wherein the predictor is determined by:

$$Prob \sim \frac{e^Y}{(1+e^Y)}$$
$$Y \sim 22.61 - 0.622 T_{0max} - 0.0626\Delta Z_0$$

wherein $T_{0max}$ is highest initial temperature and $\Delta Z_0$ is initial impedance variation.

269. Use according to Clause 205, wherein the characteristic is a predictor is of the single shot isolation PVI success rate before ablation, and wherein the predictor is determined by:

$$Prob \sim \frac{e^Y}{(1+e^Y)}$$
$$Y \sim 11.53 - 0.439\Delta T_0 - 0.0856 Z_{0mean}$$

wherein $\Delta T_0$ is initial temperature variation and $Z_{0max}$ is mean initial impedance.

270. Use according to Clause 205, wherein the characteristic is a predictor is of the single shot isolation PVI success rate before ablation, and wherein the predictor is determined by:

$$Prob \sim \frac{e^Y}{(1+e^Y)}$$
$$Y \sim 26.52 + 0.013\Delta T_0 - 0.594 T_{0max} - 0.0122\Delta Z_0 - 0.0535 Z_{0max}$$

wherein $\Delta T_0$ is initial temperature variation, $T_{0max}$ is highest initial temperature, $\Delta Z_0$ is initial impedance variation, and $Z_{0max}$ is highest initial impedance.

271. Use according to any preceding clause, wherein the characteristic is an evaluator of the single shot isolation PVI success rate post ablation, and wherein the evaluator is determined by:

$$Prob \sim \frac{e^Y}{(1+e^Y)}$$
$$Y \sim 1.562 + 0.2856\Delta T_{min} - 0.0629\Delta Z_{drop}$$

wherein $\Delta T_{min}$ is lowest temperature rise and $\Delta Z_{drop}$ is impedance drop variation.

272. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim -0.507 + 0.206\Delta T_{min} + 0.083 Z_{dropmin}$$

wherein $\Delta T_{min}$ is lowest temperature rise and $Z_{dropmin}$ is minimum impedance drop.

273. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim 1.248 + 0.2486\Delta T_{min} - 0.0594\Delta Z_{drop} + 0.0419 Z_{dropmin}$$

wherein $\Delta T_{min}$ is lowest temperature rise and $Z_{dropmin}$ is minimum impedance drop.

274. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim 1.174 + 0.2515\Delta T_{min} - 0.0564\Delta Z_{drop}\%$$

wherein $\Delta T_{min}$ is lowest temperature rise and $\Delta Z_{drop}$ is impedance drop percent variation.

275. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim -0.644 + 0.170\Delta T_{min} + 0.107\Delta Z_{drop}\%_{min}$$

wherein $\Delta T_{min}$ is lowest temperature rise and $Z_{drop}\%_{min}$ is lowest impedance drop percent.

276. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim 0.339 + 0.187\Delta T_{min} + 0.0737 Z_{drop}\%_{min} - 0.0368 \Delta Z_{drop}\%$$

wherein $\Delta T_{min}$ is lowest temperature rise, $Z_{drop}\%_{min}$ is lowest impedance drop percent, and $\Delta Z_{drop}\%$) is impedance drop percent variation.

277. Use according to any preceding clause, wherein the characteristic is an evaluator of the single shot isolation PVI success rate post ablation, and wherein the evaluator is determined by:

$$P \sim \frac{e^Y}{(1+e^Y)}$$
$$Y \sim 1.043 + 0.777 T'_{min} + 0.171\Delta T_{min} + 0.0479 Z_{drop-min} - 0.0589\Delta Z_{drop}$$

wherein $T'_{min}$ is lowest temperature slope, $\Delta T_{min}$ is lowest temperature rise, $Z_{drop}$-min is lowest impedance drop and $\Delta Z_{drop}$ is impedance drop variation.

278. Use according to Clause 205, further comprising the step of displaying a graphical representation of the independently controllable electrodes and the ablation parameters.

279. Use according to Clause 278, wherein one ablation parameter comprises impedance measured proximate each electrode.

280. Use according to Clause 279, wherein the measured impedance comprises impedance measured before ablation.

281. Use according to Clause 279, wherein the measured impedance comprises impedance measured after ablation.

282. Use according to Clause 279, wherein the measured impedance comprises impedance measured before and impedance measured after ablation.

283. Use according to Clause 278, wherein one ablation parameter comprises temperature measured proximate each electrode.

284. Use according to Clause 278, wherein one ablation parameter comprises a maximum temperature measured proximate each electrode during the ablating.

285. Use according to Clause 278, wherein one ablation parameter comprises a measured temperature rise from a beginning of ablating to an end of the ablating.

286. Use of an independently controlled multi-electrode radiofrequency balloon catheter to treat a plurality of patients for paroxysmal atrial fibrillation, comprising the steps of:

delivering the radiofrequency balloon catheter having a plurality of independently controllable electrodes for radiofrequency ablation and a multi-electrode diagnostic catheter to one or more targeted pulmonary veins;

ablating tissue of the one or more targeted pulmonary veins with one or more of the plurality of the electrodes independently controlled multi-electrode radiofrequency balloon catheter;

diagnosing the one or more targeted pulmonary veins using the multi-electrode diagnostic catheter; and achieving at least one of a predetermined clinical effectiveness and acute effectiveness of the multi-electrode radiofrequency balloon catheter and the multi-electrode diagnostic catheter in the isolation of the one or more targeted pulmonary veins, during and approximately 3 months after the ablating step.

287. Use according to Clause 286, wherein acute effectiveness is defined by confirming if there is an entrance block in all targeted pulmonary veins after adenosine and/or isoproterenol challenge.

288. Use according to Clause 287, further comprising: determining the acute effectiveness determined at approximately 3 months after the ablating step; and generating an estimated acute effectiveness at approximately 12 months after the ablating step based on the acute effectiveness determined at approximately 3 months.

289. Use according to Clause 288, wherein the estimated acute effectiveness at approximately 12 months is substantially similar to the acute effectiveness determined at approximately 3 months.

290. Use according to Clause 287, wherein the acute effectiveness is further defined by success greater than 90% for the plurality of patients.

291. Use according to Clause 287, wherein the acute effectiveness is further defined by success greater than 95% for the plurality of patients.

292. Use according to Clause 287, wherein a Type-1 error rate for power the acute effectiveness and the clinical effectiveness of all targeted veins are controlled at approximately a 5% level, the method or use further comprising:

determining whether the ablating is clinically successful for the plurality of patients if both the acute effectiveness and the clinical effectiveness indications are controlled at approximately the 5% level.

293. Use according to Clause 287, wherein the acute effectiveness is at least 80% for the plurality of patients being at least 80 patients.

294. Use according to Clause 287, wherein the acute effectiveness is at least 80% for the plurality of patients being at least 130 patients.

295. Use according to Clause 287, wherein the acute effectiveness is at least 80% for the plurality of patients being at least 180 patients.

296. Use according to Clause 287, wherein the acute effectiveness is at least 80% for the plurality of patients being at least 230 patients.

297. Use according to Clause 287, wherein the acute effectiveness is further defined by confirming if there is an entrance block in all targeted pulmonary veins after adenosine and/or isoproterenol challenge using a focal ablation catheter.

298. Use according to Clause 287, wherein the acute effectiveness is further defined by confirming if there is an entrance block in all targeted pulmonary veins after adenosine and/or isoproterenol challenge without using a focal ablation catheter.

299. Use according to Clause 286, wherein the ablating is administered on the plurality of patients diagnosed with symptomatic paroxysmal atrial fibrillation.

300. Use according to Clause 286, wherein the step of diagnosing further comprises:

electrophysiological mapping of the heart.

301. Use according to Clause 286, wherein the multi-electrode diagnostic catheter further comprises a high torque shaft with a halo-shaped tip section containing a plurality of pairs of electrodes visible under fluoroscopy.

302. Use according to Clause 286, wherein the plurality of patients is at least 80.

303. Use according to Clause 286, wherein the plurality of patients is at least 130.

304. Use according to Clause 286, wherein the plurality of patients is at least 180.

305. Use according to Clause 286, wherein the plurality of patients is at least 230.

306. Use according to Clause 286, wherein the predetermined acute effectiveness is defined by ulceration being absent in the plurality of patients after the ablating.

307. Use according to Clause 286, wherein the predetermined acute effectiveness is defined by a complication rate of approximately 13% or fewer of the plurality of patients experiencing esophageal erythema after the ablating.

308. Use according to Clause 286, wherein the predetermined acute effectiveness is defined by a complication rate of approximately 25% or fewer of the plurality of patients experiencing new asymptomatic cerebral embolic lesions after the ablating.

309. Use according to Clause 286, wherein the predetermined acute effectiveness is defined by a complication rate of approximately 20% or fewer of the plurality of patients experiencing new asymptomatic cerebral embolic lesions after the ablating.

310. Use according to Clause 286, wherein the predetermined acute effectiveness is defined by a complication rate of approximately 5-9% or fewer of the plurality of patients experiencing a primary adverse event by approximately 7 or more days after the ablating.

311. Use according to Clause 286, wherein inclusion criteria for the plurality of patients comprises:

a diagnosis with symptomatic paroxysmal atrial fibrillation; and a patient capability to comply with uninterrupted per-protocol anticoagulation requirements.

312. Use according to Clause 286, wherein the predetermined acute effectiveness is defined by a total procedure time.

313. Use according to Clause 286, wherein the predetermined acute effectiveness is defined by a total ablation time.

314. Use according to Clause 286, wherein the predetermined acute effectiveness is defined by a total RF application time.

315. Use according to Clause 286, wherein the predetermined acute effectiveness is defined by a total dwell time of the multi-electrode radiofrequency balloon catheter.

316. Use according to Clause 286, wherein the predetermined acute effectiveness is defined by a total time to isolate all targeted pulmonary veins.

317. Use according to Clause 286, wherein the predetermined acute effectiveness is defined by a number and a total time of applications by the multi-electrode radiofrequency balloon catheter per location of all targeted pulmonary veins.

318. Use according to Clause 286, wherein the predetermined acute effectiveness is defined by a number and a total time of applications by the multi-electrode radiofrequency balloon catheter per patient.

319. Use according to Clause 286, wherein the predetermined acute effectiveness is defined by a number and a total time of applications by the multi-electrode radiofrequency balloon catheter per targeted vein.

320. Use according to any preceding clause, wherein the multi-electrode radiofrequency balloon catheter comprises:

a compliant balloon with a plurality of electrodes bonded configured to deliver RF energy to tissue of the pulmonary vein and sense temperature at each electrode.

321. Use according to Clause 320, wherein clinical effectiveness is defined by an incidence of early onset of one or more adverse events within a predetermined time of the method or use being implemented.

322. Use according to Clause 321, wherein the predetermined time is at least 7 days.

323. Use according to Clause 321, wherein the one or more adverse events comprise: death, atrio-esophageal fistula, myocardial infarction, cardiac tamponade/perforation, thromboembolism, stroke, TIA (Transient Ischemic Attack), phrenic nerve paralysis, pulmonary vein stenosis, and the major vascular access bleeding.

324. Use according to Clause 321, wherein the one or more adverse events comprise: incidence of individual adverse events from a primary composite; incidence of serious adverse device effect; incidence of serious adverse events within 7 days, at least 730 days, and at least 30 days following the ablating; incidence of non-serious adverse events; incidence of pre- and post-ablation asymptomatic and symptomatic cerebral emboli as determined by MRI evaluation; and frequency, anatomic location, and size (diameter and volume) of cerebral emboli by MRI evaluations at baseline, post-ablation and during follow-up.

325. Use according to Clause 321, wherein the one or more adverse events for approximately 5-9% of the plurality of patients, the one or more adverse events comprising:

NIHSS (National Institute of Health Stroke Scale) scores at baseline, post-ablation and during follow-up;

a summary of MoCA (Montreal Cognitive Assessment) and mRS (Modified Ranking Scale) scores at baseline, 1 month and during further follow-up; a rate of hospitalization for cardiovascular events; a percentage (%) of pulmonary vein isolation touch-up by focal catheter among the one or more targeted veins;

a percentage (%) of subjects with use of focal catheter ablations for non-PV triggers;

a percentage (%) of subjects with freedom from documented symptomatic atrial fibrillation (AF), atrial tachycardia (AT), or atypical (left side) atrial flutter (AFL) episodes (episodes >30 seconds on arrhythmia monitoring device from day 91 to 180);

a percentage (%) of subjects with freedom from documented atrial fibrillation (AF), atrial tachycardia (AT), or atypical (left side) atrial flutter (AFL);

one or more episodes that endure for 30 or more seconds on an arrhythmia monitoring device from day 91 to 180 following the ablating; and one or more procedural parameters including total procedure and ablation time, balloon dwell time, RF application time, a number of RF applications, fluoroscopy time and dose.

326. Use according to Clause 320, wherein the acute safety rate includes complication rates of 10% or less and is defined by incidence of asymptomatic cerebral embolic lesions at a discharge magnetic resonance imaging (MRI).

327. Use according to Clause 320, wherein the acute effectiveness rate is 100% and is defined by electrically isolating all targeted pulmonary veins without use of a focal ablation catheter.

328. Use according to Clause 320, wherein the acute effectiveness rate is defined by a freedom from documented atrial fibrillation, atrial tachycardia, or atypical atrial flutter episodes based on electrocardiographic data through an effectiveness evaluation period (1 year).

329. Use according to Clause 320, wherein the acute effectiveness rate is defined by pulmonary vein isolation touch-up by a focal catheter among all targeted pulmonary veins.

330. Use according to Clause 320, wherein the predetermined clinical effectiveness rate is defined by 10% or less complication rates related to incidence of post-ablation symptomatic and asymptomatic cerebral emboli as compared to pre-ablation.

331. Use according to Clause 320, wherein the multi-electrode diagnostic catheter is configured for electrophysiological recording and stimulation of the atrial region of the heart and is used in conjunction with the multi-electrode radiofrequency balloon catheter.

332. Use of an independently controlled multi-electrode radiofrequency balloon catheter to treat a plurality of patients for paroxysmal atrial fibrillation, comprising:
delivering the radiofrequency balloon catheter having a plurality of independently controllable electrodes for radiofrequency ablation and a multi-electrode diagnostic catheter to one or more targeted pulmonary veins; and
ablating tissue of one or more targeted pulmonary veins with one or more of the plurality of the electrodes independently controlled multi-electrode radiofrequency balloon catheter;
diagnosing all targeted pulmonary veins using the multi-electrode diagnostic catheter; and
achieving a predetermined rate of adverse events based on use of the multi-electrode radiofrequency balloon catheter and the multi-electrode diagnostic catheter in the isolation of all targeted pulmonary veins, during and approximately 6 months after the method or use.

333. Use of an independently controlled multi-electrode radiofrequency balloon catheter to treat a plurality of patients for paroxysmal atrial fibrillation, comprising the steps of:
evaluating a number and size of all targeted pulmonary veins and anatomy of the left atrial;
puncturing the transseptal;
selectively positioning a multi-electrode esophageal temperature monitoring device in the vasculature with respect to all targeted pulmonary veins;
selectively positioning the radiofrequency balloon catheter in the vasculature with respect to all targeted pulmonary veins, the multi-electrode radiofrequency balloon catheter having a plurality of independently controllable electrodes for radiofrequency ablation;
selectively positioning a multi-electrode diagnostic catheter in the vasculature with respect to all targeted pulmonary veins;
ablating tissue of all targeted pulmonary veins with one or more of the plurality of the electrodes independently controlled multi-electrode radiofrequency balloon catheter;
confirming isolation of all targeted pulmonary veins using the multi-electrode diagnostic catheter;
confirming existence of an entrance block in all targeted pulmonary veins; achieving a predetermined clinical effectiveness and/or acute effectiveness of the method or use, based on the confirmed existence of the entrance block, regarding the isolation of all targeted pulmonary veins following the method or use.

334. Use according to any preceding clause, further comprising: mapping all targeted pulmonary veins using the diagnostic catheter.

335. Use according to any preceding clause, wherein exclusion criteria for the plurality of patients comprises at least one of the following:
atrial fibrillation secondary to electrolyte imbalance, thyroid disease, or reversible or non-cardiac cause;
previous surgical or catheter ablation for atrial fibrillation;
anticipated to receive ablation outside all targeted pulmonary veins ostia and CTI region;
previously diagnosed with persistent, longstanding atrial fibrillation and/or continuous atrial fibrillation >7 days, or >48 hrs terminated by cardioversion;
any percutaneous coronary intervention (PCI) within the past 2 months;
valve repair or replacement and presence of a prosthetic valve;
any carotid stenting or endarterectomy;
coronary artery bypass grafting, cardiac surgery, valvular cardiac surgical or percutaneous procedure within the past 6 months;
documented left atrium thrombus on baseline imaging;
LA antero posterior diameter greater than 50 mm;
any pulmonary vein with a diameter greater than or equal to 26 mm;
left ventricular ejection fraction less than 40%;
contraindication to anticoagulation;
history of blood clotting or bleeding abnormalities;
myocardial infarction within the past 2 months;
documented thromboembolic event within the past 12 months;
rheumatic heart disease;
awaiting cardiac transplantation or other cardiac surgery within the next 12 months;
unstable angina;
acute illness or active systemic infection or sepsis;
diagnosed atrial myxoma or interatrial baffle or patch;
presence of implanted pacemaker, implantable cardioverter defibrillator, tissue-embedded, or iron-containing metal fragments;
significant pulmonary disease or any other disease or malfunction of the lungs or respiratory system that produces chronic symptoms;
significant congenital anomaly;
pregnancy or lactating;
enrollment in an investigational study evaluating another device, biologic, or drug;
pulmonary vein stenosis;
presence of intramural thrombus, tumor or other abnormality that precludes vascular access, or manipulation of the catheter;
presence of an IVC filter;
presence of a condition that precludes vascular access;
life expectancy or other disease processes likely to limit survival to less than 12 months;

contraindication to use of contrast agents for MRI;
presence of iron-containing metal fragments in the patient; or
unresolved pre-existing neurological deficit.

336. Use according to any preceding clause, wherein the multi-electrode radiofrequency balloon catheter comprises:
a compliant balloon with a plurality of electrodes configured to deliver RF energy to tissue of all targeted pulmonary veins and sense temperature at each electrode.

337. Use according to Clause 336, wherein the plurality of electrodes is oriented circularly to circumferentially contact with an ostia of the pulmonary vein.

338. Use according to Clause 336, further comprising using the plurality of electrodes for visualization, stimulation, recording, and ablation.

339. Use according to Clause 336, wherein each electrode is configured so an amount of power delivered to each electrode is controlled independently.

340. Use according to Clause 336, wherein the multi-electrode radiofrequency balloon catheter further comprises a proximal handle, a distal tip, and a middle section disposed therebetween.

341. Use according to Clause 340, wherein the proximal handle is a deflection thumb knob allowing for unidirectional deflection, a balloon advancement mechanism, and a luer fitting for balloon inflation and irrigation.

342. Use according to Clause 336, wherein the multi-electrode radiofrequency balloon catheter further comprises
a high-torque shaft configured to be rotated to facilitate accurate positioning of the catheter tip to a desired; and
a unidirectional braided deflectable tip section.

343. Use according to any preceding clause, further comprising:
controlling irrigation to the multi-electrode radiofrequency balloon catheter with an irrigation pump.

344. Use according to any preceding clause, further comprising:
administering uninterrupted anticoagulation therapy at least 1 month prior to the procedure.

345. Use according to any preceding clause, wherein if the patient is receiving warfarin/coumadin therapy, the patient must have an international normalized ratio (INR)≥2 for at least 3 weeks prior to the procedure.

346. Use according to any preceding clause, wherein if the patient is receiving warfarin/coumadin therapy, the patient must be confirmed to have an international normalized ratio (INR)≥2 within 48 hours pre-procedure.

347. Use according to any preceding clause, further comprising: continuing anticoagulation therapy prior to the procedure.

348. Use according to any preceding clause, further comprising:
administering a transseptal puncture;
confirming an activated clotting time target of ≥350 sec. prior to inserting the multi-electrode radiofrequency balloon catheter into the left atrium and maintaining throughout the procedure;
introducing the multi-electrode radiofrequency balloon catheter;
introducing of a multi-electrode circular diagnostic catheter;
ablating the pulmonary vein with the multi-electrode radiofrequency balloon catheter;
determining in real time pulmonary vein isolation with the multi-electrode circular diagnostic catheter; and
confirming whether an entrance is blocked in the pulmonary vein.

349. Use according to any preceding clause, wherein the multi-electrode circular diagnostic catheter comprises:
an elongated body having a longitudinal axis;
a distal assembly distal the elongated body, the distal assembly having a helical form comprising a proximal loop and a distal loop, and a shape-memory support member extending through at least the proximal loop, the proximal loop and the distal loop being oriented obliquely at an angle relative to the longitudinal axis of the elongated body;
at least one irrigated ablation ring electrode mounted on the proximal loop;
a control handle proximal the elongated body; and
a contraction wire having a proximal end in the control handle and a distal end anchored in the proximal loop, the control handle including a first control member configured to actuate the contraction wire to contract the proximal loop,
wherein the proximal loop has a first flexibility and the distal loop has a second flexibility, and the second flexibility is greater than the first flexibility.

350. Use of an independently controlled multi-electrode radiofrequency balloon catheter of treating a plurality of patients for paroxysmal atrial fibrillation by applying energy to tissue of a subject's heart proximate to an esophagus, phrenic nerve, or lung, comprising the steps of:
achieving at least one of a predetermined clinical effectiveness and acute effectiveness of the procedure based on use of the radiofrequency balloon catheter and a multi-electrode diagnostic catheter in the isolation of the one or more targeted pulmonary veins by:
positioning an expandable member proximate to the left atrium, the expandable member of the multi-electrode radiofrequency balloon catheter having a longitudinal axis and including a plurality of electrodes disposed about the longitudinal axis, each electrode capable of being energized independently, the plurality of electrodes including a first electrode having a first radiopaque marker and a second electrode having a second radiopaque marker different from the first radiopaque marker;
viewing an image of the expandable member as well as the first and second radiopaque markers in the left atrium;
determining an orientation of the first and second radiopaque markers with respect to a portion of the left atrium closest to the esophagus, phrenic nerve, or lung, of the subject;
moving one of the first and second radiopaque markers to a portion of the left atrium
closest to the esophagus, phrenic nerve or lung;
energizing one or more electrodes indexed to the one of the radiopaque markers proximate the portion close to the esophagus, phrenic nerve, or lung, at a lower energization setting as compared to other electrodes to create a transmural lesion in the left atrium with little or no effect to adjacent anatomical structures; and
electrophysiologically recording and stimulating the atrial region of the tissue proximate to the esophagus, phrenic nerve, or lung using the multi-electrode diagnostic catheter.

351. An ablation system for electrical signal isolation in portions of organ tissues, the system comprising:
a power generator;
a catheter shaft extending along a longitudinal axis;
a plurality of electrodes disposed about the longitudinal axis to define at least a circumferential surface about the longitudinal axis, each electrode independently connected to the power generator to provide electrical energy to each independent electrode; and a processor to control power delivery of the power generator to each of the independently controlled electrodes, the processor configured to:
- (a) receive measurement signals representative of tissue temperature and tissue impedance proximate each electrode in contact with organ tissues and
- (b) provide an indication for a probability of success in isolating electrical signal propagation in a region of the organ tissues in contact with the plurality of electrodes, the probability of success being determined from the tissue temperature values and tissue impedance values.

352. The system of clause 351, in which the temperature values are selected from one or more of (a) highest initial temperature; (b) variation in initial temperature; (c) lowest temperature rise; (d) lowest temperature slope; (e) mean temperature slope; (f) mean temperature rise; and the impedance values are selected from one or more of:
- (a) variation in initial impedance; (b) highest initial impedance; (c) mean initial impedance; (d) initial impedance deviation of all electrodes from mean value; (d) variation in impedance drop; (e) lowest impedance drop; (f) lowest impedance drop percent; (g) variation in impedance drop percent.

353. The system of clause 352, in which the indication of success is approximately 90% when the initial impedance is less than about 20 ohms.

354. The system of clause 352, in which the indication of success is greater than 90% when the highest initial impedance is less than about 110Ω.

355. The system of clause 352, in which the indication of success is greater than 90% when the mean initial impedance is less than about 95Ω 356. The system of clause 352, in which the indication of success is greater than 90% when the Highest Initial temp less than about 31 degrees Celsius.

357. The system of clause 352, in which the indication of success is greater than 90% when the Initial temp variation less than about 3° Celsius.

358. The system of clause 352, in which the indication of success is greater than 90% when a number of electrodes with initial impedance deviation from mean value is zero.

359. The system of clause 352, in which the indication of success is greater than 85% Impedance drop Variation less than about 20Ω.

360. The system of clause 352, in which the indication of success is greater than 90% when the Lowest Temp rise is equal to or greater than about 6° C.

361. The system of clause 352, in which the indication of success is greater than 90% when the Lowest Impedance drop is equal to or greater than about 12Ω.

362. The system of clause 352, in which the indication of success is greater than 90% when the Lowest Impedance drop Percent is equal to or greater than about 12%.

363. The system of clause 352, in which the indication of success is greater than 90% when the Lowest Temp slope is equal to or greater than about 0.75° C./sec.

364. The system of clause 352, in which the indication of success is greater than 90% when the Mean Temp rise is equal to or greater than about 14° C.

365. The system of clause 351, in which the temperature values are selected from one or more of: (a) initial temperature variation $\Delta T_0$; (b) highest initial temperature $T_{0max}$; (c) lowest temperature rise $\Delta T_{min}$; and wherein the impedance values are selected from one or more of: (a) initial impedance variation $\Delta Z_0$; (b) highest initial impedance $Z_{0max}$; (c) mean initial impedance $Z_{0mean}$; (d) impedance drop variation $\Delta Z_{drop}$; (e) lowest impedance drop $Z_{dropmin}$; (f) impedance drop percent variation $\Delta Z_{drop}\%$; (g) lowest impedance drop percent $Z_{drop}\%_{min}$.

366. The system of clause 365, wherein the probability of success is approximately equal to $$\frac{e^Y}{(1+e^Y)}$$

where $Y \sim 4.167 - 0.220\Delta T_0 - 0.0286\Delta Z_0$.

367. The system of Clause 365, wherein the probability of success is approximately equal to $$\frac{e^Y}{(1+e^Y)}$$

where $Y \sim 9.11 - 0.208\Delta T_0 - 0.0524 Z_{0max}$.

368. The system of Clause 365, wherein the probability of success is approximately equal to $$\frac{e^Y}{(1+e^Y)}$$

where $Y \sim 11.53 - 0.219\Delta T_0 - 0.0856 Z_{0mean}$.

369. The system of Clause 365, wherein the probability of success is approximately equal to $$\frac{e^Y}{(1+e^Y)}$$

where $Y \sim 2.61 - 0.62 T_{0max} - 0.066\Delta Z_0$.

370. The system of Clause 365, wherein the probability of success is approximately equal to $$\frac{e^Y}{(1+e^Y)}$$

where $Y \sim 2.61 - 0.62 T_{0max} - 0.066\Delta Z_0$.

371. The system of Clause 365, wherein the probability of success is approximately equal to $$\frac{e^Y}{(1+e^Y)}$$

where $Y \sim 6.78 - 0.576 T_{0max} - 0.0612 Z_{0max}$.

372. The system of Clause 365, wherein the probability of success is approximately equal to $$\frac{e^Y}{(1+e^Y)}$$

where $Y \sim 7.70 - 0.520 T_{0max} - 0.0959 Z_{0mean}$.

373. The system of Clause 365, wherein the probability of success is approximately equal to $$\frac{e^Y}{(1+e^Y)}$$

where $Y \sim 6.52 + 0.013\Delta T_0 - 0.594 T_{0max} - 0.012\Delta Z_0 - 0.0315 Z_{0max}$.

374. The system of Clause 365, wherein the probability of success is approximately equal to $$\frac{e^Y}{(1+e^Y)}$$

where $Y \sim 1.562 + 0.856\Delta T_{min} - 0.069\Delta Z_{drop}$.

375. The system of Clause 365, wherein the probability of success is approximately equal to $$\frac{e^Y}{(1+e^Y)}$$

and $Y \sim -0.307 + 0.206\Delta T_{min} + 0.083\ Z_{dropmin}$

376. The system of Clause 365, wherein the probability of success is approximately equal to $$\frac{e^Y}{(1+e^Y)}$$

and $Y \sim 1.28 + 0.286\Delta T_{min} - 0.0594\Delta Z_{drop} + 0.0219\ Z_{dropmin}$ 377. The system of Clause 365, wherein the probability of success is approximately equal to $$\frac{e^Y}{(1+e^Y)}$$

and $Y \sim 1.174 + 0.315\Delta T_{min} - 0.0564\ \Delta Z_{drop}\%$

378. The system of Clause 365, wherein the probability of success is approximately equal $$\frac{e^Y}{(1+e^Y)}$$

and $Y \sim -0.624 + 0.170\Delta T_{min} + 0.107\ Z_{drop}\%_{min}$.

379. The system of Clause 365, wherein the probability of success is approximately equal $$\frac{e^Y}{(1+e^Y)}$$

and $Y \sim 0.119 + 0.1867\Delta T_{min} + 0.0717\ Z_{drop}\%_{min} - 0.0168\ \Delta Z_{drop}\%$.

380. The system of Clause 351 in which the probability of success is selected from one or more of clauses 352-379.

The method or uses, systems, and devices of this disclosure demonstrated high rates of substantial clinical effectiveness and safety in patients suffering from PAF. The specific configurations, choice of materials and the size and shape of various elements can be varied according to design specifications or constraints requiring a system or method or use constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method to treat a predetermined patient population for paroxysmal atrial fibrillation, the method comprising:
    ablating tissue of one or more targeted pulmonary veins with one or more of a plurality of electrodes of a radiofrequency balloon catheter;
    determining a characteristic, based on ablation parameters of the radiofrequency balloon catheter, of single shot pulmonary vein isolation (PVI) success rate; and
    achieving, based on the characteristic and step of ablating the tissue, a single shot isolation PVI success rate in an isolation of all targeted pulmonary veins for the predetermined patient population.

2. The method of claim 1, wherein the step of achieving the single shot isolation PVI success rate further comprises achieving at least about a 91.7% success rate by ablating with a pre-ablation mean initial impedance of less than about 95Ω.

3. The method of claim 1, wherein the step of achieving the single shot isolation PVI success rate further comprises achieving at least about 88% success rate by ablating with a pre-ablation highest initial anterior wall impedance of about 110Ω.

4. The method of claim 1, wherein the step of achieving the single shot isolation PVI success rate further comprises achieving at least about 87.5% success rate by ablating with a pre-ablation initial anterior wall impedance variation impedance range of less than about 20Ω.

5. The method of claim 1, wherein the characteristic is a predictor of the single shot isolation PVI success rate before ablation was limiting a highest initial temperature to less than about 31° C. among the plurality of electrodes of the balloon catheter.

6. The method of claim 1, wherein the step of achieving the single shot isolation PVI success rate further comprises achieving at least about a 90% success rate by ablating with a mean initial impedance of less than about 95Ω for and a highest initial impedance of less than about 110Ω.

7. The method of claim 1, wherein the characteristic is a predictor of the single shot isolation PVI success rate before ablation, the predictor being mean initial temperature, and wherein the mean initial temperature is approximately less than about 28° C. and the single shot isolation PVI success rate is at least approximately about 90%.

8. The method of claim 1, wherein the characteristic is a predictor of the single shot isolation PVI success rate before ablation, the predictor being a pre-ablation lowest temperature slope, and wherein the pre-ablation lowest temperature slope is approximately greater than about 0.75° C./sec, and the single shot isolation PVI success rate is at least approximately about 90%.

9. The method of claim 1, wherein the characteristic is a predictor of the single shot isolation PVI success rate before ablation, the predictor being a pre-ablation lowest value temperature, and wherein the pre-ablation lowest value temperature is approximately greater than about 6° C., and the single shot isolation PVI success rate is at least approximately about 90%.

10. The method of claim 1, wherein the characteristic is a predictor of the single shot isolation PVI success rate before ablation, the predictor being a pre-ablation initial impedance variation, and wherein the pre-ablation initial impedance variation comprises an optimal range of approximately less than about 20Ω, and the single shot isolation PVI success rate is at least approximately about 88.5%.

11. The method of claim 1, wherein when one or more of the plurality of electrodes with initial impedance deviation from mean value is zero, the single shot isolation PVI success rate is approximately about 92%.

* * * * *